US012667626B2

(12) United States Patent
Mitragotri et al.

(10) Patent No.: US 12,667,626 B2
(45) Date of Patent: Jun. 30, 2026

(54) COMPOSITIONS AND METHODS RELATING TO ERYTHROCYTES WITH ADHERED PARTICLES

(71) Applicant: PRESIDENT AND FELLOWS OF HARVARD COLLEGE, Cambridge, MA (US)

(72) Inventors: Samir Mitragotri, Lexington, MA (US); Anvay Ashish Ukidve, Somerville, MA (US); Zongmin Zhao, Cambridge, MA (US)

(73) Assignee: PRESIDENT AND FELLOWS OF HARVARD COLLEGE

(*) Notice: Subject to any disclaimer, the term of this patent is extended or adjusted under 35 U.S.C. 154(b) by 897 days.

(21) Appl. No.: 17/616,760

(22) PCT Filed: Jun. 4, 2020

(86) PCT No.: PCT/US2020/036040
§ 371 (c)(1),
(2) Date: Dec. 6, 2021

(87) PCT Pub. No.: WO2020/247576
PCT Pub. Date: Dec. 10, 2020

(65) Prior Publication Data

US 2022/0323603 A1 Oct. 13, 2022

Related U.S. Application Data

(60) Provisional application No. 62/858,478, filed on Jun. 7, 2019.

(51) Int. Cl.

*A61K 47/69* (2017.01)
*A61K 9/51* (2006.01)
*A61K 35/18* (2015.01)
*A61P 11/00* (2006.01)
*A61P 35/04* (2006.01)
*A61P 37/04* (2006.01)

(52) U.S. Cl.
CPC ...... *A61K 47/6901* (2017.08); *A61K 47/6937* (2017.08); *A61P 11/00* (2018.01); *A61P 35/04* (2018.01); *A61P 37/04* (2018.01)

(58) Field of Classification Search
CPC ............ A61K 47/6901; A61K 47/6937; A61K 9/5153; A61K 35/18; A61K 34/18; A61K 9/51
See application file for complete search history.

(56) References Cited

U.S. PATENT DOCUMENTS

| | | | |
|---|---|---|---|
| 6,355,270 | B1 | 3/2002 | Ferrari et al. |
| 6,998,393 | B2 | 2/2006 | Jin et al. |
| 2009/0258057 | A1 | 10/2009 | Swiston et al. |
| 2011/0038939 | A1 | 2/2011 | Lvov et al. |
| 2012/0195939 | A1 | 8/2012 | Nadal-Ginard |
| 2013/0045162 | A1 | 2/2013 | Lillard et al. |
| 2015/0010630 | A1 | 1/2015 | Llamas et al. |
| 2016/0331802 | A1 | 11/2016 | Li et al. |
| 2017/0266317 | A1 | 9/2017 | Polak et al. |
| 2018/0243440 | A1 | 8/2018 | Muzykantov et al. |
| 2020/0376137 | A1 | 12/2020 | Mitragotri et al. |

FOREIGN PATENT DOCUMENTS

| | | | | |
|---|---|---|---|---|
| WO | WO-2004032970 A2 * | 4/2004 | ....... A61K 47/48776 |
| WO | 2009134866 A2 | 11/2009 | |
| WO | 2019139892 A1 | 7/2019 | |

OTHER PUBLICATIONS

Kapoor et al., PLGA: a Unique Polymer for Drug Delivery. Therapeutic Delivery, 6(1), 41-58. (Year: 2015).*
Luk, Brian T., et al. "Safe and immunocompatible nanocarriers cloaked in RBC membranes for drug delivery to treat solid tumors." Theranostics 6.7 (2016): 1004. (Year: 2016).*
Ma, "Establishment and in vitro evaluation of CPT-11-PLGA nanoparticle erythrocyte system", Disseration of Southeast Univeristy, pp. 15-25. (Year: 2017).*
Pan et al., Nanoparticle Properties Modulate Their Attachment and Effect on Carrier Red Blood Cells. Sci Rep 8, 1615 (2018). https://doi.org/10.1038/s41598-018-19897-8 (Year: 2018).*
Ma, "Establishment and in vitro evaluation of CPT-11-PLGA nanoparticle erythrocyte system", Disseration of Southeast Univeristy, pp. 15-25. Full Translation Provided. (Year: 2017).*
Steenblock et al. "A Comprehensive Platform for Ex Vivo T-cell Expansion Based on Biodegradable Polymeric Artificial Antigen-presenting Cells." Molecular Therapy 16(4):765-772 (2008).
Anselmo et al., "Cell-mediated delivery of nanoparticles: taking advantage of circulatory cells to target nanoparticles." Journal of Controlled Release 190:531-541 (2014).
Anselmo et al., "Monocyte-mediated delivery of polymeric backpacks to inflamed tissues: a generalized strategy to deliver drugs to treat inflammation." Journal of Controlled Release 199:29-36 (2015).
Ayer et al., "Cell-mediated delivery of synthetic nano-and microparticles." Journal of Controlled Release 259:92-104 (2017).
Guo et al. "Light-driven fine chemical production in yeast biohybrids." Science 362(6416): 813-816 (2018).
Guo et al. "Modular assembly of superstructures from polyphenol-functionalized building blocks." Nature Nanotechnology 11(12): 1105-1111 (2016).
Reitzer et al. "Polyphenols at interfaces." Advances in Colloid and Interface Science 257: 31-41 (2018).
Villa et al., "Red blood cells: supercarriers for drugs, biologicals, and nanoparticles and inspiration for advanced delivery systems." Advanced Drug Delivery Reviews 106:88-103 (2016).
Von Staszewski et al. "Nanocomplex formation between β-lactoglobulin or caseinomacropeptide and green tea polyphenols: Impact on protein gelation and polyphenols antiproliferative activity." Journal of Functional Foods 4(4):800-809 (2012).

(Continued)

*Primary Examiner* — Abigail Vanhorn
(74) *Attorney, Agent, or Firm* — NIXON PEABODY LLP; David S. Resnick; Nicole D. Kling

(57) ABSTRACT

Provided herein are erythrocytes with polymeric particles (i.e., 'backpacks') adhered that provide delivery of payload therapeutic agents to subjects administered these cells.

21 Claims, 91 Drawing Sheets

(56) References Cited

OTHER PUBLICATIONS

Xu et al. "Natural polyphenols as versatile platforms for material engineering and surface functionalization." Progress in Polymer Science 87: 165-196 (2018).
Chu et al. "Photosensitization Priming of Tumor Microenvironments Improves Delivery of Nanotherapeutics via Neutrophil Infiltration" Advanced Materials 29:1701021 (2017).
Fahmy et al. "Nanosystems for Simultaneous Imaging and Drug Delivery to T Cells" The AAPS Journal 9:19 (2007).
Park et al. "Hyaluronic acid-coated nanparticles for targeted photodynamic theapy of cancer guided by near-infrared and MR imaging." Carbohydrate Polymers 157:476-483 (2016).
Steenblock et al. "An Artificial Antigen-presenting Cell with Pracrine Delivery of IL-2 Impacts the Magnitude and Direction of the T Cell Reponse." TBC 40:34883-34592 (2011).
Tang et al. "Enhancing T cell therapy through TCR signaling-responsive nanoparticle drug delivery" Nat Biotechnol 36:707-716 (2018).
Warren et al. "A novel binding assy to assess specificity of monoclonal antibodies." J Immunol Methods 305:33-38 (2005).
Zhang et al. "Hyaluronic Acid-Chitosan Nanoparticles to Deliver Gd-DTPA for MR Cancer Imaging." Nanomaterials 5:1379-1396 (2015).
Anselmo et al., "Delivering Nanoparticles to Lungs while Avoiding Liver and Spleen through Adsorption on Red Blood Cells" ACS Nano 7(12):11129-11137 (2013).
Pang et al., "Primary M1 macrophages as multifunctional carrier combined with PLGA nanoparticle delivering anticancer drug for efficient glioma therapy." Drug Delivery 25(1):1922-1931 (2018).
Rezvantalab et al., "PLGA-Based Nanoparticles in Cancer Treatment" Frontiers in Pharmacology 9:1663-9812 (2018).
Zelepukin et al., "Nanoparticle-based drug delivery via RBC-hitchhiking for the inhibition of lung metastases growth." Nanoscale 11(4):1636-1646 (2019).
Shields et al. "Induction of lymphoidlike stroma and immune escape by tumors that express the chemokine CCL21." Science 328.5979 (2010): 749-752.
Ma "Establishment and in vitro evaluation of CPT-11-PLGA nanoparticle erythrocyte system", pp. 15-25, Published date: Mar. 15, 2017 [English Translation Provided].
Brenner et al., "Red blood cel-hitchhiking boosts delivery of nanocarriers to chosen organs by orders of magnitude." Nature Communications 9(1): Dec. 1, 2018.
Shin et al., "Targeting protein and peptide therapeutics to the heart via tannic acid modification." Nature Biomedical Engineering 2(5) 304-317 (Apr. 30, 2018).
Chambers et al. "Long Circulating Nanoparticles via Adhesion on Red Blood Cells: Mechanism and Extended Circulation" Experimental Biology and Medicine 232:958-966 (2007).
Ma "Establishment and in-vitro Evaluation of CPT-11-PLGA Nanoparticles-Red Blood Cell System", Southeast University, Master's Degree Thesis Published Mar. 15, 2017.
Zhao et al. "Systemic tumour suppression via the preferential accumulation of erythrocyte-anchored chemokine-encapsulating nanoparticles in lung metastases." Nature Biomedical Engineering 5.5: 441-454 (2021).
Zhao et al. "Erythrocyte leveraged chemotherapy (ELeCt): Nanoparticle assembly on erythrocyte surface to combat lung metastasis." Science Advances 5.11: eaax9250 (2019).

* cited by examiner

COMPOSITIONS AND METHODS RELATING TO ERYTHROCYTES WITH ADHERED PARTICLES

CROSS-REFERENCE TO RELATED APPLICATIONS

This application is a 35 U.S.C. § 371 National Phase Entry Application of International Application No. PCT/US2020/036040 filed Jun. 4, 2020, which designates the U.S. and claims benefit under 35 U.S.C. § 119(e) of U.S. Provisional Application No. 62/858,478 filed Jun. 7, 2019, the contents of which are incorporated herein by reference in their entireties.

TECHNICAL FIELD

The technology described herein relates to methods and compositions relating to erythrocytes with particles adhered to their cell surface.

BACKGROUND

An ongoing problem with most pharmaceutical treatments is the difficulty in achieving targeted delivery of the therapeutic agent. Intravenous administration can provide minimally invasive administration that is capable of delivery to much of the body, but the dose received by the diseased tissue or organ is a mere fraction of the total dose. Additionally, existing administration technology will also result in the therapeutic agent being distributed to organs and tissue which are not in need of treatment, often causing deleterious side effects. Described herein are the highly effective Erythrocyte Leveraged Chemotherapy (ELeCt) and Erythrocyte Anchored Systemic Immunotherapy (EASY) platforms, consisting of biodegradable drug nanoparticles self-assembled onto the surface of erythrocytes, to permit efficient and even targeted drug delivery. For example, in one embodiment, the ELeCt platform significantly extended the circulation time of the drug nanoparticles and delivered 10-fold higher drug content to the target organ compared to the free nanoparticles.

SUMMARY

Described herein is an approach which permits a red blood cell to delivery a therapeutic agent to specific tissues and/or organs in the body. This approach is demonstrated to be more efficient, and therefore to carry less risk of side effects than dosing with the agent alone, or encapsulation of the agent in free polymeric particles.

In one aspect of any of the embodiments, described herein is an engineered cellular composition comprising: a. an erythrocyte; and b. a particle comprising PLGA and at least one therapeutic agent, wherein the particle is located on the cell surface of the erythrocyte.

In some embodiments of any of the aspects, the PLGA comprises a L:G ratio of at least 50:50 or more L. In some embodiments of any of the aspects, the PLGA comprises a L:G ratio of about 50:50. In some embodiments of any of the aspects, the PLGA comprises a L:G ratio of about 85:15. In some embodiments of any of the aspects, the PLGA comprises a L:G ratio of about 65:35.

In some embodiments of any of the aspects, the PLGA comprises ester ends and/or acid ends. In some embodiments of any of the aspects, the PLGA comprises ester ends. In some embodiments of any of the aspects, the PLGA comprises acid ends.

In some embodiments of any of the aspects, the PLGA comprises a L:G ratio of about 50:50 and ester ends. In some embodiments of any of the aspects, the PLGA comprises a L:G ratio of about 50:50 and acid ends. In some embodiments of any of the aspects, the PLGA comprises a L:G ratio of about 85:15 and ester ends. In some embodiments of any of the aspects, the PLGA comprises a L:G ratio of about 65:35 and acid ends.

In some embodiments of any of the aspects, the PLGA comprises a L:G ratio of about 50:50 and ester ends, whereby the therapeutic agent is targeted to the spleen and/or heart. In some embodiments of any of the aspects, the PLGA comprises a L:G ratio of about 50:50 and acid ends, whereby the therapeutic agent is targeted to the spleen and/or lung. In some embodiments of any of the aspects, the PLGA comprises a L:G ratio of about 85:15 and ester ends, whereby the therapeutic agent is targeted to the kidney and/or lung. In some embodiments of any of the aspects, the PLGA comprises a L:G ratio of about 65:35 and acid ends, whereby the therapeutic agent is targeted to the lung, heart and/or kidney. In some embodiments of any of the aspects, the PLGA comprises a L:G ratio of more than 50:50, whereby the therapeutic agent is targeted to the lung and/or kidney. In some embodiments of any of the aspects, the PLGA comprises a L:G ratio of less than 85:15 and ester ends, whereby the therapeutic agent is targeted to the spleen.

In some embodiments of any of the aspects, the at least one therapeutic agent is selected from a chemotherapeutic agent; an antigen; a steroid; an immunosuppressant agent; an immunostimulatory agent; a virus; a small molecule; a peptide; a nucleic acid; and a chemokine. In some embodiments of any of the aspects, the at least one chemotherapeutic agent is selected from the group consisting of doxorubicin; camptothecin; paclitaxel; docetaxel; 5-fluorouracil; gemcitabine; methotrexate; or a combination thereof.

In some embodiments of any of the aspects, the therapeutic agent is present at a concentration of at least 100 μg per $3\times10^8$ erythrocytes. In some embodiments of any of the aspects, the therapeutic agent is present at a concentration of at least 150 μg per $3\times10^8$ erythrocytes. In some embodiments of any of the aspects, the therapeutic agent is present at a concentration of at least 200 μg per $3\times10^8$ erythrocytes. In some embodiments of any of the aspects, the therapeutic agent is present at a concentration of at least 250 μg per $3\times10^8$ erythrocytes.

In some embodiments of any of the aspects, the diameter of the polymeric particle is from about 100 nm to about 10 μm. In some embodiments of any of the aspects, the diameter of the polymeric particle is from about 100 nm to about 1 μm.

In some embodiments of any of the aspects, the polymeric particle further comprises one or more cell adhesive molecules. In some embodiments of any of the aspects, the one or more cell adhesive molecules is localized to a region of the particle surface. In some embodiments of any of the aspects, the cell adhesive molecule is selected from the group consisting of an antibody reagent that binds specifically to a molecule on a red blood cell; a peptide that binds specifically to a molecule on a red blood cell; a cell adhesive polymer; a cell adhesive polyelectrolyte, and a ligand for a receptor on a red blood cell. In some embodiments of any of the aspects, the cell adhesive polyelectrolytes comprise hyaluronic acid, hyaluronic acid-aldehyde, and/or poly(allylamine) hydrochloride. In some embodiments of any of the aspects, the aspects, the hyaluronic acid is modified to comprise aldehyde groups. In some embodiments of any of the aspects, the cell adhesive polymer is a polyphenol or metal-polyphenol network.

In one aspect of any of the embodiments, described herein is a method of delivering a therapeutic agent to a cell in a subject, the method comprising administering to the subject a composition described herein. In some embodiments of any of the aspects, the cell is a cancer cell and the therapeutic agent is a chemotherapeutic agent, chemokine, or immunostimulatory agent (e.g., IFNs, IFN-γ, TNFα, TGF-β, IL-1β, IL-6, IL-4, IL-10, IL-13, IL-2, IL-12, IL-15, and IL-27, and other immunostimulatory antagonists such as CpG ODN, imiquimod, Resiquimod (R848), Monophosphoryl Lipid A (MPLA), and poly(I:C)).

In one aspect of any of the embodiments, described herein is a method of treating cancer and/or a tumor in a subject in need thereof, the method comprising administering to the subject a composition as described herein. In some embodiments of any of the aspects, the therapeutic agent is a chemotherapeutic agent or chemokine.

In some embodiments of any of the aspects, the cancer cell is in the lung of the subject and/or the subject has lung cancer. In some embodiments of any of the aspects, the PLGA comprises a L:G ratio of about 65:35 and acid ends.

In some embodiments of any of the aspects, the cancer cell is in the kidney of the subject and/or the subject has kidney cancer. In some embodiments of any of the aspects, the PLGA comprises a L:G ratio of about 85:15 and ester ends.

In some embodiments of any of the aspects, the PLGA comprises a L:G ratio of about 65:35 and acid ends. In some embodiments of any of the aspects, the PLGA comprises a L:G ratio of more than 50:50.

In some embodiments of any of the aspects, the method further comprising administering radiation or at least one chemotherapy to the subject.

In one aspect of any of the embodiments, described herein is a method of stimulating an immune response in a subject in need thereof, the method comprising administering to the subject a composition as described herein, wherein the therapeutic agent is an immunostimulatory agent or chemokine. In some embodiments of any of the aspects, the immune response is localized.

In one aspect of any of the embodiments, described herein is a method of decreasing or suppressing an immune response in a subject in need thereof, the method comprising administering to the subject a composition as described herein, wherein the therapeutic agent is an immunomodulatory agent (e.g., IL-4) or steroid. In some embodiments of any of the aspects, the immune response is localized. In some embodiments of any of the aspects, the subject is in need of an immune response in the lungs. In some embodiments of any of the aspects, the subject is in need of treatment for acute lung injury. In some embodiments of any of the aspects, the therapeutic agent is a steroid or IL-4. In some embodiments of any of the aspects, the PLGA comprises a L:G ratio of more than 50:50. In some embodiments of any of the aspects, the PLGA comprises a L:G ratio of about 65:35 and acid ends.

In some embodiments of any of the aspects, a therapeutically effective amount of the composition is administered. In some embodiments of any of the aspects, the dose of the therapeutic agent administered is 50% or less of the amount that would be administered to a subject if administered in a free form. In some embodiments of any of the aspects, the dose of the therapeutic agent administered is 40% or less of the amount that would be administered to a subject if administered in a free form. In some embodiments of any of the aspects, the dose of the therapeutic agent administered is 30% or less of the amount that would be administered to a subject if administered in a free form. In some embodiments of any of the aspects, the dose of the therapeutic agent administered is 20% or less of the amount that would be administered to a subject if administered in a free form. In some embodiments of any of the aspects, the dose of the therapeutic agent administered is 10% or less of the amount that would be administered to a subject if administered in a free form.

BRIEF DESCRIPTION OF THE DRAWINGS

FIG. 1A depicts graph of binding efficiency of different PLGA nanoparticles to erythrocytes. FIG. 1B depicts scanning electron microscopic (SEM) images of erythrocytes with different PLGA nanoparticles hitchhiked on them.

FIG. 2A depicts the percent nanoparticle detached from the carrier erythrocytes under a low shear stress (rotary shear stress, ~1 Pa). FIG. 2B depicts the net percent nanoparticles detached from erythrocytes under a high shear stress (6 Pa).

(FIG. 4A) Schematic illustration of the composition and mechanism of the biodegradable drug nanoparticle self-assembling on erythrocyte platform (EleCt) for lung metastasis treatment. (FIGS. 4B-4D) Average size (FIG. 4B), zeta potential (FIG. 4C), and drug loading contents (FIG. 4D) of plain and drug-loaded nanoparticles. (FIG. 4E) SEM images showing the morphological features of the nanoparticles. Scale bar: 200 nm. (FIG. 4F) Size distribution of plain and drug-loaded nanoparticles. (FIG. 4G) Drug release kinetics from the biodegradable nanoparticles in a complete medium (n=4). (FIGS. 4H-41) Flow cytometry plots (FIG. 4H) and confocal laser scanning microscopic images (FIG. 4I) showing the interaction of drug-loaded nanoparticles with B16F10-Luc melanoma cells. In (FIG. 4I), cell nuclei were stained using DAPI. (FIGS. 4J-4K) Dose-response curve (FIG. 4J) and $IC_{50}$ values (FIG. 4K) of B16F10-Luc cells after being treated with different formulations for 24 hours (n=6).

(FIG. 5A) Flow cytometry analysis of self-assembly of DOX-loaded PLGA nanoparticles to mouse erythrocytes at different nanoparticle to erythrocyte ratios (left to right: 0:1, 50:1, 200:1, 400:1, and 800:1). (FIG. 5B) Percentage of mouse erythrocytes carrying at least one nanoparticle. (FIG. 5C) Nanoparticle binding efficiency and (FIG. 5D) drug dose on mouse erythrocytes at different nanoparticle to mouse erythrocyte ratios. (FIG. 5E) Confocal laser scanning microscopic (CLSM) and (FIG. 5F) SEM images of mouse erythrocytes with drug-loaded nanoparticles self-assembled on them. Scale bars in (FIG. 5F): 2 μm. (FIG. 5G) CLSM and (FIG. 5H) SEM images of human erythrocytes with drug-loaded nanoparticles self-assembled on them. Scale bars in (FIG. 5H): 2 μm. (FIG. 5I) Flow cytometry assay of the self-assembly of drug-loaded nanoparticles to human erythrocytes at different nanoparticle to erythrocyte ratios (left to right: 0:1, 200:1, 800:1, and 1600:1). (FIG. 5J) Nanoparticle binding efficiency and (FIG. 5K) drug dose on human erythrocytes at different nanoparticle to erythrocyte ratios.

(FIG. 6A) Pharmacokinetics of intravenously administered doxorubicin formulations. Extended blood circulation time of doxorubicin was achieved by erythrocyte hitchhiking compared to using free drug or nanoparticles alone (n=3). Significantly different (ANOVA followed by Tukey's HSD analysis): *p<0.05, p<0.01. (FIG. 6B) Hitchhiked drug-loaded nanoparticles could specifically detach from mouse and human erythrocytes under the lung-corresponding shear stress. Samples were sheared for 20 mins (n=3). Low shear indicates rotary shear (~1 Pa) while high shear was at 6 Pa. Significantly different (Student's t test): *p<0.001. (FIG. 6C) Drug accumulation in the lungs of mice bearing B16F10-Luc lung metastasis at 20 min and 6 h after intravenous administration of different doxorubicin formulations (n=3). (FIG. 6D) Comparison of the drug concentration in the lungs of erythrocyte hitchhiking group to that of the free drug and nanoparticle alone groups (n=3). (FIG. 6E) Drug distribution in the diseased lungs 20 min after intravenous administration of doxorubicin formulations. Dashed lines indicate the edge of metastasis nodules.

(FIG. 7A) Schematic chart of the treatment schedule. (FIG. 7B) Bioluminescence images of lung metastasis at different time points. (FIG. 7C) Lung metastasis progression curve as depicted from in vivo bioluminescence signal intensity. (FIG. 7D) Quantification of lung metastasis burden at different time points (n=7). (FIG. 7E) Scatter-plot comparing the lung metastasis burden in different treatment groups as depicted from bioluminescence signal intensity on day 16 (n=7). Significantly different (Mann-Whitney test): *p<0.05, p<0.01, *p<0.001. (FIG. 7F) Scatter-plot comparison of the lung metastasis burden on day 23 (n=7). Significantly different (Mann-Whitney test): *p<0.05, p<0.01, *p<0.001; n.s.: not significantly different. (FIG. 7G) Body weight change of mice during the treatment period (n=7). (FIG. 7H) Survival of mice under different treatments as displayed by Kaplan-Meier curves (n=7). Significantly different (log-rank test): *p<0.05, p<0.01, *p<0.001; n.s.: not significantly different.

(FIG. 8A) Schematic illustration of the treatment schedule. (FIG. 8B) Bioluminescence images of lung metastasis progression at different time points. (FIG. 8C) Lung metastasis growth curve in mice treated with different doxorubicin formulations. (FIG. 8D) Quantitative analysis of lung metastasis burden as depicted from bioluminescence signal intensity (n=7). Significantly different (Mann-Whitney test): *p<0.05, p<0.01; n.s.: not significantly different. (FIG. 8E) Quantification of metastasis nodule numbers on excised lungs from mice in different treatment groups on day 16 (n=7). Significantly different (Mann-Whitney test): *p<0.001; n.s.: not significantly different. (FIG. 8F) Body weight change of mice during the treatment period (n=7). (FIG. 8G) Kaplan-Meier survival curves of mice in different treatment groups. Significantly different (log-rank test): p<0.01, *p<0.001; n.s.: not significantly different.

FIG. 9 demonstrates that other chemotherapeutic agent-loaded biodegradable nanoparticles can efficiently bind to erythrocytes. The tested chemotherapeutic agents include camptothecin, paclitaxel, docetaxel, 5-fluorouracil, gemcitabine, methotrexate, and the combination of 5-fluorouracil+methotrexate. Scale bars: 1 μm.

FIG. 11 depicts representative H&E staining images of organs of mice treated with different drug formulations. 16 days after tumor inoculation in the late-stage lung metastasis model, mice were scarified and organs were processed by H&E staining.

FIG. 12 depicts size distribution of different chemotherapeutic agent-loaded biodegradable PLGA nanoparticles.

FIG. 13 depicts a schematic illustration of Erythrocyte Anchored Systemic Immunotherapy (EASY) for immunorestoration. (a) ImmunoBait (chemokine-loaded polymeric nanoparticles) assemble onto the surface of erythrocytes. (b) ImmunoBait specifically dislodges from erythrocytes in response to the mechano-physiological shear stress and gets deposited in the vicinity of lung metastatic sites. (c) ImmunoBait modulates the local microenvironments by releasing chemokine and restoring the chemokine gradient. (d) Effector cells including Th1 CD4, effector CD8 T, and Natural Killer (NK) cells infiltrate to the lung metastatic sites to control their progression.

FIG. 14A depicts binding efficiency of different PLGA nanoparticles to erythrocytes (n=5). Significantly different (One-way ANOVA followed by Tukey's HSD test): p<0.01; &&& p<0.001 compared to all other groups. (FIG. 14R) Osmotic fragility of carrier erythrocytes after being hitchhiked by nanoparticles. Percent hemolysis of carrier erythrocytes at 73 mM NaCl was shown (n=3). Data in (FIGS. 14L, 14P, and 14R) are presented as mean±s.e.m.

(FIG. 15A) Scanning electron microscopic (SEM) images of ImmunoBait. Scale bar, 1 μm. (FIG. 15B) Transmission electron microscopic (TEM) images of ImmunoBait. Scale bar, 500 nm. (FIG. 15C) Size distribution of ImmunoBait. (FIG. 15D) Chemokine release kinetics from ImmunoBait (n=3). (FIG. 15E) CLSM images of erythrocytes with ImmunoBait assembled on them. ImmunoBait was labeled with Alexa Fluor 647 which was conjugated to chemokine. (FIG. 15F) Flow cytometry analysis of erythrocytes carrying Alexa Fluor 647 labeled ImmunoBait. ImmunoBait was labeled with Alexa Fluor 647 which was conjugated to chemokine. Dots to the left of the box: plain erythrocytes; dots within the box: erythrocytes carrying ImmunoBait. (FIG. 15G) SEM images of ImmunoBait assembled on erythrocytes. Scale bar, 1 μm. (FIG. 15H) Expression of phosphatidylserine on carrier erythrocytes after being hitchhiked by nanoparticles (n=3). Both plain nanoparticles and ImmunoBait caused negligible phosphatidylserine expression on the carrier erythrocytes. Series are, in order, plain NPs and ImmunoBait. (FIG. 15I) Agglutination of carrier erythrocytes hitchhiked by nanoparticles. 200 nm carboxylic polystyrene nanoparticles were used as a positive control in (FIG. 15H) and (FIG. 15I). (FIG. 15J) Osmotic fragility of carrier erythrocytes after being hitchhiked by nanoparticles. Percent hemolysis of carrier erythrocytes at 73 mM NaCl was shown (n=3). Data in (FIGS. 15D, 15H, and 15J) are presented as mean±s.e.m.

(FIG. 16A) SEM images of ImmunoBait hitchhiked erythrocytes before shear, after shear, or shear after fixation. Samples were sheared at a rotary shear stress of 6 Pa for 20 mins. (FIG. 16B) Percent ImmunoBait nanoparticles detached from the carrier erythrocytes when being sheared at 6 Pa for 5, 10, or 20 mins (n=3). (FIG. 16C) Biodistribution of ImmunoBait formulations 20 min or 6 h after intravenous administration in the early-stage lung metastasis model. At 20 min, n=3 for all groups. At 6 h, n=2 for NPs and NPs w/a ICAM-1; n=3 for EH-NPs and EH-NPs w/aICAM-1. Significantly different (One-way ANOVA followed by Tukey's HSD test): * $p<0.05$,  $p<0.01$, * $p<0.001$, and ** $P<0.0001$. (FIG. 16**D) Lung to blood ratio of distributed ImmunoBait nanoparticles 20 min after intravenous administration in the early-stage lung metastasis model (n=3). Significantly different (One-way ANOVA followed by Tukey's HSD test): * $p<0.05$. (FIG. 16E) IVIS fluorescent images of lungs of mice bearing early-stage lung metastasis 20 min after intravenous administration of ImmunoBait formulations. (FIG. 16F) IVIS fluorescent images of lungs of mice bearing late-stage lung metastasis 20 min after intravenous administration of ImmunoBait formulations. (FIG. 16G) CLSM images of metastatic lung sections 20 mins after intravenous administration of ImmunoBait formulations. White dash lines indicate the edge of the metastatic nodules. Nucleus were stained by DAPI. In (FIGS. 16B-16G), all nanoparticles were labeled by Alexa Fluor 647 that was conjugated to the albumin carrier protein that was encapsulated into the nanoparticles. (FIG. 16H) Schedule for monitoring the time-course change of CXCL10 chemokine gradients in mice bearing breast cancer lung metastasis. (FIG. 16I) Lung to blood ratio of CXCL10 chemokine on different days after primary tumor resection (n=5). Significantly different (One-way ANOVA followed by Tukey's HSD test): * $p<0.05$. (FIG. 16J) Schedule for the chemokine gradient assay. (FIG. 16K) Concentration of CXCL10 chemokine in the blood 20 min or 6 h after intravenous administration of CXCL10 formulations (n=4-5). (FIG. 16L) Concentration of CXCL10 chemokine in the blood 20 min or 6 h after intravenous administration of CXCL10 formulations (n=4-5). (FIG. 16M) Lung to blood ratio of CXCL10 chemokine concentration after administration (n=4-5). Significantly different (One-way ANOVA followed by Tukey's HSD test): * $p<0.05$,  $p<0.01$. Data in (FIGS. 16B-16D, 16I, 16K-16M) are presented as mean±s.e.m. Series for FIGS. 16K-16M are, in order, control, Free chemokine (5×), NPs, and RBC-NPs.

(FIG. 17A) Schedule for the efficacy study. (FIG. 17B) Representative bioluminescence images of mice receiving different treatments at different time. (FIG. 17C) Nodules number on excised lungs of mice on day 37 (n=8). Significantly different (Mann-Whitney test): p<0.01, *p<0.001. (FIG. 17D) Inhibition rate of different treatments. (FIG. 17E) Representative images of excised lungs on day 37. (FIG. 17F) Lung weight of mice on day 37 after being treated by different treatments (n=8). Significantly different (One-way ANOVA followed by Tukey's HSD test): *p<0.05. (FIG. 17G) Body weight change of mice during the treatment period (n=8). (FIG. 17H) Survival of mice under different treatments as displayed by Kaplan-Meier curves (n=6). Significantly different (log-rank test): *p<0.05. Data in (FIGS. 17C, 17F, 17G) are presented as mean±s.e.m.

(FIG. 18A) Schedule for profiling the immune cells of metastatic lungs of mice under different treatments. (FIGS. 18L-18O) Concentrations of (FIG. 18L) IFN-γ, (FIG. 18M) TNF-α, (FIG. 18N) IL-10, and (FIG. 18O) CXCL10 in the metastatic lungs of mice following different treatments. Data in (FIGS. 18C, 18E, 18I, 18K, and 18L-O) are presented as mean±s.e.m. Significantly different in (FIGS. 18C, 18E, 18G, 18I, 18K, and 18L-O) (One-way ANOVA followed by Tukey's HSD test): *p<0.05, p<0.01, **p<0.0001.

FIG. 19 depicts scanning electron microscopic (SEM) images of mouse erythrocytes carrying different PLGA nanoparticles.

(FIG. 20A) Percent carrier erythrocytes lysed during the hitchhiking process (n=3). (FIG. 20B) Osmotic fragility (hemolysis during osmotic shock) of the carrier erythrocytes with different PLGA nanoparticles hitchhiked on them (n=3). The enlarged panel shows the percent hemolysis of carrier erythrocytes at a NaCl concentration of 72.5 mM. (FIG. 20C) Percent carrier erythrocytes expressing phosphatidylserine on their surface after being hitchhiked by different PLGA nanoparticles (n=3). Data are presented as mean±s.e.m. Series for FIGS. 20A and 20C are, in order, PLGA-a, PLGA-b, PLGA-c, and PLGA-d.

FIG. 21 depicts the percent nanoparticles detached from the carrier erythrocytes under in vitro shear conditions. Erythrocytes with different PLGA nanoparticles hitchhiked on them were sheared for 20 mins using a rheometer at a high rotary stress (6 Pa) (n=2-3). Low shear indicates a rotary stress the carrier erythrocyte experienced during rotation using a revolver at 12 rpm/min. Data in are presented as mean±s.e.m. Series are, in order, low shear and high shear.

(FIG. 22A) Biodistribution of different PLGA nanoparticles either in a free form or hitchhiked to erythrocytes 20 min after intravenous administration (n=3 for NPs, n=6 for EH-NPs). Series are, in order NPs, and EH-NPs. (FIG. 22B) Biodistribution of hitchhiked PLGA-d nanoparticles with or without anti-ICAM-1 antibody at different time points after intravenous administration (n=3). Series are, in order, NPs, EH-NPs without aICAM-1, and EH-NPs with aICAM-1. Significantly different (One-way ANOVA followed by Tukey's HSD test): *p<0.05, p<0.01, *p<0.001. Data are presented as mean±s.e.m.

(FIG. 23A) Flow cytometry histogram plots of erythrocytes after being incubated with different amount of ImmunoBait nanoparticles. ImmunoBait to erythrocyte ratios used in histograms from left to right are 0:1, 50:1, 400:1, and 1000:1, respectively. (FIG. 23B) Percentage of erythrocytes carrying ImmunoBait nanoparticles after being incubated at different ImmunoBait to erythrocyte ratios (n=3). Data are presented as mean±s.e.m. (FIG. 23C) CLSM images of erythrocytes carrying ImmunoBait nanoparticles when being incubated at a ImmunoBait to erythrocyte ratio of 400:1. ImmunoBait was labeled by Alexa Fluor 647 which was conjugated to the encapsulated chemokine.

FIG. 24 demonstrates assembly of ImmunoBait carrying other immunomodulatory agents onto erythrocytes. GM-CSF, IL-2, IL-12, and IL-15 were encapsulated in ImmunoBait. Anti-PD-1 antibody was conjugated to the surface of ImmunoBait. Scale bar: 1 μm.

(FIG. 25A) SEM images of human erythrocytes with ImmunoBait nanoparticles assembled on them. Scale bar: 1 m. (FIG. 25B) Number of ImmunoBait nanoparticles assembled onto the surface of human erythrocytes at different ImmunoBait to human erythrocyte incubation ratios (n=3). Data are presented as mean±s.e.m.

FIG. 26 depicts the impact of ImmunoBait hitchhiking on the sensitivity of the carrier erythrocytes to osmotic stress. Representative osmotic fragility curves of carrier erythrocytes were shown (n=3). The carrier erythrocytes at all the tested nanoparticle concentrations exhibited similar fragility curves compared to Naive erythrocytes. Data are presented as mean±s.e.m.

FIG. 28 depicts representative images of the back side of lungs of mice on day 37 under different treatments in the early-stage lung metastasis model.

FIG. 29 depicts H&E of mouse organs following different treatments in the early-stage lung metastasis model.

(FIG. 30A) Schedule for the efficacy study in the late-stage lung metastasis model. (FIG. 30B) Nodule number on excised lungs of mice on day 50 following different treatments (n=3). Significantly different (student's t test): *p<0.05. Data are presented as mean±s.e.m. (FIG. 30C) Images of excised lungs on day 50.

(FIG. 31D) The percentage of CD86+ cell in CD45+CD11c+ dendritic cells. Data are presented as mean±s.e.m. Significantly different (One-way ANOVA followed by Tukey's HSD test): *p<0.05, p<0.01, *p<0.001.

FIG. 32 depicts a heat-map showing the concentrations of cytokines in the metastatic lungs of mice being treated by different treatments. Unit: pg/mL.

(FIG. 33A) Schedule for evaluating the local and systemic immune response. (FIG. 33P) Photographs of extracted tumors 16 days after tumor rechallenge. "EXP" indicates "Expired". In (FIGS. 33K-33P), n=8 for the "Healthy" group; n=5 for the "Control-saline" and "EASI" groups. In (FIGS. 33M-33O), significantly different (student's t test): *p<0.05, p<0.01, **p<0.0001. Data in (FIGS. 33B, 33D, 33F, 33H, 33J, and 33M-33O) are presented as mean±s.e.m.

(FIG. 34A) When erythrocytes were fixed by 2.5% glutaraldehyde. (FIG. 34B) When the surface of erythrocytes was PEGylated. (FIG. 34C) When the hitchhiking was conducted in serum. (FIG. 34D) When PLGA NPs were PEGylated. (FIG. 34E) When PLGA NPs had different surface end (different hydrogen bonding capability).

FIG. 35 depicts the percent nanoparticles detached from the carrier erythrocytes under in vitro shear conditions. Erythrocytes with different PLGA nanoparticles hitchhiked on them were sheared for 20 mins using a rheometer at a high rotary stress (6 Pa) (n=6-7). Low shear indicates a rotary stress the carrier erythrocyte experienced during rotation using a revolver at 12 rpm/min. Data in are presented as mean±s.e.m. Significantly different (two-way ANOVA): *P<0.05, p<0.01, *p<0.0001. Significantly different compared to all other groups (two-way ANOVA): && P<0.01.

(FIG. 36A) Schematic illustration of the dual-labeling strategy for the tracking of carrier erythrocytes and nanoparticles. The carrier erythrocytes were labeled with CellTrace™ Far Red and PLGA-d nanoparticles were labeled with FITC. Blood was collected at different time points after i.v. administration of the dual-labeled system. The carrier erythrocytes and the nanoparticles on them were analyzed by flow cytometry. (FIG. 36B) Representative flow plots of the blood at different time points (n=3). (FIG. 36C) Representative flow plot of the administered erythrocytes at different time points (n=3). (FIG. 36D) Percentage of the carrier erythrocytes remaining in the blood at different time points as normalized to 0 min (n=3). (FIG. 36E) Percentage of the carrier erythrocytes carrying hitchhiked nanoparticles at different time points as normalized to 0 min (n=3). (FIG. 36F) IVIS images of organs of mice 5 min after i.v. administration of the erythrocyte hitchhiking system. In (FIG. 36F), nanoparticles were labeled by encapsulating AF647 while the carrier erythrocytes were not labeled.

FIG. 37 depicts the effect of the binding of aICAM-1 antibody to EH-NP complex on the detachment of nanoparticles from carrier erythrocytes under shear stress. Erythrocytes with PLGA-d nanoparticles hitchhiked on them w/or w/o aICAM-1 binding were sheared for 20 mins using a rheometer at a high rotary stress (6 Pa) (n=4-7). Low shear indicates a rotary stress the carrier erythrocyte experienced during rotation using a revolver at 12 rpm/min. Data in are presented as mean±s.e.m. n.s.: not significantly different (two-way ANOVA).

(FIG. 38A) MALDI-TOF spectrum of native CXCL10 and CXCL10 released from ImmunoBait. (FIG. 38B) Circular Dichroism Spectrum of native CXCL10 and CXCL10 released from ImmunoBait.

FIGS. 39A-39 B demonstrate that ImmunoBait was released from carrier erythrocytes under shear. (FIG. 39A) SEM images of ImmunoBait hitchhiked erythrocytes before shear, after shear, or shear after fixation. Samples were sheared at a rotary shear stress of 6 Pa for 20 mins. (FIG. 39B) Percent ImmunoBait nanoparticles detached from the carrier erythrocytes when being sheared at low shear stress (rotary shear at 12 rpm) or high shear stress (6 Pa) for 3, 10, or 20 mins (n=3). Significantly different compared to low shear (student's t test): *p<0.001, **p<0.0001. Data in (FIG. 39B) are presented as mean±s.e.m.

FIG. 40A) Representative IVIS images of lungs. FIG. 40B) ID % of ImmunoBait NPs accumulated in the lungs. Data indicated that with the progression of lung metastasis, the amount of NPs delivered to lungs by EH remained similar. Not significantly different among all groups (One-way ANOVA followed by Tukey's HSD test): n.s. Data are presented as mean±s.e.m.

FIG. 41A) Representative IVIS images of organs of mice injected with saline, EASI, or EASI after phagocyte depletion. FIG. 41B) Total radiant efficiency per gram of organ in major organs of mice with or without phagocyte depletion. The depletion of phagocytes resulted in reduced NP accumulation in the liver and kidney, indicating NPs accumulated in these two organs were majorly entrapped in phagocytes. In contrast, the accumulation of NPs in the lung was not decreased when phagocytes were depleted, indicating the detached ImmunoBait NPs in the lung were not majorly entrapped in phagocytes. Data are presented as mean s.e.m. Significantly different (Student's t test): *$p<0.01$, $p<0.01$, *$p<0.001$.

(FIG. 42A) Concentration of RANTES chemokine in the blood (n=5). (FIG. 42B) Concentration of RANTES chemokine in the lung (n=5). (FIG. 42C) Lung to blood ratio of RANTES chemokine concentration after administration (n=5). Data are presented as mean±s.e.m. Significantly different (Student's t test): **$p<0.01$. Not significantly different (Student's t test): n.s.

(FIG. 45A) Representative images of lungs of mice on day 37 under different treatments in the early-stage lung metastasis model. (FIG. 45B) Body weight change of mice during the treatment. Data in (FIG. 45B) are presented as mean±s.e.m.

(FIG. 46A) The absolute percentage of dendritic cells in the lungs. (FIG. 46B) The percentage of CD86+ cell in CD45+CD11c+ dendritic cells. Data are presented as mean±s.e.m. Significantly different (student's t test): $p<0.01$, **$p<0.0001$.

(FIG. 47A) Protein-capped polymeric nanoparticles used for the study (different size, material or coated with different proteins). (FIG. 47B) Number of nanoparticles loaded on erythrocytes were tuned for protein loading and to induce temporary upregulation of phosphatidyl choline. (FIG. 47C) Intravenous injection of hitchhiked nanoparticles leads to high discharge in the spleen. (FIG. 47D) Upregulated phosphatidyl choline and masking CD47 improves interactions with antigen presenting cells (APCs) in the spleen. (FIG. 47E) Improved erythrocyte interactions facilitate nanoparticle uptake by the APCs while the erythrocytes return back to the circulation. (FIG. 47F) Hand-off of nanoparticles at the spleen improves both humoral and cellular immune responses.

(FIG. 48A) Scheme of protein attachment to polystyrene carboxylate (PS—COOH) nanoparticles using EDC chemistry. (FIG. 48B) Antigen attached to PS—COOH (n=12). (FIG. 48C) Particle size in nm of plain and protein capped nanoparticles (n=6). Significantly different (Student's t test): **: $p<0.0001$. (FIG. 48D) Zeta potential in mV of plain and protein capped nanoparticles (n=6). Significantly different (Student's t test): : $p<0.0001$. (FIG. 48E) Particle size distribution of plain and protein capped nanoparticles. (FIG. 48F) Scanning electron micrographs (SEM) of plain and protein capped nanoparticles. Scale bar: 200 nm. (FIG. 48**G) Dendritic cell maturation evaluated in terms of % CD80 expression (normalized to basal expression) (n=3 for all groups). Significantly different (One-way ANOVA followed by Tukey's HSD test): *: $p<0.05$, ns: not significant. Data in (FIGS. 48B-48D, 48G) are expressed as mean±s.e.m.

(FIG. 49A) Nanoparticle loaded per erythrocyte for different feed ratios of nanoparticles to erythrocytes (n=3 for all groups). (FIG. 49B) Percentage of erythrocytes carrying nanoparticles (determined by flow cytometry) for different feed ratios of nanoparticles to erythrocytes (n=3 for all groups). (FIG. 49C) Percentage of nanoparticles released from erythrocytes following in vitro shear studies at the lung corresponding shear stress (6 Pa). Significantly different (One-way ANOVA followed by Tukey's HSD test). *: $p<0.05$. (FIG. 49D) Erythrocyte damaged caused by nanoparticles, evaluated by changes in percentage of phosphatidyl serine expression, for different feed ratios of nanoparticles to erythrocytes (n=3 for all groups) Dotted line indicates positive control (polystyrene beads) mean value. Significantly different (One-way ANOVA followed by Tukey's HSD test). *: $p<0.05$, : $p<0.01$. (FIG. 49E) Optical agglutination assay demonstrating minimal aggregates induced by nanoparticles to erythrocytes. All the tested nanoparticle to erythrocyte ratios were similar to Naïve control as opposed to polystyrene beads which induced matrix shaped aggregates. (FIG. 49F) IVIS images of lungs and spleen harvested from mice, 20 minutes after being injected with erythrocytes incubated at different nanoparticle to erythrocyte ratios. Scale indicates low (maroon) to high (bright yellow) radiant efficiency. (FIG. 49**G) Lung to spleen accumulation ratios computed by using radiant efficiencies of these organs from IVIS imaging (n=3 for all groups). Dotted line indicates equal lung and spleen accumulation. Significantly different (One-way ANOVA followed by Tukey's HSD test). *: $p<0.05$. (FIG. 49H) Fraction of particles and erythrocytes remaining in circulation, evaluating by their parallel tracking using flow cytometry (n=5). (FIG. 49I) Biodistribution of free nanoparticles and hitchhiked nanoparticles in different organs, expressed in terms of % Injected Dose per gram of tissue, harvested 20 minutes after injection (n=3 for all groups). Significantly different. (Student's t test). *: $p<0.05$. First series is NP, second series is RBC-NPs. (FIG. 49J) Kinetics of spleen accumulation of free and hitchhiked nanoparticles monitored over 24 hours after injection. (n=3 for all groups). Significantly different. (Student's t test). *: p<0.05. (FIG. 49K) Effect of phagocyte depletion on hitchhiked nanoparticles biodistribution in two most important organs of the mononuclear phagocytic system, 20 minutes after injection. (n=3 for all groups). First series is +phagocytes, second series is -phagocytes. Significantly different. (Student's t test). *: p<0.05, ns: not significant. Data in (FIGS. 49A-49D, 49G-49J) are expressed as mean±s.e.m.

(FIG. 50A) Schedule for evaluating systemic antibody (humoral) responses of hitchhiked nanoparticles. (FIG. 50B) Anti-OVA IgG titer evaluated one day before first immune challenge (Day −1) and 14 days after the second immune challenge (Day 27) (n=5 for all groups). Significantly different. (One-way ANOVA followed by Tukey's HSD test). *: p<0.05. (FIG. 50C) Schedule for evaluating systemic cellular immune responses of hitchhiked nanoparticles. (FIG. 50D) Representative flow cytometry analysis images of CD3+CD8+ cells in spleen. (FIG. 50E) Quantitative analysis of percentage of CD3+ CD8+ cells in spleen. (n=4 for EDIT group, n=5 for all other groups). Significantly different. (One-way ANOVA followed by Tukey's HSD test). *: p<0.05. (FIG. 50F) Representative flow cytometry analysis images of CCR7+ CD62L+ cells in spleen. (FIG. 50G) Quantitative analysis of percentage of CCR7+ CD62L+ cells in spleen. (n=4 for EDIT group, n=5 for all other groups). Significantly different. (One-way ANOVA followed by Tukey's HSD test). : p<0.01, *: p<0.001. (FIG. 50H) Representative flow cytometry analysis images of CD25+ FOXP3+ cells in spleen. (FIG. 50I) Quantitative analysis of percentage of CD25+ FOXP3+ cells in spleen. (n=4 for EDIT group, n=5 for all other groups). Significantly different. (One-way ANOVA followed by Tukey's HSD test). *: p<0.05, : p<0.01, : p<0.0001. Data in (FIGS. 50B, 50E, 50G, 50**I) are expressed as mean±s.e.m.

(FIG. 51A) Schedule for prophylactic vaccination studies. (FIG. 51B) In vitro cell killing data post immunizations by various treatment groups evaluated as percent viability normalized to the untreated control at different effector to target ratios (n=3 mice for all groups). Significantly different: Saline-OVA vs EDIT and NPs vs EDIT. (One-way ANOVA followed by Tukey's HSD test). *: p<0.05, &: p<0.05. (FIG. 51C) Fold change in in vitro cell killing assay, comparison of fold change within each treatment group as a function of effector to target ratio. (n=3 mice for all groups). Significantly different. (One-way ANOVA followed by Tukey's HSD). *: p<0.05. On the x-axis, the first group is Saline-OVA, the second group is NP, the third group is EDIT, and the fourth group is CpG. (FIG. 51D) Tumor growth curves for mice inoculated after prophylactic vaccinations by different treatment groups. Statistical analysis within this figure was carried on day 17. (FIG. 51E) Evaluation of tumor volumes for different groups on day 13. For FIGS. 51D-51E (n=8 for EDIT and CpG groups, n=7 for Saline and NP groups. Significant different (One-way ANOVA followed by Tukey's HSD). *: p<0.05, : p<0.01, *: p<0.001. FIGS. 51F-51I Tumor growth kinetics for individual mice in (FIG. 51F) Saline, (FIG. 51G) NP, (FIG. 51H) EDIT, (FIG. 51I) CpG treatment groups. Data in (FIGS. 51B-51E) are expressed as mean±s.e.m.

(FIG. 52A) Attachment efficiency of protein to the PS—COOH. (FIG. 52B) Amount of protein attached to PS—COOH expressed in terms of μg attached per mg of particles. Data expressed as mean±s.e.m.

(FIG. 53A) Flow cytometry images of dendritic cells post internalization of Alexa Fluor 647 labelled ovalbumin, either in free form or attached to PS—COOH. (FIG. 53B) Confocal light scanning micrographs (CLSM) of dendritic cells post internalization of Alexa Fluor 647 labelled ovalbumin either in free form or attached to PS—COOH. Scale bar: 10 μm.

(FIG. 54A) Quantification of different protein attachment to different particles using EDC chemistry. Attachment of ovalbumin to 500 nm polystyrene carboxylate and 200 nm polylactic co glycolate, and attachment of KLH to 200 nm polystyrene carboxylate. (n=6 for PS-KLH-200, n=5 for all other groups). (FIG. 54B) Scanning electron micrographs of the different particles. Scale bar: 200 nm. (FIG. 54C) Confocal light scanning micrographs (CLSM) of dendritic cells post internalization of Alexa Fluor 647 labelled ovalbumin or KLH attached to different particles. Scale bar: 10 μm. (FIG. 54D) Dendritic cell maturation evaluated in terms of % CD 80 expression (normalized to basal expression) (n=3 for all groups). Significantly different (Student's t test): *: p<0.001. Data in (FIGS. 54A-54**D) are expressed as mean±s.e.m.

(FIG. 55A) Hitchhiking efficiency change when erythrocytes are fixed indicating that physical wrapping of nanoparticles is needed to achieve proper hitchhiking. (FIG. 55B) Addition of serum during hitchhiking process affects the process, indicating that even a minimum amount of serum affects the protein-protein interactions from happening, indicating they are important interactions governing hitchhiking. (FIG. 55C) Confocal laser scanning microscopy images of hitchhiked nanoparticles on erythrocytes. Scale bar: 10 μm. Data expressed in (FIG. 55A, 55B) as mean±s.e.m.

(FIG. 56A) Group of control erythrocytes. Scale bar: 10 μm. (FIG. 56B) Group of hitchhiked erythrocytes. Scale bar: 10 μm. (FIG. 56C) Single erythrocyte showing hitchhiked nanoparticles. Scale bar: 2 μm (FIG. 57A) Percentage expression of CD47 on erythrocyte membrane. Naïve cells expression indicated by dotted lines. (n=3 for all groups). Significantly different. (One-way ANOVA followed by Tukey's HSD test). *: p<0.05. (FIG. 57B) Kinetics of changes in phosphatidyl serine expression as normalized to the basal. Groups indicate hitchhiked erythrocytes before injection, tracked erythrocytes immediately after injection and tracked erythrocytes 20 mins after injection (when the nanoparticles are expected to be sheared off) (n=3). Significantly different. (One-way ANOVA followed by Tukey's HSD test). *: p<0.05. Data expressed as mean±s.e.m.

(FIG. 58A) Biodistribution at 6 h. (n=3 for all groups). Significantly different. (Student's t test). *: p<0.05, *: p<0.001. (FIG. 58**B) Biodistribution at 24 h. Data expressed as mean±s.e.m. In both, the first series is NP and the second series is RBC-NPs.

(FIG. 59A) Scanning electron micrographs of erythrocytes with hitchhiked nanoparticles (PS-OVA-500, PLGA-OVA-200, PS-KLH-200). All scale bars: 2 μm (FIG. 59B) Erythrocyte damage caused by nanoparticles, evaluated by changes in percentage of phosphatidyl serine expression, for different protein capped particles, at a nanoparticle to erythrocyte feed ratio of 300:1 (n=3 for all groups). Dotted lines indicate phosphatidyl serine expression on Naïve erythrocytes and the damaged caused by positive control (polystyrene beads). (FIG. 59C) Optical agglutination assay demonstrating damage induced by nanoparticles to erythrocytes for different protein capped particles, at a nanoparticle to erythrocyte feed ratio of 300:1. All the tested particles were similar to Naïve control as opposed to polystyrene induced matrix shaped aggregates. (FIG. 59D) Biodistribution of hitchhiked nanoparticles, 20 minutes injection, evaluated by IVIS imaging. All the hitchhiked particles showed high spleen delivery efficiency. (n=3 for all groups). Data in (FIGS. 59B, 59D) are expressed as mean±s.e.m.

(FIG. 60A) Quantitative analysis of CD8+ cells present in the lungs. (n=3 for EDIT, n=5 for all other groups). (FIG. 60B) Quantitative analysis of antigen experienced CCR7+CD62L+ cells in the lungs (n=4 for EDIT, n=5 for all other groups). Data in (FIGS. 60A, 60B) are expressed as mean±s.e.m.

DETAILED DESCRIPTION

Figure 1A:
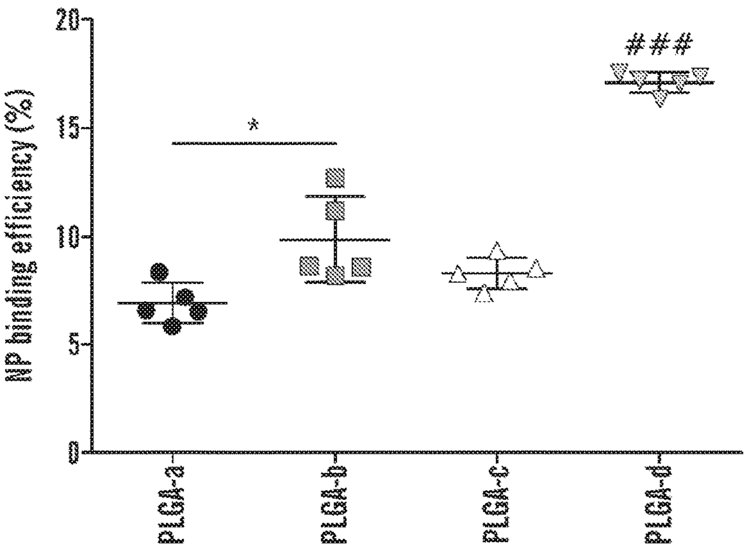
FIGS. 1A-1B depict properties of PLGA influence their binding to carrier erythrocytes.

The methods and compositions described herein relate to erythrocytes in combination with certain polymeric particles, e.g., located on the surface of the erythrocyte. These polymeric particles comprise at least therapeutic agent and PLGA. When the polymeric particles described herein are adhered to the erythrocyte and administered to a subject, they are less likely to be phagocytosed and can accumulate preferentially in a tissue or organ, providing drug delivery with increased efficiency.

In one aspect of any of the embodiments, described herein is an engineered composition (e.g., cellular composition) comprising: a. an erythrocyte; and b. a particle comprising PLGA and at least one therapeutic agent, wherein the particle is located on the cell surface of the erythrocyte. The particles can be referred to interchangeably herein as "adhered particles", "polymeric particles" or "backpacks."

An erythrocyte or red blood cell is a hematopoietic cell lacking a cell nucleus and having an oval biconcave shape in humans. Erythryocytes have high levels of hemoglobin and are the means by which oxygen is delivered throughout the body of vertebrates. In some embodiments of any of the aspects, the erythrocyte is a human erythrocyte. In some embodiments of any of the aspects, the erythrocyte is autologous to a subject—e.g., it is one of the subject's own erythrocytes to which the particle has been adhered, either in vitro or in vivo. In some embodiments of any of the aspects, the erythrocyte has not been genetically engineered and/or no exogenous material has been introduced to the cytoplasm of the erythrocyte.

The polymeric particles described herein comprise poly (lactic-co-glycolic) acid (PLGA). In some embodiments of any of the aspects, the particle comprises one or more therapeutic agents and PLGA. In some embodiments of any of the aspects, the particle consists essentially of one or more therapeutic agents and PLGA. In some embodiments of any of the aspects, the particle consists of one or more therapeutic agents and PLGA.

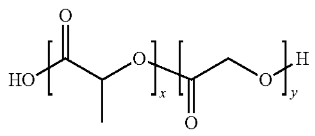

Structure of PLGA

In some embodiments of any of the aspects, the PLGA can be a random copolymer.

In some embodiments of any of the aspects, the PLGA can comprise, consist of, or consist essentially of PLGA with a molecular weight of from about 10,000 to about 90,000. In some embodiments of any of the aspects, the PLGA can comprise, consist of, or consist essentially of PLGA with a molecular weight of from about 20,000 to about 60,000. In some embodiments of any of the aspects, the PLGA can comprise, consist of, or consist essentially of PLGA with a molecular weight of from about 35,000 to about 56,000. In some embodiments of any of the aspects, the PLGA can comprise, consist of, or consist essentially of PLGA with a molecular weight of from about 38,000 to about 54,000. In some embodiments of any of the aspects, the PLGA can comprise, consist of, or consist essentially of PLGA with a molecular weight of from about 45,000 to about 80,000. In some embodiments of any of the aspects, the PLGA can comprise, consist of, or consist essentially of PLGA with a molecular weight of from about 50,000 to about 75,000. In some embodiments of any of the aspects, the PLGA can comprise, consist of, or consist essentially of PLGA with a molecular weight of from about 20,000 to about 40,000. In some embodiments of any of the aspects, the PLGA can comprise, consist of, or consist essentially of PLGA with a molecular weight of from about 24,000 to about 38,000.

In some embodiments of any of the aspects, the PLGA can comprise, consist of, or consist essentially of PLGA with a molecular weight of from 10,000 to 90,000. In some embodiments of any of the aspects, the PLGA can comprise, consist of, or consist essentially of PLGA with a molecular weight of from 20,000 to 60,000. In some embodiments of any of the aspects, the PLGA can comprise, consist of, or consist essentially of PLGA with a molecular weight of from 35,000 to 56,000. In some embodiments of any of the aspects, the PLGA can comprise, consist of, or consist essentially of PLGA with a molecular weight of from 38,000 to 54,000. In some embodiments of any of the aspects, the PLGA can comprise, consist of, or consist essentially of PLGA with a molecular weight of from 45,000 to 80,000. In some embodiments of any of the aspects, the PLGA can comprise, consist of, or consist essentially of PLGA with a molecular weight of from 50,000 to 75,000. In some embodiments of any of the aspects, the PLGA can comprise, consist of, or consist essentially of PLGA with a molecular weight of from 20,000 to 40,000. In some embodiments of any of the aspects, the PLGA can comprise, consist of, or consist essentially of PLGA with a molecular weight of from 24,000 to 38,000.

In some embodiments of any of the aspects, the PLGA comprises a L:G ratio of at least about 50:50 or more L, e.g., a L:G of at least about 50:50, about 55:45, about 60:40, about 65:35, about 70:30, about 75:25, about 80:20, about 85:15, about 90:10, or about 95:5 or more. In some embodiments of any of the aspects, the PLGA comprises a L:G ratio of at least 50:50 or more L, e.g., a L:G of at least 50:50, 55:45, 60:40, 65:35, 70:30, 75:25, 80:20, 85:15, 90:10, or 95:5 or more. In some embodiments of any of the aspects, the PLGA comprises a L:G ratio of at least from about 50:50 to about 95:5, e.g., a L:G ratio of from about 50:50 to about 85:15, of from about 50:50 to about 65:35. In some embodiments of any of the aspects, the PLGA comprises a L:G ratio of at least from 50:50 to 95:5, e.g., a L:G ratio of from 50:50 to 85:15, of from 50:50 to 65:35. In some embodiments of any of the aspects, the PLGA comprises a L:G ratio of about 50:50, about 65:35, or about 85:15. In some embodiments of any of the aspects, the PLGA comprises a L:G ratio of from 45:55 to 55:45, from 60:40 to 70:30 or from 80:20 to 90:10. In some embodiments of any of the aspects, the PLGA comprises a L:G ratio of 50:50, 65:35, or 85:15.

PLGA can terminate in an ester end or an acid end. In some embodiments of any of the aspects, the PLGA comprises ester ends and/or acid ends. In some embodiments of any of the aspects, the PLGA ends comprise at least 90% ester ends, e.g, at least 90%, at least 95%, at least 98%, at least 99% or more ester ends. In some embodiments of any of the aspects, the PLGA ends comprise at least 90% acid ends, .g, at least 90%, at least 95%, at least 98%, at least 99% or more acid ends. In some embodiments of any of the aspects, the PLGA ends consist of ester ends. In some embodiments of any of the aspects, the PLGA ends consist of acid ends.

Certain specific PLGA compositions, comprising certain L:G ratios and end identities are contemplated herein, and are demonstrated to target their polymeric particles to certain organs. Exemplary such compositions are provided in Table 3.

TABLE 3

| Particle Composition # | Ratio of L:G in PLGA | PLGA end composition | Targeted organs |
|---|---|---|---|
| 1 | About 50:50 | Comprises at least 90% ester ends | Spleen, heart |
| 2 | 45:55 to 55:45 | Comprises at least 90% ester ends | Spleen, heart |
| 3 | 50:50 | Comprises at least 90% ester ends | Spleen, heart |
| 4 | About 50:50 | Consists of ester ends | Spleen, heart |
| 5 | 45:55 to 55:45 | Consists of ester ends | Spleen, heart |
| 6 | 50:50 | Consists of ester ends | Spleen, heart |
| 7 | About 50:50 | Comprises at least 90% acid ends | Spleen, lung |
| 8 | 45:55 to 55:45 | Comprises at least 90% acid ends | Spleen, lung |
| 9 | 50:50 | Comprises at least 90% acid ends | Spleen, lung |
| 10 | About 50:50 | Consists of acid ends | Spleen, lung |
| 11 | 45:55 to 55:45 | Consists of acid ends | Spleen, lung |
| 12 | 50:50 | Consists of acid ends | Spleen, lung |
| 13 | About 85:15 | Comprises at least 90% ester ends | Kidney, lung |
| 14 | 80:20 to 90:10 | Comprises at least 90% ester ends | Kidney, lung |
| 15 | 85:15 | Comprises at least 90% ester ends | Kidney, lung |
| 16 | About 85:15 | Consists of ester ends | Kidney, lung |
| 17 | 80:20 to 90:10 | Consists of ester ends | Kidney, lung |
| 18 | 85:15 | Consists of ester ends | Kidney, lung |
| 19 | About 65:35 | Comprises at least 90% acid ends | Lung, heart, kidney |
| 20 | 60:40 to 70:30 | Comprises at least 90% acid ends | Lung, heart, kidney |
| 21 | 65:35 | Comprises at least 90% acid ends | Lung, heart, kidney |
| 22 | About 65:35 | Consists of acid ends | Lung, heart, kidney |
| 23 | 60:40 to 70:30 | Consists of acid ends | Lung, heart, kidney |
| 24 | 65:35 | Consists of acid ends | Lung, heart, kidney |
| 25 | Less than about 85:15 | Comprises at least 90% ester ends | Spleen |
| 26 | Less than 85:15 | Comprises at least 90% ester ends | Spleen |
| 27 | Less than about 85:15 | Consists of ester ends | Spleen |
| 28 | Less than 85:15 | Consists of ester ends | Spleen |
| 29 | About 50:50 to about 85:15 | Comprises at least 90% ester ends | Spleen |
| 30 | 50:50 to 85:15 | Comprises at least 90% ester ends | Spleen |
| 31 | About 50:50 to about 85:15 | Consists of ester ends | Spleen |
| 32 | 50:50 to 85:15 | Consists of ester ends | Spleen |

Alternatively, or additionally, the ratio of particles to erythrocyte during incubation to form the cellular composition can influence the delivery target for the therapeutic agent. For example, in some embodiments of any of the aspects, a cellular composition formed by incubation of particles and erythrocytes at a ratio of between about 150 and about 600 particles per erythrocyte will target the therapeutic agent to the spleen. In some embodiments of any of the aspects, a cellular composition formed by incubation of particles and erythrocytes at a ratio of between 150 and 600 particles per erythrocyte will target the therapeutic agent to the spleen. In some embodiments of any of the aspects, a cellular composition formed by incubation of particles and erythrocytes at a ratio of between about 200 and about 400 particles per erythrocyte will target the therapeutic agent to the spleen. In some embodiments of any of the aspects, a cellular composition formed by incubation of particles and erythrocytes at a ratio of between 200 and 400 particles per erythrocyte will target the therapeutic agent to the spleen. In some embodiments of any of the aspects, a cellular composition formed by incubation of particles and erythrocytes at a ratio of about 300 particles per erythrocyte will target the therapeutic agent to the spleen. In some embodiments of any of the aspects, a cellular composition formed by incubation of particles and erythrocytes at a ratio of 300 particles per erythrocyte will target the therapeutic agent to the spleen. In some embodiments of any of the aspects, the particle is a nanoparticle.

In some embodiments of any of the aspects, a cellular composition comprising more than 18 particles per erythrocyte will target the therapeutic agent to the spleen. In some embodiments of any of the aspects, a cellular composition comprising more than 20 particles per erythrocyte will target the therapeutic agent to the spleen. In some embodiments of any of the aspects, a cellular composition comprising more than 22 particles per erythrocyte will target the therapeutic agent to the spleen. In some embodiments of any of the aspects, a cellular composition comprising about 24 particles per erythrocyte will target the therapeutic agent to the spleen. In some embodiments of any of the aspects, a cellular composition comprising 24 particles per erythrocyte will target the therapeutic agent to the spleen. In some embodiments of any of the aspects, the particle is a nanoparticle.

In some embodiments of any of the aspects, a cellular composition formed by incubation of particles and erythrocytes at a ratio of below about 200 or above about 500 particles per erythrocyte will target the therapeutic agent to the lung. In some embodiments of any of the aspects, a cellular composition formed by incubation of particles and erythrocytes at a ratio of below 200 or above 500 particles per erythrocyte will target the therapeutic agent to the lung. In some embodiments of any of the aspects, a cellular composition formed by incubation of particles and erythrocytes at a ratio of below about 150 or above about 600 particles per erythrocyte will target the therapeutic agent to the lung. In some embodiments of any of the aspects, a cellular composition formed by incubation of particles and erythrocytes at a ratio of below 150 or above 600 particles per erythrocyte will target the therapeutic agent to the lung. In some embodiments of any of the aspects, the particle is a nanoparticle.

In some embodiments of any of the aspects, a cellular composition comprising less than 22 particles per erythrocyte will target the therapeutic agent to the lung. In some embodiments of any of the aspects, a cellular composition comprising less than 20 particles per erythrocyte will target the therapeutic agent to the lung. In some embodiments of any of the aspects, a cellular composition comprising 18 or less particles per erythrocyte will target the therapeutic agent to the lung. In some embodiments of any of the aspects, a cellular composition comprising about 18 particles per erythrocyte will target the therapeutic agent to the lung. In some embodiments of any of the aspects, a cellular composition comprising 18 particles per erythrocyte will target the therapeutic agent to the lung. In some embodiments of any of the aspects, the particle is a nanoparticle.

In some embodiments of any of the aspects, the diameter of the polymeric particle is about 10 nm to about 100 μm in size. In some embodiments of any of the aspects, the diameter of the polymeric particle is 10 nm to 100 μm in size. In some embodiments of any of the aspects, the diameter of the polymeric particle is about 100 nm to about 10 μm in size. In some embodiments of any of the aspects, the diameter of the polymeric particle is 100 nm to 10 μm in size. In some embodiments of any of the aspects, the diameter of the polymeric particle is about 100 nm to about 1 μm in size. In some embodiments of any of the aspects, the diameter of the polymeric particle is 100 nm to 1 μm in size.

In some embodiments of any of the aspects, the polymeric particle is substantially discoidal in shape. In some embodiments of any of the aspects, the polymeric particle is discoidal in shape. As used herein, "discoidal" refers to a particle having a disk-like shape, with substantially flat, concave or convex faces. In some embodiments of any of the aspects, the polymeric particle has a shape which is a rod, a cylinder, a cube, cuboid, hexahedron, or pyramid.

As used herein, the term "therapeutic agent" refers to any agent that can be used in the treatment, management or amelioration of a disease and/or a symptom related thereto. An agent can be selected from a group comprising: chemicals; small organic or inorganic molecules; signaling molecules; nucleic acid sequences; nucleic acid analogues; proteins; peptides; enzymes; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments of any of the aspects, the agent is any chemical, entity or moiety, including without limitation synthetic and naturally-occurring non-proteinaceous entities. Agents can be known to have a desired activity and/or property, or can be selected from a library of diverse compounds. Preferably, a therapeutic agent is an agent which is known to be useful for, or has been or is currently being used for the treatment, management or amelioration of a disease or one or more symptoms related thereto. Therapeutic compounds are known in the art for a variety of conditions, see, e.g., the database available on the world wide web at drugs.com or the catalog of FDA-approved compounds available on the world wide web at catalog.data.gov/dataset/drugsfda-database; each of which is incorporated by reference herein in its entirety. Non-limiting examples of therapeutic agents include, a peptide, a nucleic acid, an antigen (e.g., for stimulating an immune response against a cell expressing the antigen), an antibody reagent, a small molecule, a virus, a chemotherapeutic agent, a steroid, a chemokine, an immunosuppressant agent, an immunostimulatory agent, or combinations thereof.

A nucleic acid molecule, as described herein, can be a vector, an expression vector, an inhibitory nucleic acid, an aptamer, a template molecule or cassette (e.g., for gene editing), or a targeting molecule (e.g., for CRISPR-Cas technologies), or any other nucleic acid molecule that one wishes to deliver to a cell. The nucleic acid molecule can be RNA, DNA, or synthetic or modified versions thereof.

As used herein the term “chemotherapeutic agent” refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. Non-limiting examples of chemotherapeutic agents are provided elsewhere herein. In some embodiments of any of the aspects, the at least one chemotherapeutic agent can be doxorubicin; camptothecin; paclitaxel; docetaxel; 5-fluorouracil; gemcitabine; methotrexate; or a combination thereof.

The term “immunomodulatory agent” and variations thereof including, but not limited to, immunomodulatory agents, as used herein refer to an agent that modulates a host’s immune system. In certain embodiments, an immunomodulatory agent is an immunosuppressant agent. In certain other embodiments, an immunomodulatory agent is an immunostimulatory agent. As used herein, “suppression of the immune system” refers to decreasing or inhibiting the immune function of an animal, as measured by any parameter of the various immune functions of the immune system. Non-limiting examples of parameters of immune function can include the magnitude of the antibody response, the response of a B cell, the response of a T cell, the proliferation of T cells, the production of immunomodulatory cytokines, and/or the response to an antigen (e.g. to allogenic or xenogenic cells). Conversely, “stimulation of the immune system” refers to an increase or activation of the immune function of an animal, as measured by any parameter of the various immune functions of the immune system. Exemplary, non-limiting immunostimulants include immunostimulatory cytokines such as IFNs, IFN-γ, TNFα, TGF-β, IL-1β, IL-6, IL-4, IL-10, IL-13, IL-2, IL-12, IL-15, and IL-27, and other immunostimulatory antagonists such as CpG ODN, imiquimod, Resiquimod (R848), Monophosphoryl Lipid A (MPLA), and poly(I:C).

As used herein, the term “steroid” refers to a chemical substance comprising three cyclohexane rings and a cyclopentane ring. The rings are arranged to form tetracyclic cyclopentaphenanthrene, i.e. gonane. In some embodiments of any of the aspects, the steroid is a corticosteroid. As used herein, the term “corticosteroid” refers to a class of steroid hormones that are produced in the adrenal cortex or produced synthetically. Corticosteroids are involved in a wide range of physiologic systems such as stress response, immune response and regulation of inflammation, carbohydrate metabolism, protein catabolism, blood electrolyte levels, and behavior. Corticosteroids are generally grouped into four classes, based on chemical structure. Group A corticosteroids (short to medium acting glucocorticoids) include hydrocortisone, hydrocortisone acetate, cortisone acetate, tixocortol pivalate, prednisolone, methylprednisolone, and prednisone. Group B corticosteroids include triamcinolone acetonide, triamcinolone alcohol, mometasone, amcinonide, budesonide, desonide, fluocinonide, fluocinolone acetonide, and halcinonide. Group C corticosteroids include betamethasone, betamethasone sodium phosphate, dexamethasone, dexamethasone sodium phosphate, and fluocortolone. Group D corticosteroids include hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Non-limiting examples of corticosteroids include, aldosternone, beclomethasone, beclomethasone dipropionate, betametahasone, betametahasone-21-phosphate disodium, betametahasone valerate, budesonide, clobetasol, clobetasol propionate, clobetasone butyrate, clocortolone pivalate, cortisol, cortisteron, cortisone, deflazacort, dexamethasone, dexamethasone acetate, dexamethasone sodium phosphate, diflorasone diacetate, dihydroxycortison, flucinonide, fludrocortisones acetate, flumethasone, flunisolide, flucionolone acetonide, fluticasone furate, fluticasone propionate, halcinonide, halpmetasone, hydrocortisone, hydroconrtisone acetate, hydrocortisone succinate, 16α-hydroxyprednisolone, isoflupredone acetate, medrysone, methylprednisolone, prednacinolone, predricarbate, prednisolone, prednisolone acetate, prednisolone sodium succinate, prednisone, triamcinolone, triamcinolone, and triamcinolone diacetate. As used herein, the term “corticosteroid” can include, but is not limited to, the following generic and brand name corticosteroids: cortisone (CORTONE™ ACETATE™, ADRESON™, ALTESONA™, CORTELAN™, CORTISTAB™, CORTISYL™, CORTOGEN™, CORTONE™, SCHEROSON™); dexamethasone-oral (DECADRON-ORAL™, DEXAMETH™, DEXONE™, HEXADROL-ORAL™, DEXAMETHASONE™ INTENSOL™, DEXONE 0.5™, DEXONE 0.75™ DEXONE 1.5™, DEXONE 4™); hydrocortisone-oral (CORTEF™, HYDROCORTONE™); hydrocortisone cypionate (CORTEF ORAL SUSPENSION™); methylprednisolone-oral (MEDROL-ORAL™); prednisolone-oral (PRELONE™, DELTA-CORTEF™, PEDIAPRED™, ADNISOLONE™, CORTALONE™, DELTACORTRIL™, DELTASOLONE™, DELTASTAB™, DI-ADRESON F™, ENCORTOLONE™, HYDROCORTANCYL™, MEDISOLONE™, METICORTELONE™, OPREDSONE™, PANAAFCORTELONE™, PRECORTISYL™, PRENISOLONA™, SCHERISOLONA™, SCHERISOLONE™); prednisone (DELTASONE™, LIQUID PRED™, METICORTEN™, ORASONE 1™, ORASONE 5™, ORASONE 10™, ORASONE 20™, ORASONE 50™, PREDNICEN-M™, PREDNISONE INTENSOL™, STERAPRED™, STERAPRED DS™, ADASONE™, CARTANCYL™, COLISONE™, CORDROL™, CORTAN™, DACORTIN™, DECORTIN™, DECORTISYL™, DELCORTIN™, DELLACORT™, DELTADOME™, DELTACORTENE™, DELTISONA™, DIADRESON™, ECONOSONE™, ENCORTON™, FERNISONE™, NISONA™, NOVOPREDNISONE™, PANAFCORT™, PANASOL™, PARACORT™, PARMENISON™, PEHACORT™, PREDELTIN™, PREDNICORT™, PREDNICOT™, PREDNIDIB™, PREDNIMENT™, RECTODELT™, ULTRACORTEN™, WINPRED™); triamcinoloneoral (KENACORT™, ARISTOCORT™, ATOLONE™, SHOLOG A™, TRAMACORT-D™, TRI-MED™, TRIAMCOT™, TRISTOPLEX™, TRYLONE D™, U-TRILONE™). In some embodiments of any of the aspects, a corticosteroid can be dexamethasone (e.g. a compound having the structure of Formula I); prednisone (e.g. a compound having the structure of Formula II); prednisolone (e.g. a compound having the structure of Formula III); triamcinolone (e.g. a compound having the structure of Formula IV); clobetasol propionate (e.g. a compound having the structure of Formula V); betamethasone valerate (e.g. a compound having the structure of Formula VI); betamethasone dipropionate (e.g. a compound having the structure of Formula VII); or mometasone furoate (e.g. a compound having the structure of Formula VII). Methods of synthesizing steroids and corticosteroids are well known in the art and such compounds are also commercially available, e.g. dexamethasone (Cat. No. D4902, Sigma-Aldrich; St. Louis, MO) and predinsone (Cat. No. P6254, Sigma-Aldrich; St. Louis, MO).

Formula I

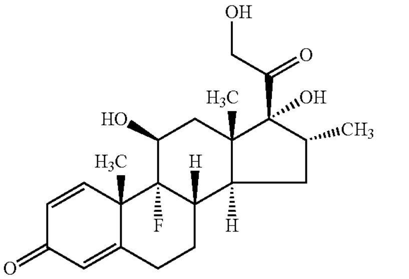

Formula II

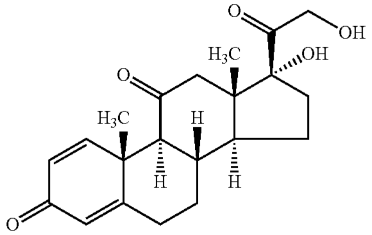

Formula III

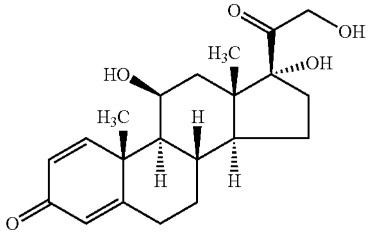

Formula IV

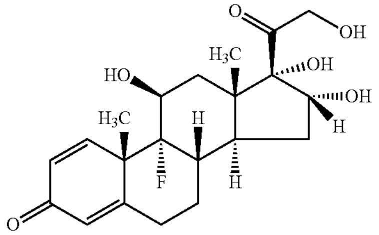

Formula IV

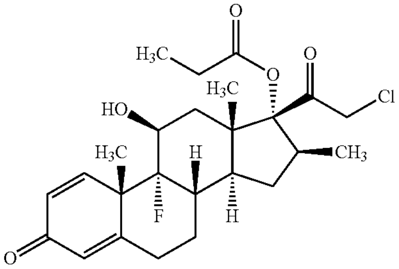

-continued

Formula V

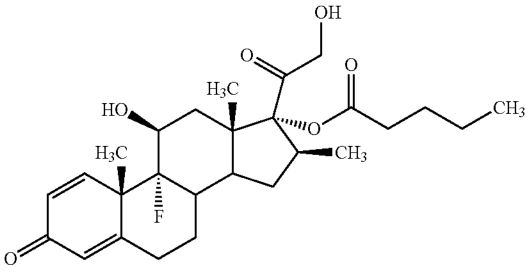

Formula VI

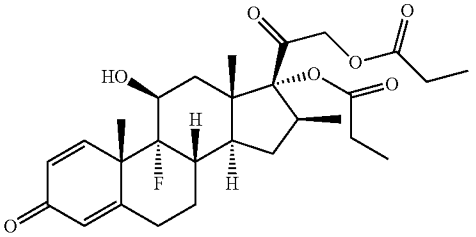

Formula VII

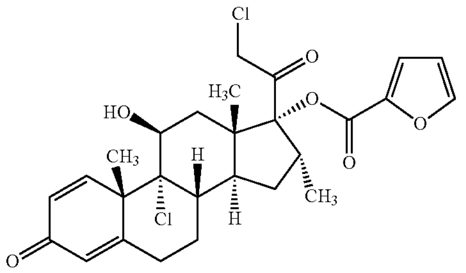

The term "chemokine" is a generic term for any of the proteins that act on white blood cells and induce them to move and/or become activated to carry out their immune system functions. Chemokines are well-known in the art. Exemplary chemokines include, for example and not for limitation, TECK, ELC, BLC-1, CTACK, RANTES, fractalkine, exotaxin, eotaxin-2, Monocyte chemoattractant protein-1 (MCP-1), MCP-2, MCP-3, MCP-4, MDC, leukotactin, SDF-1. beta., lymphotactin, TARC, ITAC, ENA-70, ENA-78, IP-10, NAP-2, interleukin-8 (IL-8), HCC-1, MIP-la, MIP-1p, MIP-16, I-309, GRO-α, GRO-β, GRO-γ, MPIF-1, I-LINK, GCP-2, CXCL9, CXCL10, CXCL11, XCL-1, and CCL-5. In some embodiments of any of the aspects, the therapeutic agent can be present at a concentration of at least about 100 μg per $3\times10^8$ erythrocytes, e.g., at least about 150 g per $3\times10^8$ erythrocytes, at least about 200 μg per $3\times10^8$ erythrocytes, or at least about 250 μg per $3\times10^8$ erythrocytes. In some embodiments of any of the aspects, the therapeutic agent can be present at a concentration of at least 100 μg per $3\times10^8$ erythrocytes, e.g., at least 150 μg per $3\times10^8$ erythrocytes, at least 200 μg per $3\times10^8$ erythrocytes, or at least 250 μg per $3\times10^8$ erythrocytes.

In some embodiments of any of the aspects, the therapeutic agent(s) is present in admixture with the PLGA. In some embodiments of any of the aspects, the therapeutic agent(s) is present only in part of the particle, e.g., it coats the surface of the particle, and/or is present in a portion of the interior volume of the particle.

In some embodiments of any of the aspects, the particle can comprise two or more different therapeutic agents. In some embodiments of any of the aspects, the cellular composition comprises two or more particles, each comprising a different therapeutic agent. In some embodiments of any of the aspects, the cellular composition comprises a mixture of two or more erythrocyte-particle combinations, each comprising a different therapeutic agent.

In some embodiments of any of the aspects, the polymeric particle further comprises one or more cell adhesive molecules. Cell adhesive molecules can be any molecule which will adhere to the surface of a cell, e.g., an erythrocyte. Non-limiting examples of suitable cell adhesive molecules include an antibody reagent that binds specifically to a molecule on a red blood cell; a peptide that binds specifically to a molecule on a red blood cell; a cell adhesive polymer; a cell adhesive polyelectrolyte, and a ligand for a receptor on a red blood cell.

Characteristics that can enhance cell adhesion include, e.g., high surface free energy, hydrophilic protein content, low surface hydration, and low surface charge density. Exemplary, non-limiting cell adhesive molecules can include poly (glycidyl methacrylate) (PGMA); polycaprolactone (PCL); polydimethylsiloxane (PDMS); poly(hexamethyldisiloxane) (PHMDSO); superhydrophobic perfluoro-substituted PEDOT (PEDOT-F); superhydrophobic polystyrene (PS); plasma-treated poly (methyl methacrylate) (PMMA); plasma-treated poly-3-hydroxybutyrate (P3HB); phosphatidylethanolamine (PE); and carboxymethyl chitin (CMCH). Cell adhesive molecules can also include, or comprise, e.g., RGD peptides, collagen, fibronectin, gelatin, and collagen. Further discussion of cell adhesive molecules can be found, e.g., at Lih et al. Progress in *Polymer Science* 44:28-61 (2015) and Chen et al. Materials Today (2017); which are incorporated by reference herein in their entireties.

In some embodiments of any of the aspects, cell adhesive polyelectrolytes comprise hyaluronic acid, poly(allylamine) hydrochloride, and/or hyaluronic acid modified to comprise aldehyde groups.

In some embodiments of any of the aspects, cell adhesive polymers can be a polyphenol or metal-polyphenol network.

Ligands for the receptors on a given cell surface and/or which target a red blood cell are known in the art and can include natural or synthetic ligands. Exemplary ligands for red blood cells can include, by way of non-limiting example, glucose transporter ligands like glucose, BAND3 ligands like lectin, glycophorin A ligands like EBA-175, glycophorin B ligands like EBL-1, glycophorin C ligands like EBA-140, complement receptor 1 ligands like Rh4, basigin ligands like Rh5, and CD59 ligands like C9.

In some embodiments of any of the aspects, the cell adhesive molecules can be specific for one or more cell types, e.g., red blood cells. However, the particles can be adhered to isolated cell populations in vitro, and thus such specificity is not required in all embodiments. In some embodiments of any of the aspects, the cell adhesive molecules are not specific for red blood cells.

In some embodiments of any of the aspects, the cell adhesive molecule(s) is present in admixture with the PLGA. In some embodiments of any of the aspects, the cell adhesive molecule(s) is present only in part of the particle, e.g., it coats the surface of the particle. In some embodiments of any of the aspects, the particle can comprise two or more different cell adhesive molecules. In some embodiments of any of the aspects, the cellular composition comprises two or more particles, each comprising a different cell adhesive molecule. In some embodiments of any of the aspects, the cellular composition comprises a mixture of two or more erythrocyte-particle combinations, each comprising a different cell adhesive molecule.

As used herein, the term "polymer" refers to oligomers, co-oligomers, polymers and copolymers, e.g., random block, multiblock, star, grafted, gradient copolymers and combination thereof. The average molecular weight of the polymer, as determined by gel permeation chromatography, can range from 500 to about 500,000, e.g., from 20,000 to about 500,000.

In some embodiments of any of the aspects, the particle can comprise one or more additional polymers. Without limitation, any polymeric material known in the art can be used in the invention. Accordingly, In some embodiments of any of the aspects, the polymer is selected from the group consisting of polysaccharides, polypeptides, polynucleotides, copolymers of fumaric/sebacic acid, poloxamers, polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, polymethyl methacrylate, chitin, chitosan, copolymers of polylactic acid and polyglycolic acid, poly (glycerol sebacate) (PGS), gelatin, collagen, silk, alginate, cellulose, poly-nucleic acids, cellulose acetates (including cellulose diacetate), polyethylene, polypropylene, polybutylene, polyethylene terphthalate (PET), polyvinyl chloride, polystyrene, polyamides, nylon, polycarbonates, polysulfides, polysulfones, hydrogels (e.g., acrylics), polyacrylonitrile, polyvinylacetate, cellulose acetate butyrate, nitrocellulose, copolymers of urethane/carbonate, copolymers of styrene/maleic acid, poly(ethylenimine), hyaluron, heparin, agarose, pullulan, and copolymers, terpolymers, and copolymers comprising any combinations thereof. Exemplary polymers can include, by way of non-limiting example polylactide (PLA): polyglycolide (PGA); poly-(ε-caprolactone) (PCL); polyvinyl alcohol (PVA), poly(lactic-co-caprolactone) (PLCL), hyaluronic acid (HA), gelatin, collagen; poly(glycerol sebacate) (PGS); polyphosphazenes; polyorthoesters; polyanhydrides; poly(α-hydroxy esters); poly (ether esters); copolymers comprising lactide of glycolide and ε-caprolactone or trimethylene carbonate; poly(polyol sebacate) elastomers; elastomers; poly(polyol citrate); polyesters; poly(glycolic acid); poly(lactic acid); poly(caprolactone); poly(lactic-co-glycolic acid); poly(butylene succinate); poly(trimethylene carbonate); poly(β-dioxanone); poly(butylene terephthalate); poly(ester amide)s; Hybrane™ S1200; DegraPol™; polyurethanes; polyanhydrides; poly [(caboxyphenoxy) propane-sebacic acid]; polyphsophoesters; poly[bis(hydroxyethyl) terephthalate-ethyl orthophosphorylate/terephthaloyl chloride]; poly(ortho esters); poly (alkyl cyanoacrylates); poly(butyl cyanoacrylate); polyethers; poly(ethylene glycol); poly(amino acids); tyrosine derived polycarbonate; microbial polyesters; poly(β-hydroxyalkanoate); poly(hydroxybutyrate); poly(hydroxybutyrate-co-hydroxyvalerate); collagen; albumin; gluten; chitosan; hyaluronate; cellulose; alginate; and starch. Suitable structural polymers are discussed in more detail at, e.g., Bat et al. *Regen. Med.* 9:385-398 (2014) and Marin et al. *Int. J. Nanomedicine* 8:3071-3091 (2013); which are incorporated by reference herein in their entireties.

In some embodiments of any of the aspects, the polymer is a biocompatible polymer. As used herein, the term "biocompatible" means exhibition of essentially no cytotoxicity or immunogenicity while in contact with body fluids or tissues. The term "biocompatible polymer" refers to polymers which are non-toxic, chemically inert, and substantially non-immunogenic when used internally in a subject and which are substantially insoluble in blood. The biocompatible polymer can be either non-biodegradable or preferably biodegradable. Preferably, the biocompatible polymer is also non-inflammatory when employed in situ.

Biodegradable polymers are disclosed in the art. Examples of suitable biodegradable polymers include, but are not limited to, linear-chain polymers such as polypeptides, polynucleotides, polysaccharides, polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, polymethyl methacrylate, chitin, chitosan, copolymers of polylactic acid and polyglycolic acid, poly(glycerol sebacate) (PGS), fumaric acid, sebacic acid, and copolymers, terpolymers including one or more of the foregoing. Other biodegradable polymers include, for example, gelatin, collagen, silk, chitosan, alginate, cellulose, poly-nucleic acids, etc.

Suitable non-biodegradable biocompatible polymers include, by way of example, cellulose acetates (including cellulose diacetate), polyethylene, polypropylene, polybutylene, polyethylene terphthalate (PET), polyvinyl chloride, polystyrene, polyamides, nylon, polycarbonates, polysulfides, polysulfones, hydrogels (e.g., acrylics), polyacrylonitrile, polyvinylacetate, cellulose acetate butyrate, nitrocellulose, copolymers of urethane/carbonate, copolymers of styrene/maleic acid, poly(ethylenimine), Poloxamers (e.g., Pluronic such as Poloxamers 407 and 188), hyaluronic acid, heparin, agarose, Pullulan, and copolymers including one or more of the foregoing, such as ethylene/vinyl alcohol copolymers (EVOH). In some embodiments of any of the aspects, the biocompatible polymer is a copolymer of polylactic acid and polyglycolic acid, poly(glycerol sebacate) (PGS), poly(ethylenimine), Pluronic (Poloxamers 407, 188), hyaluronic acid, heparin, agarose, or Pullulan.

In some embodiments of any of the aspects, the polymer is a homopolymer, a copolymer or a block polymer. In some embodiments of any of the aspects, the polymer comprises side chains selected from the group consisting of amide or ester groups. In some embodiments of any of the aspects, the polymer is biodegradable, biocompatible, and non-toxic.

The polymer can be derivatized with a second polymer and the first polymer and the second polymer can be the same or different. For example, the polymer can be derivatized with a polyethylene glycol (PEG).

In some embodiments of any of the aspects, polymers or portions of polymers can be connected by linkers. In some embodiments of any of the aspects, components of a polymeric particle, e.g., a therapeutic agent and/or cell adhesive molecule can be connected via a linker. As used herein, the term "linker" refers to a moiety that connects two parts of a compound. Linkers typically comprise a direct bond or an atom such as oxygen or sulfur, a unit such as $NR_1$, C(O), C(O)O, $C(O)NR_1$, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R_1)_2$, C(O), cleavable linking group, substituted or unsubstituted aryl, substituted or unsubstituted heteroaryl, substituted or unsubstituted heterocyclic; where $R_1$ is hydrogen, acyl, aliphatic or substituted aliphatic.

The linker can be a branched linker. The branch-point of the branched linker can be at least divalent, but can be a trivalent, tetravalent, pentavalent or hexavalent atom, or a group presenting such multiple valencies. In certain embodiments, the branch-point can be, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments of any of the aspects, the branch-point can be an acrylate, cyanoacrylate, or methylacrylate.

In various embodiments, the linker is a cleavable linker. A cleavable linker means that the linker can be cleaved to release the two parts the linker is holding together. A cleavable linker can be susceptible to cleavage agents, such as, but not limited to, enzymes, pH, redox potential or the presence of degradative molecules. Examples of such agents: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

In some embodiments of any of the aspects, the linker is polyethylene glycol. In some embodiments of any of the aspects, the linker is a peptide comprising the sequence DEVD (SEQ ID NO: 1). In a further embodiment, the linker is a peptide comprising the sequence KDEVDAP (SEQ ID NO: 2). In still a further embodiment, the linker is a peptide comprising the sequence GKDEVDAP (SEQ ID NO: 3). In some embodiments of any of the aspects, the cleavable linker is cleavable by an enzyme.

In some embodiments of any of the aspects, the cleavable linker is selected from a group consisting of small molecules. In some preferred embodiments, the cleavable linker is selected from a group consisting of peptides or polypeptides.

Exemplary methods of making the particles and adhering them to erythrocytes are provided in the examples herein.

In one aspect of any of the embodiments, described herein is a method of delivering a therapeutic agent to a cell in a subject, the method comprising administering to the subject a cellular composition as described herein. In some embodiments of any of the aspects, the cell is a cancer cell and the therapeutic agent is a chemotherapeutic agent, chemokine, or immunostimulatory agent (e.g., IFN).

In one aspect of any of the embodiments, described herein is a method of treating cancer and/or a tumor in a subject in need thereof, the method comprising administering to the subject a cellular composition as described herein, wherein the therapeutic agent is a chemotherapeutic agent, chemokine, or immunostimulatory agent (e.g., IFN).

In some embodiments of any of the aspects, the cancer cell is in the lung of the subject and/or the subject has lung cancer. In some embodiments of any of the aspects, the cancer cell is in the lung of the subject and/or the subject has lung cancer and the PLGA is composition selected from Table 3 which targets the lung, e.g., wherein the PLGA comprises a L:G ratio of about 65:35 and acid ends.

In some embodiments of any of the aspects, the cancer cell is in the kidney of the subject and/or the subject has kidney cancer. In some embodiments of any of the aspects, the cancer cell is in the kidney of the subject and/or the subject has kidney cancer and the PLGA is composition selected from Table 3 which targets the kidney, e.g., wherein the PLGA comprises a L:G ratio of about 85:15 and ester ends or the PLGA comprises a L:G ratio of about 65:35 and acid ends.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastatses. Cancers that migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulvar cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

In some embodiments of any of the aspects, described herein is a method of stimulating an immune response in a subject in need thereof, the method comprising administering to the subject a a cellular composition as described herein, wherein the therapeutic agent is an antigen, immunostimulatory agent or chemokine. In some embodiments of any of the aspects, the immune response is localized.

As described in the Examples herein, delivery of an antigen using one of the cellular compositions described herein can provide a vaccination effect. That is, the therapeutic agent is an antigen and the cellular composition stimulates the immune response to provide vaccination against the antigen.

As further described herein, the cellular compositions described herein can provide a vaccination effect without the use of a further adjuvant. As used herein in the context of immunization, immune response and vaccination, the term "adjuvant" refers to any substance than when used in combination with a specific antigen that produces a more robust immune response than the antigen alone. When incorporated into a vaccine formulation, an adjuvant acts generally to accelerate, prolong, or enhance the quality of specific immune responses to the vaccine antigen(s). Accordingly, in some embodiments of any of the aspects, a cellular composition described herein comprising an antigen is administered without a further adjuvant. In some embodiments of any of the aspects, a cellular composition described herein comprising an antigen does not comprise a further adjuvant. In some embodiments of any of the aspects, a composition comprising a cellular composition described herein comprising an antigen does not comprise a further adjuvant. In some embodiments of any of the aspects, the further adjuvant can be any of alum, aluminium hydroxide, aluminium phosphate, calcium phosphate hydroxide, paraffin oil, squalene, a detergent, a plant saponin, a cytokine, Freund's complete adjuvant, Freund's incomplete adjuvant, or an analgesic. In some embodiments of any of the aspects, a composition comprising a cellular composition described herein comprising an antigen does not comprise exogenous or ectopic alum, aluminium hydroxide, aluminium phosphate, calcium phosphate hydroxide, paraffin oil, squalene, a detergent, a plant saponin, a cytokine, Freund's complete adjuvant, Freund's incomplete adjuvant, or analgesic. In some embodiments of any of the aspects, a cellular composition described herein comprising an antigen does not comprise exogenous or ectopic alum, aluminium hydroxide, aluminium phosphate, calcium phosphate hydroxide, paraffin oil, squalene, a detergent, a plant saponin, a cytokine, Freund's complete adjuvant, Freund's incomplete adjuvant, or analgesic.

As described herein, an "antigen" is a molecule that is specifically bound by a B cell receptor (BCR), T cell receptor (TCR), and/or antibody, thereby activating an immune response. An antigen can be pathogen-derived, or originate from a pathogen. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

In some embodiments of any of the aspects, the cellular composition can be a subunit vaccine, including a recombinant subunit vaccine. A subunit vaccine does not comprise entire disease-causing microbes, but only a subset of antigens obtained from or derived from the disease-causing microbe. A subunit vaccine can comprise multiple different antigens. Subunit vaccines in which the antigens are produced via recombinant technologies are termed recombinant subunit vaccines.

Exemplary, non-limiting vaccines suitable for use in the methods and compositions described herein can include a coronavirus vaccine; a SARS-CoV-2 vaccine; a pneumococcal vaccine; a hepatitis B (HBV) vaccine; an acellular pertussis (aP) vaccine; a diphtheria tetanus acellular pertussis (DTaP) vaccine; a hepatitis A (HAV) vaccine; a meningococcal (MV) vaccine; and/or pneumococcal conjugate vaccine (PCV)13. In some embodiments of any of the aspects, the antigen can be an antigen of (obtained from, originating from, or found in) a coronavirus; a SARS-CoV-2; a pneumococcus; a hepatitis B (HBV) virus; *Clostribium tetani; Bordetella pertussis; Corynebacterium diphtheria*; a hepatitis A (HAV) virus; and/or a meningococcus.

In some embodiments of any of the aspects, multiple antigens are administered. In some embodiments of any of the aspects, multiple vaccines are administered.

The compositions and methods described herein can be administered to a subject in need of vaccination, immunization, and/or stimulation of an immune response. In some embodiments of any of the aspects, the methods described herein comprise administering an effective amount of compositions described herein, e.g. to a subject in order to stimulate an immune response or provide protection against the relevant pathogen the antigen was derived from. Providing protection against the relevant pathogen is stimulating the immune system such that later exposure to the antigen (e.g., on or in a live pathogen) triggers a more effective immune response than if the subject was naïve to the antigen. Protection can include faster clearance of the pathogen, reduced severity and/or time of symptoms, and/or lack of development of disease or symptoms. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or topical, administration. Administration can be local or systemic. In some embodiments of any of the aspects, the administration can be intramuscular or subcutaneous.

In some embodiments of any of the aspects, when the therapeutic agent is an antigen, the cellular composition is targeted to the spleen. Cellular compositions can be targeted the spleen when, e.g., the PGLA of the composition comprises: a) a L:G ratio of about 50:50 and ester ends; b) a L:G ratio of about 50:50 and acid ends, or c) a L:G ratio of less than 85:15 and ester ends.

Alternatively, or additionally, the ratio of particles to erythrocyte during incubation to form the cellular composition can influence the delivery target for the therapeutic agent. For example, in some embodiments of any of the aspects, a cellular composition formed by incubation of particles and erythrocytes at a ratio of between about 150 and about 600 particles per erythrocyte will target the therapeutic agent to the spleen. In some embodiments of any of the aspects, a cellular composition formed by incubation of particles and erythrocytes at a ratio of between 150 and 600 particles per erythrocyte will target the therapeutic agent to the spleen. In some embodiments of any of the aspects, a cellular composition formed by incubation of particles and erythrocytes at a ratio of between about 200 and about 400 particles per erythrocyte will target the therapeutic agent to the spleen. In some embodiments of any of the aspects, a cellular composition formed by incubation of particles and erythrocytes at a ratio of between 200 and 400 particles per erythrocyte will target the therapeutic agent to the spleen. In some embodiments of any of the aspects, a cellular composition formed by incubation of particles and erythrocytes at a ratio of about 300 particles per erythrocyte will target the therapeutic agent to the spleen. In some embodiments of any of the aspects, a cellular composition formed by incubation of particles and erythrocytes at a ratio of 300 particles per erythrocyte will target the therapeutic agent to the spleen. In some embodiments of any of the aspects, the particle is a nanoparticle.

In some embodiments of any of the aspects, a cellular composition comprising more than 18 particles per erythrocyte will target the therapeutic agent to the spleen. In some embodiments of any of the aspects, a cellular composition comprising more than 20 particles per erythrocyte will target the therapeutic agent to the spleen. In some embodiments of any of the aspects, a cellular composition comprising more than 22 particles per erythrocyte will target the therapeutic agent to the spleen. In some embodiments of any of the aspects, a cellular composition comprising about 24 particles per erythrocyte will target the therapeutic agent to the spleen. In some embodiments of any of the aspects, a cellular composition comprising 24 particles per erythrocyte will target the therapeutic agent to the spleen. In some embodiments of any of the aspects, the particle is a nanoparticle.

In some embodiments of any of the aspects, described herein is a method of decreasing or suppressing an immune response in a subject in need thereof, the method comprising administering to the subject a a cellular composition as described herein, wherein the therapeutic agent is an immunosuppressant agent or steroid. In some embodiments of any of the aspects, the immune response is localized.

In some embodiments of any of the aspects, the immune response to be stimulated, decreased, or suppressed is in or to be in the lung of the subject. In some embodiments of any of the aspects, the immune response to be stimulated, decreased, or suppressed is in or to be in the lung of the subject and the PLGA is composition selected from Table 3 which targets the lung, e.g., wherein the PLGA comprises a L:G ratio of about 65:35 and acid ends.

As used herein, an "immune response" refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus (e.g., to an a disease, an antigen, or healthy cells, e.g., in the case of autoimmunity). In some embodiments of the aspects described herein, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response. Stimulation of an immune response refers to an induction or increase of the immune response. Suppression of an immune response refers to an elimination or decrease of the immune response.

An immune response to an antigen can be the development in a subject of a humoral and/or a cell-mediated immune response to molecules present in the antigen or vaccine composition of interest. For purposes of the present invention, a "humoral immune response" is an antibody-mediated immune response and involves the induction and generation of antibodies that recognize and bind with some affinity for the antigen, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+ T helper cells or CD8+ cytotoxic lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) J. Immunol. 151:4189-4199; and Doe et al. (1994) Eur. J. Immunol. 24:2369-2376.

The engineered cellular compositions can comprise cells (e.g, erythrocytes), which are autologous to or heterologous to the subject to be treated. In some embodiments of any of the aspects, the method of treatment can comprise a first step of obtaining the cell from a donor and/or the subject and contacting the cell with the polymeric particle ex vivo. The cell can be isolated, e.g., isolated from a blood sample obtained from the donor/subject prior to performing the contacting/adhering step, or the contacting/adhering can take place in a sample comprising multiple cell types, e.g., in a blood sample.

The compositions and methods described herein can be administered to a subject having or diagnosed as having one of the conditions described herein. In some embodiments of any of the aspects, the methods described herein comprise administering an effective amount of compositions described herein, e.g. an engineered cellular composition to a subject in order to alleviate a symptom of a condition described herein. In some embodiments of any of the aspects, a therapeutically effective dose of the composition is administered. As used herein, "alleviating a symptom" is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to parenteral, intravenous, intramuscular, subcutaneous, transdermal, airway (aerosol), pulmonary, cutaneous, injection, or intratumoral administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular therapeutic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g. for tumor size and/or immune response markers, among others. The dosage can be determined by a physician and adjusted, as necessary, to suit observed effects of the treatment.

In some embodiments of any of the aspects, the dose of the therapeutic agent administered is 50% or less of the amount that would be administered to a subject if administered in a free form (e.g., not in a particle and/or not adhered to a erythrocyte). In some embodiments of any of the aspects, the dose of the therapeutic agent administered is 40% or less of the amount that would be administered to a subject if administered in a free form (e.g., not in a particle and/or not adhered to a erythrocyte). In some embodiments of any of the aspects, the dose of the therapeutic agent administered is 30% or less of the amount that would be administered to a subject if administered in a free form (e.g., not in a particle and/or not adhered to a erythrocyte). In some embodiments of any of the aspects, the dose of the therapeutic agent administered is 20% or less of the amount that would be administered to a subject if administered in a free form (e.g., not in a particle and/or not adhered to a erythrocyte). In some embodiments of any of the aspects, the dose of the therapeutic agent administered is 10% or less of the amount that would be administered to a subject if administered in a free form (e.g., not in a particle and/or not adhered to a erythrocyte).

In some embodiments of any of the aspects, a composition described herein can be a pharmaceutical composition. In some embodiments of any of the aspects, the technology described herein relates to a pharmaceutical composition comprising an engineered cellular composition as described herein, and optionally a pharmaceutically acceptable carrier. In some embodiments of any of the aspects, the active ingredients of the pharmaceutical composition comprise an engineered cellular composition as described herein. In some embodiments of any of the aspects, the active ingredients of the pharmaceutical composition consist essentially of an engineered cellular composition as described herein. In some embodiments of any of the aspects, the active ingredients of the pharmaceutical composition consist of an engineered cellular composition as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, as described herein.

In some embodiments of any of the aspects, the pharmaceutical composition comprising an engineered cellular composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry or lyophilized products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an engineered cellular composition as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, the engineered cellular composition described herein is administered as a monotherapy, e.g., another treatment for the condition is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, FK506, vorinostat, acriflavine, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., *Agnew. Chem. Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside (“Ara-C”); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In certain embodiments, an effective dose of a composition comprising a cellular composition as described herein can be administered to a patient once. In certain embodiments, an effective dose of a composition can be administered to a patient repeatedly. In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the composition. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an engineered cellular composition as described herein can be administered over a period of time, such as over a 5 minute, 10 minute, 15 minute, 20 minute, or 25 minute period.

The dosage ranges for the administration of the compositions described herein, according to the methods described herein depend upon, for example, the potency of the cells, and the extent to which symptoms, markers, or indicators of a condition described herein are desired to be reduced, for example the percentage reduction desired for tumor growth is desired to be induced. The dosage should not be so large as to cause adverse side effects, such as excessive inflammation or immunosuppression. Generally, the dosage will vary with the age, condition, and sex of the patient and can be determined by one of skill in the art. The dosage can also be adjusted by the individual physician in the event of any complication.

The efficacy of an cellular composition in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g., pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g., tumor growth, tumor size, inflammation, wound size, etc.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

The terms "compound" and "agent" refer to any entity which is normally not present or not present at the levels being administered and/or provided to a cell, tissue or subject. An agent can be selected from a group comprising: chemicals; small organic or inorganic molecules; signaling molecules; nucleic acid sequences; nucleic acid analogues; proteins; peptides; enzymes; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments of any of the aspects, the agent is any chemical, entity or moiety, including without limitation synthetic and naturally occurring non-proteinaceous entities. In certain embodiments the agent is a small molecule having a chemical moiety. For example, chemical moieties include unsubstituted or substituted alkyl, aromatic, or heterocyclyl moieties including macrolides, leptomycins and related natural products or analogues thereof. Agents can be known to have a desired activity and/or property or can be selected from a library of diverse compounds.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the terms "protein" and "polypeptide" are used interchangeably herein to designate a series of amino acid residues, connected to each other by peptide bonds between the alpha-amino and carboxyl groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. the M1-polarizing activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments of any of the aspects, the polypeptide described herein (or a nucleic acid encoding such a polypeptide) can be a functional fragment of one of the amino acid sequences described herein. As used herein, a "functional fragment" is a fragment or segment of a peptide, which retains at least 50% of the wild type reference polypeptide's activity according to the assays described below herein. A functional fragment can comprise conservative substitutions of the sequences disclosed herein.

In some embodiments of any of the aspects, the polypeptide described herein can be a variant of a sequence described herein. In some embodiments of any of the aspects, the variant is a conservatively modified variant.

Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (*Gene* 42:133, 1986); Bauer et al. (*Gene* 37:73, 1985); Craik (*BioTechniques*, January 1985, 12-19); Smith et al. (Genetic Engineering: Principles and Methods, *Plenum. Press,* 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

Antibodies and/or antibody reagents can include an immunoglobulin molecule, a monoclonal antibody, a chimeric antibody, a CDR-grafted antibody, a humanized antibody, a fully human antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As used herein, the term "nanobody" or single domain antibody (sdAb) refers to an antibody comprising the small single variable domain (VHH) of antibodies obtained from camelids and dromedaries. Antibody proteins obtained from members of the camel and dromedary (*Camelus baclrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994; which is incorporated by reference herein in its entirety).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520; each of which is incorporated by reference herein in its entirety. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies being extremely thermostable, stable to extreme pH and to proteolytic digestion, and poorly antigenic. See U.S. patent application 20040161738 published Aug. 19, 2004; which is incorporated by reference herein in its entirety. These features combined with the low antigenicity to humans indicate great therapeutic potential.

As used herein, "inhibitory nucleic acid" refers to a nucleic acid molecule which can inhibit the expression of a target, e.g., double-stranded RNAs (dsRNAs), inhibitory RNAs (iRNAs), and the like.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route, which results in at least partial delivery of the agent at a desired site. Pharmaceutical compositions comprising the compounds disclosed herein can be administered by any appropriate route, which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

In some events, such as with Hylauronic acid with adehyde modifications, the specific binding can be accompanied by covalent binding to strengthen the cell/particle interaction.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example".

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloffs Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An engineered cellular composition comprising:
   a. an erythrocyte; and
   b. a particle comprising PLGA and at least one therapeutic agent, wherein the particle is located on the cell surface of the erythrocyte.
2. The composition of paragraph 1, wherein the PLGA comprises a L:G ratio of at least 50:50 or more L.
3. The composition of paragraph 2, wherein the PLGA comprises a L:G ratio of about 50:50.
4. The composition of paragraph 2, wherein the PLGA comprises a L:G ratio of about 85:15.
5. The composition of paragraph 2, wherein the PLGA comprises a L:G ratio of about 65:35.
6. The composition of any of paragraphs 1-5, wherein the PLGA comprises ester ends and/or acid ends.
7. The composition of any of paragraphs 1-6, wherein the PLGA comprises ester ends.
8. The composition of any of paragraphs 1-6, wherein the PLGA comprises acid ends.
9. The composition of paragraph 2, wherein the PLGA comprises a L:G ratio of about 50:50 and ester ends.
10. The composition of paragraph 2, wherein the PLGA comprises a L:G ratio of about 50:50 and acid ends.
11. The composition of paragraph 2, wherein the PLGA comprises a L:G ratio of about 85:15 and ester ends.
12. The composition of paragraph 2, wherein the PLGA comprises a L:G ratio of about 65:35 and acid ends.
13. The composition of any of paragraphs 1-8, wherein the PLGA comprises a L:G ratio of about 50:50 and ester ends, whereby the therapeutic agent is targeted to the spleen and/or heart.
14. The composition of any of paragraphs 1-8, wherein the PLGA comprises a L:G ratio of about 50:50 and acid ends, whereby the therapeutic agent is targeted to the spleen and/or lung.
15. The composition of any of paragraphs 1-8, wherein the PLGA comprises a L:G ratio of about 85:15 and ester ends, whereby the therapeutic agent is targeted to the kidney and/or lung.
16. The composition of any of paragraphs 1-8, wherein the PLGA comprises a L:G ratio of about 65:35 and acid ends, whereby the therapeutic agent is targeted to the lung, heart and/or kidney.
17. The composition of any of paragraphs 1-8, wherein the PLGA comprises a L:G ratio of more than 50:50, whereby the therapeutic agent is targeted to the lung and/or kidney.
18. The composition of any of paragraphs 1-8, wherein the PLGA comprises a L:G ratio of less than 85:15 and ester ends, whereby the therapeutic agent is targeted to the spleen.
19. The composition of any of paragraphs 1-18, wherein the at least one therapeutic agent is selected from:
   a chemotherapeutic agent; an antigen; a steroid; an immunosuppressant agent; an immunostimulatory agent; a virus; a small molecule; a peptide; a nucleic acid; and a chemokine.
20. The composition of paragraph 19, wherein the at least one chemotherapeutic agent is selected from the group consisting of:
   doxorubicin; camptothecin; paclitaxel; docetaxel; 5-fluorouracil; gemcitabine; methotrexate; or a combination thereof.
21. The composition of any of paragraphs 1-20, wherein the therapeutic agent is present at a concentration of at least 100 μg per $3\times10^8$ erythrocytes.
22. The composition of any of paragraphs 1-21, wherein the therapeutic agent is present at a concentration of at least 150 μg per $3\times10^8$ erythrocytes.
23. The composition of any of paragraphs 1-22, wherein the therapeutic agent is present at a concentration of at least 200 μg per $3\times10^8$ erythrocytes.
24. The composition of any of paragraphs 1-23, wherein the therapeutic agent is present at a concentration of at least 250 μg per $3\times10^8$ erythrocytes.
25. The composition of any of paragraphs 1-24, wherein the diameter of the polymeric particle is from about 100 nm to about 10 μm.
26. The composition of any of paragraphs 1-24, wherein the diameter of the polymeric particle is from about 100 nm to about 1 μm.
27. The composition of any of paragraphs 1-26, wherein the polymeric particle further comprises one or more cell adhesive molecules.
28. The composition of paragraph 27, wherein the one or more cell adhesive molecules is localized to a region of the particle surface.
29. The composition of any of paragraphs 27-28, wherein the cell adhesive molecule is selected from the group consisting of:
   an antibody reagent that binds specifically to a molecule on a red blood cell; a peptide that binds specifically to a molecule on a red blood cell; a cell adhesive polymer; a cell adhesive polyelectrolyte, and a ligand for a receptor on a red blood cell.
30. The composition of paragraph 29, wherein the cell adhesive polyelectrolytes comprise hyaluronic acid, hyaluronic acid-aldehyde, and/or poly(allylamine) hydrochloride.
31. The composition of paragraph 30, wherein the hyaluronic acid is modified to comprise aldehyde groups.
32. The composition of paragraph 29, wherein the cell adhesive polymer is a polyphenol or metal-polyphenol network.
33. A method of delivering a therapeutic agent to a cell in a subject, the method comprising administering to the subject a composition of any of paragraphs 1-32.
34. The method of paragraph 33, wherein the cell is a cancer cell and the therapeutic agent is a chemotherapeutic agent, chemokine, or immunostimulatory agent (e.g., IFNs, IFN-γ, TNFα, TGF-β, IL-1β, IL-6, IL-4, IL-10, IL-13, IL-2, IL-12, IL-15, and IL-27, and other immunostimulatory antagonists such as CpG ODN, imiquimod, Resiquimod (R848), Monophosphoryl Lipid A (MPLA), and poly(I:C)).
35. A method of treating cancer and/or a tumor in a subject in need thereof, the method comprising administering to the subject a composition of any of paragraphs 1-32.
36. The method of paragraph 35, wherein the therapeutic agent is a chemotherapeutic agent or chemokine.
37. The method of any of paragraphs 33-36, wherein the cancer cell is in the lung of the subject and/or the subject has lung cancer.

38. The method of paragraph 37, wherein the PLGA comprises a L:G ratio of about 65:35 and acid ends.
39. The method of any of paragraphs 33-36, wherein the cancer cell is in the kidney of the subject and/or the subject has kidney cancer.
40. The method of paragraph 39, wherein the PLGA comprises a L:G ratio of about 85:15 and ester ends.
41. The method of paragraph 39, wherein the PLGA comprises a L:G ratio of about 65:35 and acid ends.
42. The method of any of paragraphs 33-41, wherein the PLGA comprises a L:G ratio of more than 50:50.
43. The method of any of paragraphs 33-42, further comprising administering radiation or at least one chemotherapy to the subject.
44. A method of stimulating an immune response in a subject in need thereof, the method comprising administering to the subject a composition of any of paragraphs 1-32, wherein the therapeutic agent is an immunostimulatory agent or chemokine.
45. The method of paragraph 44, wherein the immune response is localized.
46. A method of decreasing or suppressing an immune response in a subject in need thereof, the method comprising administering to the subject a composition of any of paragraphs 1-32, wherein the therapeutic agent is an immunomodulatory agent (e.g., IL-4) or steroid.
47. The method of paragraph 46, wherein the immune response is localized.
48. The method of any of paragraphs 44-47, wherein the subject is in need of an immune response in the lungs.
49. The method of any of paragraphs 46-48, wherein the subject is in need of treatment for acute lung injury.
50. The method of any of paragraphs 46-49, wherein the therapeutic agent is a steroid or IL-4.
51. The method of any of paragraphs 46-50, wherein the PLGA comprises a L:G ratio of more than 50:50.
52. The method of any of paragraphs 46-51, wherein the PLGA comprises a L:G ratio of about 65:35 and acid ends.
53. The method of any of paragraphs 33-52, wherein a therapeutically effective amount of the composition is administered.
54. The method of any of paragraphs 33-53, wherein the dose of the therapeutic agent administered is 50% or less of the amount that would be administered to a subject if administered in a free form.
55. The method of any of paragraphs 33-53, wherein the dose of the therapeutic agent administered is 40% or less of the amount that would be administered to a subject if administered in a free form.
56. The method of any of paragraphs 33-53, wherein the dose of the therapeutic agent administered is 30% or less of the amount that would be administered to a subject if administered in a free form.
57. The method of any of paragraphs 33-53, wherein the dose of the therapeutic agent administered is 20% or less of the amount that would be administered to a subject if administered in a free form.
58. The method of any of paragraphs 33-57, wherein the dose of the therapeutic agent administered is 10% or less of the amount that would be administered to a subject if administered in a free form.

Some embodiments of the technology described herein can be defined according to any of the following numbered paragraphs:

1. An engineered cellular composition comprising:
   a. an erythrocyte; and
   b. a particle comprising PLGA and at least one therapeutic agent, wherein the particle is located on the cell surface of the erythrocyte.
2. The composition of paragraph 1, wherein the PLGA comprises a L:G ratio of at least 50:50 or more L.
3. The composition of paragraph 2, wherein the PLGA comprises a L:G ratio of about 50:50.
4. The composition of paragraph 2, wherein the PLGA comprises a L:G ratio of about 85:15.
5. The composition of paragraph 2, wherein the PLGA comprises a L:G ratio of about 65:35.
6. The composition of any of paragraphs 1-5, wherein the PLGA comprises ester ends and/or acid ends.
7. The composition of any of paragraphs 1-6, wherein the PLGA comprises ester ends.
8. The composition of any of paragraphs 1-6, wherein the PLGA comprises acid ends.
9. The composition of paragraph 2, wherein the PLGA comprises a L:G ratio of about 50:50 and ester ends.
10. The composition of paragraph 2, wherein the PLGA comprises a L:G ratio of about 50:50 and acid ends.
11. The composition of paragraph 2, wherein the PLGA comprises a L:G ratio of about 85:15 and ester ends.
12. The composition of paragraph 2, wherein the PLGA comprises a L:G ratio of about 65:35 and acid ends.
13. The composition of any of paragraphs 1-8, wherein the PLGA comprises a L:G ratio of about 50:50 and ester ends, whereby the therapeutic agent is targeted to the spleen and/or heart.
14. The composition of any of paragraphs 1-8, wherein the PLGA comprises a L:G ratio of about 50:50 and acid ends, whereby the therapeutic agent is targeted to the spleen and/or lung.
15. The composition of any of paragraphs 1-8, wherein the PLGA comprises a L:G ratio of about 85:15 and ester ends, whereby the therapeutic agent is targeted to the kidney and/or lung.
16. The composition of any of paragraphs 1-8, wherein the PLGA comprises a L:G ratio of about 65:35 and acid ends, whereby the therapeutic agent is targeted to the lung, heart and/or kidney.
17. The composition of any of paragraphs 1-8, wherein the PLGA comprises a L:G ratio of more than 50:50, whereby the therapeutic agent is targeted to the lung and/or kidney.
18. The composition of any of paragraphs 1-8, wherein the PLGA comprises a L:G ratio of less than 85:15 and ester ends, whereby the therapeutic agent is targeted to the spleen.
19. The composition of any of paragraphs 1-18, wherein the at least one therapeutic agent is selected from:
   a chemotherapeutic agent; an antigen; a steroid; an immunosuppressant agent; an immunostimulatory agent; a virus; a small molecule; a peptide; a nucleic acid; and a chemokine.
20. The composition of paragraph 19, wherein the at least one chemotherapeutic agent is selected from the group consisting of:
   doxorubicin; camptothecin; paclitaxel; docetaxel; 5-fluorouracil; gemcitabine; methotrexate; or a combination thereof.
21. The composition of any of paragraphs 1-20, wherein the therapeutic agent is present at a concentration of at least 100 μg per $3\times10^8$ erythrocytes.

22. The composition of any of paragraphs 1-21, wherein the therapeutic agent is present at a concentration of at least 150 μg per $3\times10^8$ erythrocytes.
23. The composition of any of paragraphs 1-22, wherein the therapeutic agent is present at a concentration of at least 200 μg per $3\times10^8$ erythrocytes.
24. The composition of any of paragraphs 1-23, wherein the therapeutic agent is present at a concentration of at least 250 μg per $3\times10^8$ erythrocytes.
25. The composition of any of paragraphs 1-24, wherein the diameter of the polymeric particle is from about 100 nm to about 10 μm.
26. The composition of any of paragraphs 1-24, wherein the diameter of the polymeric particle is from about 100 nm to about 1 μm.
27. The composition of any of paragraphs 1-26, wherein the polymeric particle further comprises one or more cell adhesive molecules.
28. The composition of paragraph 27, wherein the one or more cell adhesive molecules is localized to a region of the particle surface.
29. The composition of any of paragraphs 27-28, wherein the cell adhesive molecule is selected from the group consisting of:
    an antibody reagent that binds specifically to a molecule on a red blood cell; a peptide that binds specifically to a molecule on a red blood cell; a cell adhesive polymer; a cell adhesive polyelectrolyte, and a ligand for a receptor on a red blood cell.
30. The composition of paragraph 29, wherein the cell adhesive polyelectrolytes comprise hyaluronic acid, hyaluronic acid-aldehyde, and/or poly(allylamine) hydrochloride.
31. The composition of paragraph 30, wherein the hyaluronic acid is modified to comprise aldehyde groups.
32. The composition of paragraph 29, wherein the cell adhesive polymer is a polyphenol or metal-polyphenol network.
33. A method of delivering a therapeutic agent to a cell in a subject, the method comprising administering to the subject a composition of any of paragraphs 1-32.
34. The method of paragraph 33, wherein the cell is a cancer cell and the therapeutic agent is a chemotherapeutic agent, chemokine, or immunostimulatory agent (e.g., IFNs, IFN-γ, TNFα, TGF-β, IL-1β, IL-6, IL-4, IL-10, IL-13, IL-2, IL-12, IL-15, and IL-27, and other immunostimulatory antagonists such as CpG ODN, imiquimod, Resiquimod (R848), Monophosphoryl Lipid A (MPLA), and poly(I:C)).
35. A method of treating cancer and/or a tumor in a subject in need thereof, the method comprising administering to the subject a composition of any of paragraphs 1-32.
36. The method of paragraph 35, wherein the therapeutic agent is a chemotherapeutic agent or chemokine.
37. The method of any of paragraphs 33-36, wherein the cancer cell is in the lung of the subject and/or the subject has lung cancer.
38. The method of paragraph 37, wherein the PLGA comprises a L:G ratio of about 65:35 and acid ends.
39. The method of any of paragraphs 33-36, wherein the cancer cell is in the kidney of the subject and/or the subject has kidney cancer.
40. The method of paragraph 39, wherein the PLGA comprises a L:G ratio of about 85:15 and ester ends.
41. The method of paragraph 39, wherein the PLGA comprises a L:G ratio of about 65:35 and acid ends.
42. The method of any of paragraphs 33-41, wherein the PLGA comprises a L:G ratio of more than 50:50.
43. The method of any of paragraphs 33-42, further comprising administering radiation or at least one chemotherapy to the subject.
44. A method of stimulating an immune response in a subject in need thereof, the method comprising administering to the subject a composition of any of paragraphs 1-32, wherein the therapeutic agent is an antigen, immunostimulatory agent, or chemokine.
45. The method of paragraph 44, wherein the immune response is localized.
46. The method of any of paragraphs 44-45 wherein the therapeutic agent is an antigen and the PGLA comprises: a) a L:G ratio of about 50:50 and ester ends; b) a L:G ratio of about 50:50 and acid ends, or c) a L:G ratio of less than 85:15 and ester ends.
47. A method of decreasing or suppressing an immune response in a subject in need thereof, the method comprising administering to the subject a composition of any of paragraphs 1-32, wherein the therapeutic agent is an immunomodulatory agent (e.g., IL-4) or steroid.
48. The method of paragraph 47, wherein the immune response is localized.
49. The method of any of paragraphs 44-48, wherein the subject is in need of an immune response in the lungs.
50. The method of any of paragraphs 44-49, wherein the subject is in need of treatment for acute lung injury.
51. The method of any of paragraphs 47-50, wherein the therapeutic agent is a steroid or IL-4.
52. The method of any of paragraphs 47-51, wherein the PLGA comprises a L:G ratio of more than 50:50.
53. The method of any of paragraphs 47-51, wherein the PLGA comprises a L:G ratio of about 65:35 and acid ends.
54. The method of any of paragraphs 33-53, wherein a therapeutically effective amount of the composition is administered.
55. The method of any of paragraphs 33-54, wherein the dose of the therapeutic agent administered is 50% or less of the amount that would be administered to a subject if administered in a free form.
56. The method of any of paragraphs 33-54, wherein the dose of the therapeutic agent administered is 40% or less of the amount that would be administered to a subject if administered in a free form.
57. The method of any of paragraphs 33-54, wherein the dose of the therapeutic agent administered is 30% or less of the amount that would be administered to a subject if administered in a free form.
58. The method of any of paragraphs 33-54, wherein the dose of the therapeutic agent administered is 20% or less of the amount that would be administered to a subject if administered in a free form.
59. The method of any of paragraphs 33-54, wherein the dose of the therapeutic agent administered is 10% or less of the amount that would be administered to a subject if administered in a free form.
60. A composition of any of paragraphs 1-32 for use in a method of delivering a therapeutic agent to a cell in a subject, the method comprising administering to the subject the composition of any of paragraphs 1-32.
61. The composition of paragraph 60, wherein the cell is a cancer cell and the therapeutic agent is a chemotherapeutic agent, chemokine, or immunostimulatory agent (e.g., IFNs, IFN-γ, TNFα, TGF-β, IL-1β, IL-6, IL-4, IL-10, IL-13, IL-2, IL-12, IL-15, and IL-27, and other immunostimulatory antagonists such as CpG ODN, imiquimod, Resiquimod (R848), Monophosphoryl Lipid A (MPLA), and poly(I:C)).

62. A composition of any of paragraphs 1-32 for use in a method of treating cancer and/or a tumor in a subject in need thereof, the method comprising administering to the subject the composition of any of paragraphs 1-32.
63. The composition of paragraph 62, wherein the therapeutic agent is a chemotherapeutic agent or chemokine.
64. The composition of any of paragraphs 62-63, wherein the cancer cell is in the lung of the subject and/or the subject has lung cancer.
65. The composition of paragraph 64, wherein the PLGA comprises a L:G ratio of about 65:35 and acid ends.
66. The composition of any of paragraphs 62-65, wherein the cancer cell is in the kidney of the subject and/or the subject has kidney cancer.
67. The composition of paragraph 66, wherein the PLGA comprises a L:G ratio of about 85:15 and ester ends.
68. The composition of paragraph 66, wherein the PLGA comprises a L:G ratio of about 65:35 and acid ends.
69. The composition of any of paragraphs 60-68, wherein the PLGA comprises a L:G ratio of more than 50:50.
70. The composition of any of paragraphs 60-69, further comprising administering radiation or at least one chemotherapy to the subject.
71. A composition of any of paragraphs 1-32 for use in a method of stimulating an immune response in a subject in need thereof, the method comprising administering to the subject the composition of any of paragraphs 1-32, wherein the therapeutic agent is an antigen, immunostimulatory agent, or chemokine.
72. The composition of paragraph 71, wherein the immune response is localized.
73. The composition of any of paragraphs 71-72, wherein the therapeutic agent is an antigen and the PGLA comprises: a) a L:G ratio of about 50:50 and ester ends; b) a L:G ratio of about 50:50 and acid ends, or c) a L:G ratio of less than 85:15 and ester ends.
74. A composition of any of paragraphs 1-32 for use in a method of decreasing or suppressing an immune response in a subject in need thereof, the method comprising administering to the subject the composition of any of paragraphs 1-32, wherein the therapeutic agent is an immunomodulatory agent (e.g., IL-4) or steroid.
75. The composition of paragraph 74, wherein the immune response is localized.
76. The composition of any of paragraphs 74-75, wherein the subject is in need of an immune response in the lungs.
77. The composition of any of paragraphs 74-76, wherein the subject is in need of treatment for acute lung injury.
78. The composition of any of paragraphs 74-77, wherein the therapeutic agent is a steroid or IL-4.
79. The composition of any of paragraphs 74-78, wherein the PLGA comprises a L:G ratio of more than 50:50.
80. The composition of any of paragraphs 74-78, wherein the PLGA comprises a L:G ratio of about 65:35 and acid ends.
81. The composition of any of paragraphs 60-80, wherein a therapeutically effective amount of the composition is administered.
82. The composition of any of paragraphs 60-80, wherein the dose of the therapeutic agent administered is 50% or less of the amount that would be administered to a subject if administered in a free form.
83. The composition of any of paragraphs 60-80, wherein the dose of the therapeutic agent administered is 40% or less of the amount that would be administered to a subject if administered in a free form.
84. The composition of any of paragraphs 60-80, wherein the dose of the therapeutic agent administered is 30% or less of the amount that would be administered to a subject if administered in a free form.
85. The composition of any of paragraphs 60-80, wherein the dose of the therapeutic agent administered is 20% or less of the amount that would be administered to a subject if administered in a free form.
86. The composition of any of paragraphs 60-80, wherein the dose of the therapeutic agent administered is 10% or less of the amount that would be administered to a subject if administered in a free form.

EXAMPLES

Example 1

Four PLGA compositions were tested with the erythrocyte-nanoparticle approach described herein. The four PLGA candidates differ in two parameters: L:G ratio and end-group, which determine their hydrophobicity and ability to form hydrogen-bond. PLGA with a higher L:G ratio is more hydrophobic. PLGA with an ester-end is more hydrophobic. Overall, the two parameters control the location of delivery of erythrocyte hitchhiked PLGA nanoparticles via tuning the binding strength of nanoparticles to erythrocytes and shear-dependent detachment of nanoparticles from the carrier erythrocytes. Table 1 depicts the four PLGA compositions, with the ratio of L:G provided as a molar ratio.

TABLE 1

| | PLGA-a | PLGA-b | PLGA-c | PLGA-d |
|---|---|---|---|---|
| L:G ratio | 50:50 | 50:50 | 85:15 | 65:35 |
| End-group | Ester-end | Acid-end | Ester-end | Acid-end |

Figure 1B:
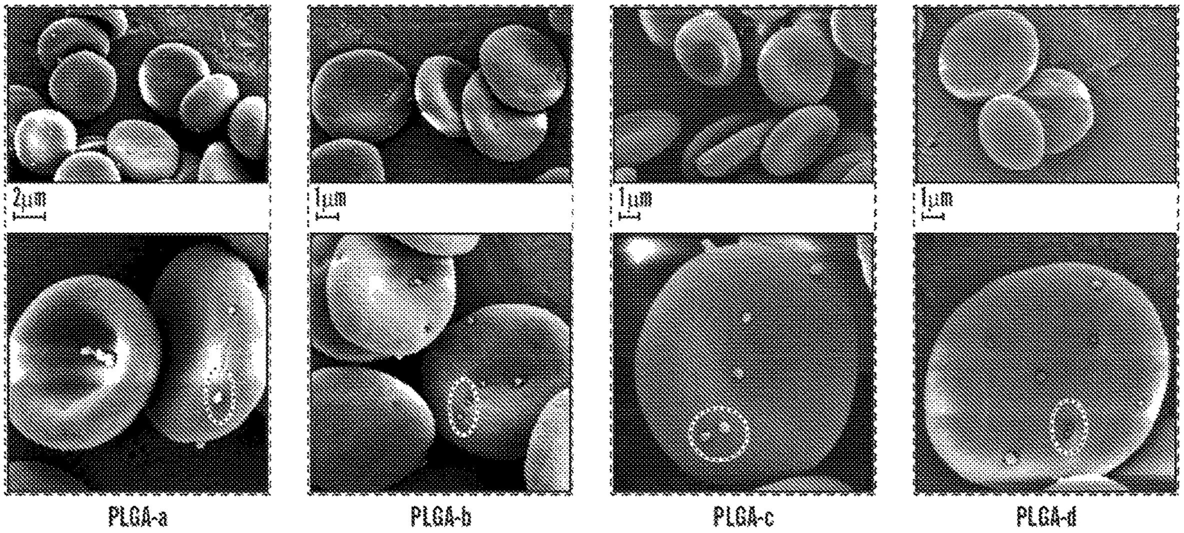

Binding efficiency data indicated that both hydrophobic interaction and hydrogen-bonding are necessary for more PLGA nanoparticles to bind to erythrocytes (FIG. 1A). SEM data indicated that acid-end PLGA nanoparticles went deeper on erythrocytes than ester-end PLGA nanoparticles (FIG. 1B). Variation of L:G ratio and end-group are correlated to the detachment of PLGA nanoparticles from carrier erythrocytes, and engineering both parameters can tune the binding strength and shear-dependent detachment of PLGA nanoparticles (FIGS. 2A-2B).

Figure 2A:
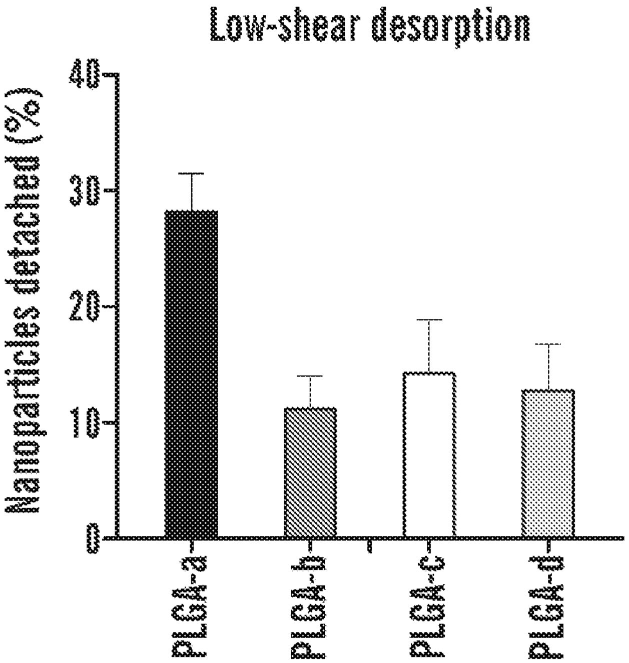
FIGS. 2A-2B demonstrate that properties of PLGA influence their binding and detachment on carrier erythrocytes.
Figure 2B:
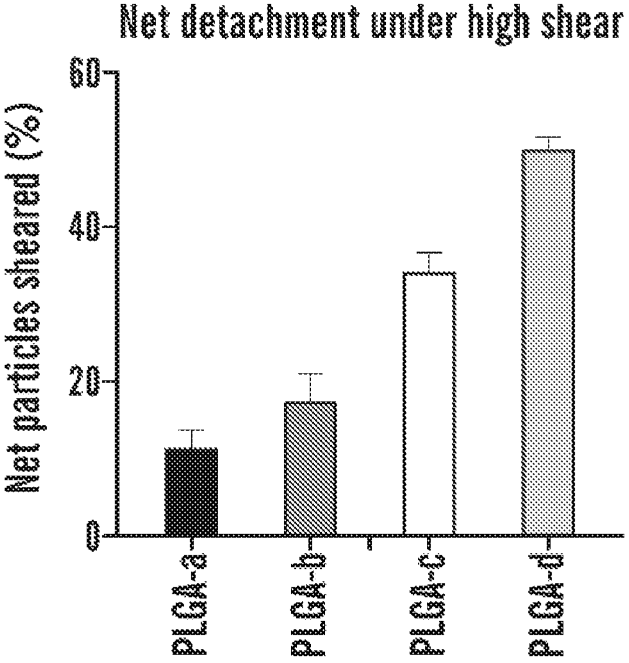
Figure 3:
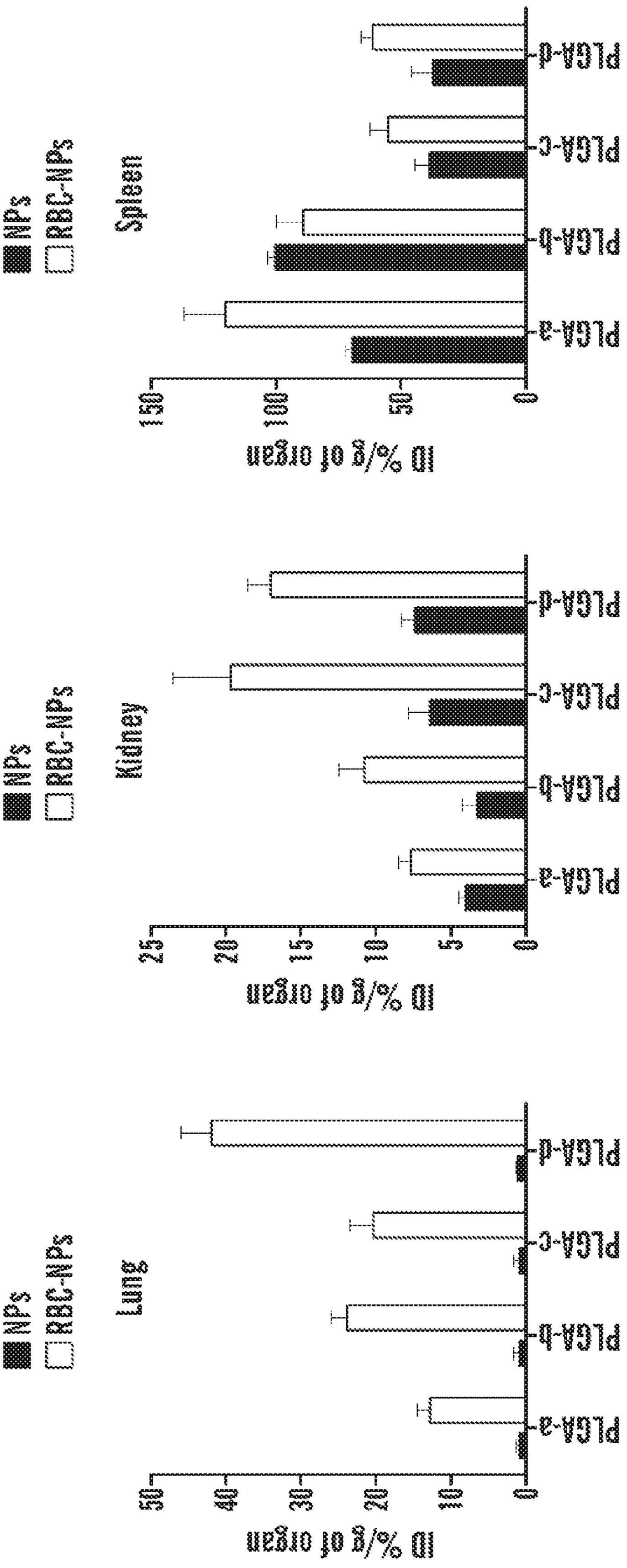
FIG. 3 demonstrates that properties of PLGA hitchhiked on erythrocytes influence their delivery to specific organs. The biodistribution of nanoparticles and erythrocyte hitchhiked nanoparticles in lung, kidney, spleen, liver, heart, and brain is shown.
Figure 3:
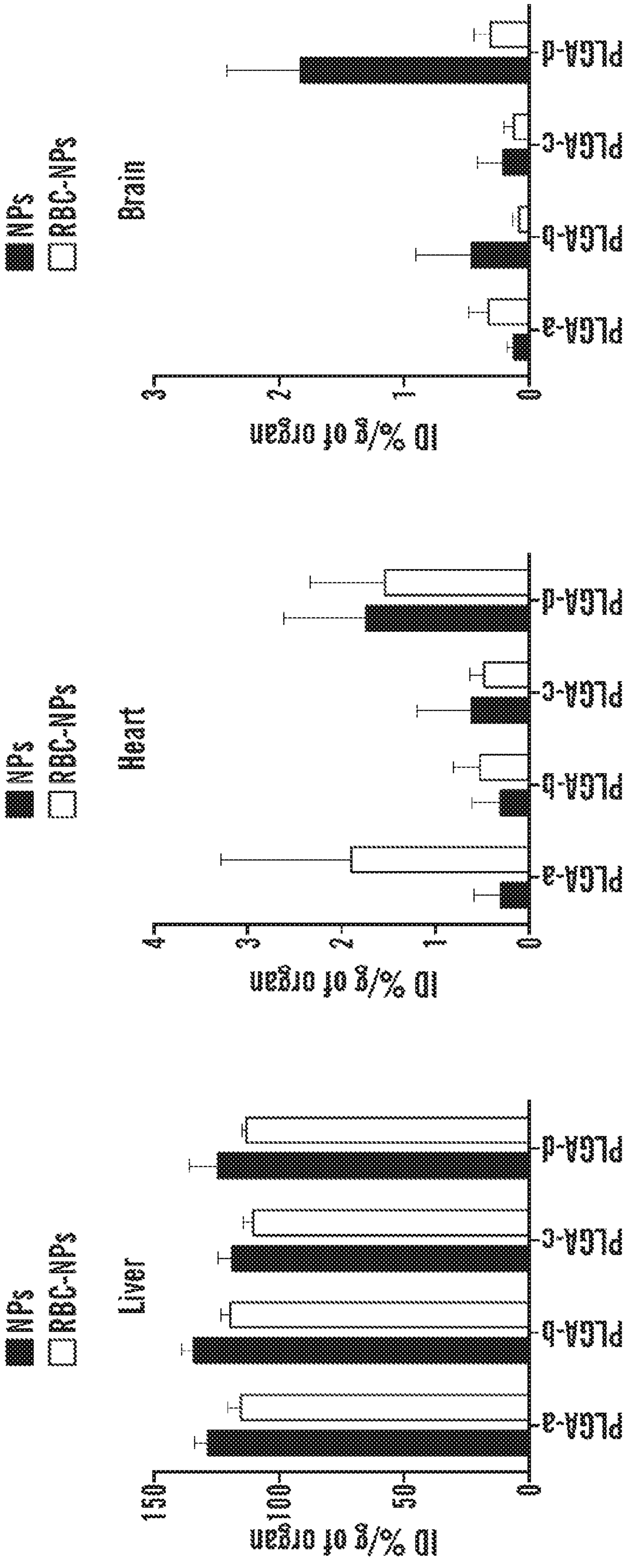

The biodistribution data is correlated to the in vitro shear study data (FIGS. 2A-2B). Erythrocyte hitchhiking delivers PLGA nanoparticles to specific organs depending on the properties of PLGA (FIG. 3). Delivery of PLGA nanoparticles to high shear organs (lung and kidney) is correlated to the net nanoparticle detachment from erythrocytes under high shear stress. For example, PLGA-c and PLGA-d showed the highest detachment efficiency under high shear stress and were more delivered to the lung and kidney. Delivery of PLGA nanoparticles to low shear organs (spleen) is related to the premature nanoparticle release under low shear stress. For example, PLGA-a showed the highest premature detachment under low shear stress and were more delivered to the spleen.

Example 2: Erythrocyte Leveraged Chemotherapy (ELeCt): Erythrocyte Surface Assembled Biodegradable Nanoparticles to Combat Lung Metastasis In spite of being a mainstay of cancer treatment, chemotherapy has shown limited efficacy for the treatment of lung metastasis due to ineffective targeting and poor tumor accumulation. Described herein is a highly effective Erythrocyte Leveraged Chemotherapy (ELeCt) platform, consisting of biodegradable drug nanoparticles self-assembled onto the surface of erythrocytes, to permit chemotherapy for lung metastasis treatment. The ELeCt platform significantly extended the circulation time of the drug nanoparticles and delivered 10-fold higher drug content to the lung compared to the free nanoparticles. In both the early- and late-stage melanoma lung metastasis models, the ELeCt platform enabled substantial inhibition of tumor growth that resulted in significant improvement of survival. Further, the ELeCt platform can be used to deliver numerous approved chemotherapeutic drugs. Altogether, the findings indicate that the ELeCt platform offers a versatile strategy to enable chemotherapy for effective lung metastasis treatment.

Introduction

Cancer has been one of the leading causes of mortality over the last few decades.[1] While early detection of tumor cells in specific tissues or the blood has improved the survival of cancer patients, current standard of care interventions including surgery, radiation therapy or chemotherapy have limited efficacy of cancer is not detected early.[1-4] Early detection, however, is not often feasible and in most patients tumors have metastasized to secondary locations by the time of diagnosis.[2, 4]

According to National Cancer Institute (NCI), the most common site of metastasis for a variety of primary cancers is the lung, owing to its high vascular density. Lung metastasis is highly fatal if not treated and currently there is no specific treatment it.[5, 6] Systemic chemotherapy is one of the standard treatment options for lung metastasis.[7, 8] However, its efficacy has been far from desirable attributing to the ineffective targeting and poor accumulation to the lungs. Nanotechnology has played a pivotal role in enhancing the treatment of advanced metastatic cancers[9-11] and therefore can be applied in the case of lung metastasis as well. However, traditional nanoparticle delivery often fails to accumulate at the desired site of action due to the existence of biological barriers that impede the intravascularly injected nanoparticles.[12-17] Active targeting using tissue specific ligands has often been explored as a strategy to improve tissue accumulation but has only resulted in modest improvement of therapeutic efficacy and decreased translational capability due to increased cost of production. [18-26]

Figure 4A:
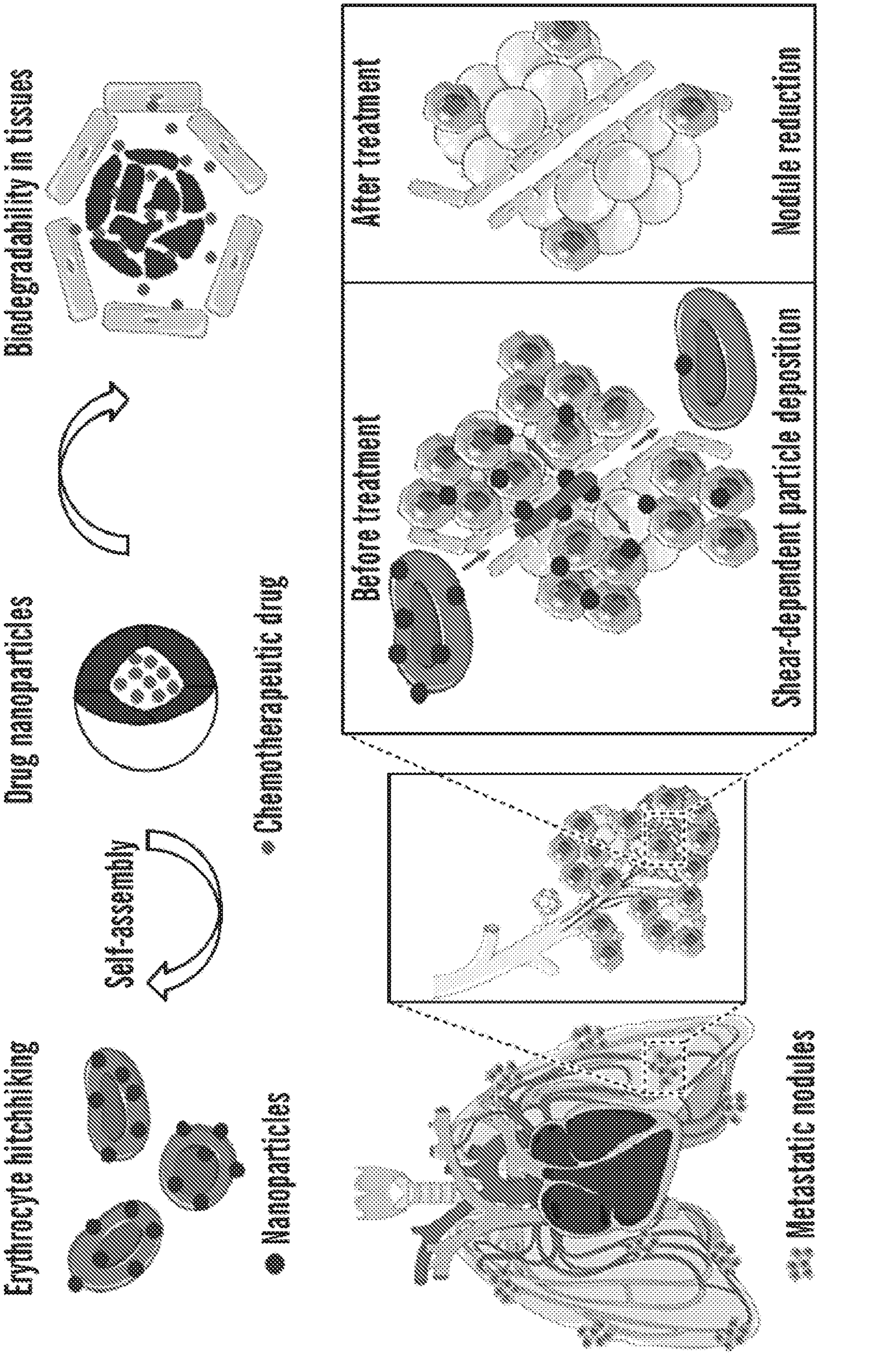
FIGS. 4A-4K depict a schematic illustration of the Erythrocyte Leveraged Chemotherapy (EleCt) platform and characterization of drug (doxorubicin)-loaded biodegradable PLGA nanoparticles.

To achieve efficient drug delivery to enable chemotherapy for effective lung metastasis treatment, the unique physiology of the target site was considered herein and a two-pronged strategy (Erythrocyte Leveraged Chemotherapy (ELeCt))-biodegradable drug nanoparticles self-assembled on the surface of erythrocyte was developed (FIG. 4A). Erythrocytes act as a primary drug delivery system, capable of responsively dislodging the particles in the lung endothelium and tumor nodules in response to the high shear stress experienced by erythrocytes in narrow lung capillaries.[27, 28] The biodegradable nanoparticles themselves are capable of encapsulating large amounts of chemotherapeutics and having a characteristic controlled release mechanism.[29, 30] They act as a secondary drug delivery system enabling sustained delivery of the cargo. In this study, superior accumulation and therapeutic efficacy of this lung physiology-assisted nanoparticle strategy was demonstrated using a model chemotherapeutic-doxorubicin. This concept was successfully used to combat lung metastasis and improve survival in early and late stage melanoma-lung metastasis model. The ability to incorporate a plethora of FDA-approved chemotherapy drugs and drug combinations in the biodegradable nanoparticles and subsequently self-assemble onto the erythrocytes was demonstrated. The particles also readily self-assemble to human erythrocytes and dislodge in a shear-dependent manner. Put altogether, Erythrocyte Leveraged Chemotherapy (ELeCt) offers a versatile, potent and translatable platform to combat lung metastasis.

Results

Figure 4B:
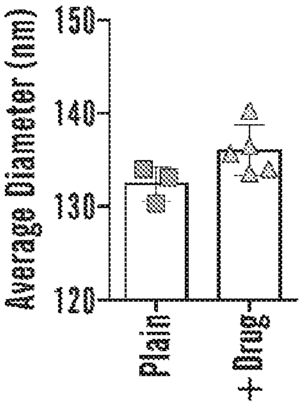
Figure 4C:
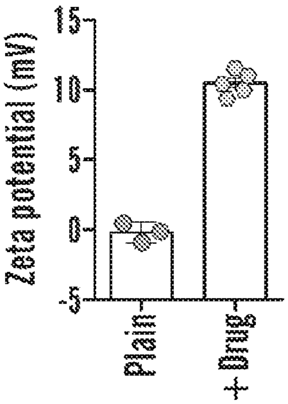
Figure 4D:
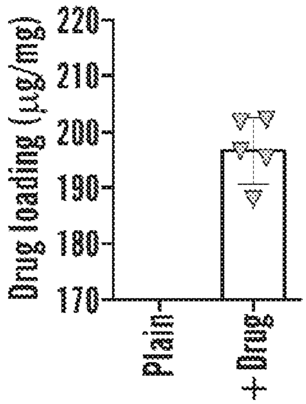
Figure 4E:
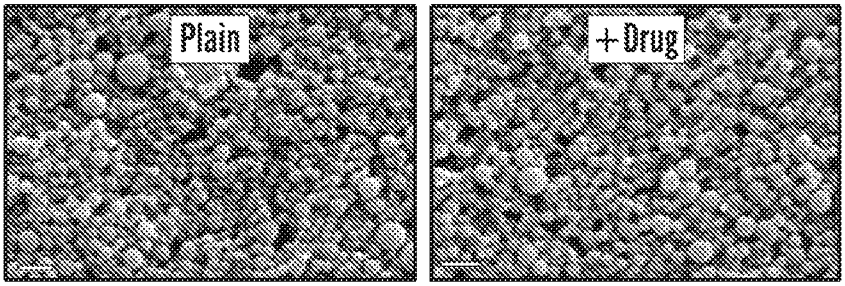
Figure 4F:
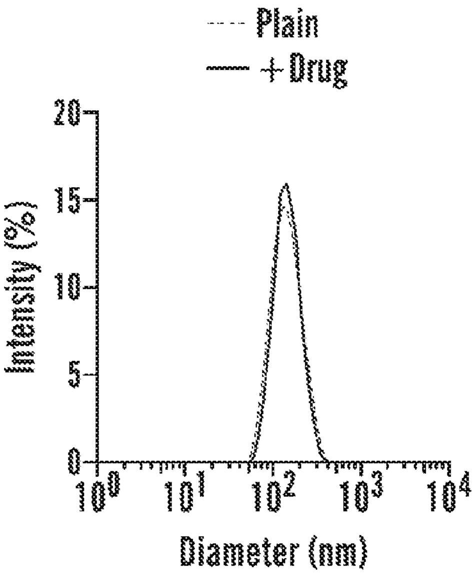
Figure 4G:
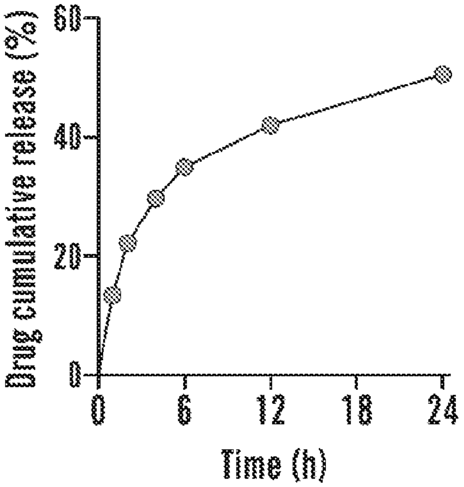
Figure 4H:
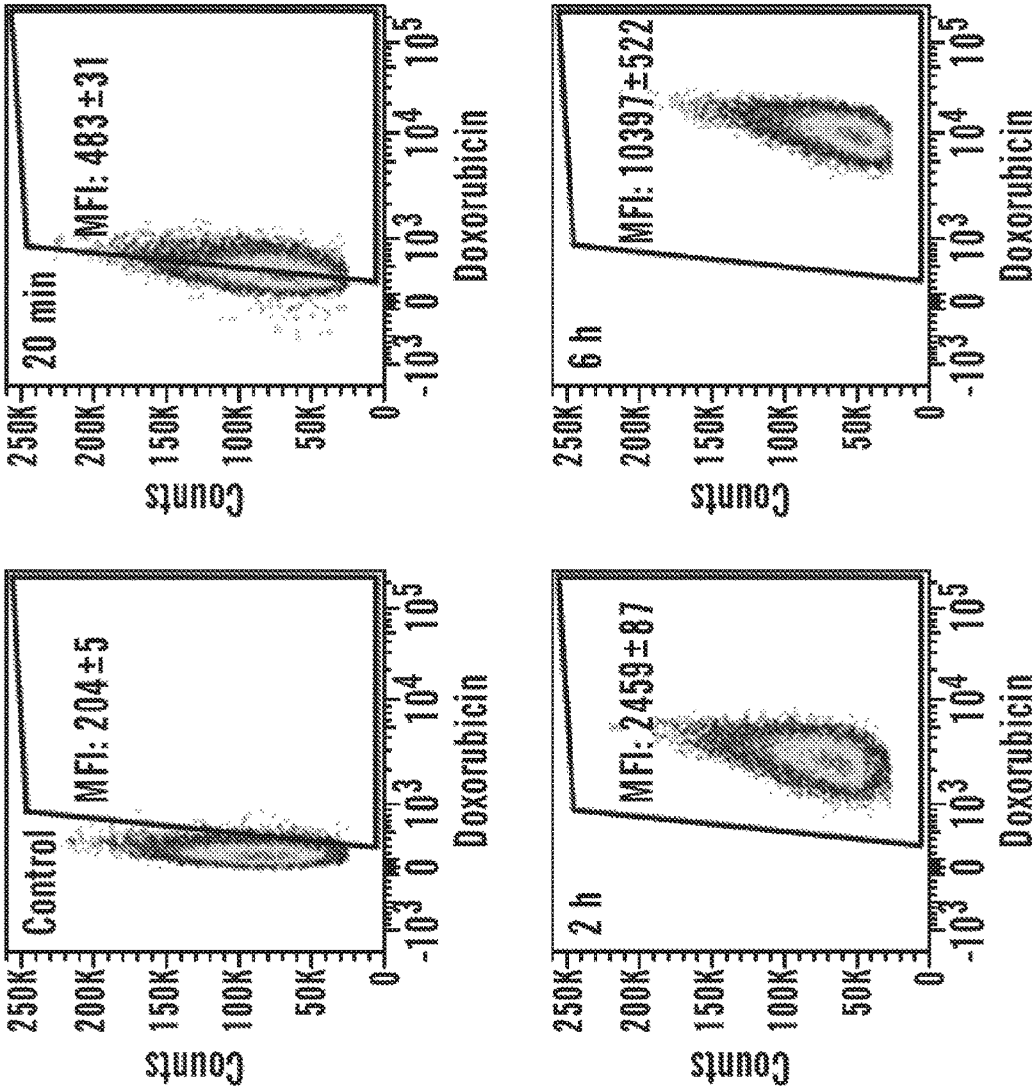
Figure 4I:
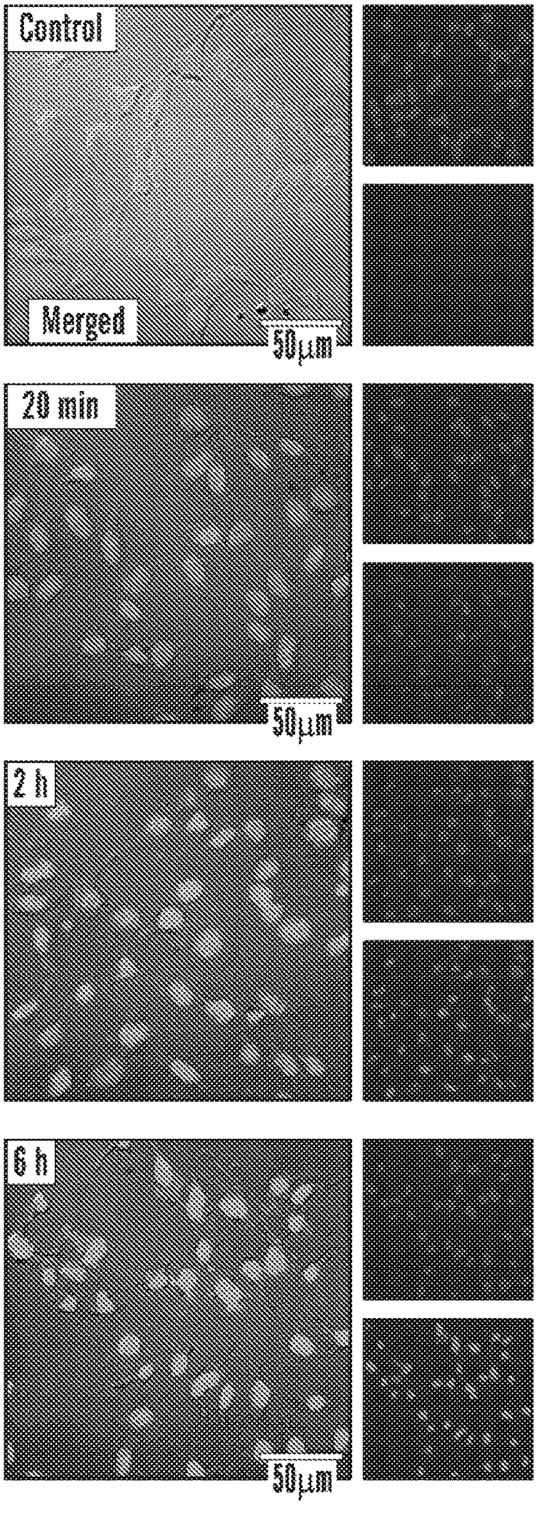
Figure 4J:
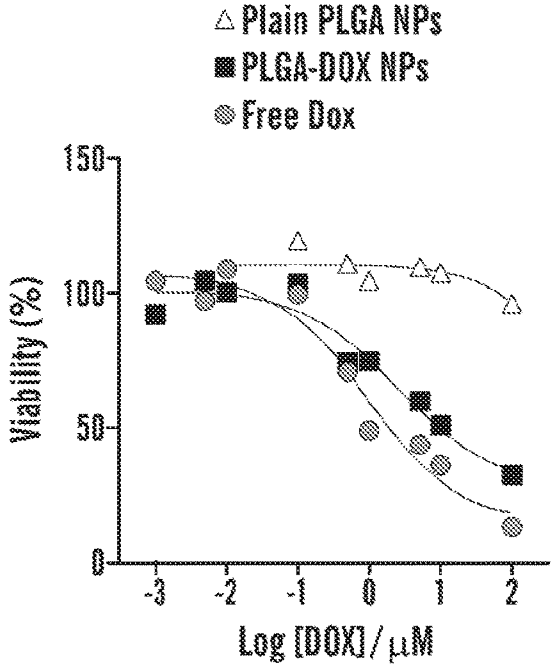
Figure 4K:
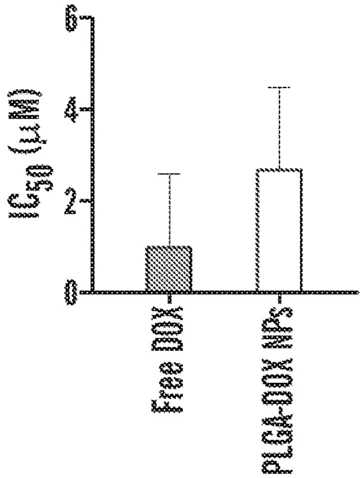

Drug-loaded biodegradable nanoparticles can efficiently interact with target cancer cells. Doxorubicin was used as a model drug and prepared drug-loaded biodegradable polymeric (poly(lactic-co-glycolic acid) (PLGA)) nanoparticles using the nanoprecipitation method. The drug-loaded PLGA nanoparticles had a diameter of 136.0±2.7 nm, which is slightly larger than the plain nanoparticles (FIG. 4B). Interestingly, the encapsulation of doxorubicin made the surface of the drug-loaded nanoparticles slightly positive (10.45±0.84 mV) (FIG. 4C), and this can be attributed to the presence of doxorubicin on the nanoparticle surface. The drug-loaded PLGA nanoparticles exhibited a high drug loading capacity (196.7±5.8 mg/g) (FIG. 4D). The morphology of nanoparticles was characterized using scanning electron microscopy (SEM). SEM images shown in FIG. 4E reveal that both the plain and the drug-loaded PLGA nanoparticles are spherical and relatively mono-dispersed. The dynamic light scattering (DLS) data (FIG. 4F) confirmed the uniform size distribution of the prepared nanoparticles. To test whether the drug can be released from the PLGA nanoparticles, their release profile was assayed in a complete medium. A burst followed by sustained release profile was observed and most of the drug was released within the first 6 hours (FIG. 4G). Efficient interaction of drug nanoparticles with the target cancer cells is critical for successful drug delivery and efficacy. In this study, B16F10-Luc melanoma cells were used as a model to evaluate the interaction between the drug-loaded biodegradable PLGA nanoparticles and the target cancer cells. As shown in FIG. 4H, the drug-loaded PLGA nanoparticles appeared to be internalized by B16F10-Luc cells quickly and efficiently. Within 20 mins of the incubation, a substantial portion of the cells had drug-loaded nanoparticles in them. The confocal laser scanning microscopy (CLSM) images shown in FIG. 4I confirmed the efficient interaction between the nanoparticles and the B16F10-Luc cells. Noticeably, the increase of doxorubicin fluorescence within the cell nucleus indicated an effective intracellular delivery and sufficient release of the loaded drug. The in vitro antitumor efficacy of the drug-loaded PLGA nanoparticles was further evaluated in a 2D culture of the same cell line. As indicated by the dose-response curve (FIG. 4J) and $IC_{50}$ values (FIG. 4K), the drug-loaded PLGA nanoparticles exhibited a slightly weaker cell killing efficacy compared to the free drug. However, the difference between them is insignificant.

Figure 5A:
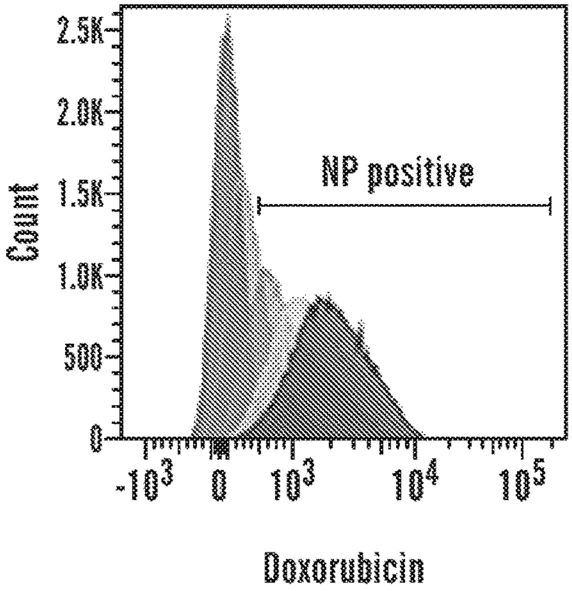
FIGS. 5A-5K demonstrate that doxorubicin-loaded biodegradable PLGA nanoparticles efficiently self-assemble to mouse and human erythrocytes.
Figure 5B:
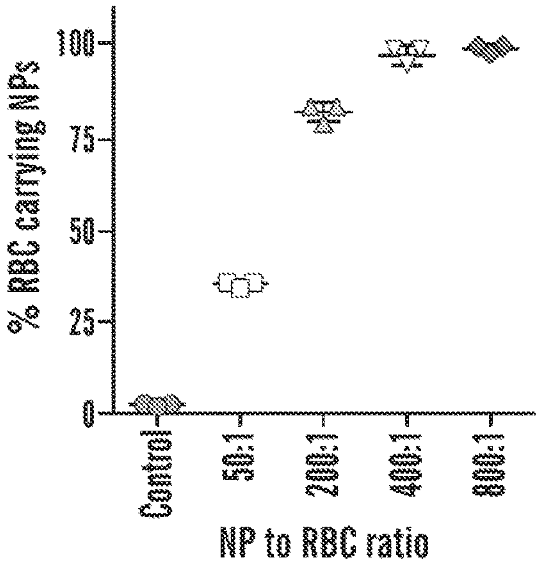
Figure 5C:
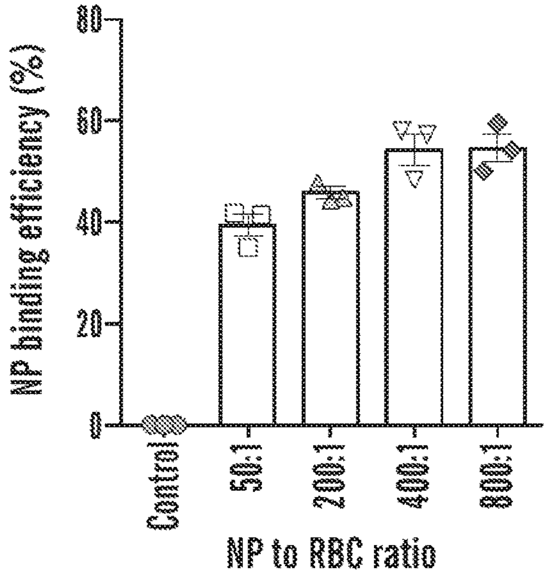
Figure 5D:
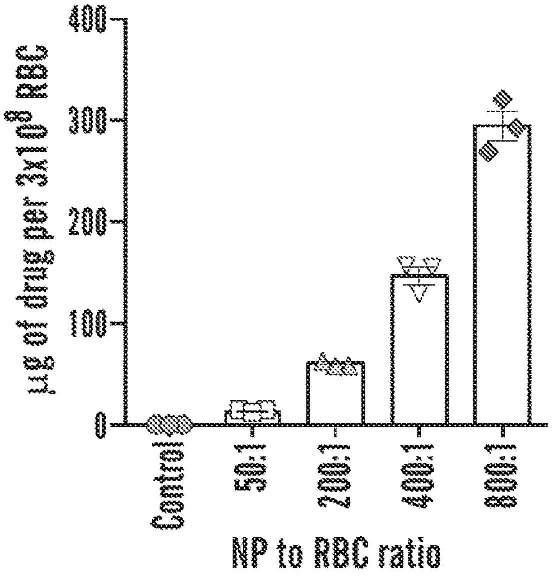
Figure 5E:
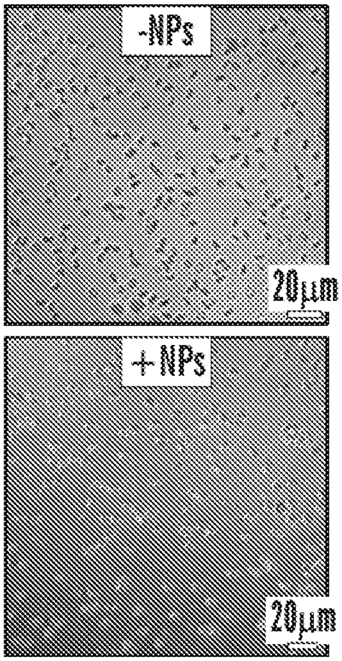
Figure 5F:
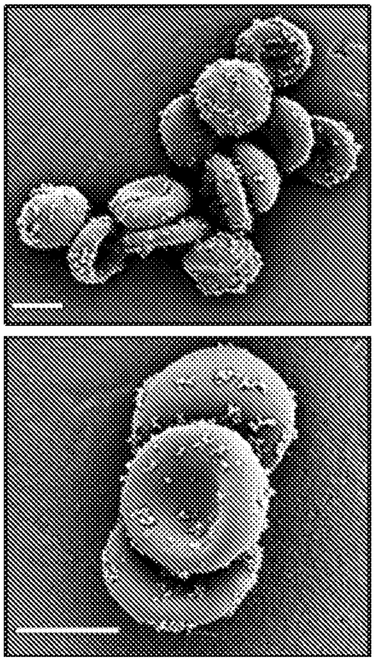
Figure 5G:
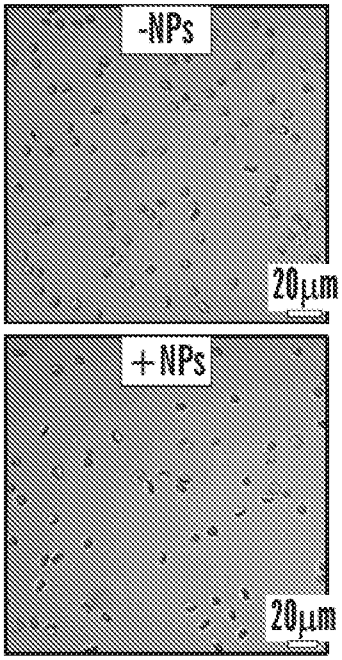
Figure 5H:
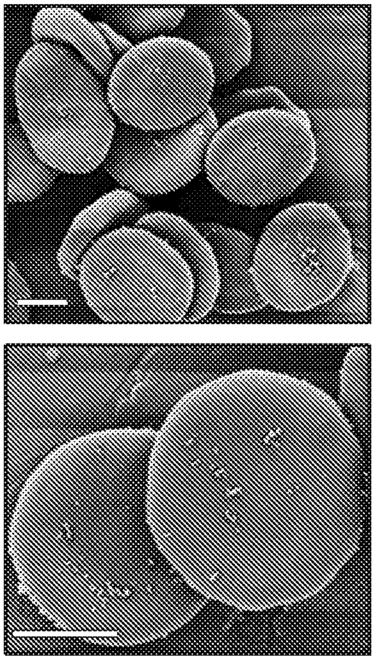
Figure 5I:
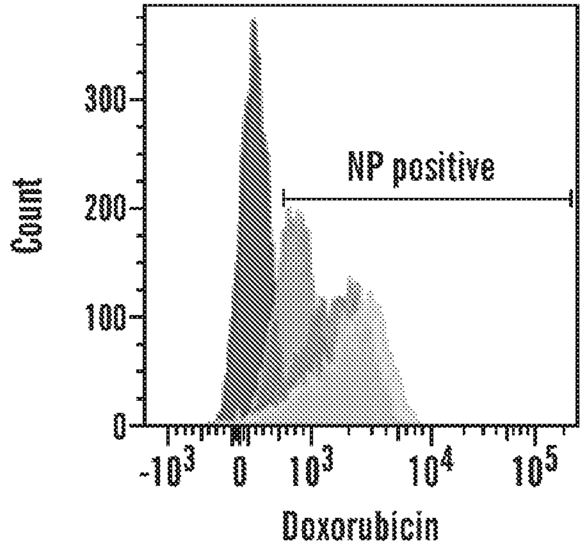

Drug-Loaded Biodegradable Nanoparticles Efficiently Self-Assembled onto Erythrocytes It was first evaluated whether the drug-loaded PLGA nanoparticles can efficiently self-assemble onto the mouse erythrocytes. To do this, mouse erythrocytes were incubated with the nanoparticles at a range of nanoparticle to erythrocyte ratios (50:1 to 800:1) and the binding of nanoparticles detected using flow cytometry. As shown in FIGS. 5A and 5B, the drug-loaded PLGA nanoparticles indeed self-assembled onto the mouse erythrocytes efficiently. Particularly, 81.6% of erythrocytes were found to carry nanoparticles when being incubated with nanoparticles at a ratio of 200:1, and this number increased to >96% on further increasing the incubation ratio. The binding efficiency of the nanoparticles to the erythrocytes was also quantified. Surprisingly, a substantial portion (39.3-54.5%) of the incubated nanoparticles self-assembled onto the mouse erythrocytes, depending on the feed ratio of the nanoparticles to the erythrocytes (FIG. 5C). Because of this high binding efficiency and the high drug loading capacity of the nanoparticles, the mouse erythrocytes were able to carry a high drug dose (as high as 294.1 μg per $3\times10^8$ erythrocytes) (FIG. 5D). In addition, the drug dose on the mouse erythrocytes can be easily tuned by manipulating the feed ratio of the nanoparticles to the erythrocytes. Next, the self-assembly of drug-loaded PLGA nanoparticles onto the mouse erythrocytes was visualized using CLSM and SEM. As shown in FIGS. 5E and 5F, both the CLSM and SEM data confirmed the efficient self-assembly of the nanoparticles onto the mouse erythrocytes. Meanwhile, the mouse erythrocytes maintained their bi-concave shapes after being hitchhiked by the drug-loaded PLGA nanoparticles (FIGS. 5E and 5F), indicating the self-assembly of the nanoparticles has caused minimal damage to the carrier erythrocytes. To test the translational potential of the erythrocyte hitchhiking platform, the self-assembly of the drug-loaded PLGA nanoparticles onto the human erythrocytes was evaluated. Both the CLSM and SEM images shown in FIGS. 5G and 5H indicated that the drug nanoparticles efficiently self-assemble onto the human erythrocytes as well.

Figure 5J:
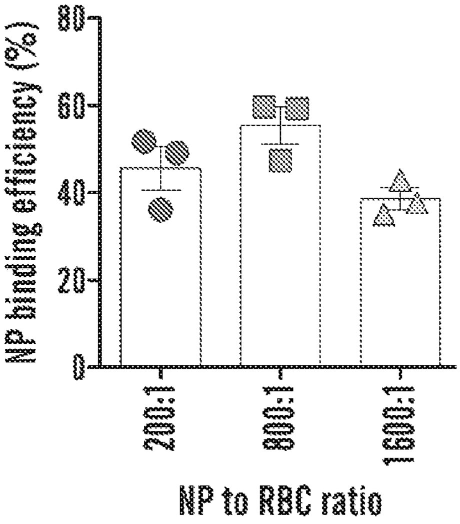
Figure 5K:
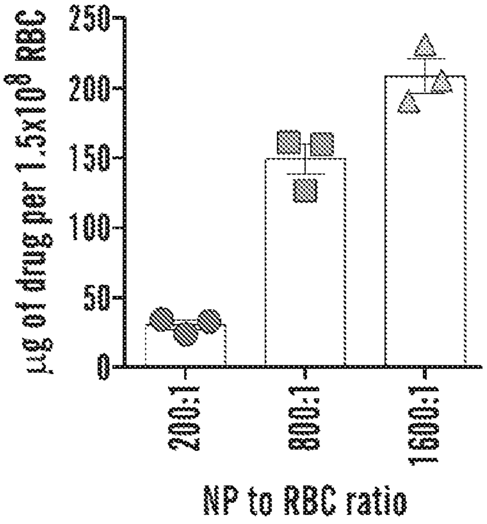

In addition, the self-assembly of drug-loaded PLGA nanoparticles to human erythrocytes at different nanoparticle to erythrocyte feed ratios (200:1 to 1600:1) was also evaluated). Similar to the murine counterparts, the drug-loaded PLGA nanoparticles self-assembled onto the human erythrocytes with high efficiency (38.7-45.7%) at various nanoparticle to erythrocyte feed ratios (FIGS. 51 and 5J). Moreover, the drug dose on human erythrocytes is tunable by changing the incubation ratio and a very high drug dose (209.1 μg per $1.5\times10^8$ erythrocytes) can be hitchhiked to human erythrocytes when being incubated at a 1600:1 nanoparticle to erythrocyte ratio (FIG. 5K).

Figure 6A:
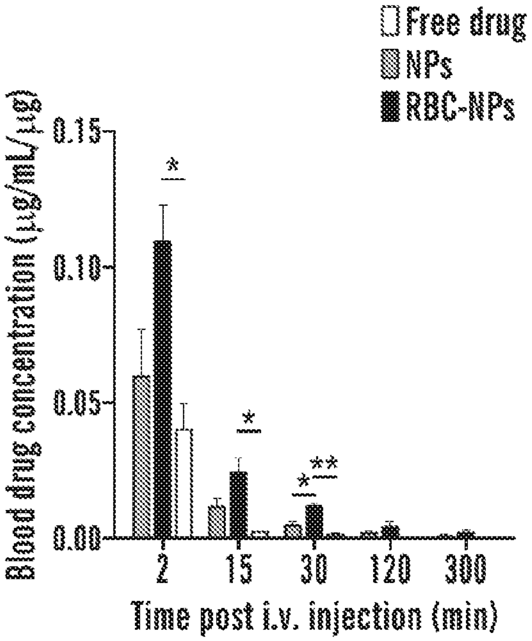
FIGS. 6A-6E demonstrate that the ELeCt platform enables enhanced and targeted delivery of nanoparticle drugs to the lungs bearing metastasis.
Figure 6B:
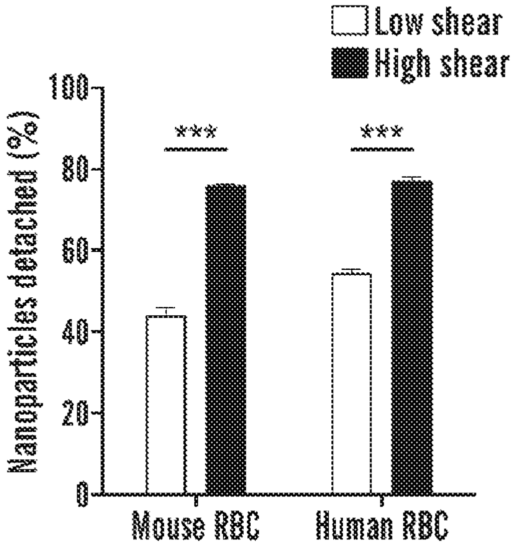
Figure 6C:
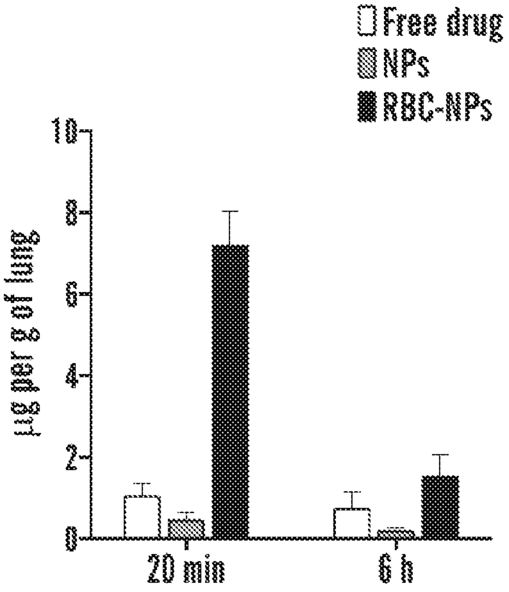
Figure 6D:
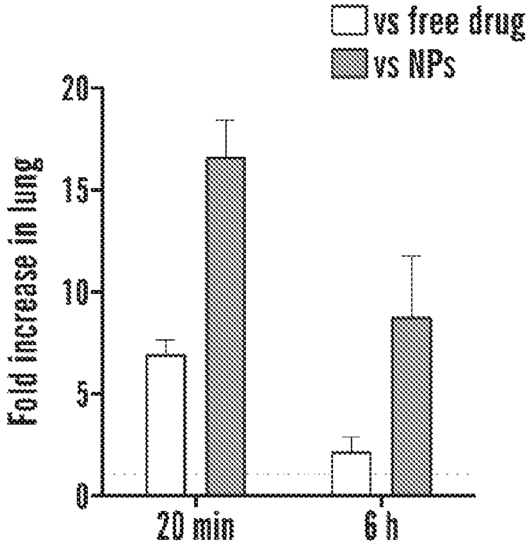

Erythrocyte Leveraged Chemotherapy (ELeCt) enables enhanced and targeted delivery of the nanoparticle drugs to the lungs bearing metastasis. A pharmacokinetic study was first conducted to examine the blood circulation time of different drug formulations. As shown in FIG. 6A, by self-assembling drug nanoparticles to erythrocytes, a higher drug concentration in the blood was achieved at all the tested time points, indicating an extended circulation time of the hitchhiked formulation. Mouse lung capillaries have an average diameter of 5 μm, narrowing down up to sizes as small as 1 μm, 3-4 times smaller than the mouse erythrocyte diameter.[27] Upon intravenous administration, the drug-loaded nanoparticles self-assembled onto the erythrocytes are expected to detach from the carrier erythrocytes because of the high shear stress and be deposited in the narrow lung capillaries. To test this hypothesis, an in vitro shear study was first performed in which the erythrocytes carrying the drug-loaded nanoparticles were sheared for 20 mins at a low (~1 Pa) or high (6 Pa) shear stress. As shown in FIG. 6B, detachment of the drug nanoparticles from the mouse erythrocytes is evidently shear-dependent, providing a basis for specific delivery of drug nanoparticles to the diseased lungs. Particularly, 76% of the hitchhiked drug nanoparticles were sheared off at the lung-corresponding shear stress (6 Pa), using a rheometer. Moreover, this shear-dependent detachment of drug nanoparticles was also observed with the human erythrocytes, bolstering the translational potential of this ELeCt platform. To test whether the drug nanoparticles can be sheared-off and deposited in the lungs that bear metastasis in vivo, a biodistribution study was conducted in mice bearing B16F10-Luc melanoma lung metastasis and the amount of drug was quantified, in this case, doxorubicin. Remarkably, as shown in FIGS. 6C and 6D, by self-assembly on erythrocytes, the drug-loaded nanoparticles delivered 16.6-fold higher drug content to the diseased lungs as compared to their free nanoparticle counterparts, 20 mins after administration. Even at a longer time point (6 h), erythrocyte hitchhiking deposited 8.7-fold higher drug content in the lungs as compared to their un-hitchhiked counterparts. In addition, erythrocyte hitchhiking delivered a 6.9-fold higher drug content to the lungs with melanoma metastasis as compared to the free drug injection, 20 mins after administration.

Figure 6E:
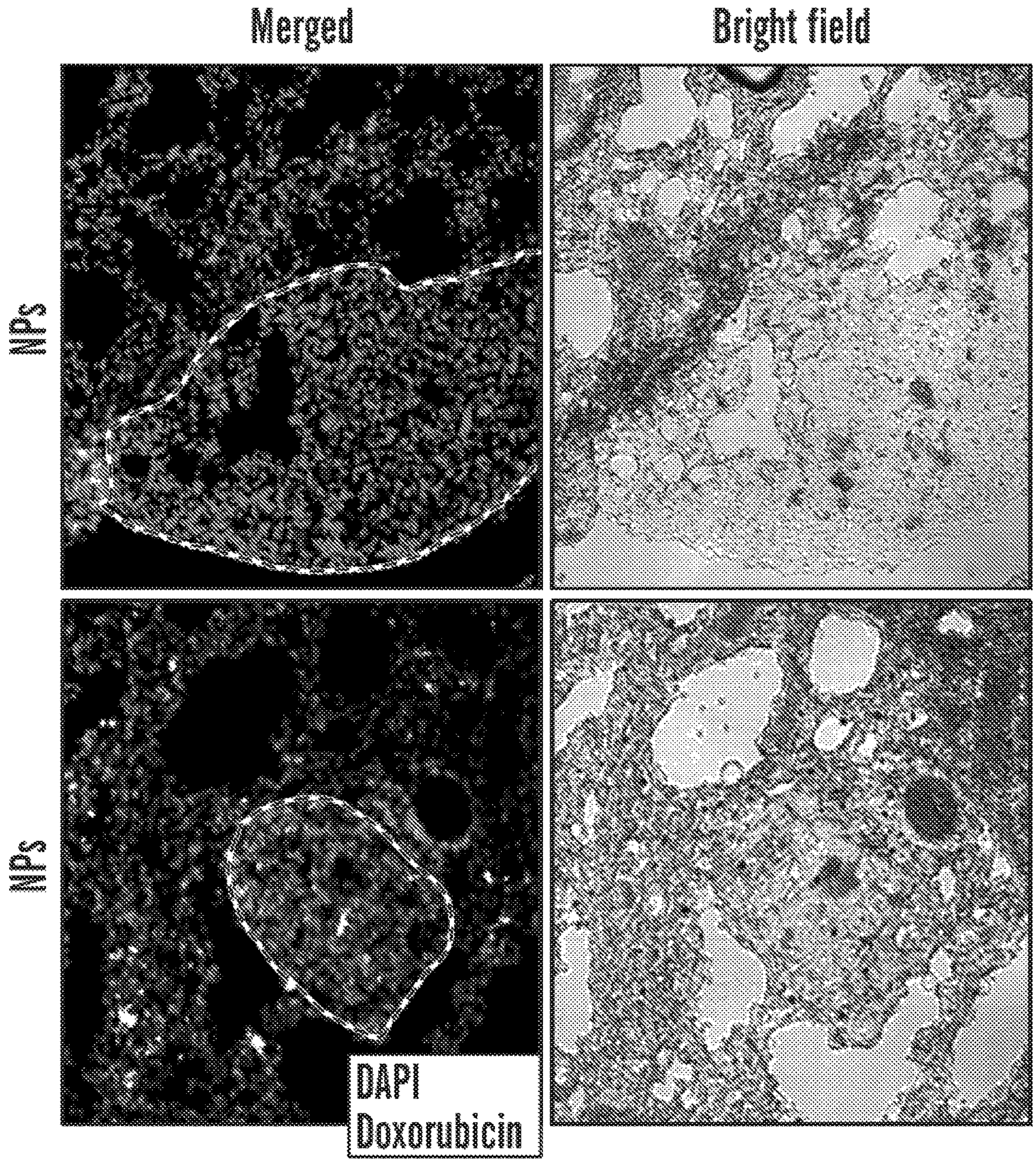

Next, the distribution of the drug nanoparticles sheared-off from the carrier erythrocytes within the lungs bearing metastasis was investigated. As shown in FIG. 6E, consistent with the biodistribution data, remarkably more drug nanoparticles were found in the lung section being treated with erythrocytes with nanoparticles self-assembled on them compared to that being treated with the nanoparticles alone. Evidently, a substantial portion, though not all, of the deposited nanoparticles went deep into the tumor metastasis nodules, indicating the biodegradable drug nanoparticle self-assembling on erythrocyte is able to precisely deliver the payload chemotherapeutic agents to their desired site of action.

Figure 7A:
FIGS. 7A-7H demonstrate that the ELeCt platform inhibits lung metastasis progression and improves survival in the early-stage B16F10-Luc metastasis model.
Figure 7B:
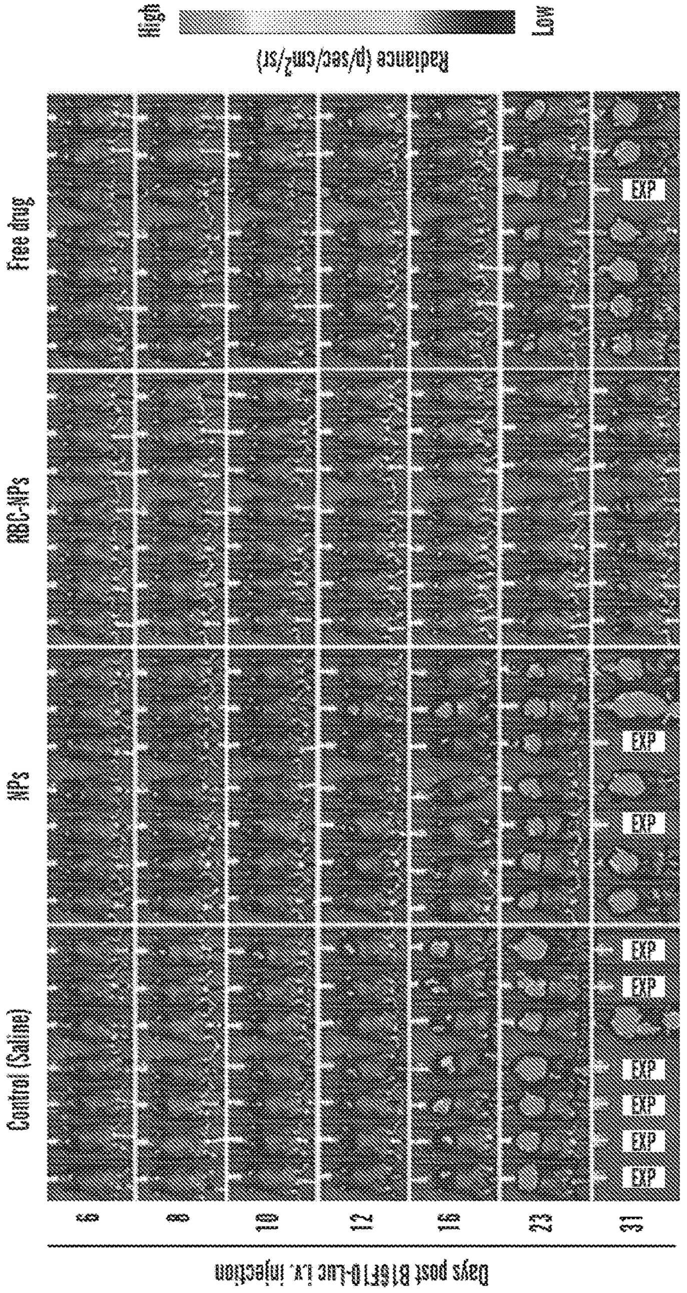
Figure 7C:
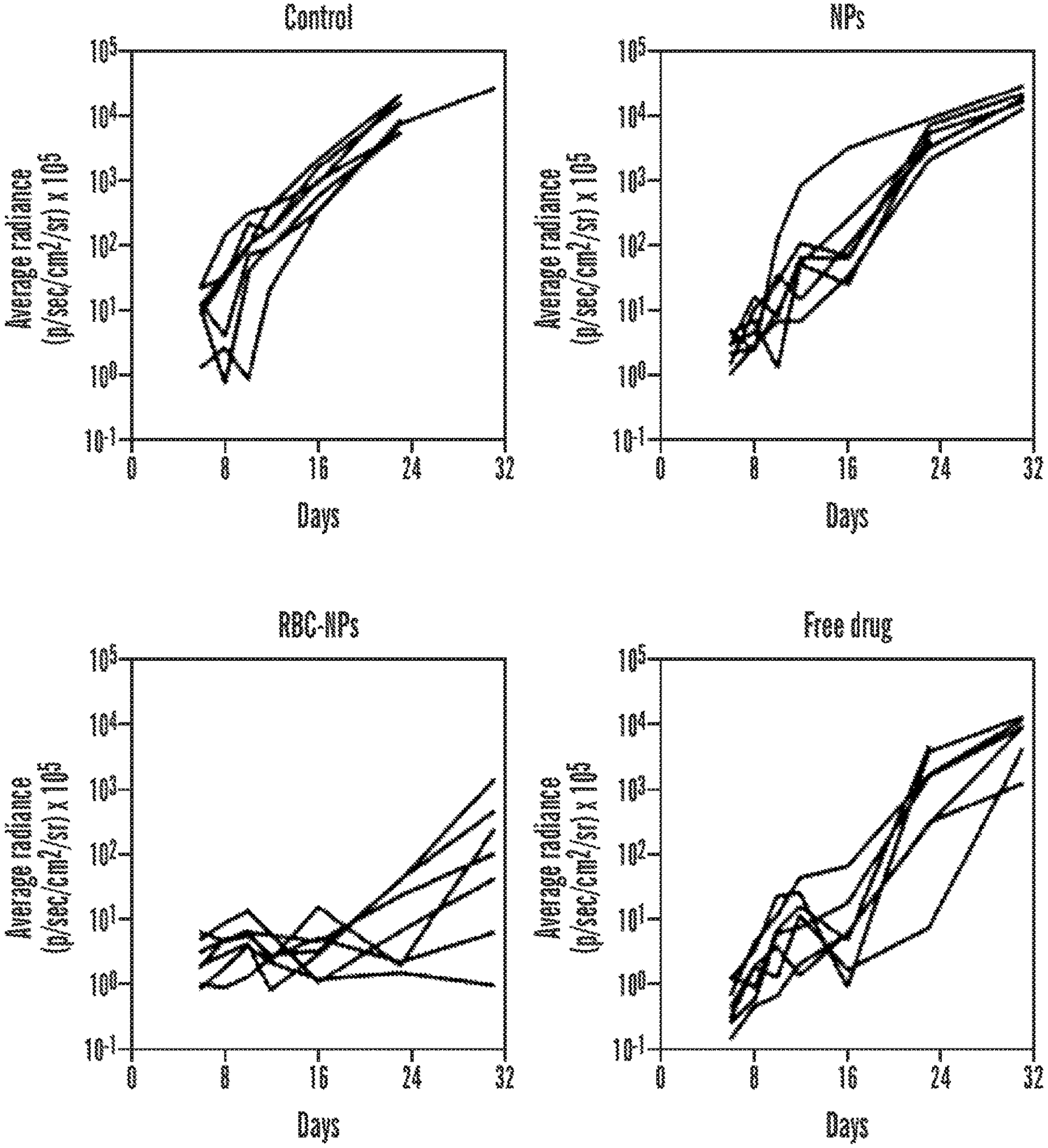
Figure 7D:
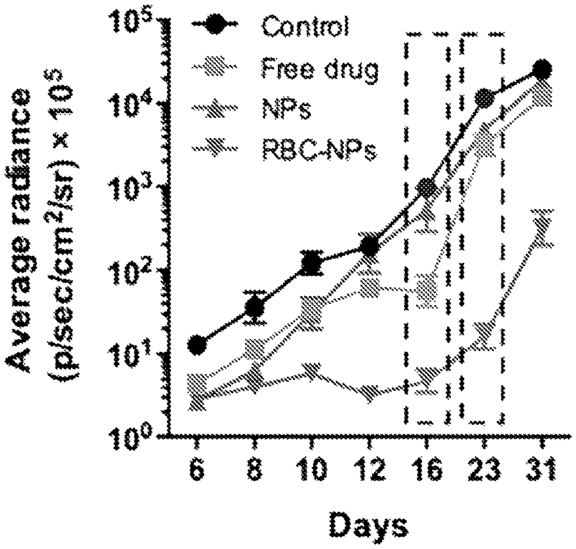
Figure 7G:
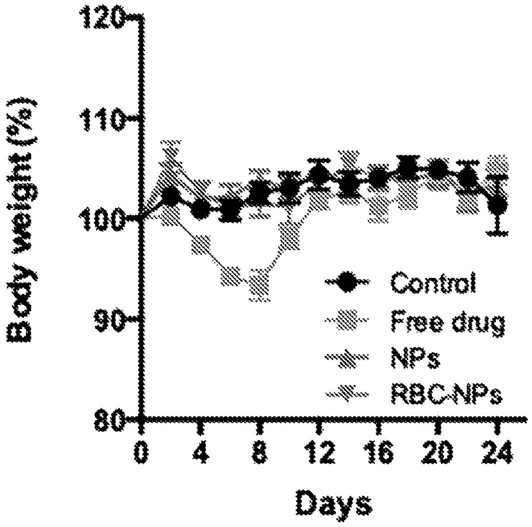
Figure 7E:
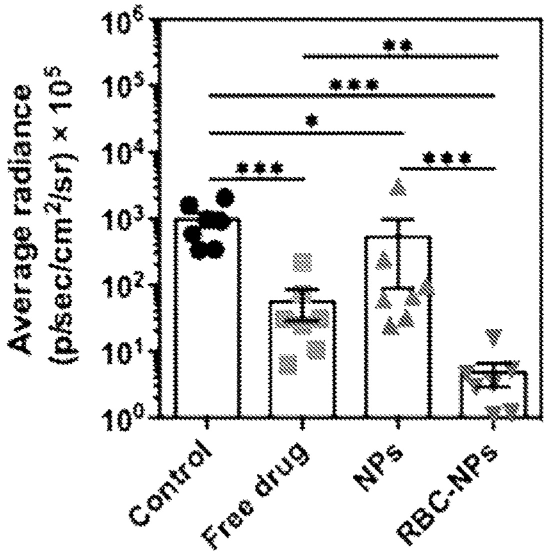
Figure 7F:
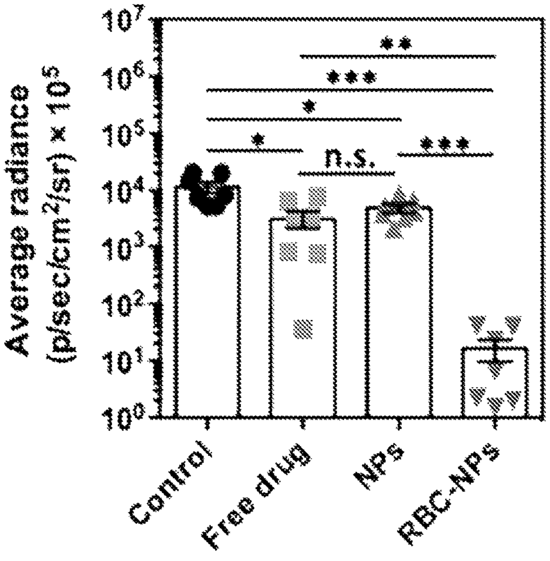
Figure 7H:
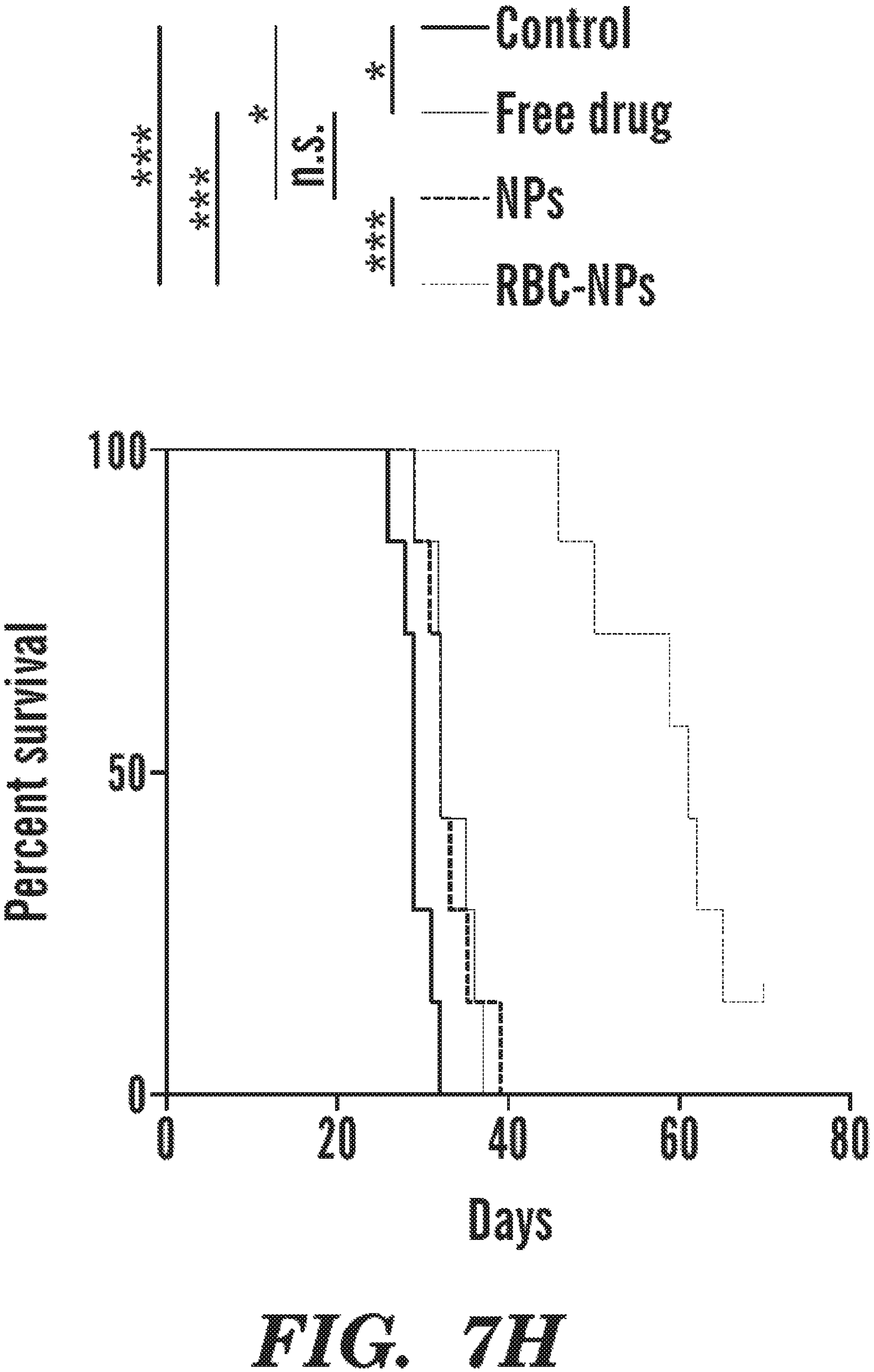

The Erythrocyte Leveraged Chemotherapy (ELeCt) platform inhibits lung metastasis progression and improves survival. To evaluate the efficacy of the biodegradable drug nanoparticle self-assembly on erythrocyte platform, a B16F10-Luc melanoma lung metastasis model was established and used to test the anti-metastatic efficacies in both the early- and the late-stage of the same model. The efficacy of the developed platform was tested in controlling early-stage lung metastasis. As shown in FIG. 7A, the lung metastasis model was established by intravenously injecting B16F10-Luc cells via the tail vein. Four doses of treatments were given every other day with the first dose being administered one day after the tumor cell injection. The lung metastasis burden was measured by the bioluminescence intensity in the lung. As indicated by the bioluminescence images (FIG. 7B) and lung metastasis burden growth curve of individual mouse (FIG. 7C), a significantly better inhibition of the lung metastasis progression was achieved by the ELeCt as compared to using the free drug or nanoparticles alone. Surprisingly, two mice remained completely free of lung metastasis after being treated with the drug nanoparticles self-assembled on erythrocytes up to day 31 post tumor inoculation. The overall lung metastasis burden was calculated based on the bioluminescence intensity in the lungs. As shown in FIG. 7D, in the first 23 days after tumor inoculation, lung metastasis was almost completely inhibited in all mice being treated with the drug nanoparticles self-assembled on erythrocytes. Particularly, as shown in FIG. 7E, on day 16, 94.2% and 45.6% of the lung metastasis burden was inhibited with the mice being treated with free drug or drug nanoparticles alone, respectively. In a sharp contrast, the ELeCt achieved a metastasis inhibition rate of 99.5%. Similar finding was also observed on day 23. As shown in FIG. 7F, compared to using the drug nanoparticles alone, the treatment using drug nanoparticles self-assembled on erythrocytes led to a 42.3% higher inhibition rate of the lung metastasis burden. The Kaplan-Meier survival analysis (FIG. 7H) further confirmed the significantly improved survival benefit of the ELeCt approach over using the nanoparticles alone. Using the free drug or nanoparticles alone only improved the survival slightly, increasing the median survival time from 29 to 32 days. In a sharp comparison, by the treatment with drug nanoparticles self-assembled on erythrocytes, the animal median survival time was extended from 29 days to 61 days. Moreover, one out of seven mice continued to survive for at least 70 days. The body weight change of mice was monitored during the entire treatment period. No significant body weight loss was detected for any of the treatments as compared to a sharp decline in the body weight during the free drug treatment (FIG. 7G), indicating that only the free drug administration caused obvious toxicity at the current drug dose.

Figure 8A:
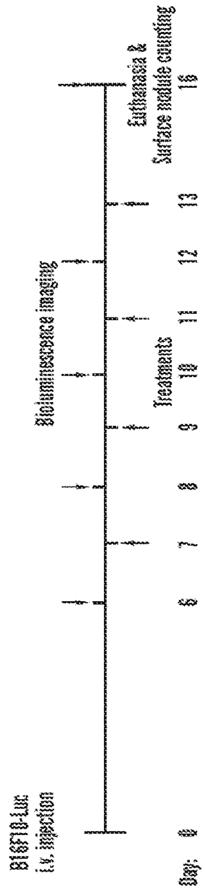
FIGS. 8A-8G demonstrate that the ELeCt platform inhibits lung metastasis progression and extends survival in the late-stage B16F10-Luc metastasis model.
Figure 8B:
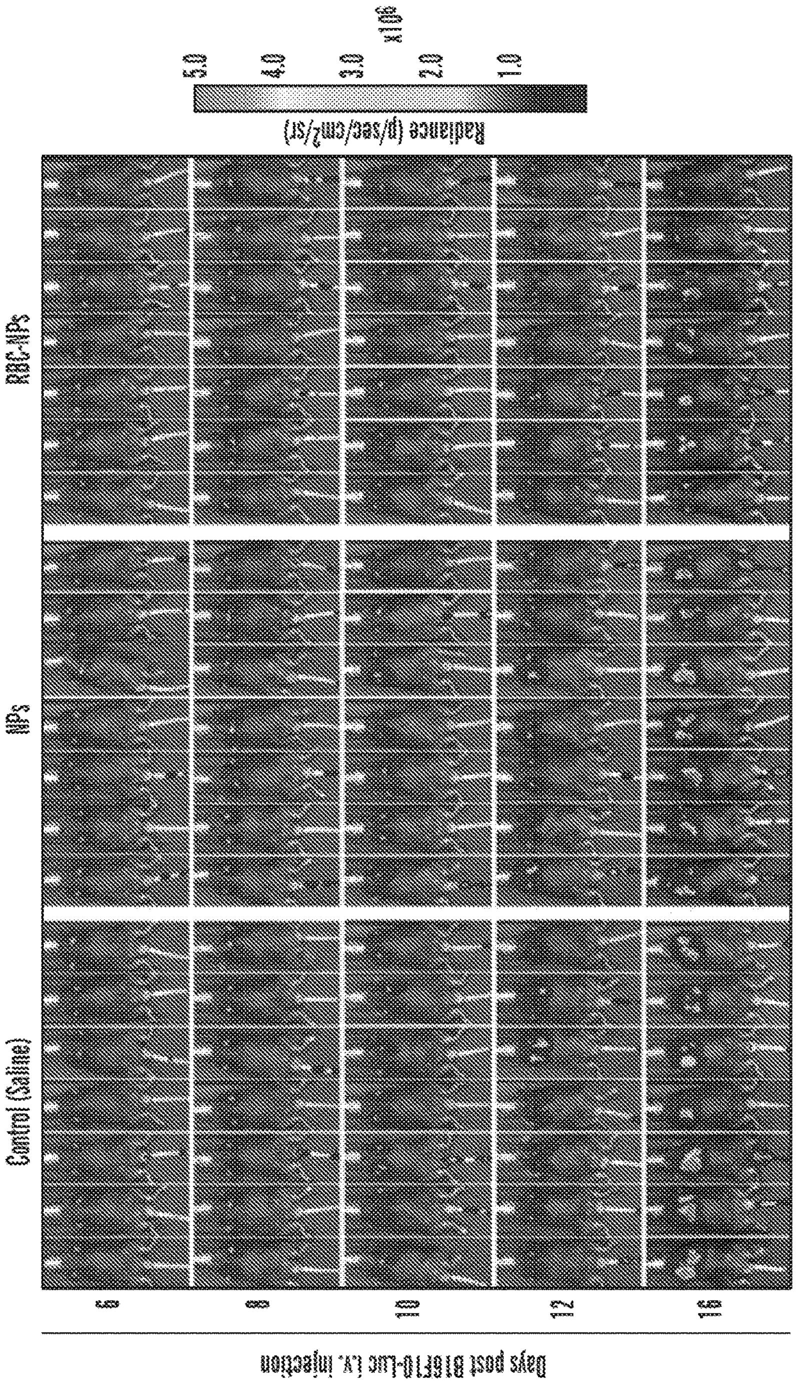
Figure 8C:
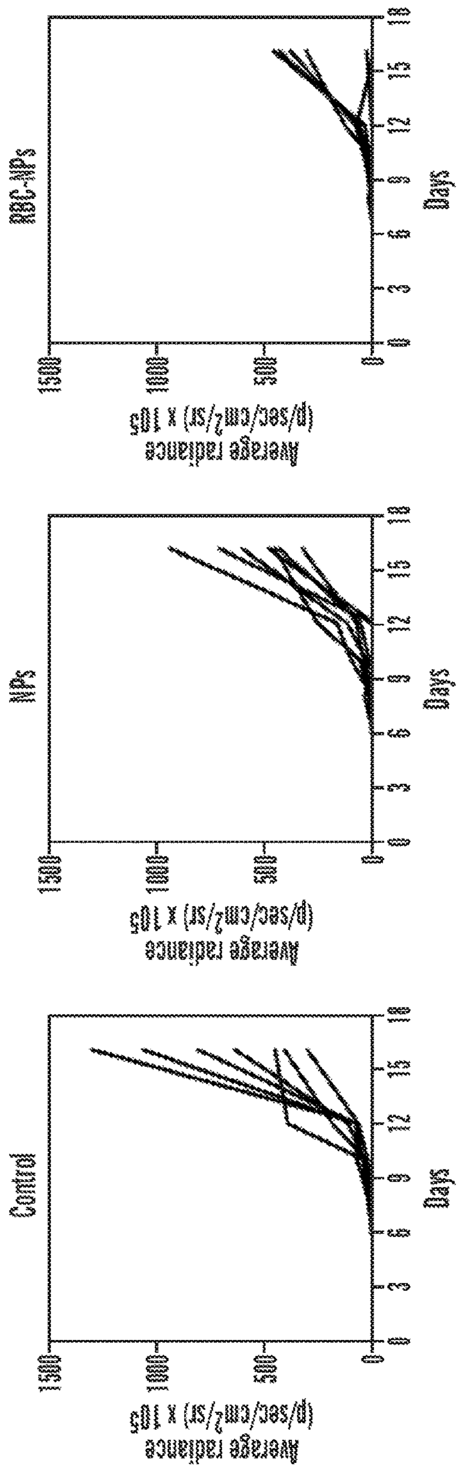
Figure 8D:
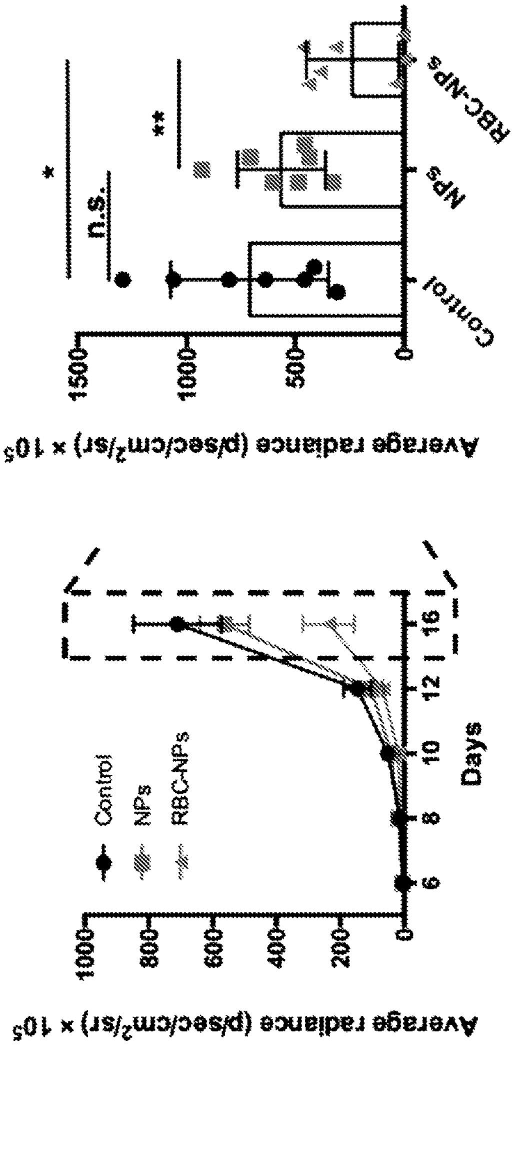
Figure 8E:
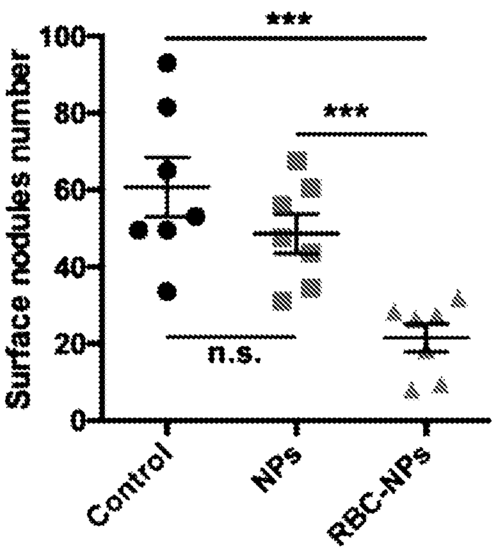
Figure 8F:
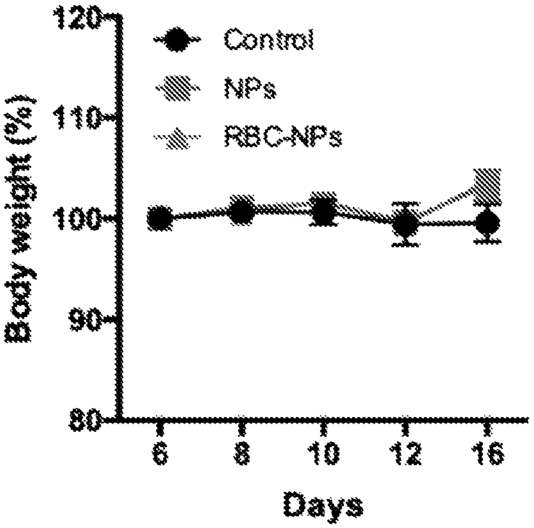
Figure 8G:
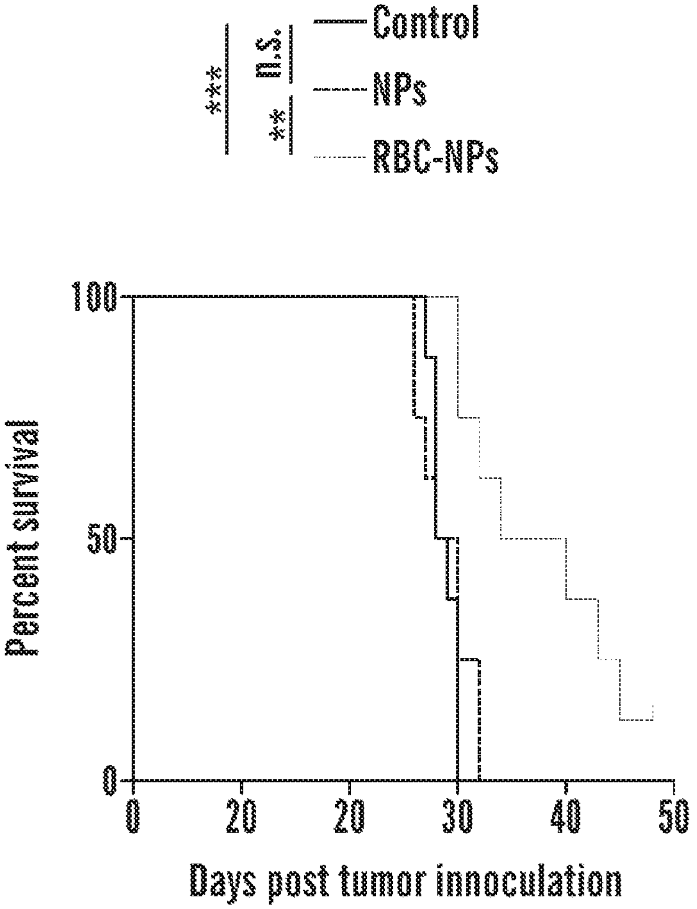
Figure 10A:
FIGS. 10A-10C depict representative H&E staining images of lungs of mice. Mice treated with (FIG. 10A) control (Saline), (FIG. 10B) DOX-loaded nanoparticles, and (FIG. 10C) drug nanoparticles self-assembled on erythrocytes (RBC-NPs) were scarified 16 days after tumor inoculation in the late-stage lung metastasis model. Lungs were processed by H&E staining.
Figure 10B:
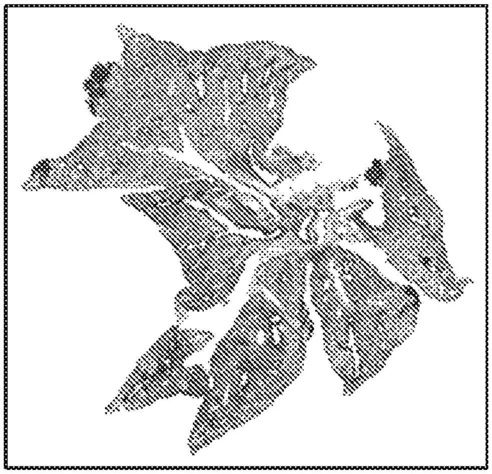
Figure 10C:
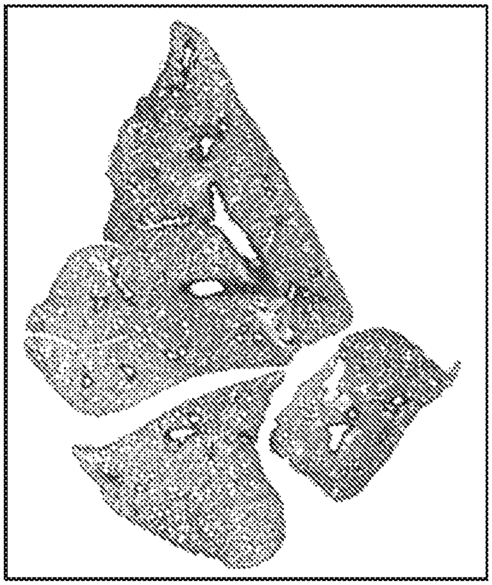
Figure 11:
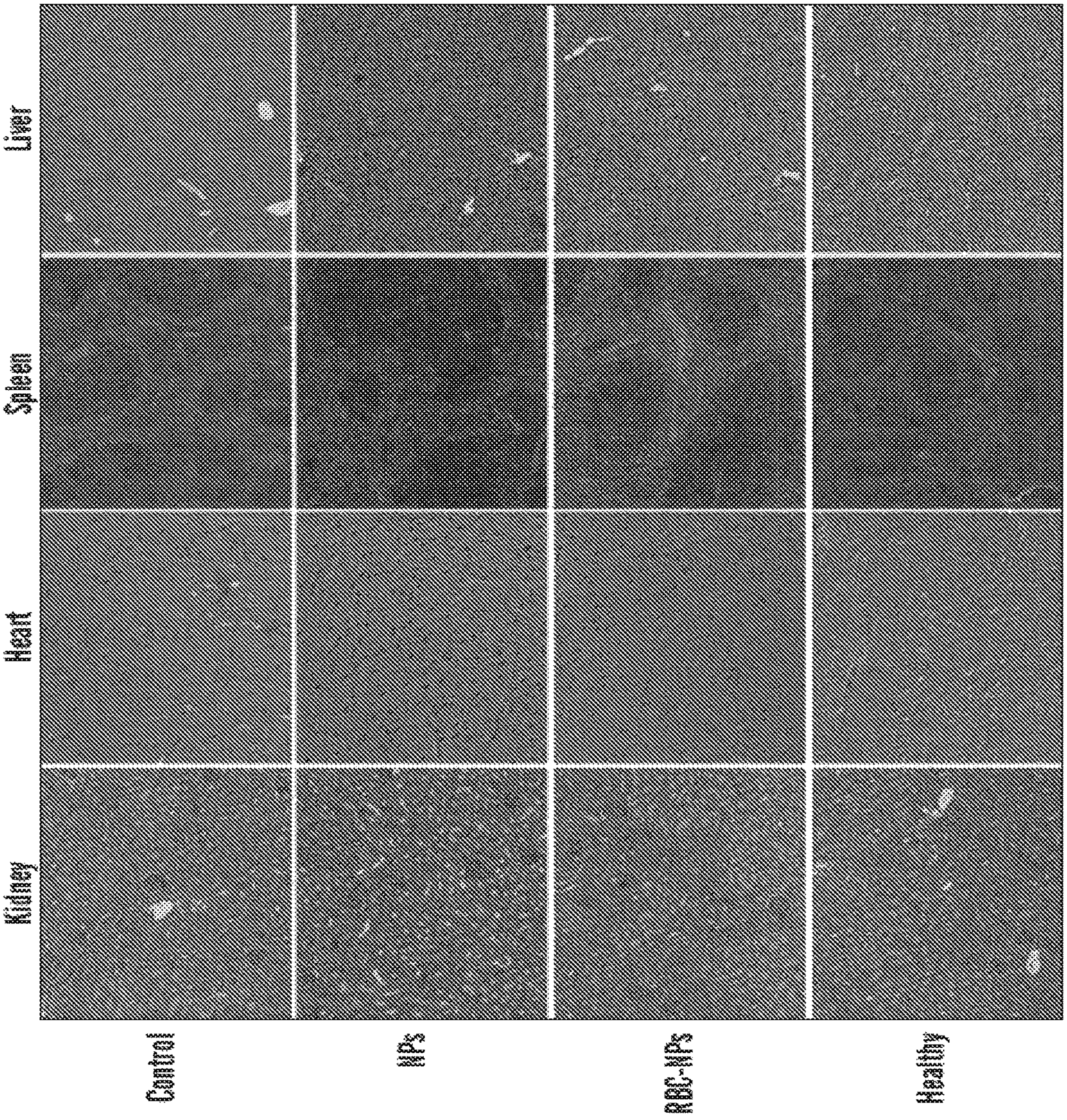

Next, the anti-metastatic activity of the developed therapies was investigated in late-stage lung metastasis. As shown in FIG. 8A, after intravenous tumor cell injection, mice were received four doses of therapies every other day with the first dose being administered a week after inoculation (day 7). According to the bioluminescence images (FIG. 8B) and lung metastasis growth curve (FIG. 8C) of individual mouse, using the drug nanoparticles alone did not lead to significant inhibition of lung metastasis progression. However, the drug nanoparticle self-assembled on erythrocyte (ELeCt) was able to slow down the lung metastasis progression, although not as strikingly as in the early-stage metastasis model. Particularly, two out of seven mice that received the treatment of drug nanoparticles self-assembled on erythrocytes remained completely free from lung metastasis up to day 16 after tumor inoculation. The overall lung metastasis burden data shown in FIG. 8D confirmed the better efficacy of the hitchhiked drug nanoparticles over using the nanoparticles alone. Especially, on day 16 after tumor inoculation, the hitchhiked drug nanoparticles exhibited a 2.4-fold better efficacy in terms of inhibiting metastasis growth. On day 16, the lungs were excised and the surface metastatic nodules on the lungs were counted. The surface nodules data shown in FIG. 8E are consistent with the bioluminescence metastasis burden data evaluated with bioluminescence. A 2.3-fold better efficacy in reducing surface nodules was achieved by self-assembling the drug nanoparticles to the erythrocytes. The H&E analysis of the lungs of mice confirmed this result (FIG. 10). In addition, the body weight change data shown in FIGS. 8F and H&E analysis data shown in FIG. 11 indicated that no significant toxicity was associated with any of the treatments. A separate study was conducted to evaluate the efficacy of the therapies in terms of extending the animal survival time. As shown in FIG. 8G, unlike in the early-stage metastasis model, the use of drug nanoparticles alone did not provide any survival benefit. However, the treatment using drug nanoparticles self-assembled on the erythrocytes (ELeCt) significantly improved the animal survival, extending the median survival time from 28.5 days to 37 days. Especially, one out of eight mice received the hitchhiked drug nanoparticles continued to survive for at least 48 days.

Figure 9:
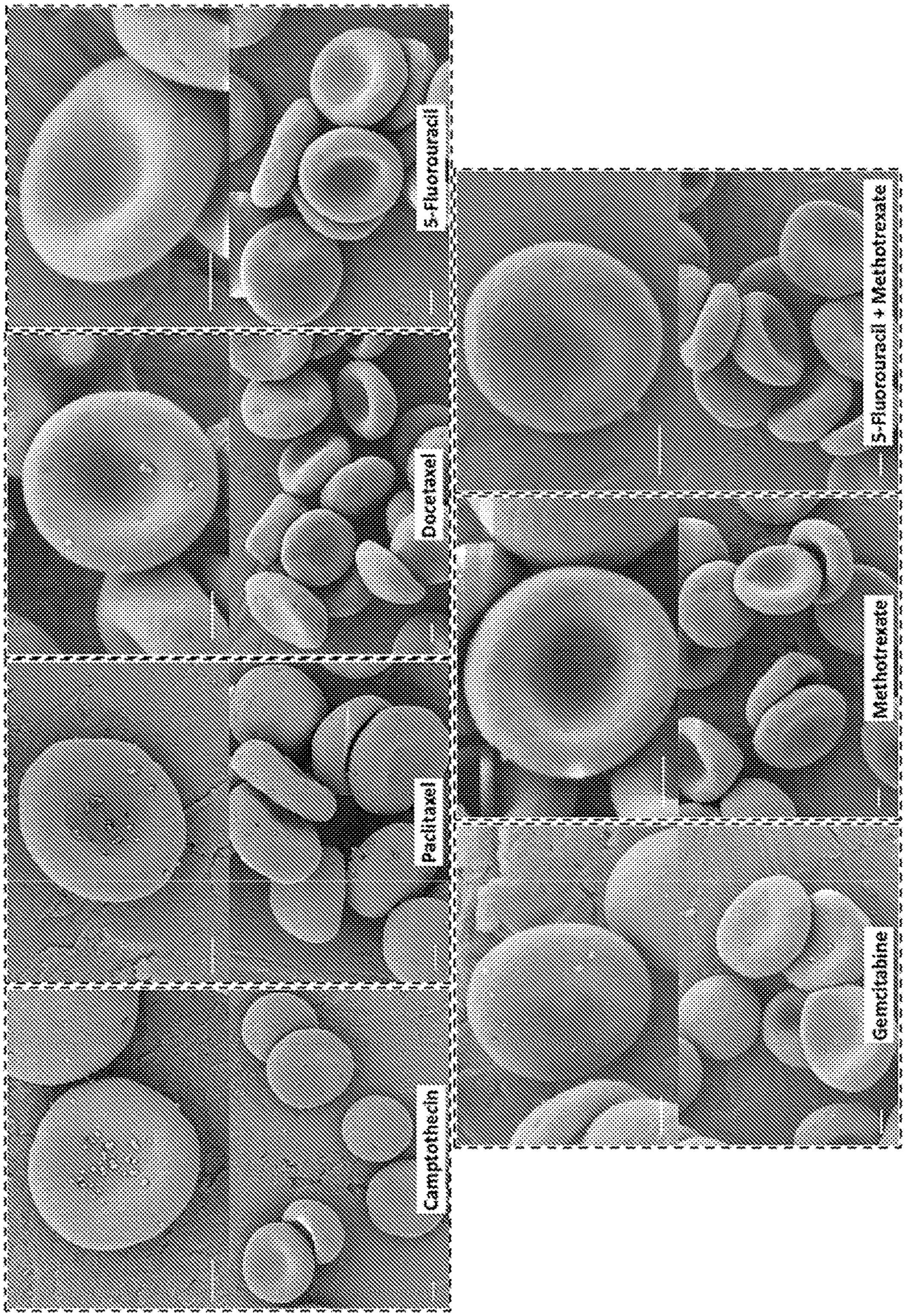
Figure 12:
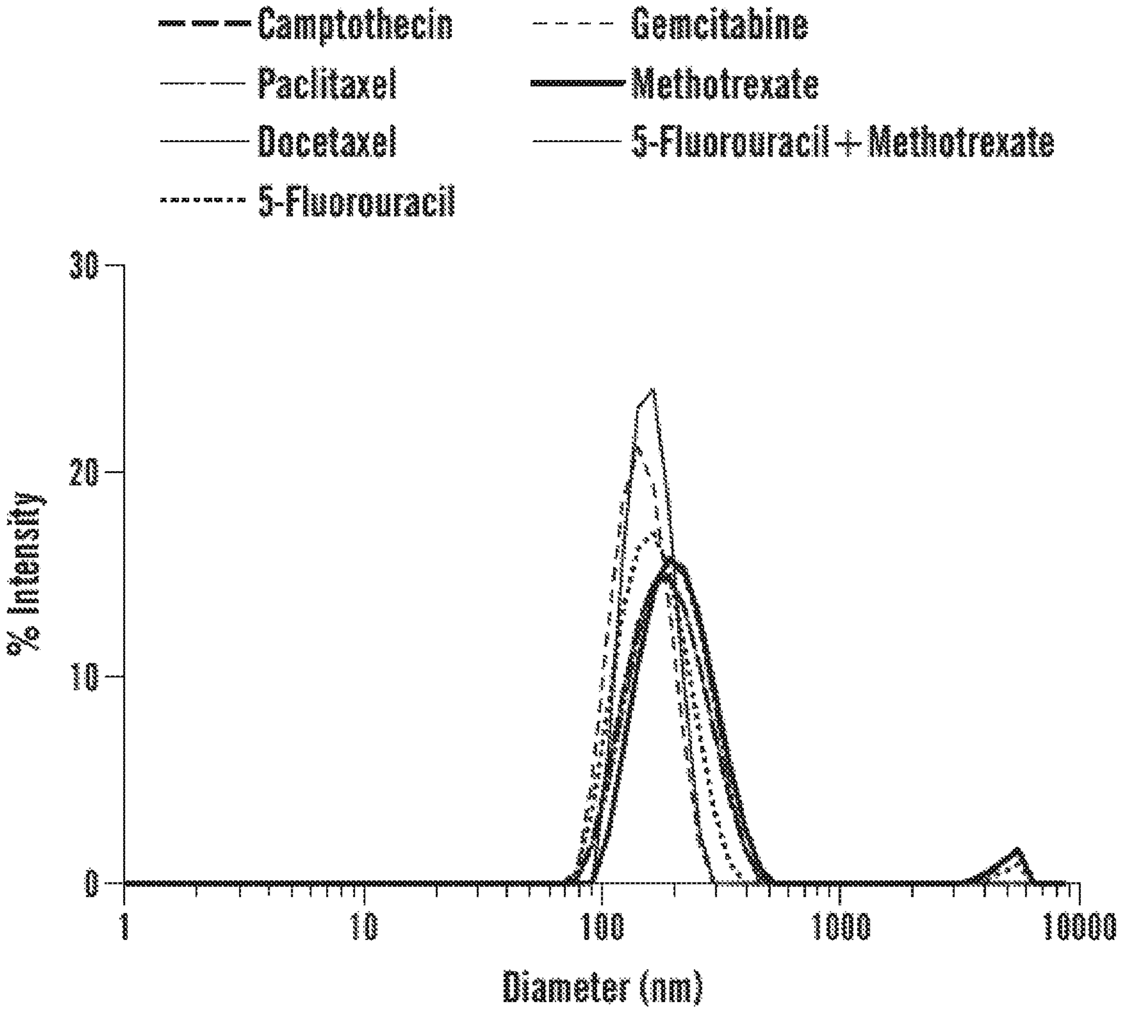

Several chemotherapeutic agent can be loaded biodegradable nanoparticles efficiently self-assembled onto the erythrocytes. To test the feasibility of using ELeCt platform for delivery of other chemotherapeutic agents, six other common chemotherapeutic agents or their combinations were selected, including camptothecin, paclitaxel, docetaxel, 5-fluorouracil, gemcitabine, methotrexate, and combination of 5-fluorouracil+methotrexate and loaded them into the biodegradable PLGA nanoparticles. In spite of possessing diverse physicochemical properties (shown in FIG. 12 and Table 2), the different chemotherapeutic agent-loaded nanoparticles were able to self-assemble to erythrocytes, though at different binding efficiency (FIG. 9). These data support that the biodegradable drug nanoparticle self-assembling to erythrocyte approach (ELeCt) is a versatile platform to deliver selected chemotherapies to lung metastasis originated from different primary tumors.

Discussion

Due to its unique physiological features like high blood throughput and high density of narrow capillaries, the lung is one of the major organs into which the evaded tumor cells from primary tumor sites can spread.[31] In fact, 30-55% of advanced cancer patients have lung metastasis.[32]Treating lung metastasis is more challenging than treating the primary tumors because it typically progresses more aggressively.[33] Systemic chemotherapy is one standard treatment option for lung metastasis. However, its efficacy is usually far from desirable, attributing to its ineffective targeting and poor accumulation in the lungs. Conventional nanoparticle mediated drug delivery also fails to achieve good localization with the desired site of action.[34] Described herein is an erythrocyte hitchhiking platform-ELeCt consisting of drug-loaded biodegradable nanoparticles self-assembled on erythrocytes for promoting chemotherapy for effective lung metastasis treatment.

Conventional nanomedicines employ the attachment of active targeting ligands to enhance the targeted delivery of chemotherapeutic payloads.[10, 11, 35-39] The ELeCt platform developed in this work exploits a completely new paradigm, taking advantage of the unique physiology of the target sites (high shear stress) and responsive dislodging of the chemotherapeutic payloads. Our pharmacokinetic and biodistribution data indicate that the ELeCt platform possesses two important features compared to the free drug and nanoparticles alone—extended blood circulation time and improved accumulation to lung metastasis. Actually, both features are favorable for lung metastasis treatment. The extended circulation time is consistent with previous reports.[27, 40] By hitchhiking to erythrocytes, nanoparticles experience less immune recognition by the reticuloendothelial system (RES) organs, enabling them to stay in circulation for a longer time.[27, 28, 40] The higher concentration of payload drug in the blood endowed by the ELeCt would allow more drug to interact with and kill the circulating tumor cells. The in vitro shear study data provided herein demonstrates that the detachment of drug nanoparticles from erythrocytes is shear-dependent, and this is the basis for employing the platform to precisely deliver payload chemotherapeutics to the target lung metastasis sites. It should be noticed that a substantial portion of the drug nanoparticles were also detached at the low shear stress. This factor emphasized the need for investigating the surface modification of the drug nanoparticles to modulate the binding strength of drug nanoparticles to erythrocytes for future explorations with this technology. Our biodistribution data indicated that the biodegradable nanoparticle self-assembly on erythrocyte (ELeCt) platform was able to deliver a high concentration of payload chemotherapeutics to the lung metastatic sites in a short period of time. Impressively, the ELeCt platform delivered 16.6-fold more drug to the lungs bearing metastasis in 20 mins compared to using the drug nanoparticles alone. In comparison, the conventional targeted nanomedicine approach using targeting ligands can rarely achieve a such high delivery enhancement.[17, 41] Moreover, it usually shows a maximum tumor accumulation at a significantly longer time point (12-24 hours), depending on the properties of the nanomedicine.[42] The quick and targeted delivery of drug nanoparticles by the ELeCt platform would bring benefits for inhibiting tumor growth. For instance, typical nanomedicines, independent of their material origins, usually have an initial burst drug release and thus cause premature drug leakage,[43] potentially attenuating the therapeutic efficacy and often leading to toxicity. The quick and targeted delivery achieved by the EleCt platform has the potential to circumvent this issue. In addition, not surprisingly, the lung section imaging indicated that the deposited nanoparticles were distributed throughout the lung sections, both the inside and the outside of the lung metastatic nodules. The nanoparticles deposited outside of the metastasis nodules have the potential to serve as a drug reservoir to release drug that can relocate to the metastatic nodules within close proximity.

Our in vivo efficacy data indicate that the enhanced and targeted delivery of chemotherapeutics by the ELeCt platform can bring benefits for inhibiting both the early-stage and the late-stage lung metastasis growth. In the early-stage lung metastasis model, the treatments using free drug or drug nanoparticles alone exhibited some slow-down of the progression of lung metastasis. However, their anti-metastatic efficacy is not potent enough to significantly extend the animal survival. In comparison, the ELeCt platform was able to provide a 100-300-fold better anti-metastatic efficacy compared to using the free drug or drug nanoparticles alone. More importantly, its improved anti-metastatic efficacy led to a significantly extended animal survival, extending the median survival time of mice bearing lung metastasis by 32 days, compared to the control group. The data indicated that the ELeCt platform has the potential to enable chemotherapy for effective treatment of early-stage lung metastasis. In the late-stage metastasis model, the administration of drug nanoparticles alone failed to significantly inhibit the lung metastasis growth and to improve the survival time. The ELeCt platform is able to significantly slow down the lung metastasis progression and modestly improved the animal survival. Evidently, the anti-metastatic efficacy of the therapies is closely related to the start-time of the therapies. The efficacy of the developed therapies to treat in an even later stage lung metastasis has not been known yet. In addition, future studies may also need to be done to unveil the effect of drug dose and schedule of the therapies on their anti-metastatic efficacy.

Based on the current understanding, hydrophobic interactions, electrostatic interactions, and hydrogen bonding may contribute to the self-assembly of drug-loaded biodegradable nanoparticles to erythrocytes[27]. Our drug nanoparticle binding data indicate that the model drug-loaded nanoparticles, in this case, doxorubicin, can self-assemble onto the mouse erythrocytes at a very high binding efficiency. This feature is critical for making the ELeCt platform work. The number of erythrocytes that can be administered has an upper limit and only having a high drug dose on individual erythrocyte can achieve the therapeutic concentration of chemotherapeutics. In addition, our data also indicate that the drug dose on erythrocytes can be tuned by changing the feed incubation ratios of drug nanoparticles to erythrocytes, thus providing the possibility of changing drug dosage according to specific lung metastasis conditions. Other than doxorubicin, different commonly-used chemotherapeutic agents or their combinations were able to be loaded to the biodegradable nanoparticles. Moreover, these drug-loaded nanoparticles self-assemble onto the mouse erythrocytes as well, though at different binding efficiencies. This opens a new window to employ the ELeCt platform to treat lung metastasis originating from different primary sites. Lung metastasis can have different primary tumor origins like breast cancer, bladder cancer, melanoma, and many others. The metastasis derived from different origins is preferably treated by specific chemotherapeutic agents.[44, 45] The ELeCt platform has the potential to be a versatile platform to treat different lung metastasis by loading optimal chemotherapeutic agents according to their primary tumor origins. More interestingly, our data also indicate that the drug-loaded biodegradable nanoparticles efficiently self-assembled onto human erythrocytes and were detached from them under lung-corresponding shear stress. In addition, the material used to prepare the biodegradable nanoparticles (PLGA) is part of several FDA approved products.[46] Therefore, this platform technology has a translational potential.

In summary, Erythrocyte Leveraged Chemotherapy (ELeCt) platform, drug-loaded biodegradable nanoparticle self-assembling on erythrocyte, was developed which enables lung physiology assisted shear-responsive targeted delivery of chemotherapeutic agents to treat lung metastasis. The drug nanoparticles self-assembled on erythrocytes can be precisely dislodged in the lungs bearing metastasis in response to the intrinsic mechanical high shear stress. Various commonly-used chemotherapeutic agents can be loaded into the biodegradable nanoparticles and further made to successfully self-assemble onto the erythrocytes. This platform successfully delivered one order of magnitude higher content of the model drug (doxorubicin) to the diseased lungs as compared to using the nanoparticles alone. Most importantly, this platform enabled chemotherapy to effectively inhibit lung metastasis growth and significantly improve the survival. All in all, the ELeCt platform can be a versatile strategy to treating lung metastasis originating from different primary tumors, with a strong translational potential.

Materials and Methods

Nanoparticle preparation and characterization. PLGA nanoparticles encapsulating doxorubicin (DOX) were prepared using a nanoprecipitation method. Briefly, 5 mg of DOX was dissolved in 500 μL of methanol and 5 μL of Triethylamine (TEA). This was added to 1 mL of acetone containing 20 mg of PLGA. The mixture was then injected into 10 mL of 1% polyvinyl alcohol (PVA) solution under constant stirring using a syringe pump at 1 mL/min. The particles were kept under constant stirring overnight before removing the organic solvents using rotary evaporation. The formed particles were centrifuged at 12000 g for 15 mins and the supernatant was analyzed for quantifying drug loading. The particles were then resuspended in deionized water and assessed for their size, zeta potential and polydispersity index using dynamic light scattering (Malvern Zen3600) and scanning electron microscopy (Zeiss FESEM Supra 55VP, Zeiss FESEM Ultra 55). The nanoparticles were washed for a total of two washes with deionized water before their final resuspension in PBS. Nanoparticles containing other chemotherapeutic drugs were prepared using the similar nanoprecipitation technique described above with minor modifications.

Blood collection and processing. Murine whole blood was collected via cardiac puncture using a heparin pre-coated syringe and stored in BD Microtainer® blood collection tubes prior to use. Whole blood was centrifuged at 1000 g for 10 mins at 4° C. to remove the serum and the buffy coat layers from the erythrocyte compartment. The isolated erythrocytes were further washed 3 times with cold PBS and centrifuged at 650 g for 15 min at 4° C. before their final resuspension at a concentration of 10% hematocrit in PBS (erythrocyte stock solution). Human whole blood obtained from BioIVT (NY, USA) was processed and stored using the same procedure as murine blood. Freshly processed erythrocytes were used for every experiment in this study.

Self-assembly of drug nanoparticles to erythrocytes and characterization. Equal volumes of erythrocyte stock solution and drug nanoparticle suspension were mixed in Axygen™ 1.5 mL Self-Standing Screw Cap Tubes and further thoroughly mixed by inversion and pipetting. The tubes were then allowed to rotate on a tube revolver (Thermo Fisher Scientific) for 40 mins. The hitchhiked erythrocytes were then pelleted by centrifugation at 100 g for 5 mins at 4° C., unabsorbed particles were carefully removed, and the pellet was washed again with 1 mL of 1×PBS to remove loosely bound particles. The hitchhiked erythrocytes were finally resuspended at 10% v/v in 1×PBS and used for further characterization or in vivo studies.

Hitchhiking efficiency and the drug loading on erythrocytes were determined using fluorescence measurements. For quantification using fluorescence, 25 μL of erythrocytes were lysed using deionized water and the drug content was quantified using DOX fluorescence (Ex/Em 470/590 nm) on a plate reader (Tecan Safire 2®, NC, USA). The percentage of erythrocytes carrying nanoparticles for different nanoparticle to erythrocyte ratios was determined using flow cytometry (BD LSR Analyser II™, CA, USA) using DOX fluorescence (Em/Ex 470/590 nm) and confirmed by confocal microscopy (Upright Zeiss LSM 710 NLO™ ready, Germany). Nanoparticle self-assembly to erythrocytes was confirmed using scanning electron microscopy (Zeiss FESEM Supra 55VP™, Zeiss FESEM Ultra 55). Briefly, the hitchhiked erythrocytes were fixed using 2.5% glutaraldehyde solution and washed in an increasing ethanol gradient before being chemically dried using hexamethyldisilazane (HMDS). Finally, the samples were sputter coated (EMT 150T ES metal sputter coater, PA, USA) prior to imaging.

In vitro serum stability and shear studies. For serum stability studies, hitchhiked murine and human erythrocytes were incubated in 1 mL of fetal bovine serum (FBS) or human serum (from BioIVT) on a tube revolver at 12 rpm at 37° C. These conditions simulate low shear physiological environment. After incubation for 20 mins, the cells were pelleted by centrifugation at 250 g for 5 mins and resuspended to 10% v/v in 1×PBS. 25 μL of erythrocytes were then lysed using deionized water and the remaining drug content was quantified using DOX fluorescence (Ex/Em 470/590 nm) on a plate reader (Tecan Safire 2®).

For shear studies, hitchhiked murine and human erythrocytes were incubated in 10 mL of FBS or human serum. A rotatory shear (6 Pa) was applied to erythrocytes in serum using a cylindrical coquette viscometer (1 mm gap, AR-G2 rheometer, TA instruments, DE, USA) for 20 mins. The samples were maintained at 37° C. during the application of shear using a water jacket. These conditions simulate lung-corresponding high shear physiological environment. After 20 mins, the cells were pelleted by centrifugation at 250 g for 10 mins and resuspended to 10% v/v in 1×PBS. 25 μL of erythrocytes were then lysed using deionized water and the remaining drug content was quantified using DOX fluorescence (Ex/Em 470/590 nm) on a plate reader (Tecan Safire 2®).

Animals. Female C57BL/6 mice (7-9 weeks of age) were purchased from Charles River Laboratories (MA, USA). All experiments were performed according to the approved protocols by the Institutional Animal Care and Use Committee (IACUC) of the Faculty of Arts and Sciences (FAS), Harvard University, Cambridge.

In vivo pharmacokinetics and biodistribution studies. For the pharmacokinetics (PK) study, healthy female C57BL/6 mice were used. Free DOX, DOX-loaded nanoparticles (NPs) and drug nanoparticles self-assembled on erythrocytes (RBC-NPs) (n=3 for all groups) were injected intravenously into the tail vein at a dose of 5.2 mg/kg. Blood samples were collected from the mice by submandibular bleed at 2 mins, 15 mins, 30 mins, 2 h, and 5 h after the injection. The plasma was separated from the cellular component by centrifuging at 5000 rpm for 10 mins. DOX was extracted from both the compartments (30 μL) using 150 μL of acetonitrile. The drug content was quantified using a reversed phase liquid chromatography-mass spectroscopy (LC-MS, Agilent 1290/6140 UHPLC, CA, USA) ran through Agilent C-18 column (Poroshell™ 120, EC-C18, 3.0×100 mm, 2.7 μm) employing a gradient mobile solvent.

For the biodistribution studies, $1\times10^5$ B16F10-Luc cells were injected intravenously into the tail vein of female C57BL/6 mice. 14 days after inoculation, mice were intravenously injected with free DOX, DOX-loaded nanoparticles (NPs) and drug nanoparticles self-assembled on erythrocytes (RBC-NPs) (n=3 for all groups) into the tail vein at a dose of 5.2 mg/kg. Mice were sacrificed at 20 mins and 6 h after the injection and organs were harvested for further processing. 1 mL of cold deionized water was added to each organ and the organs were homogenized using a high shear homogenizer (IKA T-10 Basic® Ultra turrax, NC, USA). DOX was extracted from the homogenates using acetonitrile (1:4 homogenate:acetonitrile) and the drug content was quantified using DOX fluorescence (Em/Ex 470/590 nm) on a plate reader (Tecan Safire 2®) The data is expressed as drug content (μg) normalized to the organ weight.

For nanoparticle distribution within the diseased lungs, $1\times10^5$ B16F10-Luc cells were injected intravenously into the tail vein of female C57BL/6 mice. 28 days after inoculation, mice were injected with DOX-loaded nanoparticles (NPs) and drug nanoparticles self-assembled on erythrocytes (RBC-NPs). 20 mins after the injection, the mice were euthanized, and the intact lungs were collected. Lungs were washed twice with cold 1×PBS before being fixed in a 4% paraformaldehyde solution overnight. The fixed lungs were then frozen in Tissue Tek OCT™ compound (Sakura Finetek) and sectioned using a cryostat (Leica CM1950™, IL, USA). The sectioned tissue was mounted using Fluroshield® to stain for DAPI (Ex/Em 340/488 nm) and were analyzed using confocal microscope (Upright Zeiss LSM 710 NLO™ ready).

Efficacy studies on in vivo experimental lung metastasis model. Experimental lung metastasis model was established by intravenous injection of $1\times10^5$ B16F10-Luc cells in to the tail vein of female C57BL/6 mice. Efficacy for the treatment groups was evaluated in an early stage and late stage metastatic models. Mice were randomized based on the bioluminescence intensity in the lungs one day before the first injection of therapies. A control (Saline) group and three treatment groups (DOX-NPs, RBC-NPs, free DOX) at a dose of 5.2 mg/kg were evaluated for their efficacy (n=7 for all groups, unless otherwise specified).

For the early-stage metastatic model, treatments were given starting the day after the inoculation. Four injections were given over six days, i.e. day 1, 3, 5 and 7 after inoculation. On days 6, 8, 10, 12, 18, 23, 31 after inoculation, the mice were imaged using in vivo imaging (Perkin Elmer IVIS Spectrum™, MA, USA). Briefly, mice were injected intraperitoneally with 150 μL of 30 mg/mL Xenolight™-D-luciferin in saline. 15 mins after the injection, mice were imaged using in vivo imaging. The average radiance (bioluminescence intensity) was evaluated using the software Living System®. The animals were further monitored for their survival.

For the late-stage metastatic model, treatments were given one week after the inoculation. Four injections were given over six days, i.e. day 7, 9, 11, and 13 after the inoculation. The mice were imaged on days 6, 8, 10, 12, and 16 using in vivo imaging as described above. The average radiance was evaluated using the software Living System®. On day 16, the mice were euthanized, and the lungs were excised and fixed using 10% formalin. The fixed lungs were used for counting of the surface nodules and H&E analysis. Survival in the late-stage model was evaluated by having the injection schedule as described above. (n=8 for control and the treatment groups).

Statistical analysis. All data are presented as mean±SEM. Student's t test, one-way ANOVA with Tukey's HSD analysis, or Mann-Whitney test were used to determine significance. All statistical analyses were carried out using Graphpad Prism™ 6 software. For the analysis of Kaplan-Meier survival curves, Log-rank (Mantel-Cox) analysis was used. p values represent different levels of significance; $p<0.05$*; $p<0.01$; $p<0.001$*. All the flow cytometry analyses were carried out using FlowJo™ software.

REFERENCES

[1] R. L. Siegel, K. D. Miller, A. Jemal, Cancer statistics, 2019, CA Cancer J Clin 69(1) (2019) 7-34.
[2] J. D. Emery, K. Shaw, B. Williams, D. Mazza, J. Fallon-Ferguson, M. Varlow, L. J. Trevena, The role of primary care in early detection and follow-up of cancer, Nat Rev Clin Oncol 11(1) (2014) 38-48.
[3] S. A. Eccles, D. R. Welch, Metastasis: recent discoveries and novel treatment strategies, Lancet 369(9574) (2007) 1742-57.
[4] A. C. Society, Cancer Prevention & Early Detection Facts & FIGS. 2019-2020. 2019).
[5] F. Cardoso, E. Senkus-Konefka, L. Fallowfield, A. Costa, M. Castiglione, E. G. W. Group, Locally recurrent or metastatic breast cancer: ESMO Clinical Practice Guidelines for diagnosis, treatment and follow-up, Ann Oncol 21 Suppl 5 (2010) v15-9.
[6] M. Reck, S. Popat, N. Reinmuth, D. De Ruysscher, K. M. Kerr, S. Peters, E. G. W. Group, Metastatic non-small-cell lung cancer (NSCLC): ESMO Clinical Practice Guidelines for diagnosis, treatment and follow-up, Ann Oncol 25 Suppl 3 (2014) iii27-39.
[7] G. Morgan, R. Ward, M. Barton, The contribution of cytotoxic chemotherapy to 5-year survival in adult malignancies, Clin Oncol (R Coll Radiol) 16(8) (2004) 549-60.
[8] B. A. Chabner, T. G. Roberts, Jr., Timeline: Chemotherapy and the war on cancer, Nat Rev Cancer 5(1) (2005) 65-72.
[9] A. Schroeder, D. A. Heller, M. M. Winslow, J. E. Dahlman, G. W. Pratt, R. Langer, T. Jacks, D. G. Anderson, Treating metastatic cancer with nanotechnology, Nat Rev Cancer 12(1) (2011) 39-50.
[10] D. Peer, J. M. Karp, S. Hong, O. C. FaroKHzad, R. Margalit, R. Langer, Nanocarriers as an emerging platform for cancer therapy, Nat Nanotechnol 2(12) (2007) 751-760.
[11] J. Shi, P. W. Kantoff, R. Wooster, O. C. Farokhzad, Cancer nanomedicine: progress, challenges and opportunities, Nat Rev Cancer 17(1) (2017) 20-37.
[12] Z. Zhao, A. Ukidve, V. Krishnan, S. Mitragotri, Effect of physicochemical and surface properties on in vivo fate of drug nanocarriers, Adv Drug Deliv Rev (2019).
[13] E. Blanco, H. Shen, M. Ferrari, Principles of nanoparticle design for overcoming biological barriers to drug delivery, Nat Biotechnol 33(9) (2015) 941-51.
[14] S. Mitragotri, P. A. Burke, R. Langer, Overcoming the challenges in administering biopharmaceuticals: formulation and delivery strategies, Nat Rev Drug Discov 13(9) (2014) 655-72.
[15] S. Barua, S. Mitragotri, Challenges associated with Penetration of Nanoparticles across Cell and Tissue Barriers: A Review of Current Status and Future Prospects, Nano Today 9(2) (2014) 223-243.
[16] J. W. Nichols, Y. H. Bae, Odyssey of a cancer nanoparticle: from injection site to site of action, Nano Today 7(6) (2012) 606-618.
[17] S. Wilhelm, A. J. Tavares, Q. Dai, S. Ohta, J. Audet, H. F. Dvorak, W. C. W. Chan, Analysis of nanoparticle delivery to tumours, Nat Rev Mater 1(5) (2016).
[18] Y. Zhong, F. Meng, C. Deng, Z. Zhong, Ligand-directed active tumor-targeting polymeric nanoparticles for cancer chemotherapy, Biomacromolecules 15(6) (2014) 1955-69.
[19] X. H. Peng, Y. Q. Wang, D. H. Huang, Y. X. Wang, H. J. Shin, Z. J. Chen, M. B. Spewak, H. Mao, X. Wang, Y. Wang, Z. Chen, S. M. Nie, D. M. Shin, Targeted Delivery of Cisplatin to Lung Cancer Using ScFvEGFR-Heparin-Cisplatin Nanoparticles, Acs Nano 5(12) (2011) 9480-9493.
[20] F. Pastorino, C. Brignole, D. Di Paolo, B. Nico, A. Pezzolo, D. Marimpietri, G. Pagnan, F. Piccardi, N. Cilli, R. Longhi, D. Ribatti, A. Corti, T. M. Allen, M. Ponzoni, Targeting liposomal chemotherapy via both tumor cell-specific and tumor vasculature-specific ligands potentiates therapeutic efficacy, Cancer Res 66(20) (2006) 10073-10082.
[21] J. D. Byrne, T. Betancourt, L. Brannon-Peppas, Active targeting schemes for nanoparticle systems in cancer therapeutics, Adv Drug Deliv Rev 60(15) (2008) 1615-26.
[22] R. Kanasty, J. R. Dorkin, A. Vegas, D. Anderson, Delivery materials for siRNA therapeutics, Nat Mater 12(11) (2013) 967-77.
[23] T. Lammers, W. E. Hennink, G. Storm, Tumour-targeted nanomedicines: principles and practice, Br J Cancer 99(3) (2008) 392-7.
[24] N. Bertrand, J. Wu, X. Xu, N. Kamaly, O. C. Farokhzad, Cancer nanotechnology: the impact of passive and active targeting in the era of modern cancer biology, Adv Drug Deliv Rev 66 (2014) 2-25.
[25] Y. Zou, Y. Liu, Z. Yang, D. Zhang, Y. Lu, M. Zheng, X. Xue, J. Geng, R. Chung, B. Shi, Effective and Targeted Human Orthotopic Glioblastoma Xenograft Therapy via a Multifunctional Biomimetic Nanomedicine, Adv Mater 30(51) (2018) e1803717.

[26] S. Wang, G. Yu, Z. Wang, O. Jacobson, R. Tian, L. S. Lin, F. Zhang, J. Wang, X. Chen, Hierarchical Tumor Microenvironment-Responsive Nanomedicine for Programmed Delivery of Chemotherapeutics, Adv Mater (2018) e1803926.
[27] A. C. Anselmo, V. Gupta, B. J. Zern, D. Pan, M. Zakrewsky, V. Muzykantov, S. Mitragotri, Delivering Nanoparticles to Lungs while Avoiding Liver and Spleen through Adsorption on Red Blood Cells, Acs Nano 7(12) (2013) 11129-11137.
[28] J. S. Brenner, D. C. Pan, J. W. Myerson, O. A. Marcos-Contreras, C. H. Villa, P. Patel, H. Hekierski, S. Chatterjee, J. Q. Tao, H. Parhiz, K. Bhamidipati, T. G. Uhler, E. D. Hood, R. Y. Kiseleva, V. S. Shuvaev, T. Shuvaeva, M. Khoshnejad, I. Johnston, J. V. Gregory, J. Lahann, T. Wang, E. Cantu, W. M. Armstead, S. Mitragotri, V. Muzykantov, Red blood cell-hitchhiking boosts delivery of nanocarriers to chosen organs by orders of magnitude, Nat Commun 9 (2018).
[29] Z. Zhao, S. Lou, Y. Hu, J. Zhu, C. Zhang, A Nano-in-Nano Polymer-Dendrimer Nanoparticle-Based Nanosystem for Controlled Multidrug Delivery, Mol Pharm 14(8) (2017) 2697-2710.
[30] S. Rezvantalab, N. I. Drude, M. K. Moraveji, N. Guvener, E. K. Koons, Y. Shi, T. Lammers, F. Kiessling, PLGA-Based Nanoparticles in Cancer Treatment, Front Pharmacol 9 (2018) 1260.
[31] F. van Zijl, G. Krupitza, W. Mikulits, Initial steps of metastasis: cell invasion and endothelial transmigration, Mutat Res 728(1-2) (2011) 23-34.
[32] S. D S, Secondary Lung Tumors. 2019 2019).
[33] N. K. Altorki, G. J. Markowitz, D. C. Gao, J. L. Port, A. Saxena, B. Stiles, T. McGraw, V. Mittal,
The lung microenvironment: an important regulator of tumour growth and metastasis, Nat Rev Cancer 19(1) (2019) 9-31.
[34] S. Ramalingam, C. Belani, Systemic chemotherapy for advanced non-small cell lung cancer: Recent advances and future directions, Oncologist 13 (2008) 5-13.
[35] V. P. Chauhan, R. K. Jain, Strategies for advancing cancer nanomedicine, Nat Mater 12(11) (2013) 958-962.
[36] S. A. Costa, D. Mozhdehi, M. J. Dzuricky, F. J. Isaacs, E. M. Brustad, A. Chilkoti, Active Targeting of Cancer Cells by Nanobody Decorated Polypeptide Micelle with Bio-orthogonally Conjugated Drug, Nano Lett 19(1) (2019) 247-254.
[37] S. S. He, C. Le, Q. F. Zhang, J. X. Ding, X. J. Liang, X. S. Chen, H. H. Xiao, X. Y. Chen, D. F. Zhou, Y. B. Huang, Tailoring Platinum(IV) Amphiphiles for Self-Targeting All-in-One Assemblies as Precise Multimodal Theranostic Nanomedicine, Acs Nano 12(7) (2018) 7272-7281.
[38] P. Guo, J. Yang, D. Liu, L. Huang, G. Fell, J. Huang, M. A. Moses, D. T. Auguste, Dual complementary liposomes inhibit triple-negative breast tumor progression and metastasis, Sci Adv 5(3) (2019) eaav5010.
[39] A. K. Kosmides, J. W. Sidhom, A. Fraser, C. A. Bessell, J. P. Schneck, Dual Targeting Nanoparticle Stimulates the Immune System To Inhibit Tumor Growth, Acs Nano 11(6) (2017) 5417-5429.
[40] E. Chambers, S. Mitragotri, Long circulating nanoparticles via adhesion on red blood cells: Mechanism and extended circulation, Exp Biol Med 232(7) (2007) 958-966.
[41] Q. Dai, S. Wilhelm, D. Ding, A. M. Syed, S. Sindhwani, Y. W. Zhang, Y. Y. Chen, P. MacMillan, W. C. W. Chan, Quantifying the Ligand-Coated Nanoparticle Delivery to Cancer Cells in Solid Tumors, Acs Nano 12(8) (2018) 8423-8435.
[42] D. Rosenblum, N. Joshi, W. Tao, J. M. Karp, D. Peer, Progress and challenges towards targeted delivery of cancer therapeutics, Nat Commun 9 (2018).
[43] N. Kamaly, B. Yameen, J. Wu, O. C. Farokhzad, Degradable Controlled-Release Polymers and Polymeric Nanoparticles: Mechanisms of Controlling Drug Release, Chem Rev 116(4) (2016) 2602-2663.
[44] P. S. Steeg, Targeting metastasis, Nat Rev Cancer 16(4) (2016) 201-218.
[45] Y. Gao, J. J. Xie, H. J. Chen, S. E. Gu, R. L. Zhao, J. W. Shao, L. Jia, Nanotechnology-based intelligent drug design for cancer metastasis treatment, Biotechnol Adv 32(4) (2014) 761-777.
[46] H. K. Makadia, S. J. Siegel, Poly Lactic-co-Glycolic Acid (PLGA) as Biodegradable Controlled Drug Delivery Carrier, Polymers-Basel 3(3) (2011) 1377-1397.

Materials. Poly(lactic-co-glycolic acid) (PLGA) (65:35) Resomer® 653, methotrexate, camptothecin, 5-fluorouracil, sodium heparin, Fluroshield®, DMEM, fetal bovine serum (FBS), Penicillin Streptomycin (Pen Strep) were obtained from Sigma Aldrich (MO, USA). Doxorubicin hydrochloride, docetaxel, paclitaxel and gemcitabine hydrochloride were obtained from L.C. Laboratories (MA, USA). Nunc™ Lab-Tek™ II Chamber Slide™ System, cell staining buffer, puromycin, phosphate buffered saline (1×), Axygen™ 1.5 mL Self-Standing Screw Cap tubes were obtained from Thermo Fischer Scientific (MA, USA). B16-F10 melanoma cell line (B16F10-Luc) expressing luciferase were obtained from Imanis Life Sciences (MN, USA). Human whole blood and serum was obtained from BioIVT (NY, USA). Xenolight-D-luciferin potassium salt was obtained from Perkin Elmer (MA, USA). Lithium heparin coated microtainer tubes were obtained from BD medical technology (NJ, USA). CellTiter 96® AQueous One Solution Cell Proliferation Assay (MTS) kit was obtained from Promega (CA, USA). Tissue Tek OCT compound was obtained from Sakura Finetek (CA, USA). 0.9% saline solution was obtained from Teknova (CA, USA). Paraformaldehyde was obtained from Electron Microscopy sciences (PA, USA). All other chemicals were reagent grade and obtained from Sigma Aldrich (MO, USA).

Cell culture. B16F10-Luc cells were cultured in a humidified incubator maintained at 37° C. and 5% CO2. They were cultured in DMEM media supplemented with 10% FBS, 1% Pen Strep and 1 μg/mL Puromycin. Cells were passaged 3-4 times before their use.

In vitro drug release study. DOX containing nanoparticles were resuspended in 1 mL complete medium (DMEM+10% FBS) and incubated at 37° C. on a tube revolver. At regular time points, the particles were centrifuged at 12000 g for 15 mins and the supernatant was collected for analysis. The particles were further resuspended in 1 mL of fresh release media and incubated at 37° C. until the next time point. Samples were taken at 1, 2, 4, 6, 12 and 24 h after starting the incubation. The cumulative release was quantified using DOX as fluorophore (Ex/Em 470/590 nm) on a plate reader (Tecan Safire 2®, NY, USA).

Particle internalization and cytotoxicity studies. Particle internalization was confirmed using flow cytometry and confocal microscopy. For flow cytometry analysis, 2×106 B16F10-Luc cells were plated in a 12-well plate and allowed to adhere overnight. Plates were then aspirated, and 1 mL of fresh media was added to each well. 30 μg of nanoparticles were added to each well and allowed to incubate for 20 mins, 2 h or 6 h at 37° C. in an incubator. After the stipulated time points, media in the wells was completely aspirated and washed 3 times with PBS and the cells were detached from plate using 0.25 Trypsin/EDTA solution. After being washed with PBS, these cells were analyzed by flow cytometry (BD LSR Analyser II, CA, USA) using DOX fluorophore.

For confocal microscopy, 2×105 B16F10-Luc cells were plated in individual chambers of Nunc™ Lab-Tek™ II Chamber Slide™ System (Thermo Fischer Scientific) and allowed to adhere overnight. Plates were then aspirated, and 1 mL of fresh media was added to each well. 30 μg of nanoparticles were added to each well and allowed to incubate for 20 mins, 2 h or 6 h at 37° C. in an incubator. After the stipulated time points, media in the wells was completely aspirated and cells were washed 3 times with PBS before fixing with 4% paraformaldehyde. The fixed cells were mounted using Fluroshield® to stain for DAPI (Ex/EM 340/488 nm) and were analyzed using confocal microscopy (Upright Zeiss LSM 710 NLO ready, Germany).

The cytotoxicity of loaded PLGA particles, unloaded PLGA particles and free DOX was assessed using CellTiter 96® AQueous One Solution Cell Proliferation Assay (MTS) according to manufacturer's instructions. Briefly, 2000 B16-F10-Luc cells were seeded in a 96-well plate and allowed to adhere overnight. The media was then aspirated and replaced with media containing various formulations at different concentrations and allowed to incubate for 24 h at 37° C. 20 μl of CellTiter 96® AQueous One Solution reagent was added to the wells and allowed to incubate in a humidified incubator at 37° C. for 4 h. The absorbance was read at 490 nm using a plate reader (Epoch II, Biotek systems, VT, USA). Dose response curves were fit to each formulation with the Variable slope model (Four parameter-dose response curve) using Graphpad Prism 6 and IC50 values were calculated using the same software.

Preparation of different chemotherapeutic agent-loaded biodegradable PLGA nanoparticles. All chemotherapeutic agent-loaded biodegradable PLGA nanoparticles were prepared using a nanoprecipitation method with minor modifications. To prepare nanoparticles loaded with methotrexate, 5-fluorouracil, 5-fluorouracil+methotrexate, and camptothecin, 2 mg of drug (1 mg of each for 5-fluorouracil+methotrexate) was dissolved in 200 μL of DMSO. The drug solution was then mixed with 20 mg of PLGA dissolving in 1 mL acetone. The following steps are same as in preparing DOX-loaded PLGA nanoparticles. To prepare nanoparticles loaded with docetaxel and paclitaxel, 20 mg of PLGA and 2 mg of drug was dissolved in 1 mL acetone to form the organic phase. The following steps are as in preparing DOX-loaded PLGA nanoparticles. To prepare nanoparticles loaded with gemcitabine, 2 mg of gemcitabine hydrochloride was dissolved in 0.5 mL methanol and 5 μL Triethylamine (TEA), and this drug solution was added to 20 mg of PLGA dissolved in 1 mL acetone. The following steps are same as in preparing DOX-loaded PLGA nanoparticles. All particles were collected at 12000 g for 15 mins and washed three times using deionized water. Nanoparticle size and zeta potential were measured using dynamic light scattering (Malvern Zen3600).

TABLE 2

Physicochemical properties of different chemotherapeutic agent-loaded PLGA nanoparticles

| | Average diameter (nm) | Zeta-potential (mV) | PDI |
|---|---|---|---|
| Camptothecin | 231.3 ± 6.5 | −27.9 ± 1.3 | 0.250 ± 0.038 |
| Paclitaxel | 222.0 ± 9.7 | −30.3 ± 1.4 | 0.342 ± 0.043 |
| Docetaxel | 182.2 ± 8.1 | −26.5 ± 1.2 | 0.256 ± 0.092 |
| 5-Fluorouracil | 167.7 ± 4.7 | −29.4 ± 0.5 | 0.196 ± 0.020 |
| Gemcitabine | 139.5 ± 1.8 | −28.0 ± 0.8 | 0.068 ± 0.044 |
| Methotrexate | 211.1 ± 2.5 | −21.8 ± 0.5 | 0.236 ± 0.016 |
| 5-Fluorouracil + Methotrexate | 197.7 ± 6.2 | −25.7 ± 0.3 | 0.278 ± 0.021 |

PLGA a: 50:50, ester-end, random copolymer, molecular weight—38000-54000. PLGA b: 50:50, acid-end, random copolymer, molecular weight—38000-54000. PLGA c: 85:15, ester-end, random copolymer, molecular weight—50000-75000. PLGA d: 65:35, acid-end, random copolymer, molecular weight—24000-38000.

Example 3: Erythrocyte Anchored Systemic Immunotherapy (EASY): Systemic Administration-Enabled Local Immuno-Restoration for Lung Metastasis Treatment Local immuno-restoration in tumor microenvironments is a promising strategy to employ body's own immune system to treat tumors in patients with advanced stage cancers like lung metastasis. Described herein is a new strategy, Erythrocyte Anchored Systemic Immunotherapy (EASY), that enables local immuno-restoration in the hard-to-reach metastatic sites for controlling lung metastasis progression. Briefly, ImmunoBait, nanoparticles pre-loaded with chemokine, assembled onto erythrocytes, hitch a ride, and are precisely deposited in the vicinity of metastatic sites. ImmunoBait gradually releases chemokine, modulates the local microenviroment by restoring the chemokine gradient and subsequently leads to significant enhancement in the infiltration of effector immune cells to the metastatic sites. EASY markedly inhibited the progression of lung metastasis and significantly extended the animal survival in a spontaneous breast cancer lung metastasis model. Our findings indicate that EASY is a potent strategy for local immunomodulation at the hard-to-reach lung metastatic sites to combat lung metastasis.

Immunomodulation, fine tuning of the immune system to accomplish the desired outcome, has been at the forefront of therapeutic research in recent times.[1-8] Controlling body's own immune system by manipulating the phenotype of immune cells can drastically impact the pathological outcome of disease conditions.[2, 4, 5, 9-12] To that effect, significant scientific effort has been devoted towards spatial control of immunomodulation, i.e. local alteration of immune microenvironment.[13-16] Conventionally, local immunomodulation has been a challenge, primarily due to lack of site-specific delivery of immunomodulatory agents and limited accessibility to the deeper tissues of the body.[15] Intravenous administrations do facilitate direct access to most of the tissues, but often fail at spatially restricting the immunomodulatory effect. Even with the advent of nanotechnology, targeted immunomodulation has been a challenge, owing to the mononuclear phagocytic system of the body, which often entraps nanocarriers encapsulating immunomodulatory agents, making the effects systemic rather than local.[17, 18]

Cancer immunotherapy has been a great beneficiary of immunodepletion strategies that convert the tumor microenvironment from a "cold" to a "hot" type.[11, 19-23] According to the cancer-immunity cycle described by Chen and Mellman, right from the apoptotic cancer cell death to release antigens, antigen presentation to dendritic cells, cell homing to lymph nodes, development of antigen specific responses, site-specific homing of effector immune cells to the eventual apoptotic tumor cell death caused by cytotoxic immune responses, every step is capable of being immunologically intervened to drive more potent therapeutic responses.[24] Of all these stages in the cancer-immunity cycle, site-specific homing of effector immune cells is a promising target for achieving effective anti-tumor response but has remained a great challenge.[11, 20, 22] This can be largely attributed to the tumor microenvironment endogenously depleting itself of chemoattractant biologics, chemokines, and the lack of strategies that can locally achieve immune-restoration to re-establish the chemokine gradient and thus to achieve successful homing of effector immune cells.[25, 26]

Figure 13:
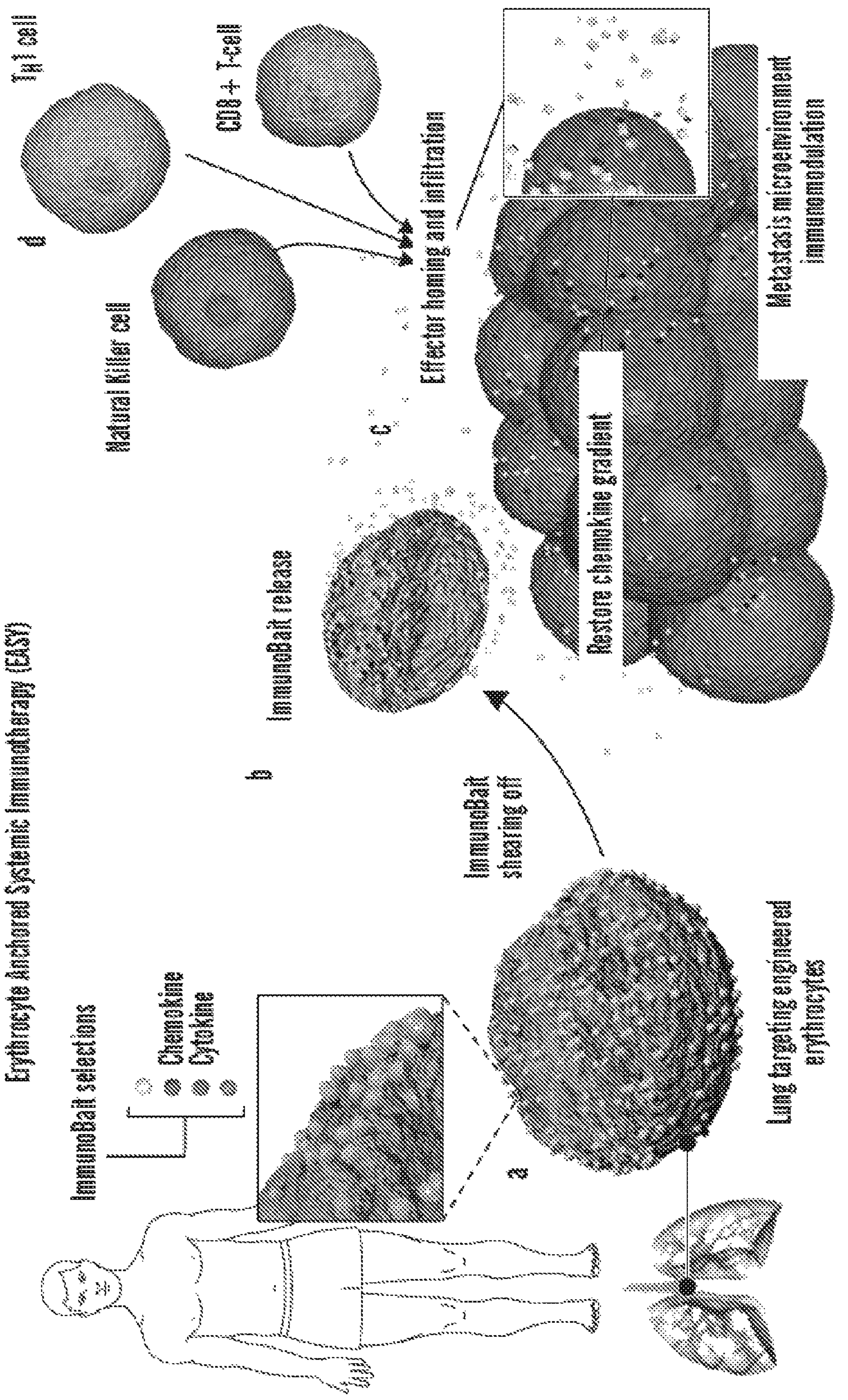

Described herein is a new approach, Erythrocyte Anchored Systemic Immunotherapy (EASY), capable of achieving local immuno-restoration post systemic administration, in advanced lung metastasis model (FIG. 13). The nanoparticles anchored on erythrocytes dislodge specifically in lungs, in a shear dependent manner and accumulate in great amounts, in otherwise hard to reach metastatic sites. A CXC type chemokine, CXCL10, capable of attracting effector immune cells, was encapsulated into PLGA nanocarriers (ImmunoBait). The site-specific delivery of ImmunoBait in the vicinity of metastatic nodules restores the local chemokine gradient and is able to attract effector immune cells to illicit cytotoxic yet local immune responses. This immune-restoration results in decrease in the number of surface metastatic nodules and improved survival in a breast cancer spontaneous lung metastasis model, highlighting the ability of EASY to achieve systemic administration enabled local modulation of the microenvironment to drive potent therapeutic responses.

Figure 14A:
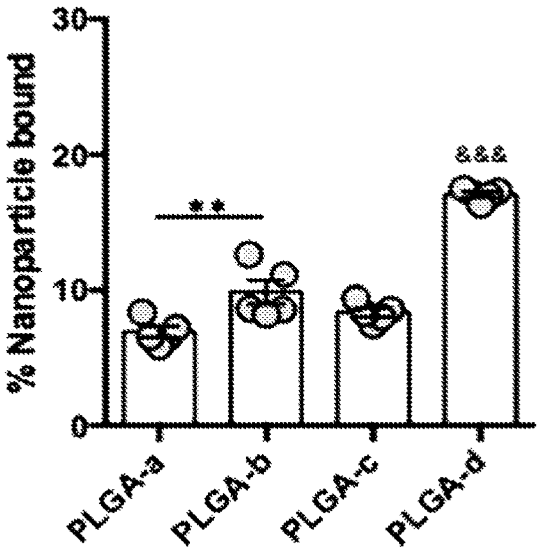
FIGS. 14A-14R demonstrate modulation of the material properties of PLGA nanoparticles led to optimal targeted delivery to the lung.
Figure 14B:
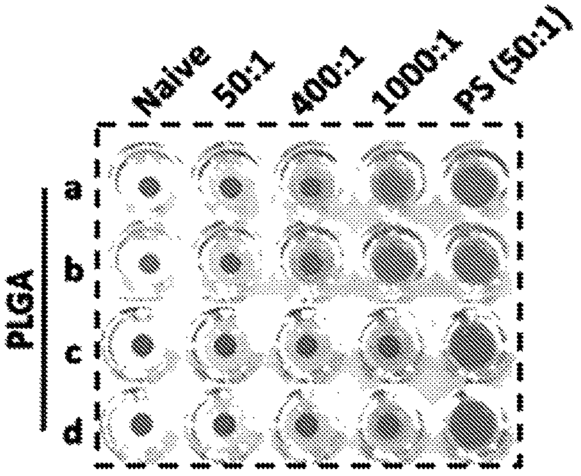
(FIG. 14B) Agglutination of the carrier erythrocytes after being hitchhiked by different PLGA nanoparticles. 200 nm polystyrene (PS) nanoparticles were used as a positive control.
Figure 14C:
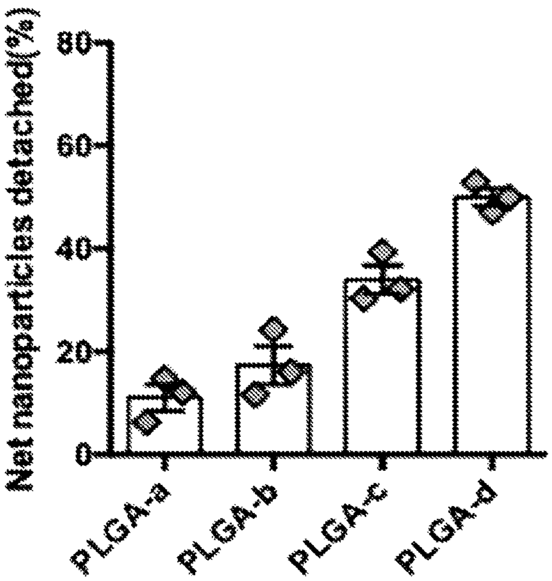
(FIG. 14C) Net percent nanoparticles detached from erythrocytes when experiencing a high rotary shear stress (6 Pa) (n=3). Nanoparticles were fluorescently labeled by encapsulating Alexa Fluor 647-ovalbumin.
Figure 14D:
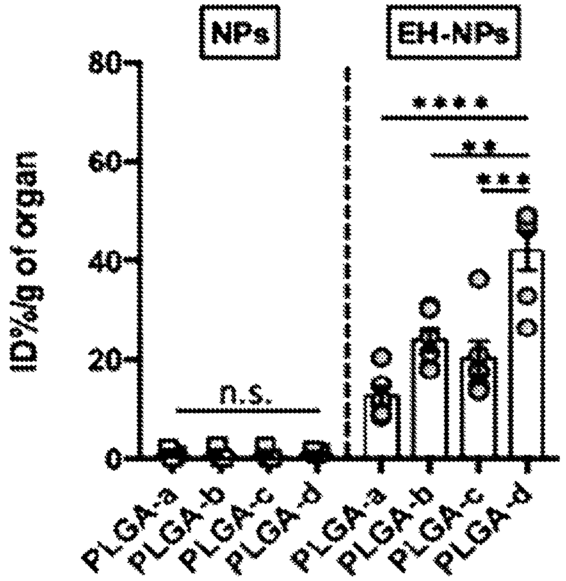
(FIG. 14D) The amount (ID %/g of organ) of different PLGA nanoparticles deposited in the lung 20 mins after being intravenously administered (n=3 for free nanoparticles, n=6 for hitchhiked nanoparticles). Significantly different (One-way ANOVA followed by Tukey's HSD test): p<0.01, *p<0.001, **p<0.0001; n.s: not significantly different.
Figure 14E:
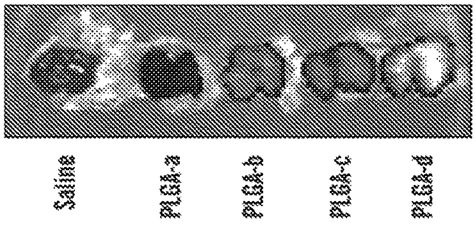
(FIG. 14E) IVIS fluorescent images of excised mouse lungs 20 min after the administration of different PLGA nanoparticles hitchhiked on erythrocytes.
Figure 19:
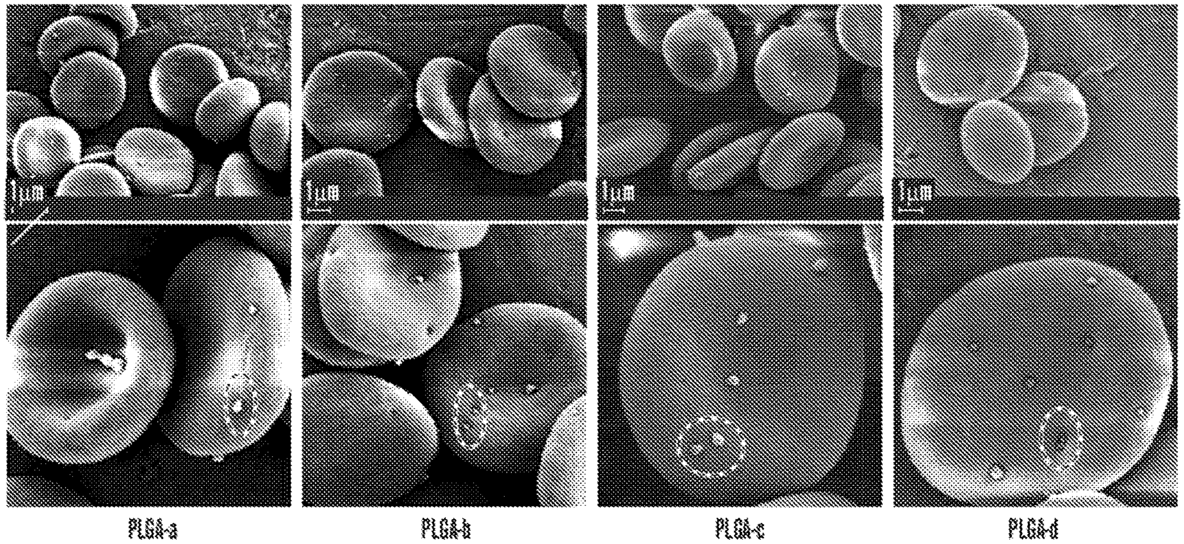
Figure 20C:
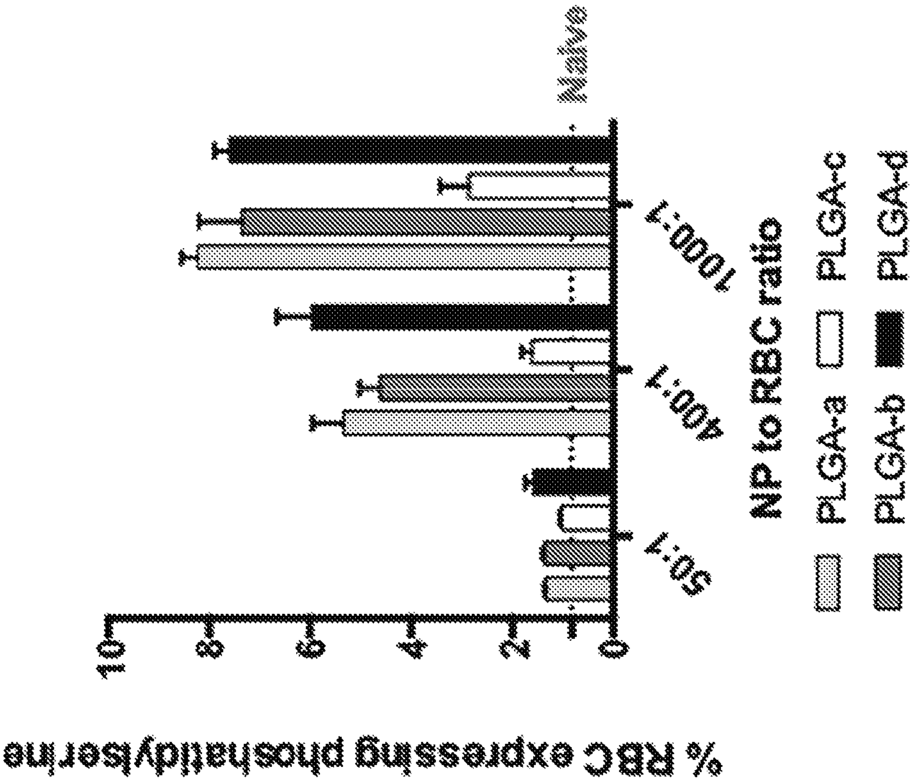
FIGS. 20A-20C demonstrate the effect of different PLGA nanoparticles on the carrier erythrocytes.
Figure 20A:
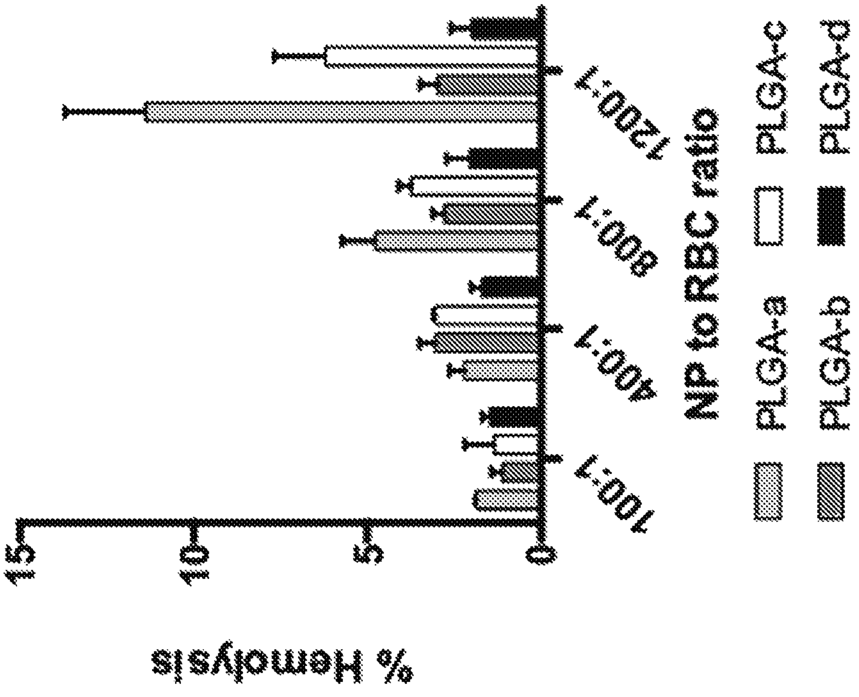
Figure 20B:
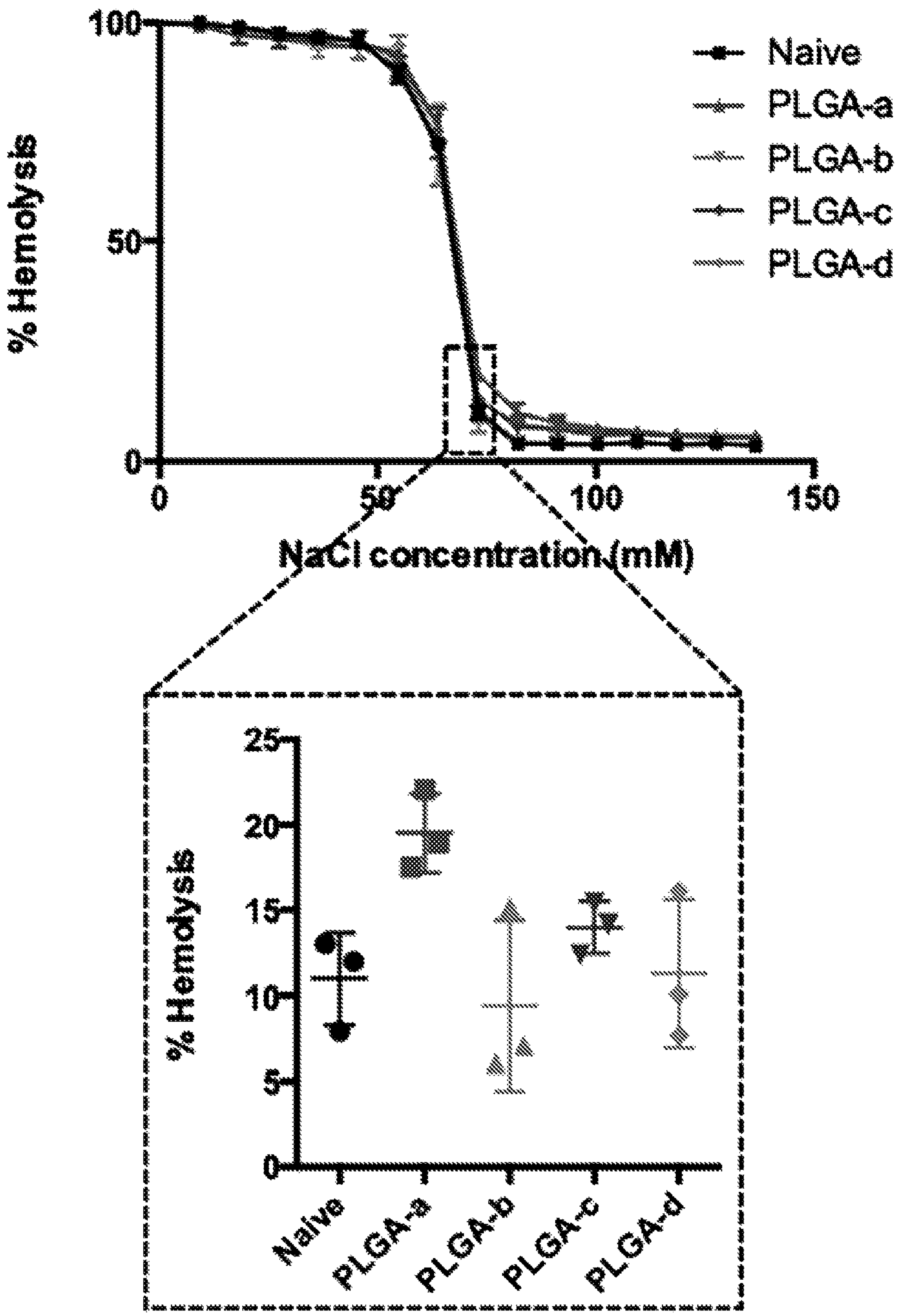
Figure 21:
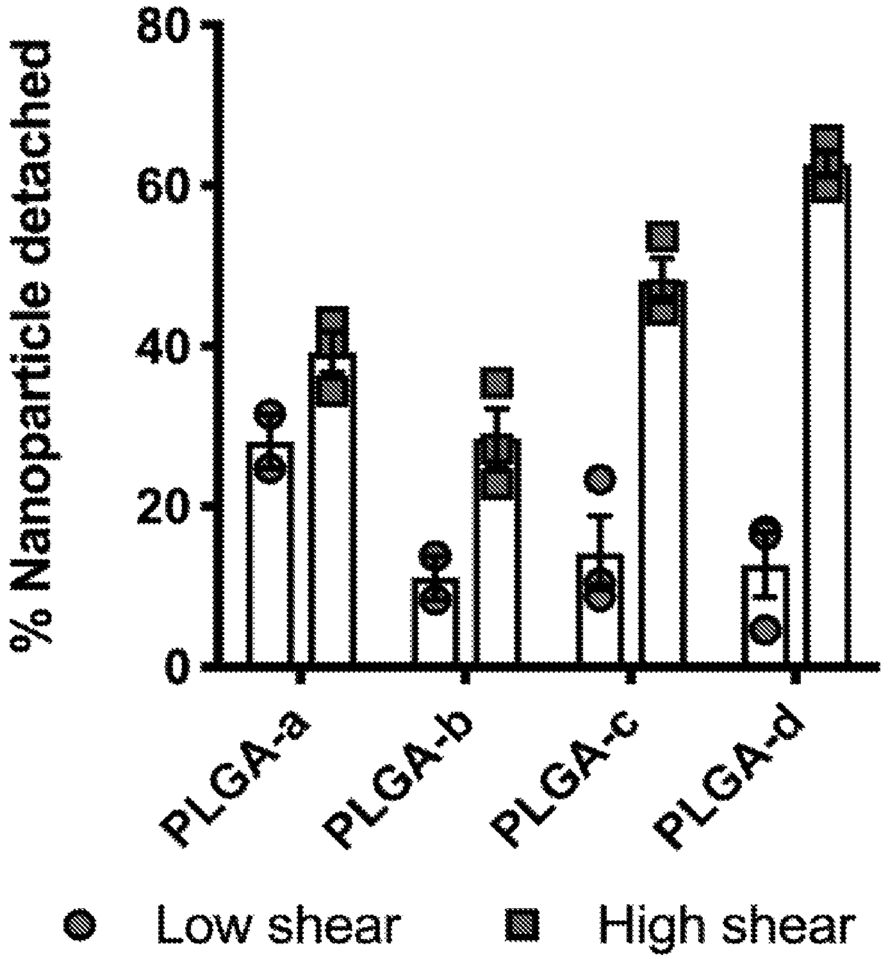
Figure 22A:
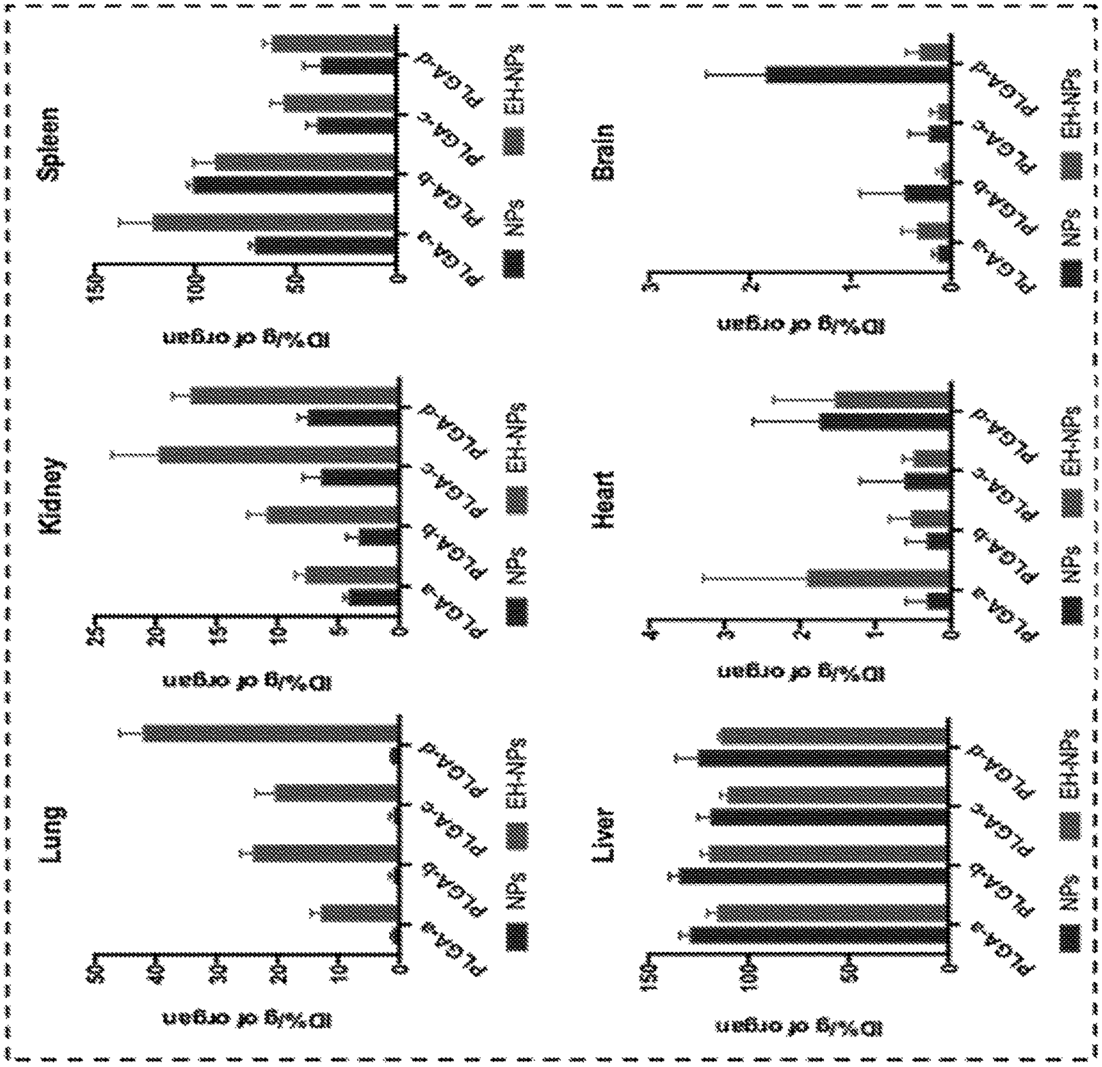
FIG. 22A-22B depict the biodistribution of PLGA nanoparticles.

Engineering of the material properties of PLGA nanoparticles for optimal lung targeting A set of experiments was conducted to achieve optimal lung targeting through material design of PLGA nanoparticles. Composition (lactic to glycolic acid ratio, L:G ratio) and surface chemistry (acid or ester end), two of the most important material properties of PLGA polymers,[27] were selected as parameters for optimization. To that effect, four different PLGA polymers (Table 4) were selected to prepare nanoparticles. Though different PLGA nanoparticles assemble onto the erythrocytes (FIG. 19), the PLGA nanoparticle with a high L:G ratio and an acid-end (PLGA-d), exhibited the highest binding efficiency to erythrocytes (FIG. 14A). The biocompatibility assays (FIG. 14B and FIG. 20A-20C) indicated that PLGA-d caused relatively minimal damage to the carrier erythrocytes compared to the other counterparts. Interestingly, according to the in vitro shear study experiments, an acid-ended polymer with a higher L:G ratio led to a higher percentage of nanoparticle detachment at a high shear stress (6 Pa) and a lower premature detachment at a low shear stress (FIG. 14C and FIG. 21). PLGA-d showed the highest detachment at the high shear stress among all the PLGA candidates. Furthermore, in vivo biodistribution data (FIG. 22A) indicated that organ-specific targeting of different PLGA nanoparticles hitchhiked onto erythrocytes correlates with the in vitro shear data. Specifically, nanoparticles having high premature detachment (PLGA-a) were targeted to low shear organs like spleen, while nanoparticles showing high net nanoparticle detachment (PLGA-c and PLGA-d) exhibited enhanced accumulation in high shear organs like lung and kidney. Especially, PLGA-d exhibited the best lung targeting ability while being assembled onto erythrocytes (FIGS. 14D and 14E). Considering its high binding efficiency, minimal damage to the carrier erythrocytes and excellent targeting to the lung, PLGA-d (65:35 L:G ratio, acid-end) was established as the lead candidate for further studies.

Figure 14F:
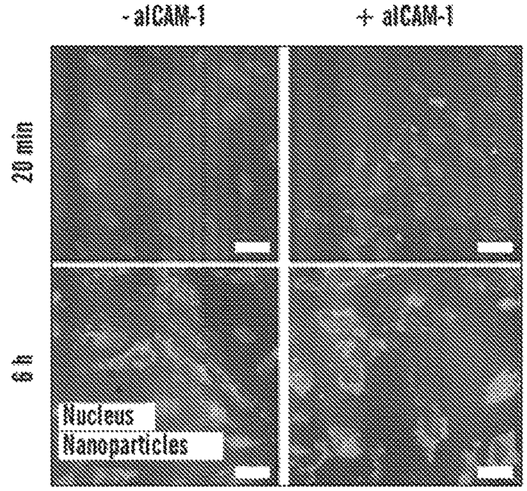
(FIG. 14F) Confocal laser scanning microscopic (CLSM) images of lung microvascular endothelial cells after being treated with PLGA-d nanoparticles with or without anti-ICAM-1 antibody for 20 min or 6 h. Nanoparticles were labeled with Alexa Fluor 647 while cell nucleus was stained by DAPI. Scale bar: 30 μm.
Figure 14G:
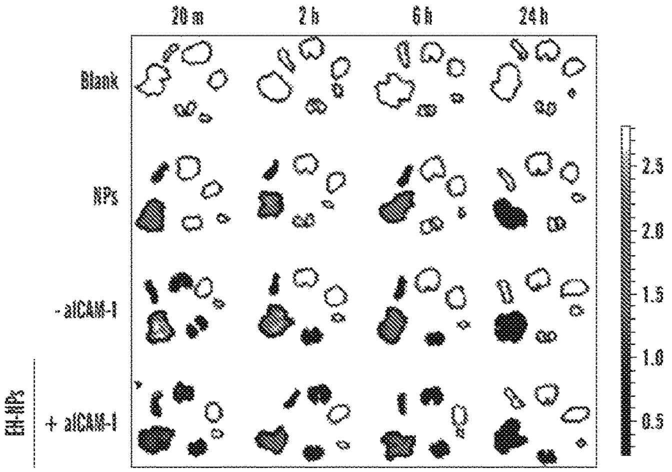
(FIG. 14G) IVIS fluorescent images of excised organs at different time points after intravenous administration of PLGA-d nanoparticle formulations.
Figure 14H:
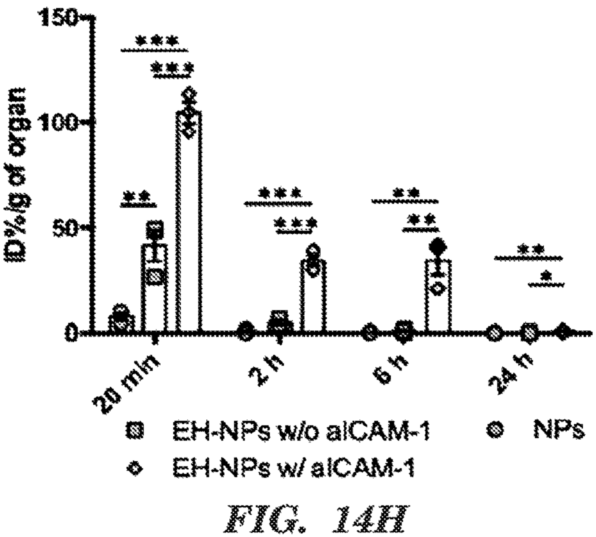
(FIG. 14H) Kinetics of the amount (ID %/g of organ) of PLGA-d nanoparticles deposited in the lung (n=3). Series are, in order, NPs, EH-NPs without aICAM-1, and EH-NPs with aICAM-1. Significantly different (One-way ANOVA followed by Tukey's HSD test): * $p<0.05$,  $p<0.01$, * $p<0.001$. In (FIGS. 14D, 14E, 14G, and 14H), nanoparticles were fluorescently labeled by encapsulating Alexa Fluor 750-ovalbumin. Data in (FIG. 14A, 14C, 14D, 14H) are presented as mean±s.e.m.
Figure 22B:
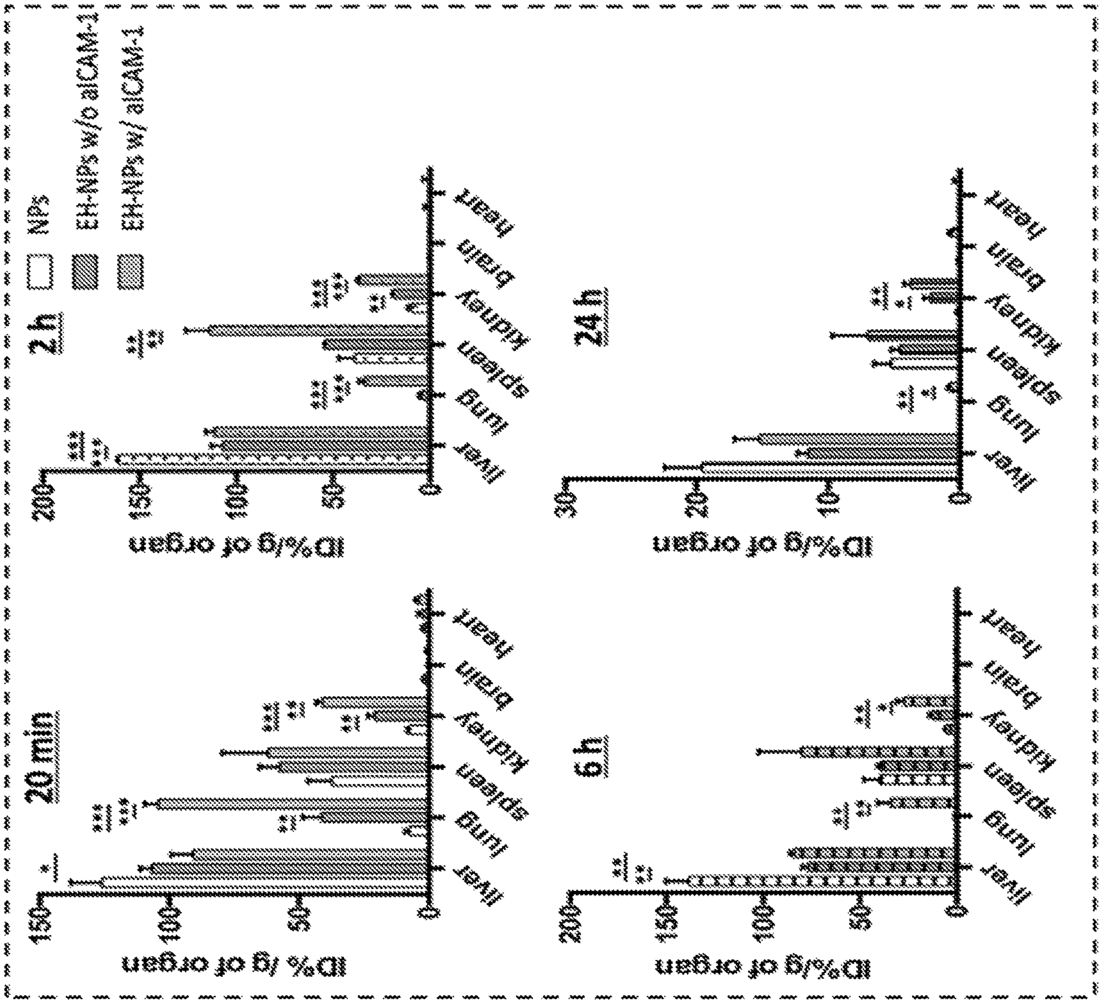

Quick, efficient interactions between nanoparticles and lung endothelium are a prerequisite for nanoparticles' long retention after being sheared off from the carrier erythrocytes. ICAM-1 has been reported to be overexpressed in the lung endothelium, especially in the diseased lungs.[28-30] Based on this, it was explored whether the attachment of anti-ICAM-1 antibody could enhance the interactions between the detached nanoparticles and the lung endothelium. In a 2-D cell culture study, the CLSM imaging data (FIG. 14F) indicated that the attachment of anti-ICAM-1 antibody to the PLGA nanoparticles led to their faster and enhanced interactions with the lung endothelial cells. Moreover, the time-course biodistribution data (FIG. 22B and FIGS. 14G-14H) revealed that, in the absence of anti-ICAM-1 antibody, erythrocyte hitchhiking delivered significantly more nanoparticles to the lung compared to the free nanoparticles alone, but the nanoparticles only stayed for up to 20 mins. In a sharp comparison, the attachment of anti-ICAM-1 antibody to nanoparticles significantly extended their retention in the lung, for at least up to 6 hours.

ImmunoBait Self-Assembly onto Erythrocytes

Figure 15A:
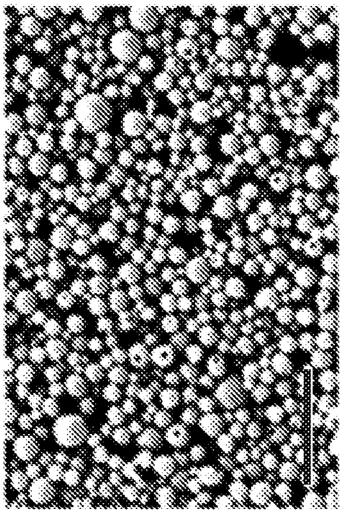
FIGS. 15A-15J demonstate that ImmunoBait assembled onto erythrocytes without causing obvious side effects to the carrier erythrocytes.
Figure 15B:
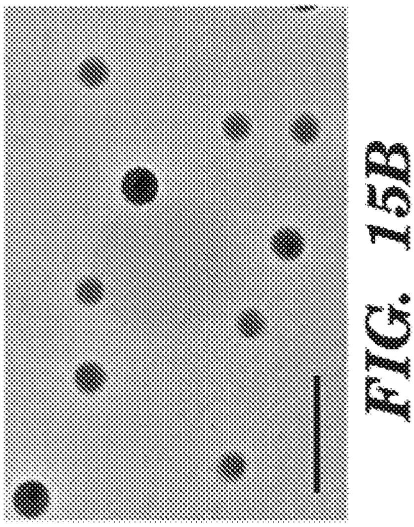
Figure 15C:
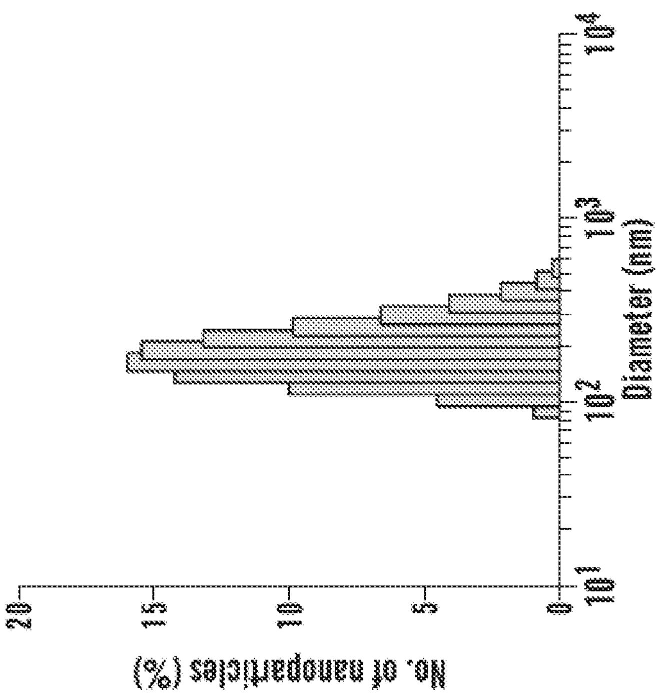
Figure 15D:
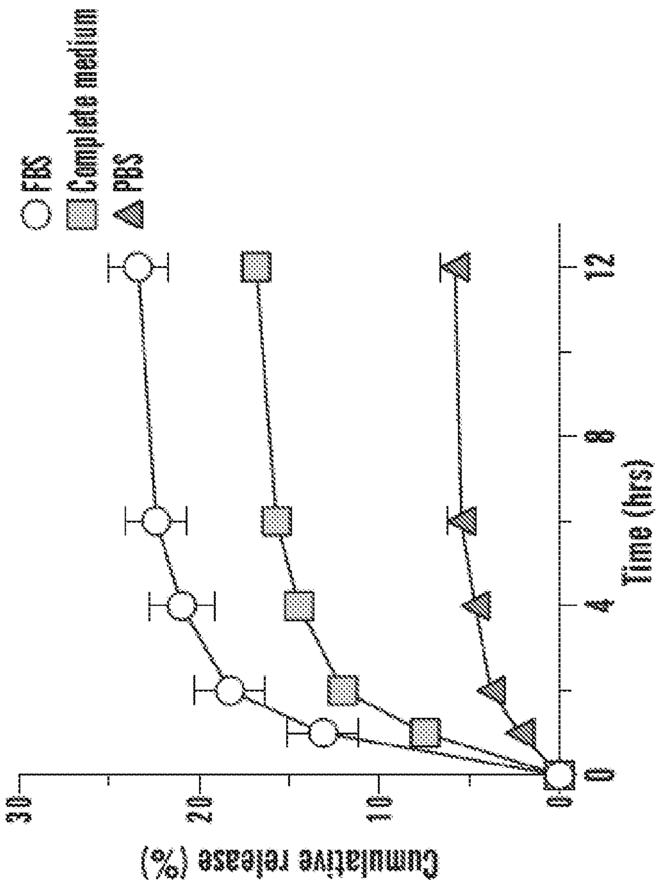
Figure 15E:
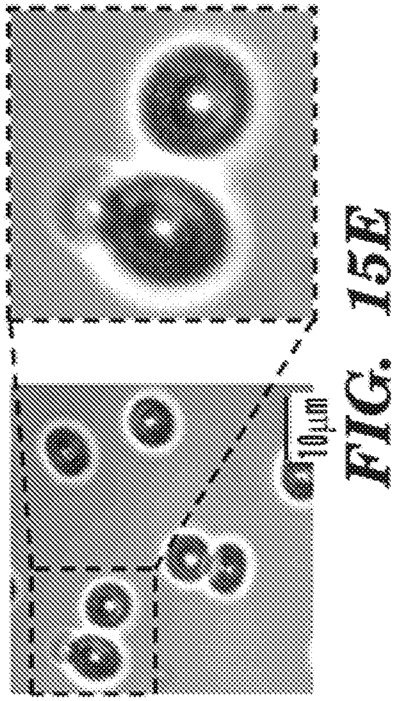
Figure 15F:
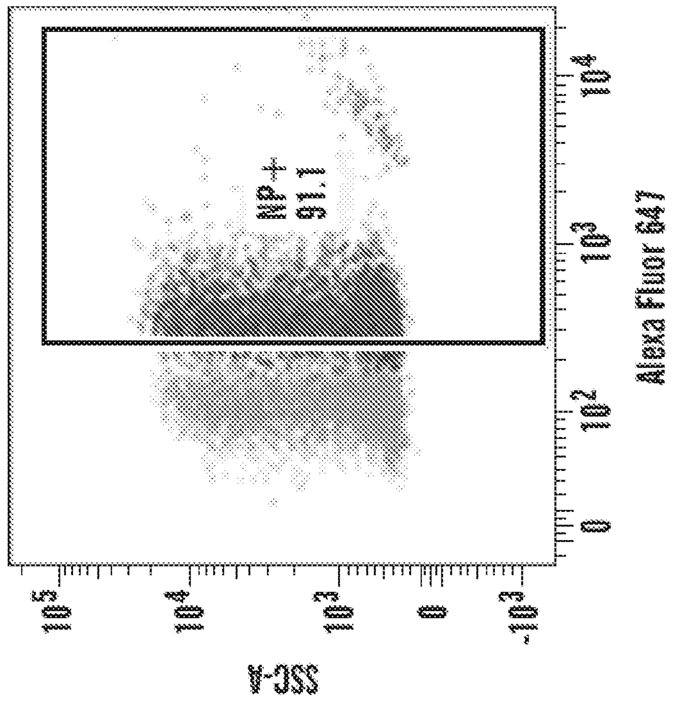
Figure 15G:
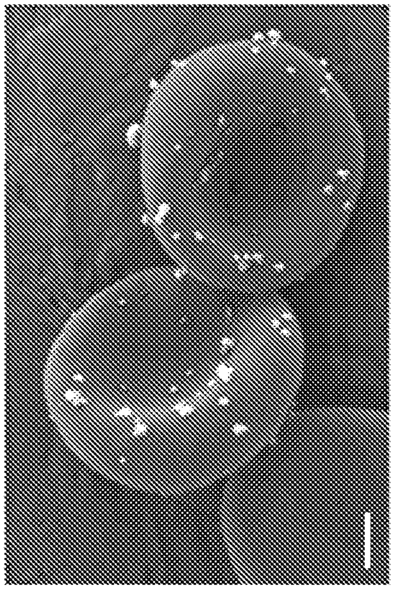
Figure 23A:
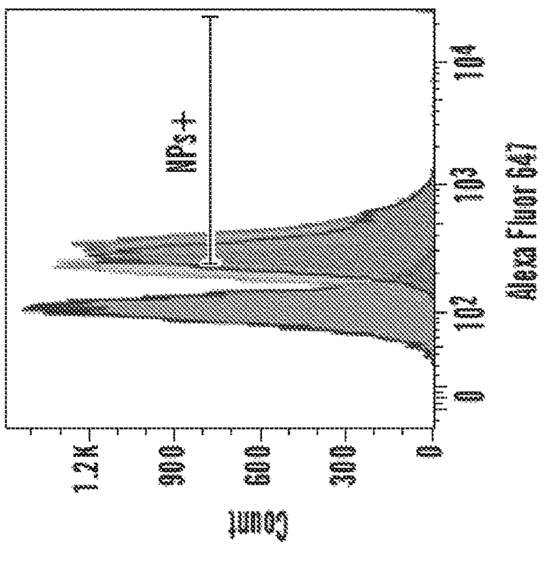
FIGS. 23A-23C depict the assembly of ImmunoBait onto the surface of mouse erythrocytes.
Figure 23B:
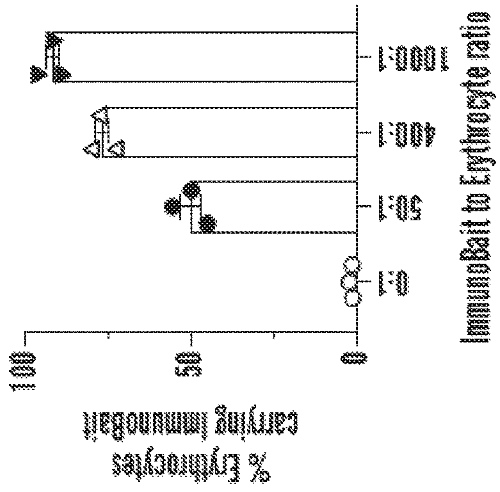
Figure 23C:
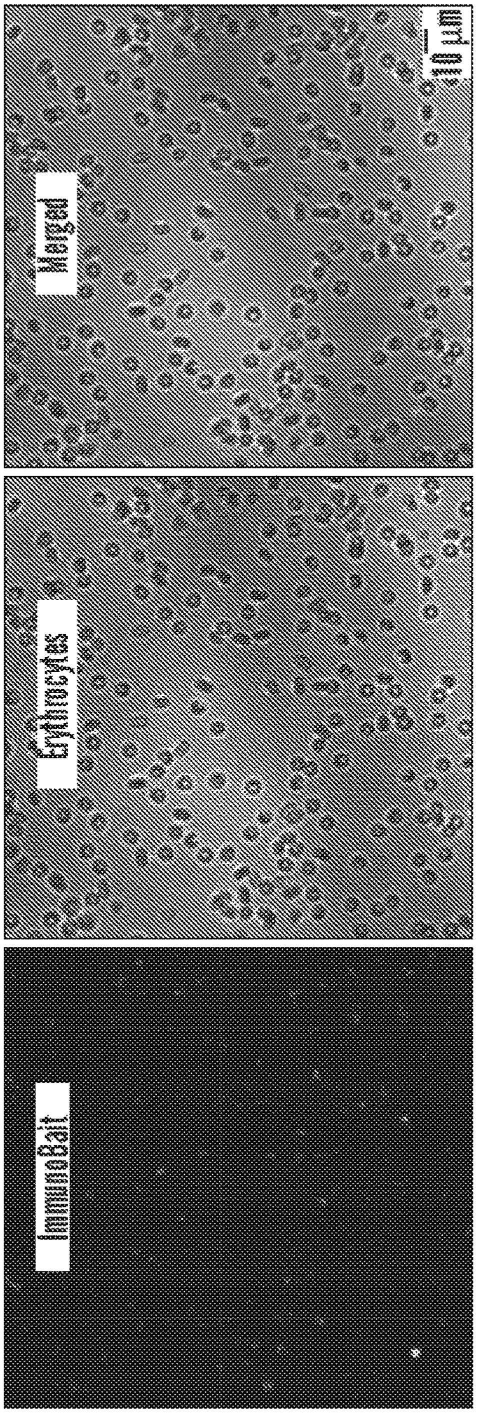
Figure 24:
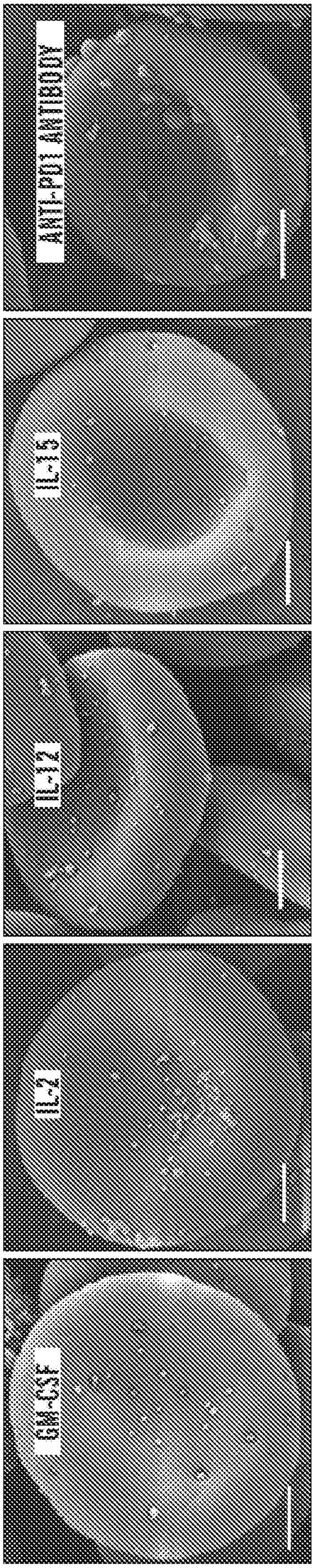
Figure 25B:
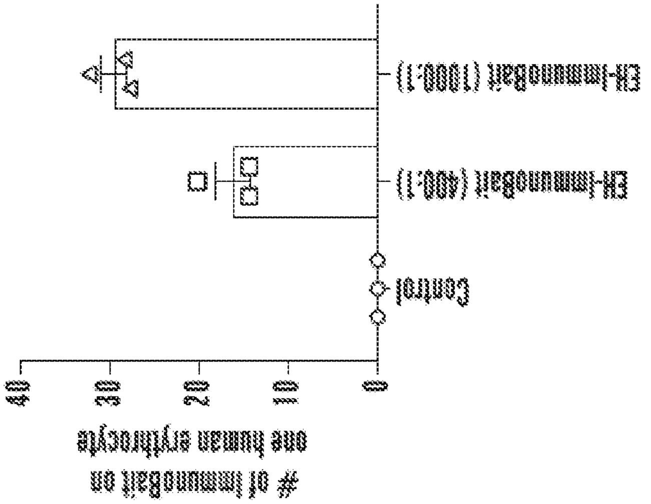
FIGS. 25A-25B demonstrate assembly of ImmunoBait to human erythrocytes.
Figure 25A:
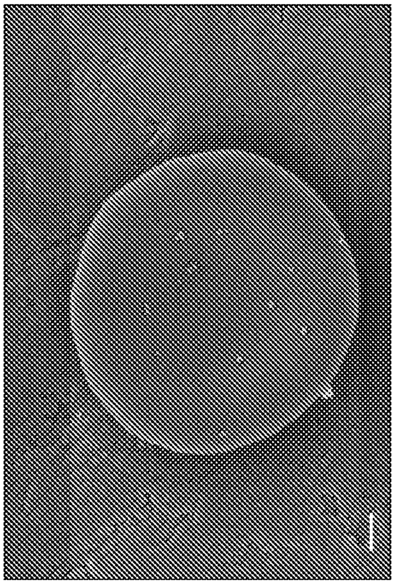

ImmunoBait, chemokine loaded PLGA nanoparticles, with a loading of 1.88 μg/mg chemokine and encapsulation efficiency of 75%, were prepared using a double-emulsion method. Monodisperse, spherical ImmunoBait nanoparticles had an average diameter of 187.3 nm and a zeta-potential of −24.5 mV. (FIG. 15A-15C). Release of chemokine from ImmunoBait in PBS, FBS, and complete medium, which stimulates the in vitro hitchhiking condition, serum environment, and local tissue environment, respectively, exhibited a burst followed sustained release pattern, with most of the releasable payloads being released within 6 hours (FIG. 15D). In addition, chemokine was released much slower in PBS than in FBS and complete medium, which is beneficial for minimizing the chemokine loss during the hitchhiking process. To test whether ImmunoBait can efficiently assemble onto the erythrocytes, chemokine was labeled with a fluorescent probe, Alexa Fluor 647. The CLSM data shown in FIG. 15E indicated efficient assembly of ImmunoBait nanoparticles onto mouse erythrocytes. By increasing the ratio of ImmunoBait nanoparticles to mouse erythrocytes, the percentage of mouse erythrocytes carrying ImmunoBait nanoparticles increased significantly (FIG. 23A-23C). Particularly, >90% of the mouse erythrocytes carried ImmunoBait nanoparticles at an ImmunoBait to erythrocyte ratio of 1000:1 (FIG. 15F). The SEM imaging data confirmed the efficient assembly of ImmunoBait nanoparticles onto mouse erythrocytes (FIG. 15G). Apart from CXCL10, ImmunoBait carrying other chemokine (GM-CSF), cytokines (IL-2, IL-12, and IL-15), and immune checkpoint inhibitor (anti-PD-1 antibody) were also efficiently bound to mouse erythrocytes (FIG. 24). Furthermore, ImmunoBait nanoparticles also assemble onto human erythrocytes, though at a lower binding efficiency (FIG. 25A-25B).

Figure 15I:
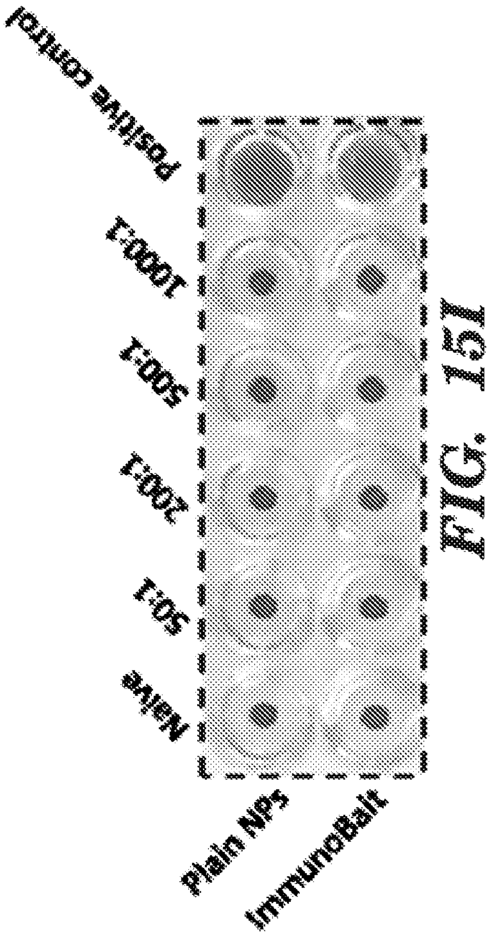
Figure 15J:
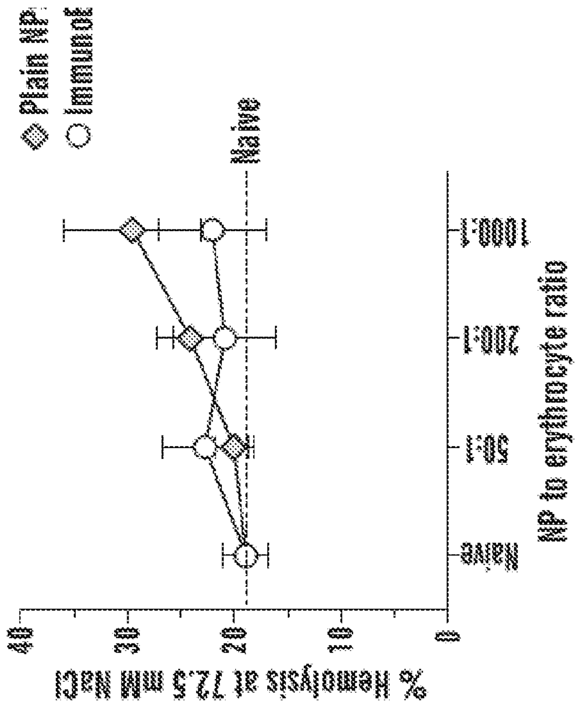
Figure 15H:
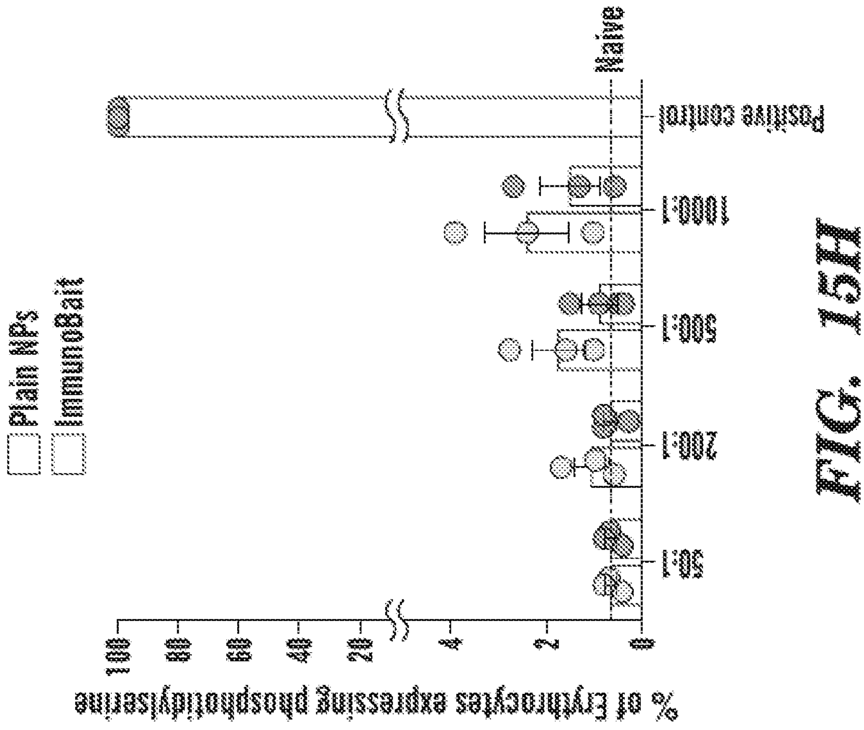
Figure 26:
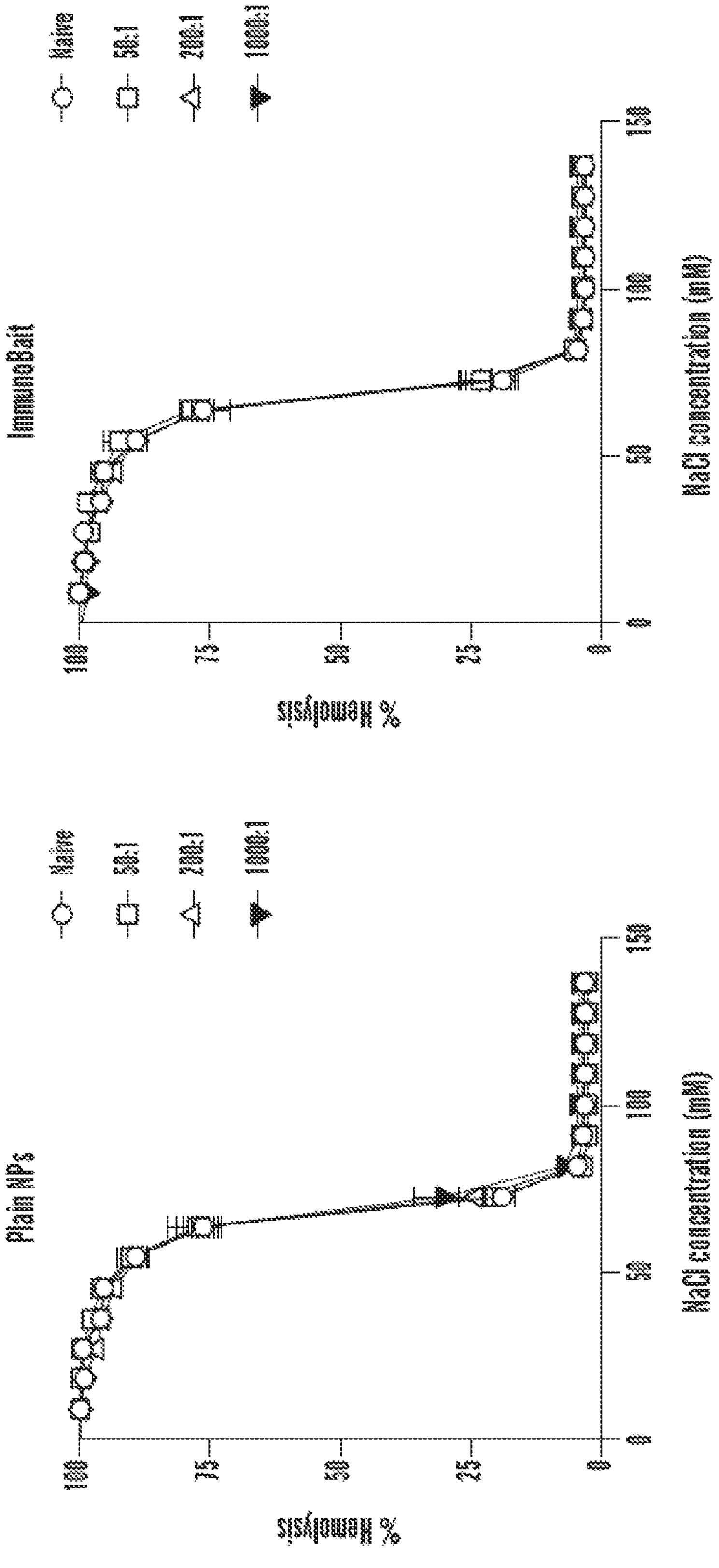

Next, a set of assays was performed to detect, if any, adverse effects caused to the carrier erythrocytes by the hitchhiking of ImmunoBait nanoparticles. Surface expression of phosphatidylserine marks erythrocytes as senescent or damaged and accelerates their in vivo clearance.[31, 32] As shown in FIG. 15H, hitchhiking of ImmunoBait nanoparticles at all tested ratios did not cause obvious overexpression of surface phosphatidylserine on the carrier erythrocytes. In addition, the data from the agglutination assay[33] (FIG. 15I) and osmotic fragility assay[34] (FIG. 26 and FIG. 15J) revealed that hitchhiking of ImmunoBait nanoparticles resulted in insignificant changes to the agglutination and sensitivity to osmotic stress of the carrier erythrocytes. These biocompatibility studies indicated that the assembly of ImmunoBait nanoparticles onto erythrocytes caused minimal damage to the carrier erythrocytes.

Targeted Delivery of ImmunoBait into to the Lung Metastatic Sites Using EASY

Figure 16A:
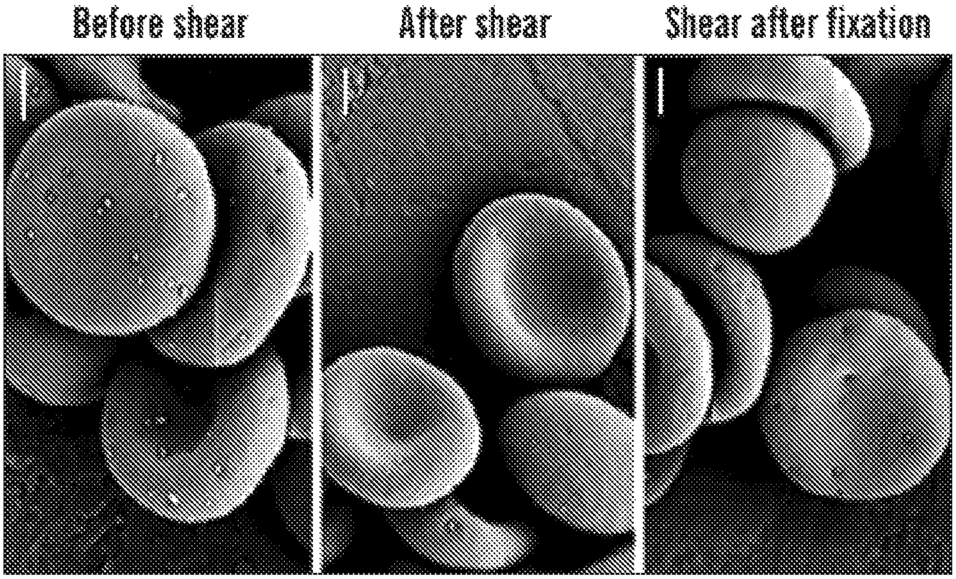
FIGS. 16A-16M demonstrate that EASY precisely delivered ImmunoBait to the lungs bearing metastasis and achieved immuno-restoration.
Figure 16B:
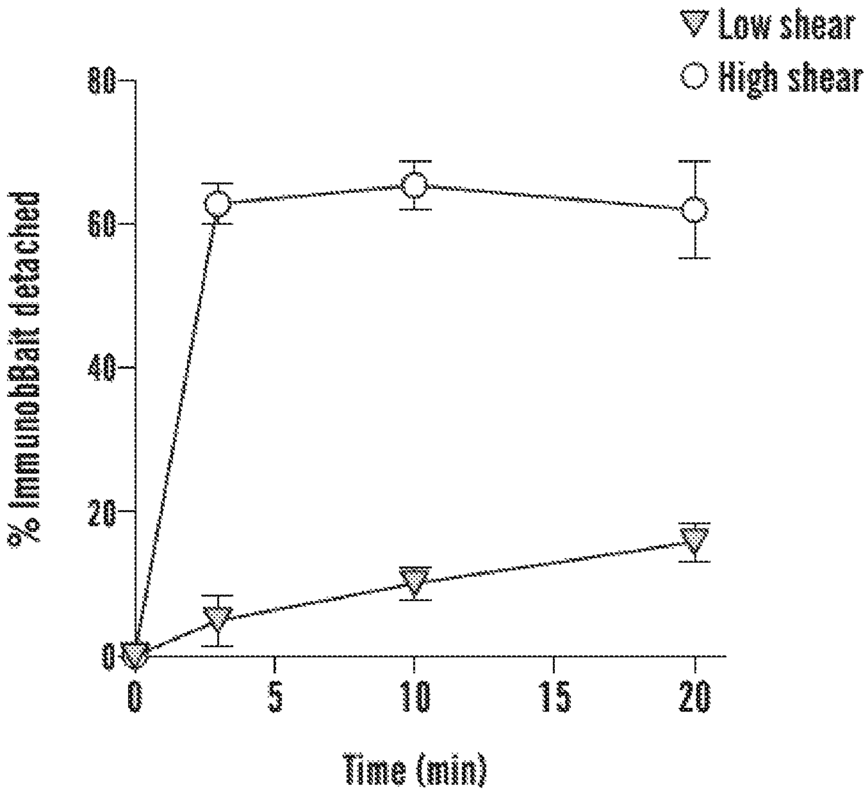

To test whether ImmunoBait can detach from the carrier erythrocytes in response to the physiological lung corresponding high shear stress, an in vitro shear study was first conducted in which erythrocytes carrying the ImmunoBait were sheared for 3, 10, or 20 mins. The SEM imaging data (FIG. 16A) revealed that the number of nanoparticles present on the surface of erythrocytes markedly decreased after shear. Quantitative analysis confirmed this finding (FIG. 16B). The detachment of ImmunoBait is shear-dependent and >60% of the nanoparticles were released within 3 mins when being sheared at the lung corresponding shear stress (6 Pa).

Figure 16C:
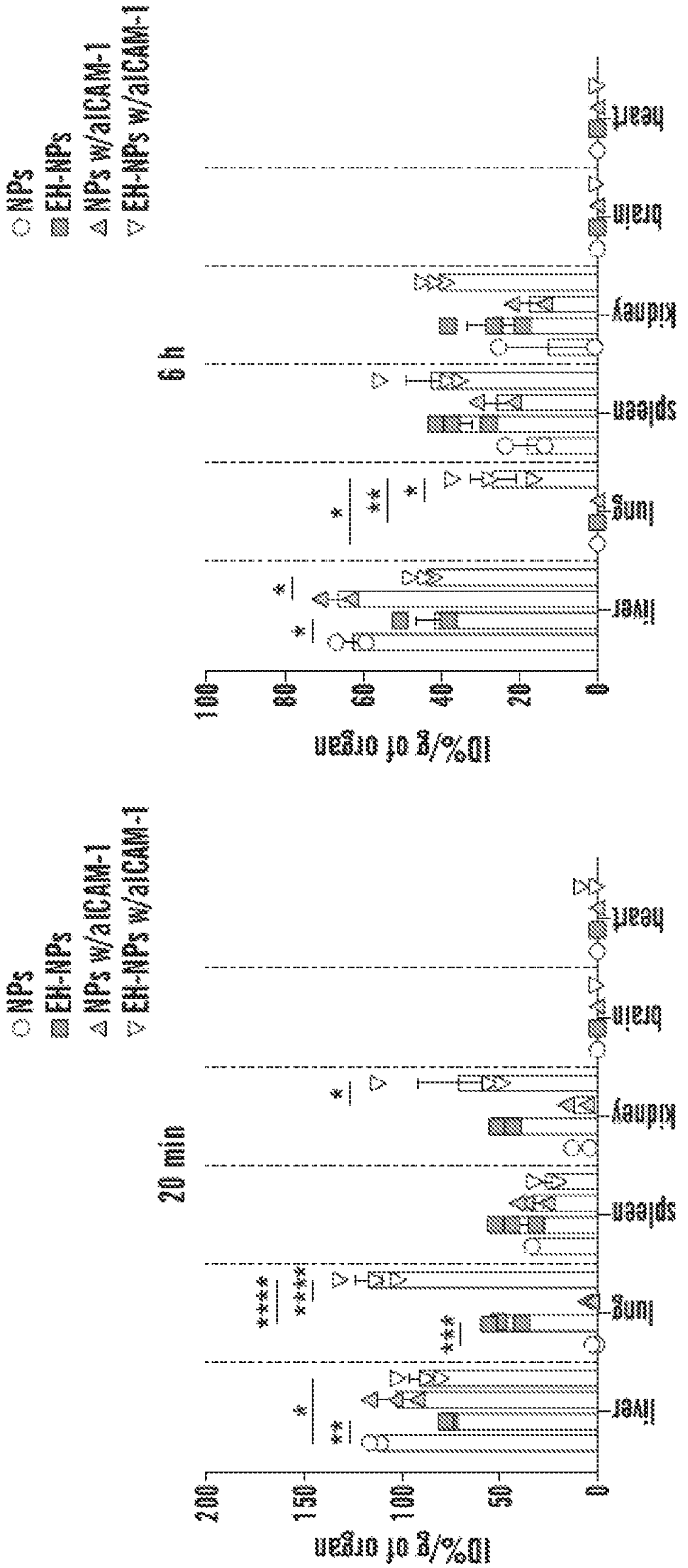
Figure 16F:
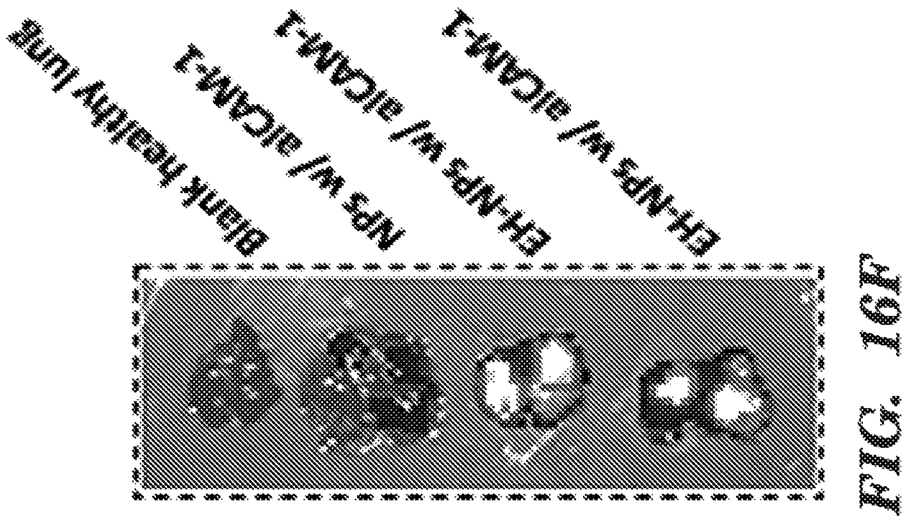
Figure 16E:
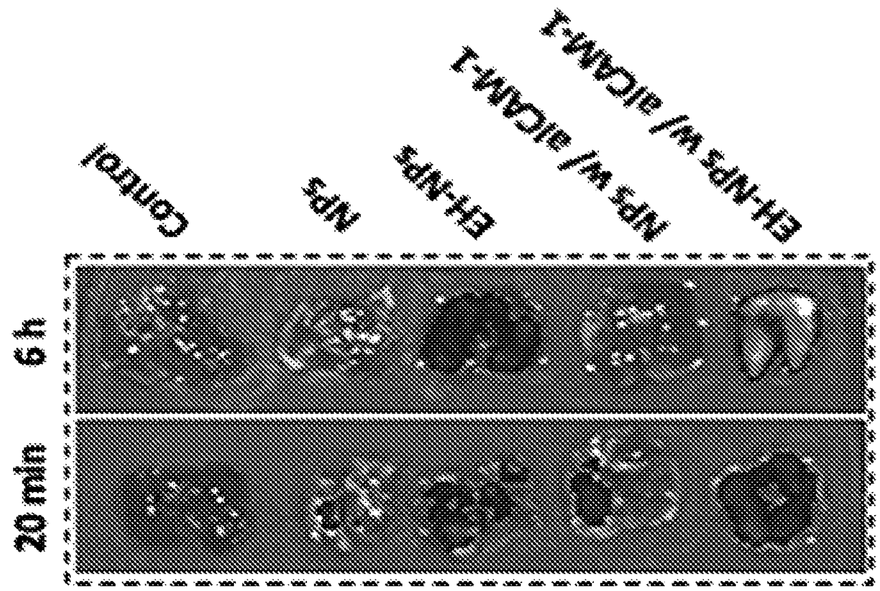
Figure 16D:
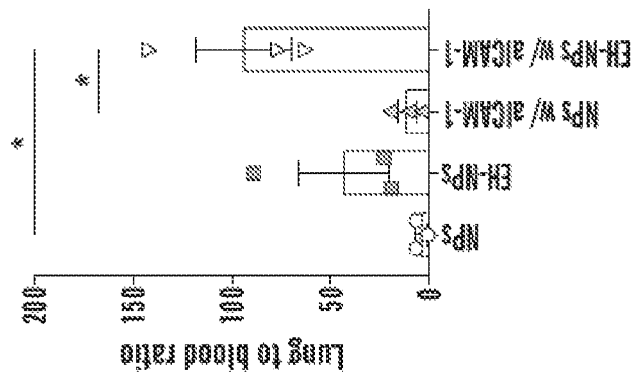

Next, a biodistribution study was conducted in an early-stage breast cancer spontaneous lung metastasis model. As shown in FIGS. 16C-16E, by hitchhiking ImmunoBait nanoparticles to the erythrocytes, a decreased number of nanoparticles were accumulated in the liver, which is consistent with the previous reports.[33, 35] In addition, similar to that in a healthy mouse model, significantly more ImmunoBait was delivered to the lungs bearing metastasis when being assembled onto erythrocytes as compared to their free counterparts. In particular, in the presence of anti-ICAM-1 antibody, ~27-fold more ImmunoBait accumulated in the diseased lung when being assembled onto erythrocytes as compared to their free counterparts, 20 mins following their intravenous administration. Furthermore, ImmunoBait retained in the lung bearing metastasis for at least 6 hours. As shown in FIG. 16D, the enhanced delivery of ImmunoBait to the metastatic lung resulted in a high lung to blood ratio, as high as 94, forming a basis for the establishment of payload gradients. Further biodistribution study in a late-stage lung metastasis model indicated that the ImmunoBait could also be deposited in the late-stage metastatic lungs in response to the physiological high shear stress even under advanced pathological conditions (FIG. 16F).

Figure 16G:
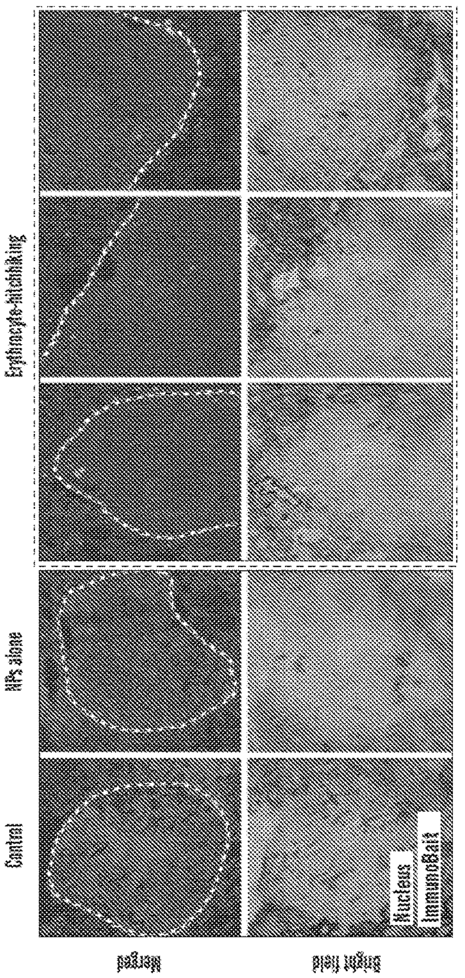

Lung sections were next analyzed to investigate the distribution of ImmunoBait within the lungs bearing metastasis. As shown in FIG. 16G, the erythrocyte hitchhiking approach was able to deliver a substantial amount of ImmunoBait to the "hard to reach" metastatic sites. Particularly, most of the ImmunoBait was distributed around the metastatic nodules while some also went deep into the metastatic nodules.

Immuno-Restoration Enabled by Erythrocyte Anchored Systemic Immunotherapy (EASY)

Figure 16H:
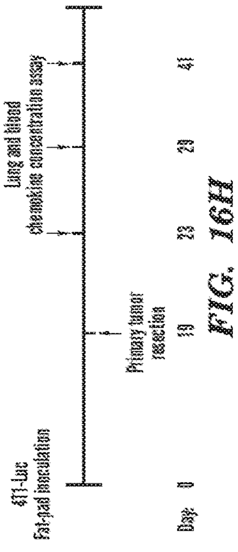
Figure 16I:
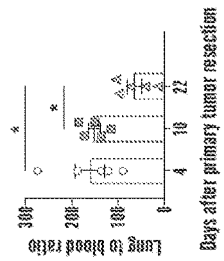
Figure 16J:
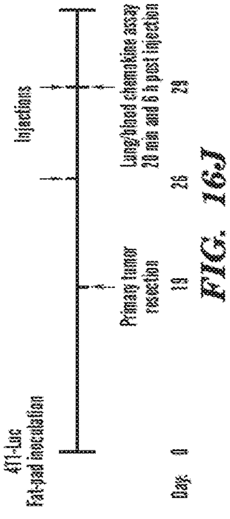
Figure 16M:
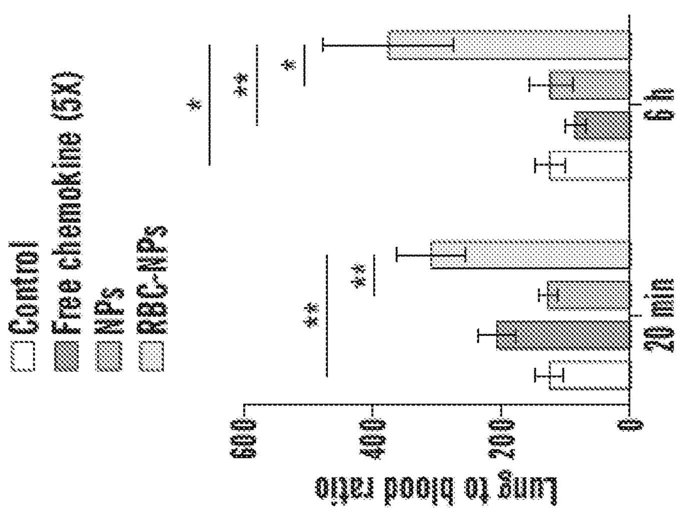
Figure 16L:
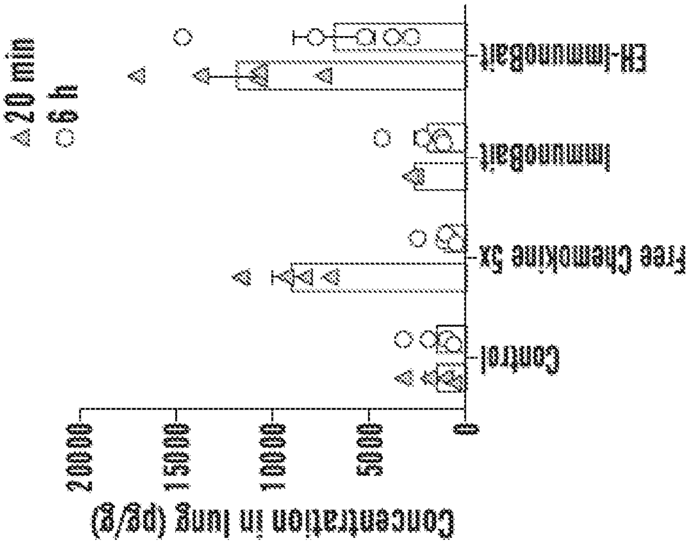
Figure 16K:
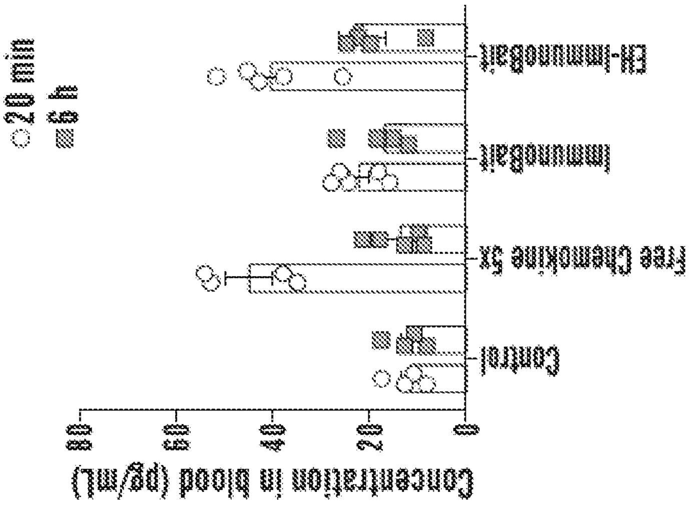
Figure 27A:
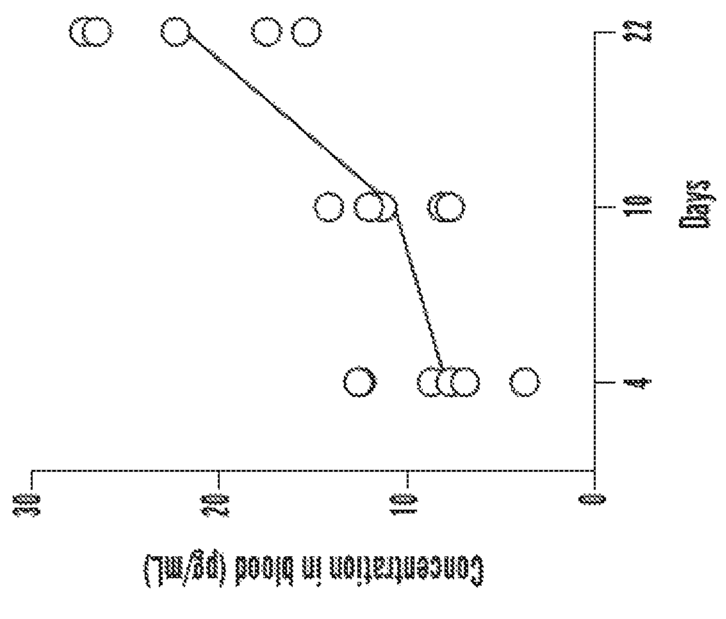
FIGS. 27A-27B depict concentrations of the CXCL10 chemokine in the blood and lung of mice bearing breast cancer lung metastasis at different time after primary tumor resection.
Figure 27B:
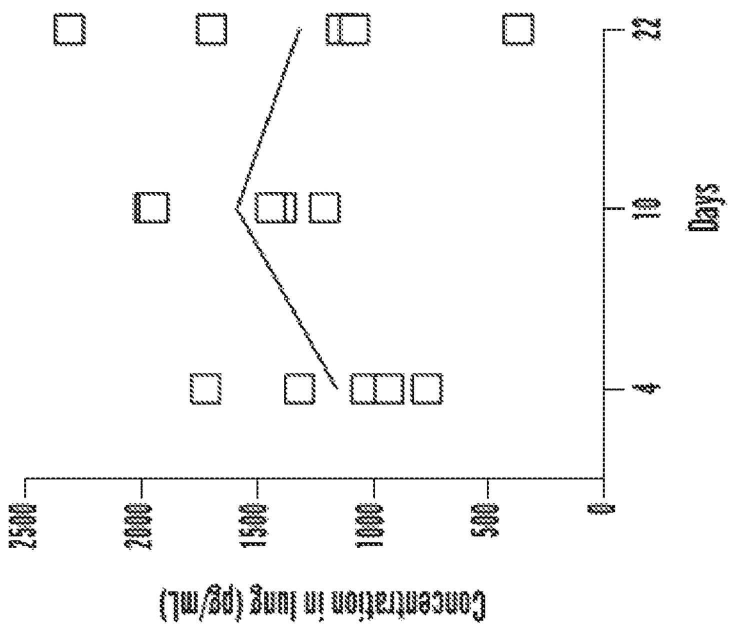

Previous studies have reported that with the progression of melanoma lung metastasis, the infiltration of effector immune cells, like effector T cells, into the metastatic sites is significantly inhibited, which is largely attributed to the loss of chemokine (CXCL9 and CXCL10) gradients.[36] A time-course study was conducted to monitor the CXCL10 chemokine gradients in the breast cancer spontaneous lung metastasis model (FIG. 16H). As shown in FIG. 27A-27B and FIG. 16I, the lung to blood CXCL10 chemokine gradient significantly dropped with the progression of lung metastasis, indicating the development of immune-inhibition in the metastatic lungs. To test whether the ImmunoBait delivered by EASY can lead to immuno-restoration, a chemokine gradient assay was performed (FIG. 16J). Specifically, 20 min or 6 h after the intravenous administration of chemokine formulations, mice were sacrificed and the CXCL10 chemokine concentrations in the lung and blood were assayed. As shown in FIG. 16K-16M, only the ImmunoBait delivered by EASY led to long-lasting restoration of chemokine gradients. The free ImmunoBait with anti-ICAM-1 antibody was not able to deliver enough chemokine to the lung and failed to establish a strong chemokine gradient. A challenging comparative control of delivering 5-fold higher dose of free chemokine was used. The 5× free chemokine formulation delivered high contents of chemokine to both the blood and lung, by virtue of high bioavailability, and created a weak chemokine gradient 20 mins after administration. However, this gradient could not be maintained. In a sharp comparison, the ImmunoBait delivered by EASY was able to deliver high concentrations of CXCL10 chemokine to the lungs and a strong chemokine gradient could be maintained for at least 6 hours.

In Vivo Treatment Efficacy of Erythrocyte Anchored Systemic Immunotherapy (EASY)

Figure 17A:
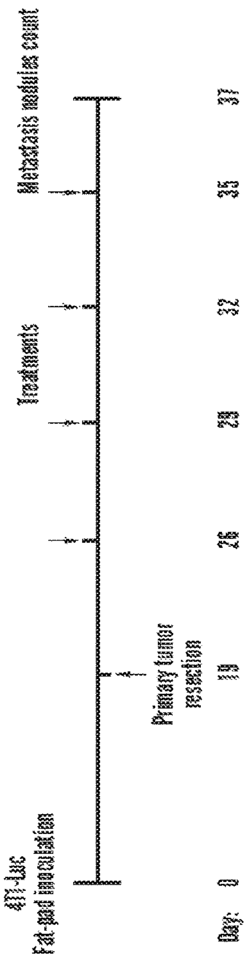
FIGS. 17A-17H demonstrate that EASY led to significant inhibition of progression of lung metastasis and improvement of survival in a breast cancer lung metastasis model.
Figure 17B:
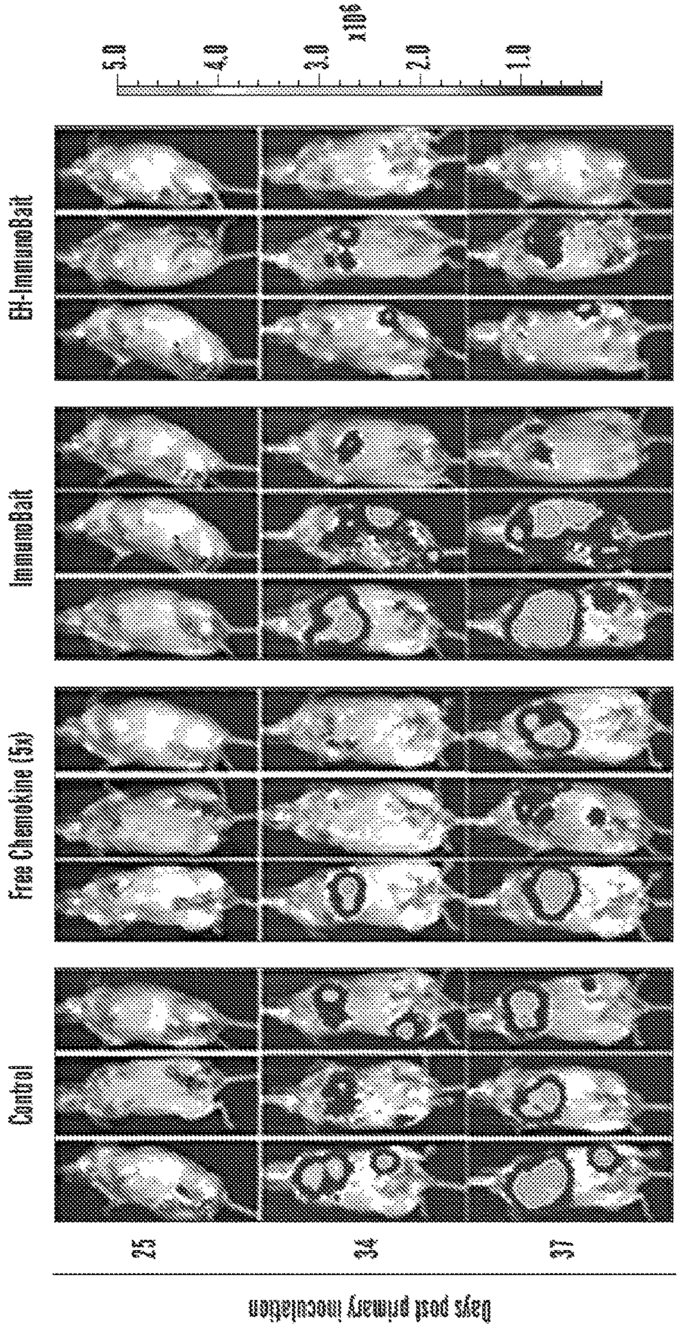
Figure 17C:
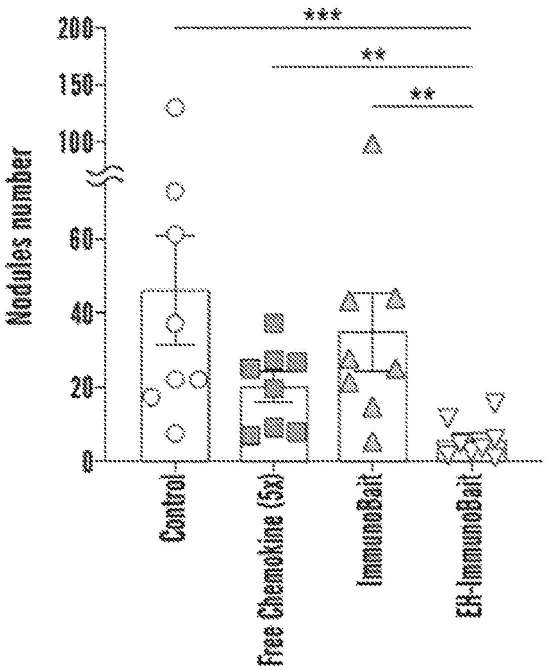
Figure 17D:
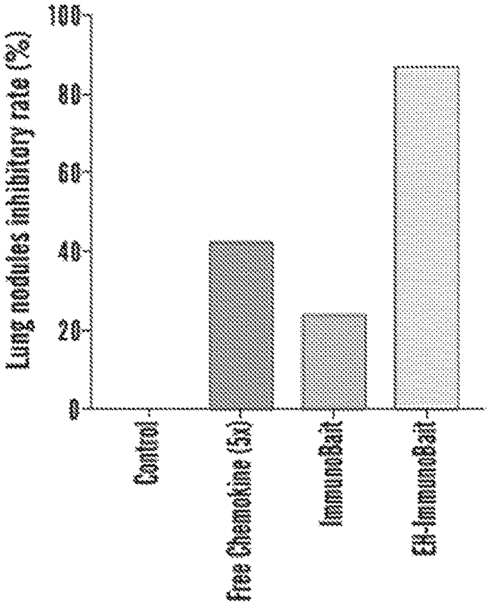
Figure 17E:
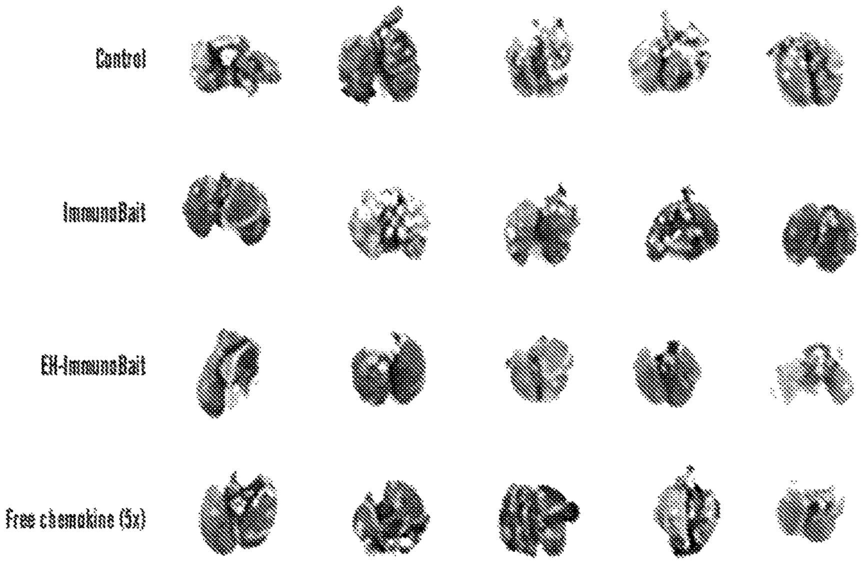
Figure 17F:
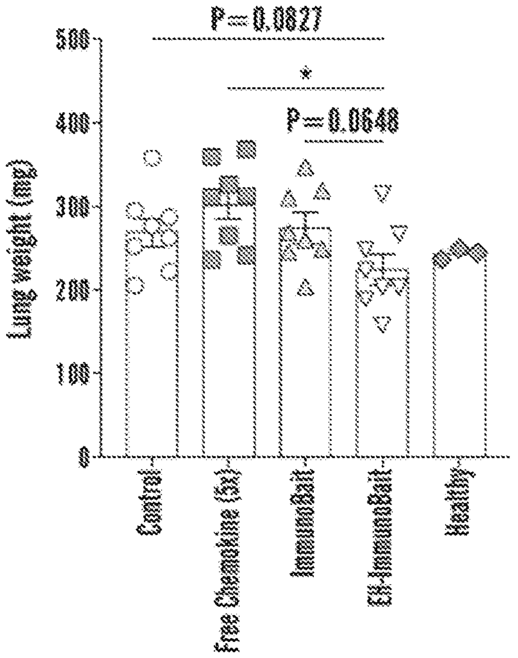
Figure 17G:
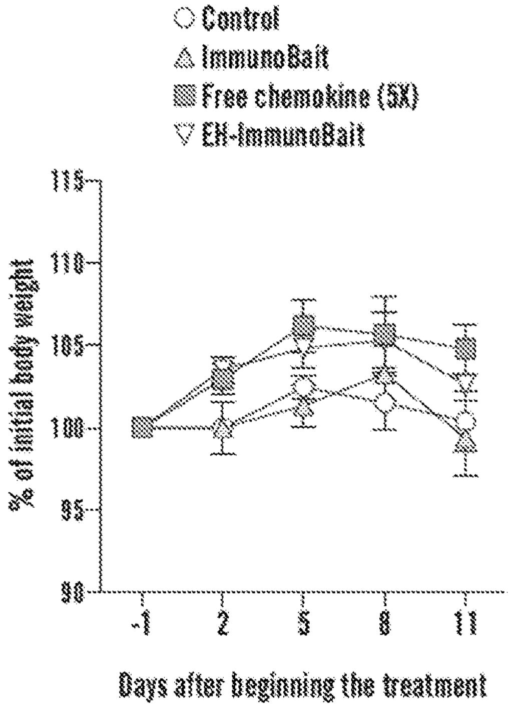
Figure 17H:
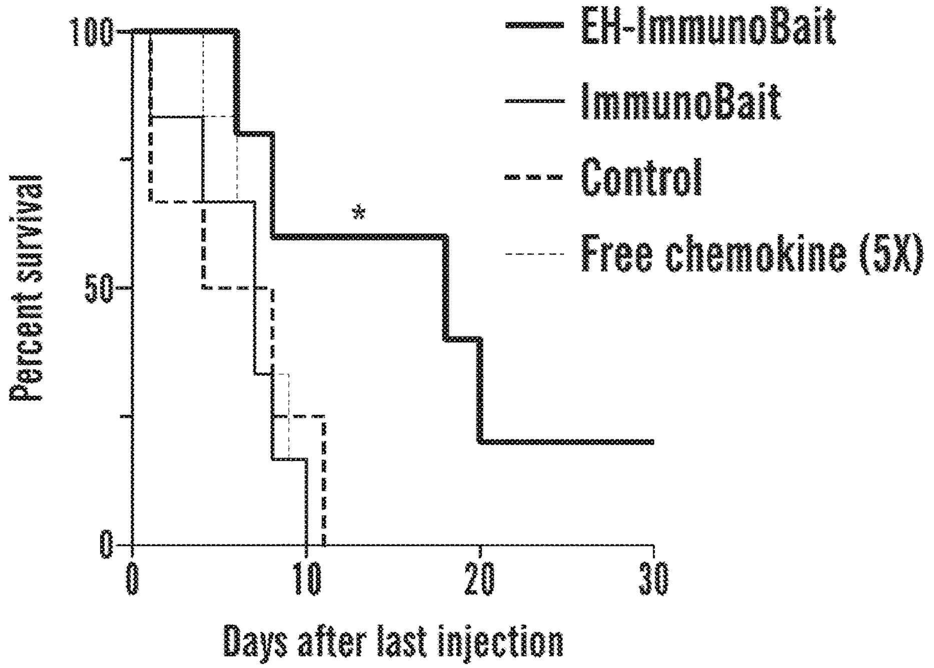
Figure 28:
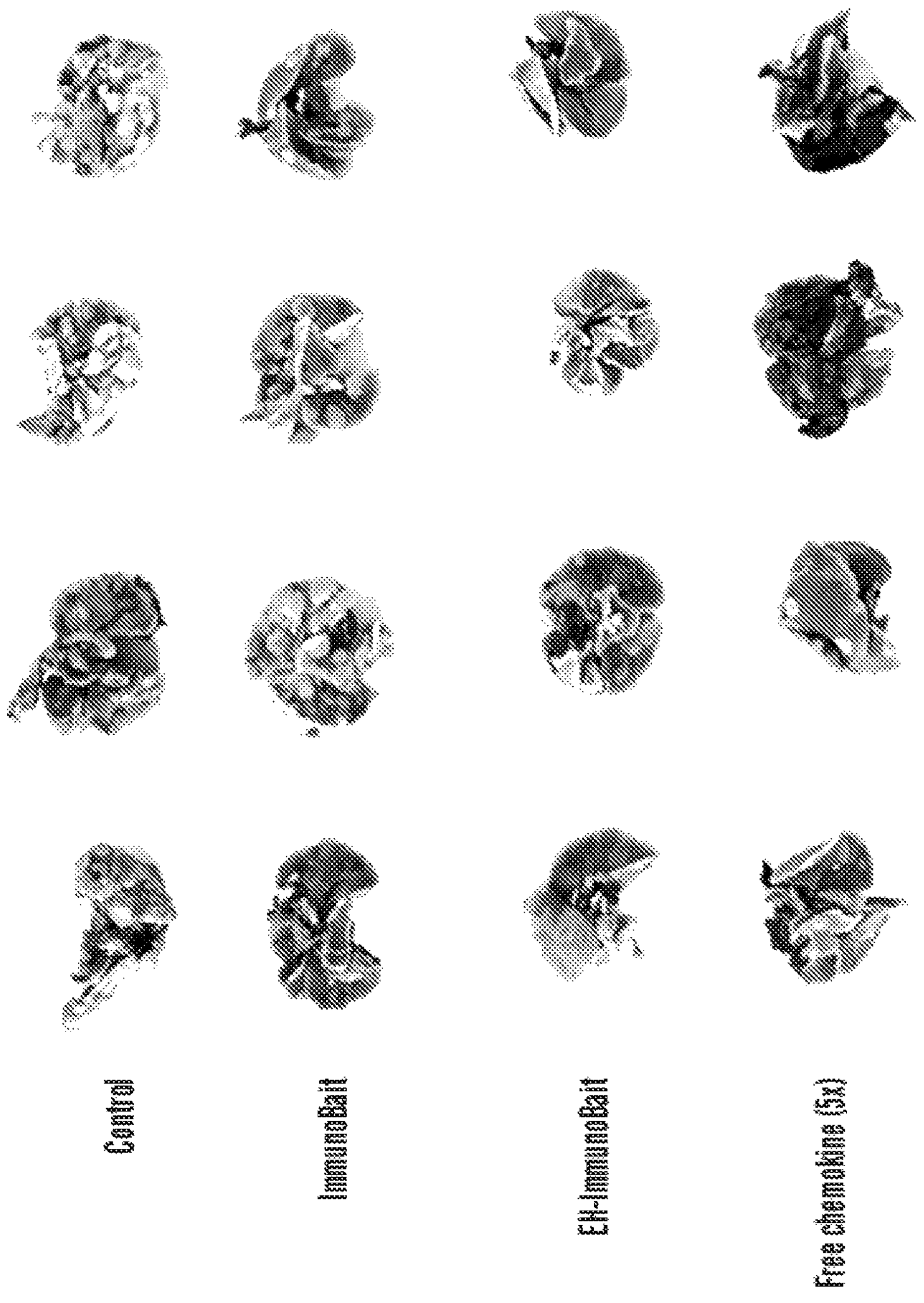
Figure 29:
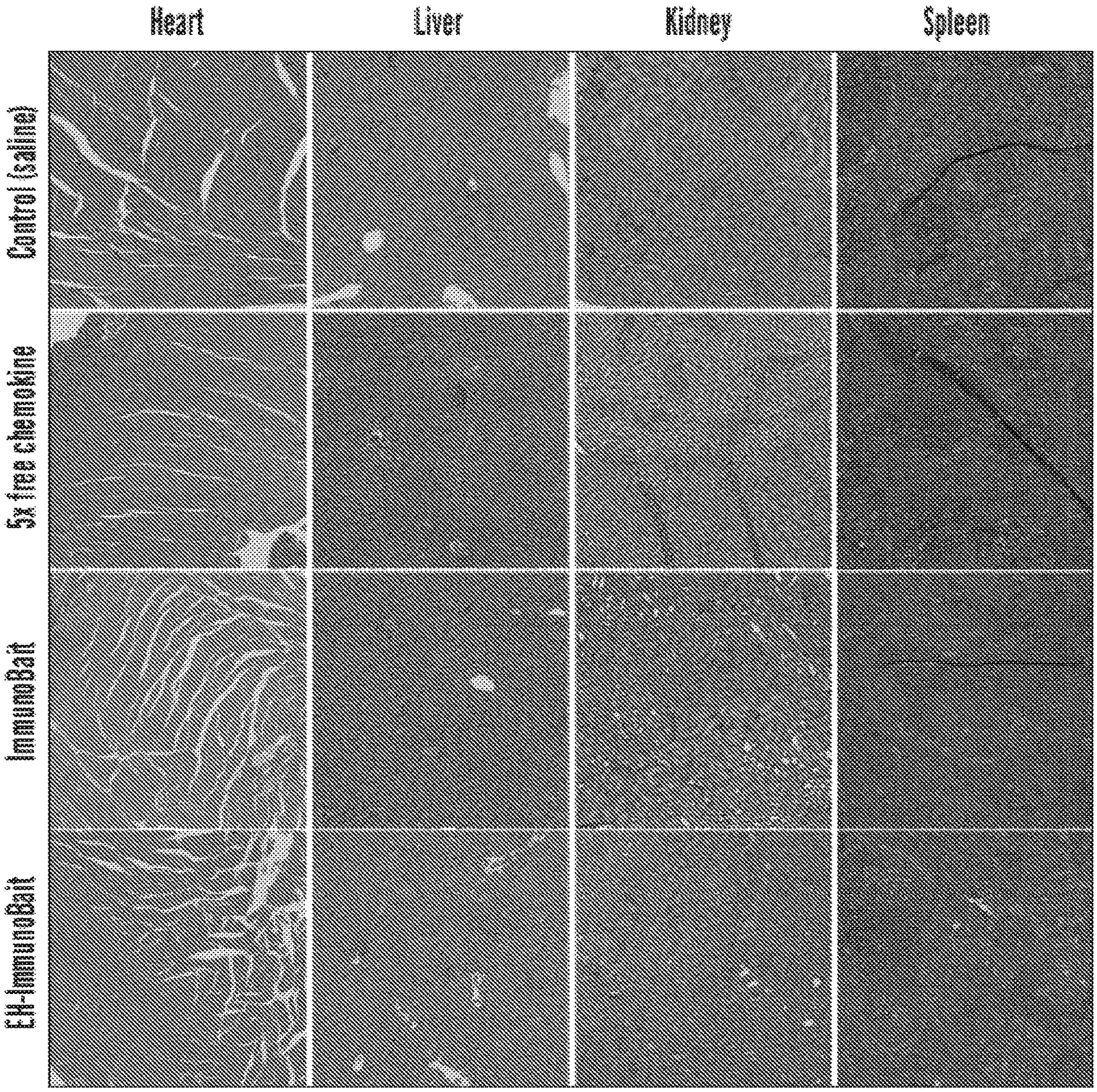
Figure 30A:
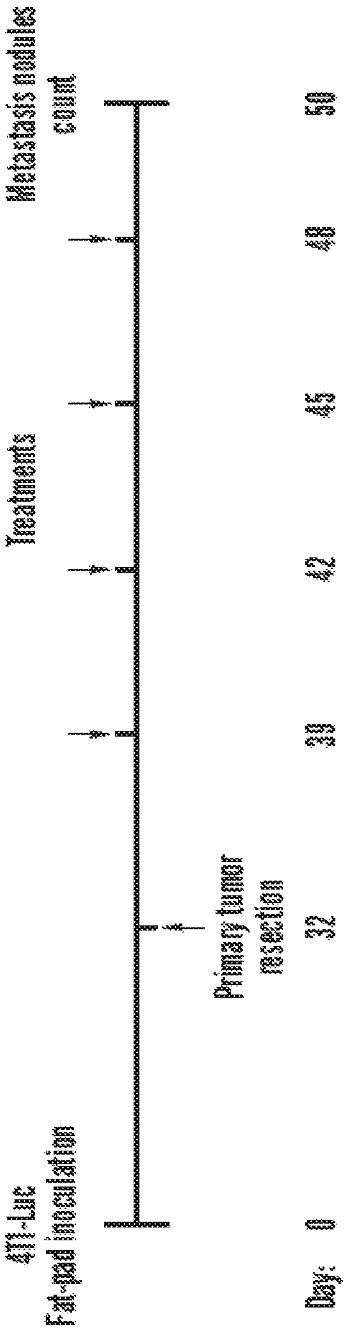
FIGS. 30A-30C depict the efficacy of EASY in inhibition of lung metastasis in a late-stage breast cancer lung metastasis model.
Figure 30B:
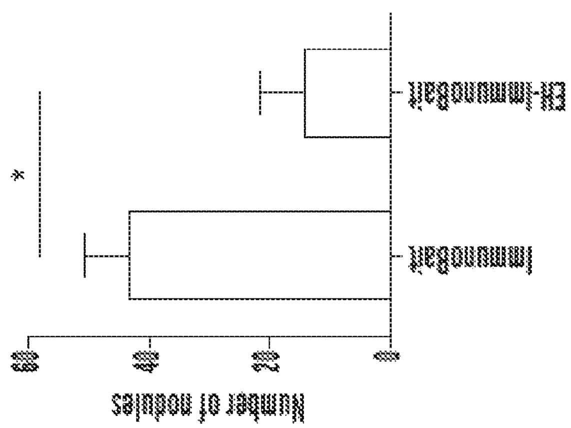
Figure 30C:
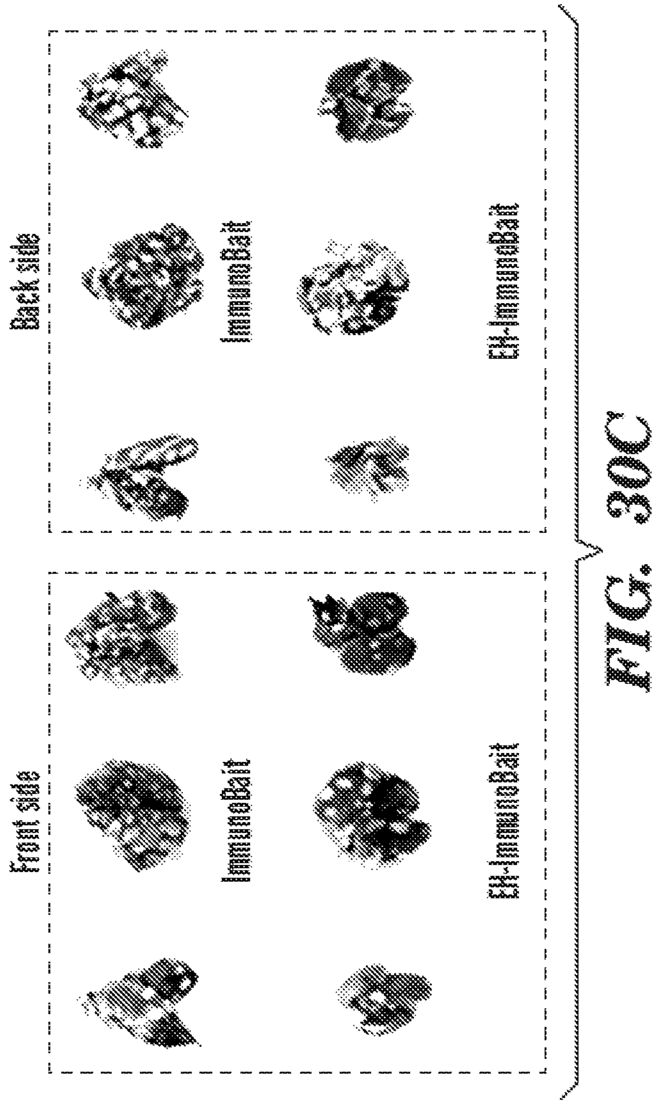

Immuno-restoration at the lung metastatic sites can modulate the local microenvironment to a "hot" state favoring cytotoxic immune responses and have the potential to control the progression of lung metastasis.[36-38] To test this hypothesis, the efficacy of EASY for controlling lung metastasis was evaluated in a breast cancer spontaneous lung metastasis model. As shown in FIG. 17A, mice received a total of 4 doses of therapies over 10 days, with the first dose being administered 7 days after the resection of the primary tumors. As indicated by the bioluminescence imaging data (FIG. 17B), the EH-ImmunoBait group exhibited remarkably slower progression of lung metastasis compared to other groups. Two days after the last dose, mice were scarified and the surface nodules on excised lungs were counted. As shown in FIG. 17C, only the EH-ImmunoBait resulted in a significantly lower lung metastasis burden compared to the control group. Specifically, EH-ImmunoBait exhibited a 3.5-fold and 6.0-fold better efficacy in inhibiting the progression of lung metastasis as compared to the 5× free chemokine and free ImmunoBait groups, respectively. The overall lung metastasis inhibition rate achieved by the EH-ImmunoBait was as high as 87.4% (FIG. 17D). Moreover, two out of eight mice in the EH-ImmunoBait group had less than 2 visible lung nodules on day 37. The qualitative images of excised lungs confirmed higher efficacy of EH-ImmunoBait over other treatments (FIG. 17E and FIG. 28). Furthermore, the lung weight of mice treated by EH-ImmunoBait is remarkably lower than that of the control and other treatment groups and is closer to that of the healthy mice (FIG. 17F). Significant body weight loss was not observed in any of the treatment groups during the entire treatment, indicating no obvious toxicity was associated with the treatments (FIG. 17G). The H&E staining data of mouse organs confirmed the safety of the treatments (FIG. 29). Next, a survival study was conducted to evaluate whether the EASY approach can extend the survival time of mice bearing breast cancer spontaneous lung metastasis. Mice received therapies according to the same schedule as shown in FIG. 17A. The treatment by EH-ImmunoBait significantly improved the animal survival compared to the control and other treatment groups, extending the median survival time by almost 3-fold (FIG. 17H). In addition, one out of six mice survived for at least 65 days. Next, the efficacy of EASY in treating late-stage lung metastasis in a late-stage breast cancer spontaneous lung metastasis model was studied (FIG. 30A). As shown in FIG. 30B-30C, the EH-ImmunoBait resulted in a significantly reduced lung metastasis burden compared to the free ImmunoBait alone, indicating EASY also showed efficacy in the late-stage metastasis model.

Figure 18A:
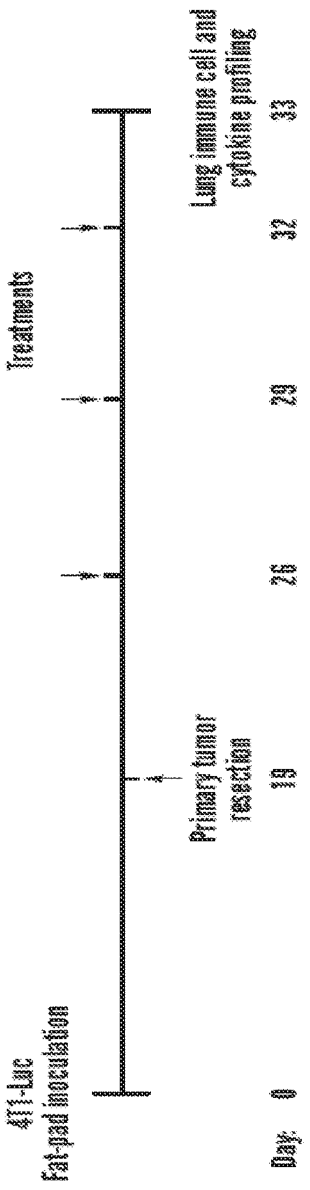
FIGS. 18A-18O demonstrate that EASY resulted in enhanced infiltration of effector immune cells into the metastatic lungs.
Figure 18B:
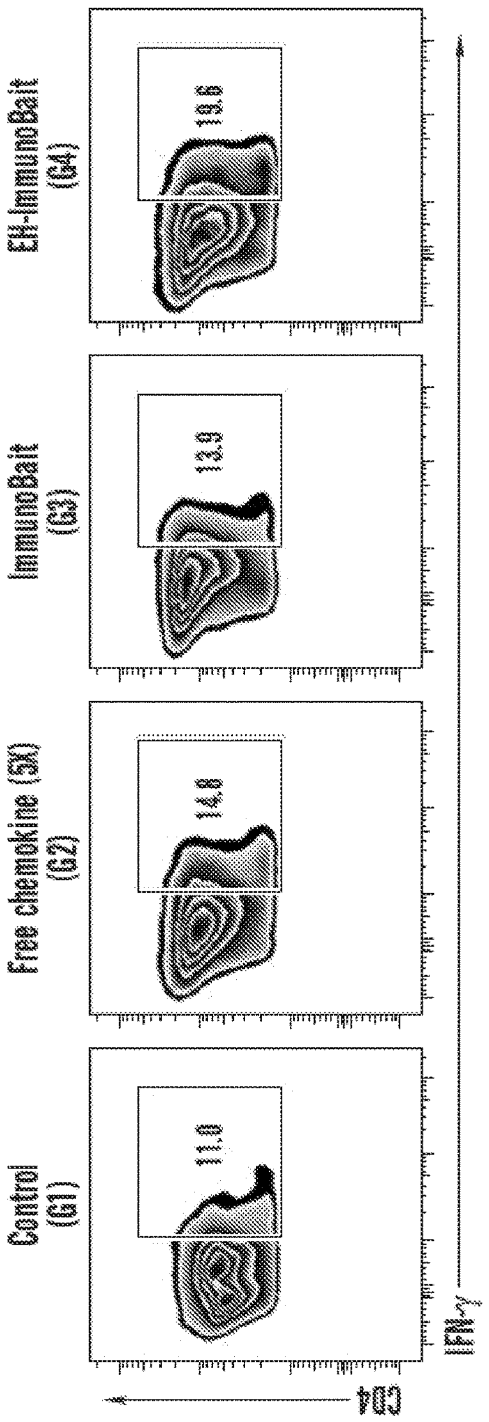
(FIG. 18B) Representative flow cytometry analysis images of CD4+IFN-γ+ cells.
Figure 18D:
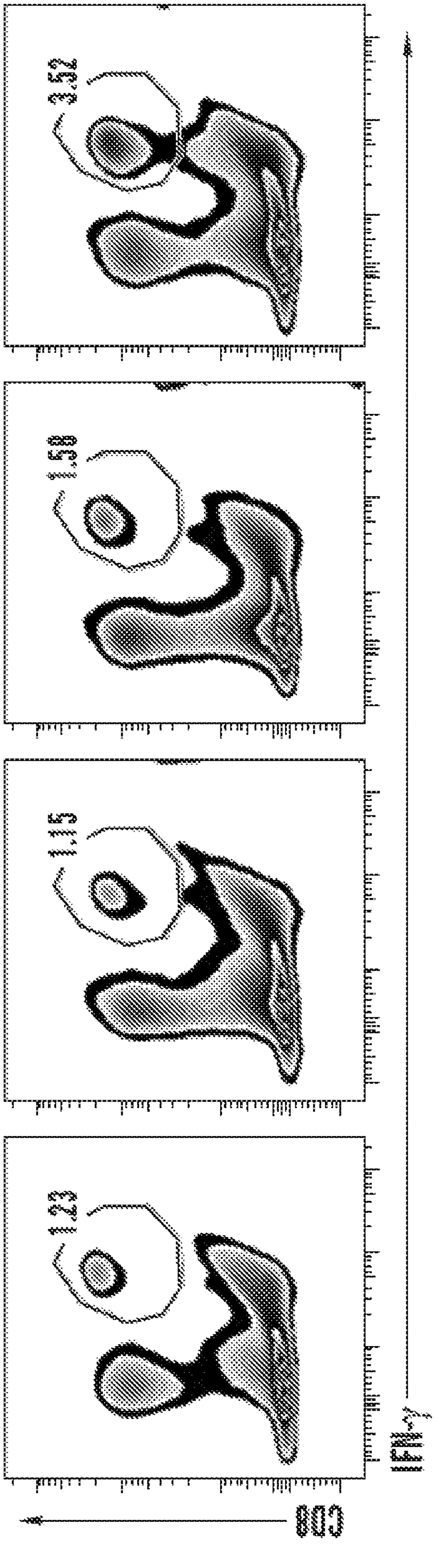
(FIG. 18D) Representative flow cytometry analysis images of CD8+ IFN-γ+ cells.
Figure 18E:
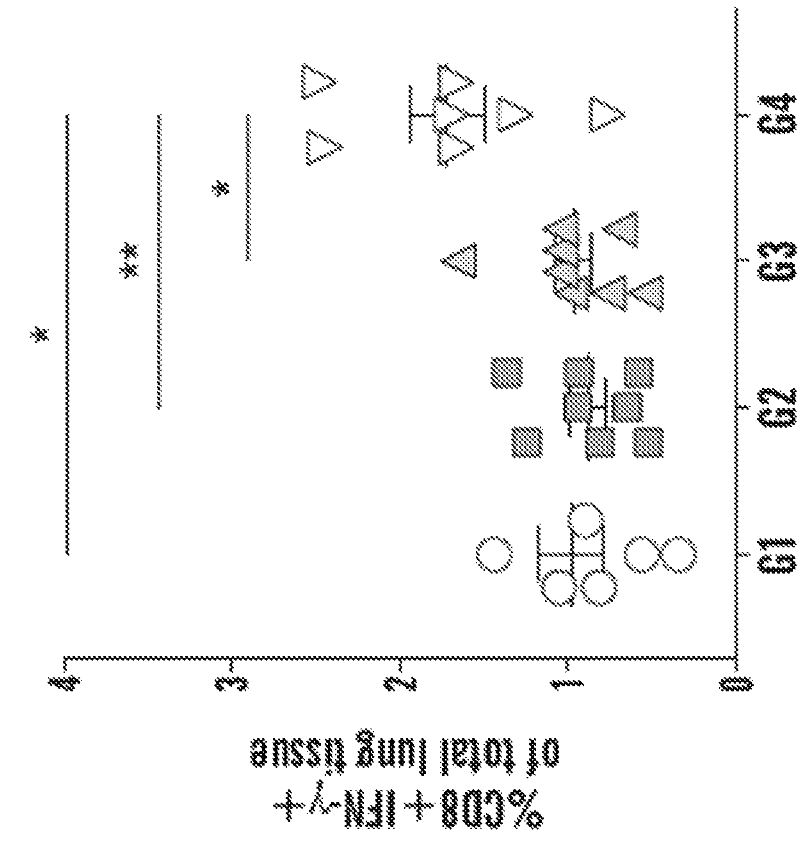
(FIG. 18E) The absolute percentage of IFN-γ+ CD8 cells in the lung (n=7-8).
Figure 18C:
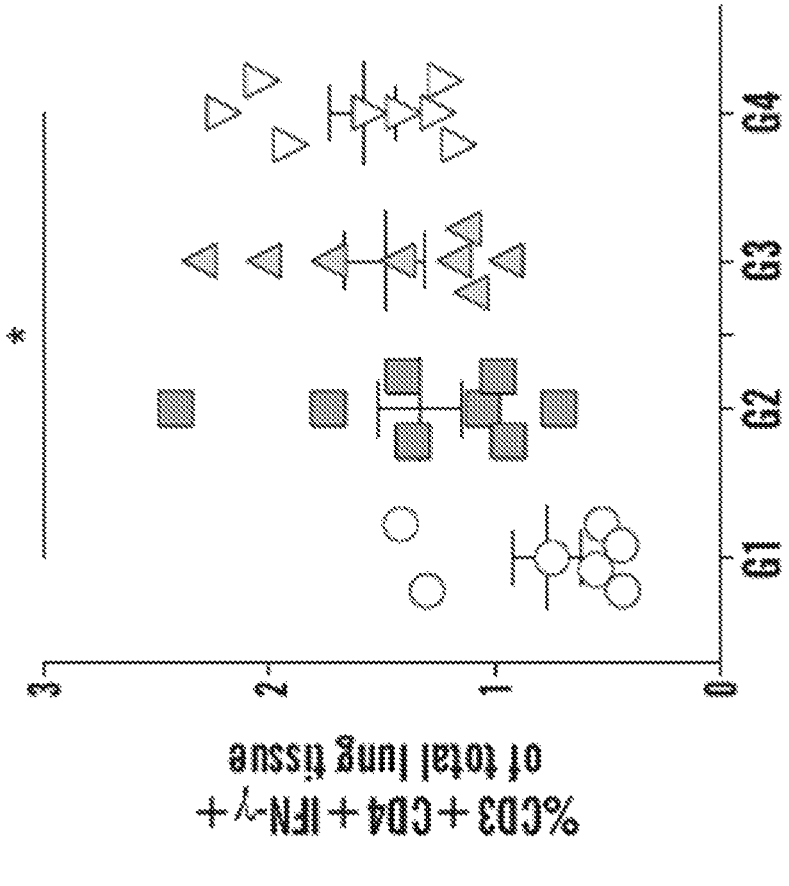
(FIG. 18C) The absolute percentage of IFN-γ+ Th1 CD4 cells in the lung (n=7-8).
Figure 18F:
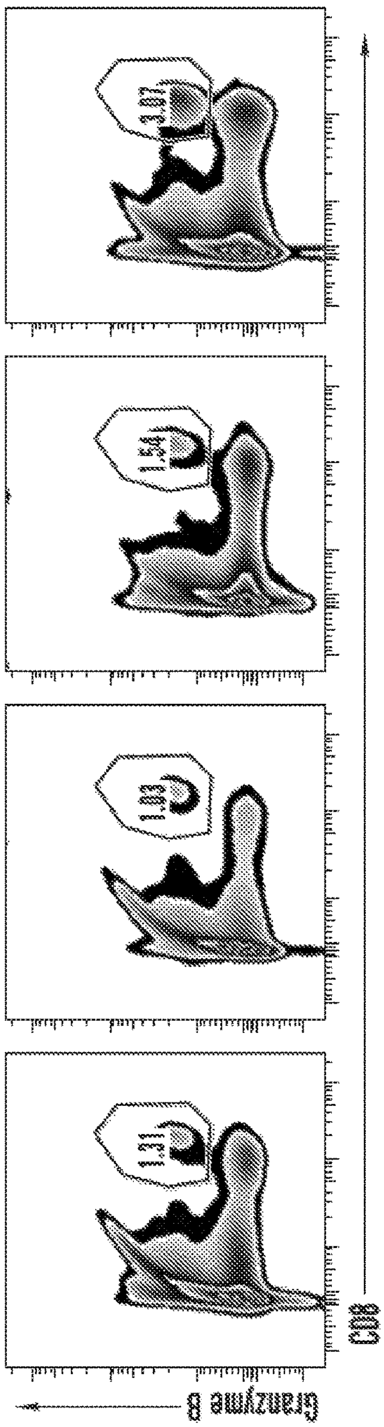
(FIG. 18F) Representative flow cytometry analysis images of Granzyme B+ CD8 cells.
Figure 18H:
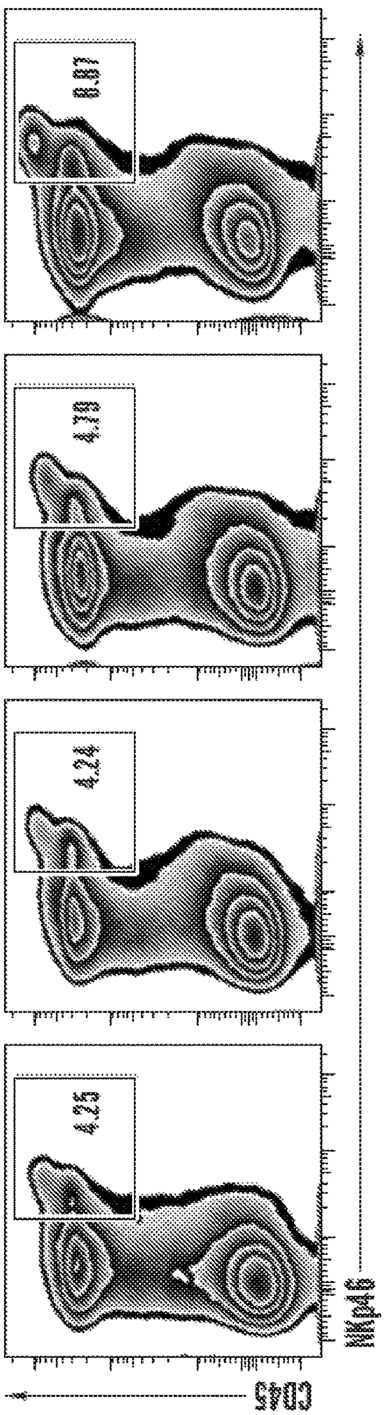
(FIG. 18H) Representative flow cytometry analysis images of CD45+NKp46+ cells.
Figure 18G:
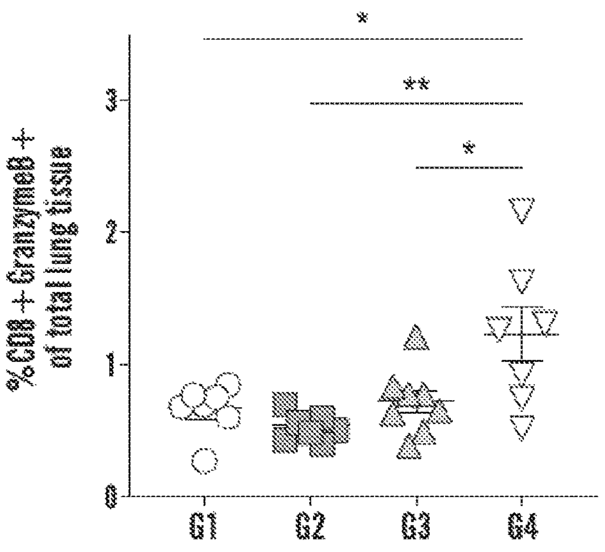
(FIG. 18G) The absolute percentage of Granzyme B+ effector CD8 cells in the lung (n=7-8).
Figure 18I:
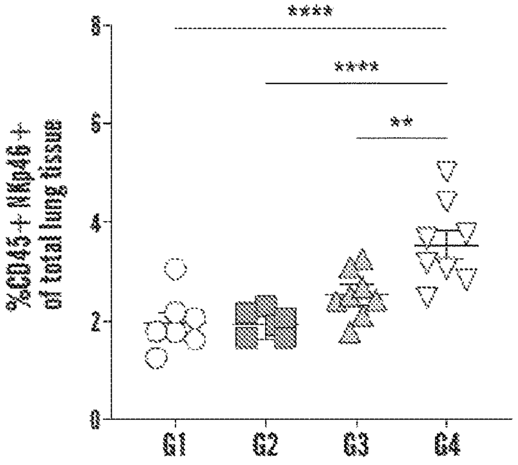
(FIG. 18I) The absolute percentage of NKp46+NK cells in the lung (n=7-8).
Figure 18K:
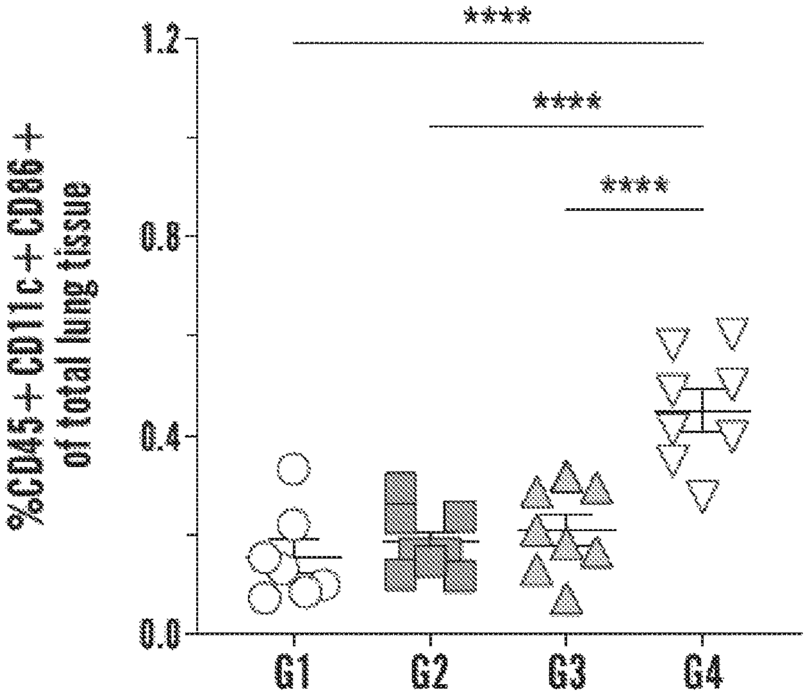
(FIG. 18K) The absolute percentage of activated (CD86+) dendritic cells in the lung (n=7-8).
Figure 18J:
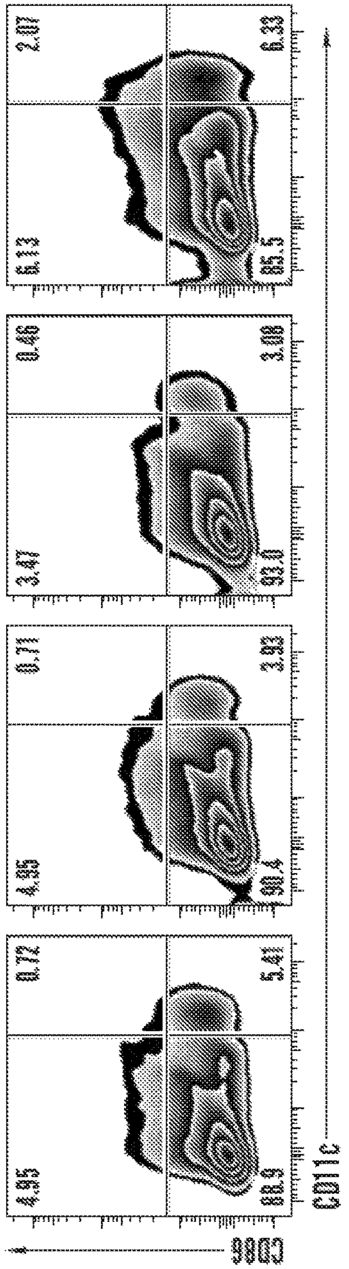
(FIG. 18J) Representative flow cytometry analysis images of CD11c+CD86+ cells.
Figure 18L:
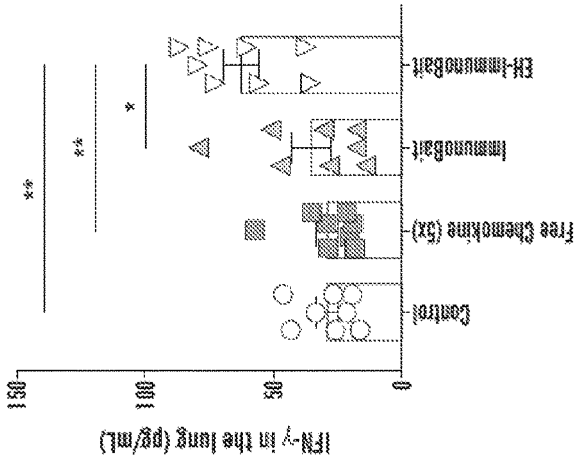
Figure 18M:
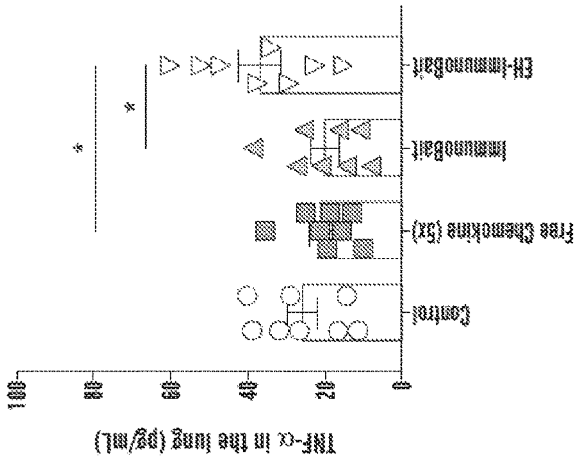
Figure 18N:
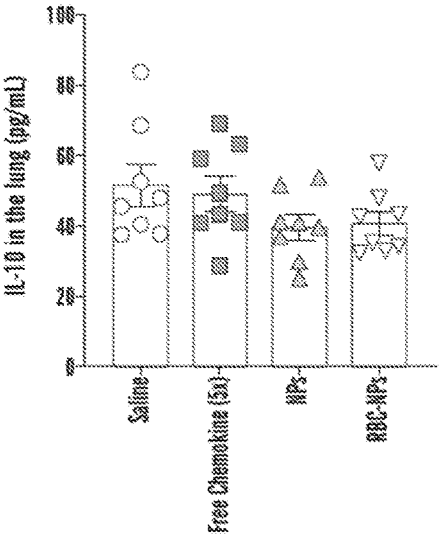
Figure 18O:
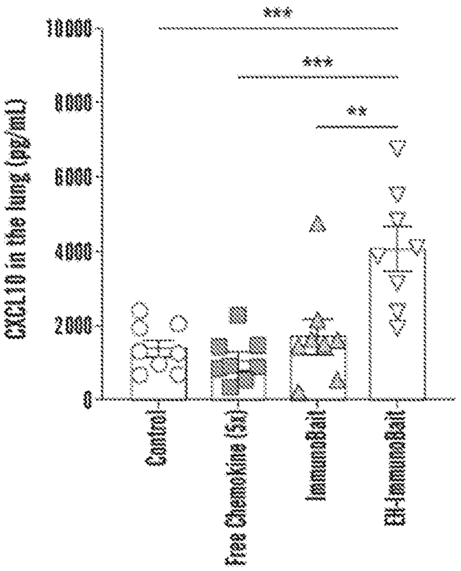
Figure 31A:
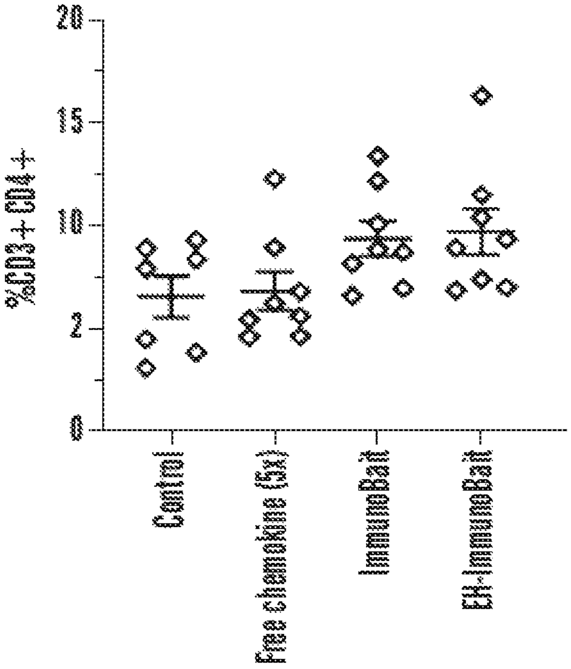
FIG. 31A-31D Immune cells in the metastatic lungs of mice under different treatments. The absolute percentage of (FIG. 31A) CD4, (FIG. 31B) CD8, and (FIG. 31C) dendritic cells in the lungs were shown.
Figure 31B:
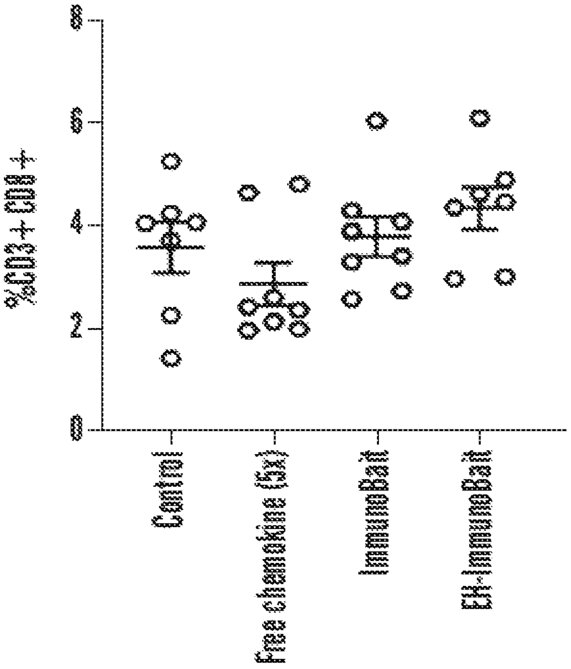
Figure 31C:
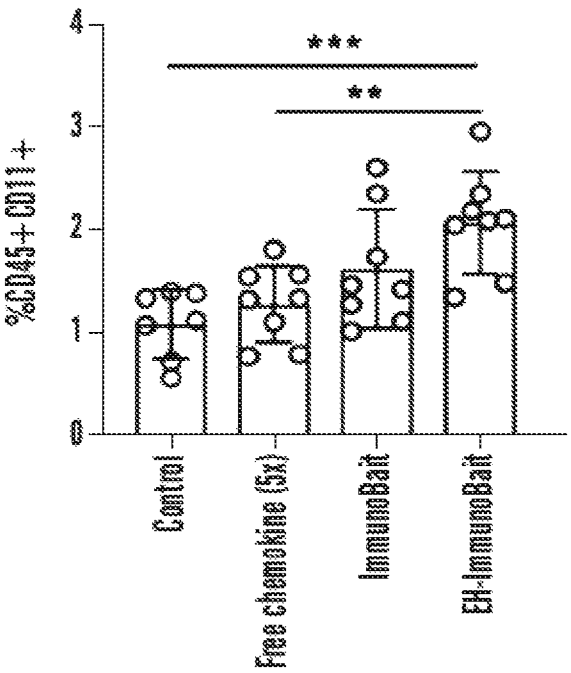
Figure 31D:
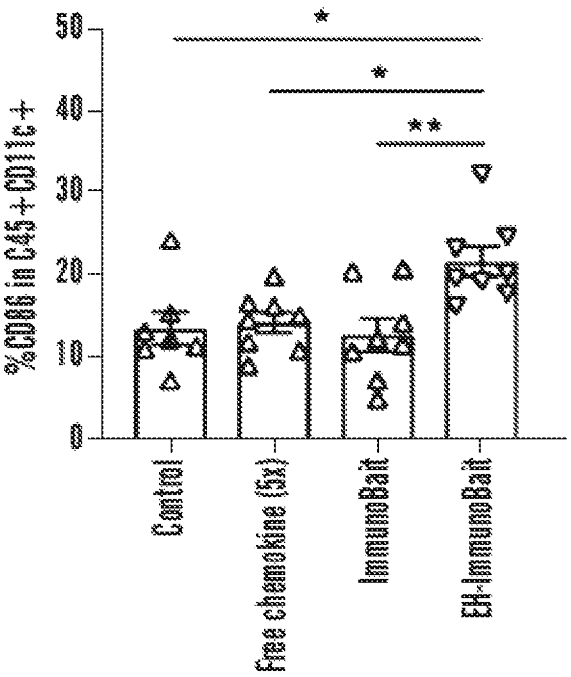
Figure 32:
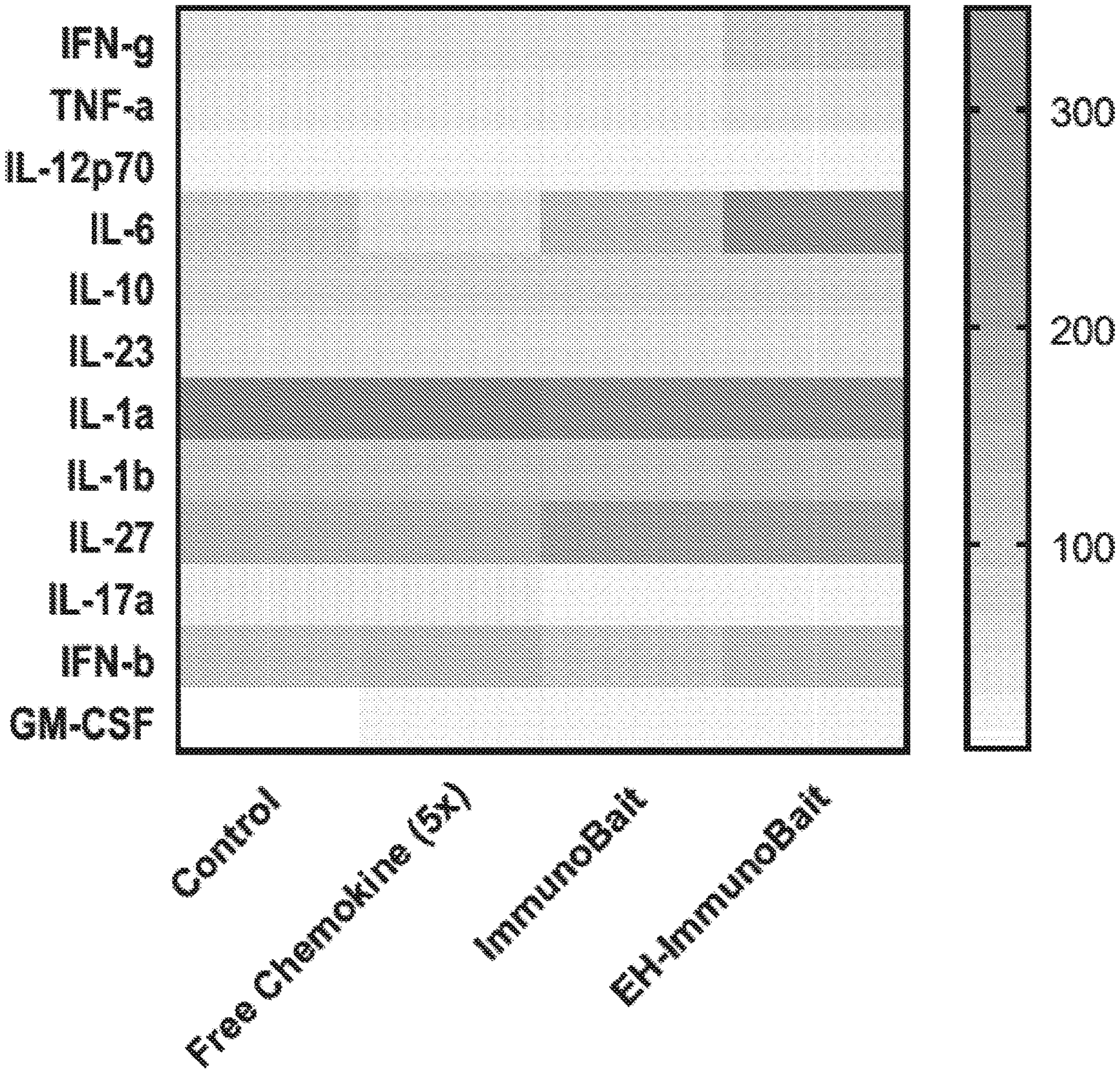

Mechanism of Immuno-Restoration Enabled by EASY for Inhibiting Lung Metastasis Progression To understand the underlying cellular mechanism of the observed anti-metastatic efficacy of the ImmunoBait delivered by EASY, a study to profile the immune cells in the metastatic lungs following different treatments was conducted (FIG. 18A). CXCL10 is a strong chemoattractant to specific classes of immune cells expressing CXCR3 receptors like Th1 CD4, effector CD8, and NK cells, all of which favor an anti-tumor response.[25, 39-41] As shown in FIG. 31A, the EH-ImmunoBait led to a 1.5-fold increase in the total CD4 cells as compared to the control (saline). Moreover, significantly more (2.0-fold increase) IFN-γ+Th1 CD4 cells were observed in the mouse metastatic lungs treated by the EH-ImmunoBait as compared to the saline group (FIG. 18B). Th1 CD4 cells secrete type 1 cytokines like IFN-γ and TNF-α, maintaining a pro-inflammatory environment that is favorable for the immunological control of tumors.[1, 42] The total CD8 T cells in the metastatic lungs were not significantly different among various treatment groups (FIG. 31B). However, EH-ImmunoBait induced significantly enhanced infiltration of effector CD8 T cells into the metastatic lungs over the other groups (FIG. 18D-18G). Specifically, a 1.7-2.0-fold increase in IFN-γ+ CD8 cells and a 1.7-2.3-fold increase in Granzyme B+CD8 cells was achieved by EH-ImmunoBait as compared to the control and other treatments. Apart from the adaptive immune cells, it was also observed that the ImmunoBait delivered by EASY significantly changed the infiltration of innate immune cells into the metastatic lungs, especially the NK and the dendritic cells (FIG. 18H-18J and FIG. 31C). As shown in FIG. 18H-18I, following the administration of EH-ImmunoBait, a significantly improved infiltration of NK cells to the metastatic lungs was observed. The total number of NK cells in the EH-ImmunoBait group was 1.4-1.8-fold higher than that in the control and other treatment groups. Notably, a remarkably higher amount of CD11c+ dendritic cells was also observed in the EH-ImmunoBait group over other groups (FIG. 31C). Moreover, the infiltrated CD11c+ dendritic cells in the EH-ImmunoBait group were in a significantly more activated state (CD86+) as compared to those in the control and other treatment groups (FIG. 31D and FIG. 18K). This finding is unexpected since CXCL10 is not a strong chemoattractant for dendritic cells. It is contemplated herein that the tumor cell death caused by the infiltration of Th1, effector CD8 and NK cells generated more tumor associated antigens, leading to the infiltration of dendritic cells and their subsequent activation.[43, 44] The above immune cell profiling data evidently indicated that the immuno-restoration enabled by EASY significantly enhanced the infiltration of effector immune cells into the metastatic lungs. Furthermore, the improved infiltration of effector immune cells significantly modulated the cytokine profile in the metastatic lungs. The inflammatory cytokine levels in EH-ImmunoBait group were generally higher than in the control and other treatment groups (FIG. 32). Especially, the concentration of IFN-γ and TNF-α in the EH-ImmunoBait group is significantly higher than that in the control or other treatment groups (FIG. 18L-18M). In addition, the level of the anti-inflammatory cytokine IL-10 was lower in the EH-ImmunoBait group than in the other groups (FIG. 18N). More interestingly, the concentration of CXCL10 chemokine in the EH-ImmunoBait group was also remarkably higher than in other groups (FIG. 18O), further confirming the successful immuno-restoration.

Discussion

In summary, described herein is Erythrocyte Anchored Systemic Immunotherapy (EASY), an erythrocyte-mediated systemic administration approach that permits local immuno-restoration at the "hard to reach" lung metastatic sites for the management of lung metastasis. EASY consists of ImmunoBait (chemokine-loaded nanoparticles) anchored onto the surface of erythrocytes. Following systemic intravenous administration, the ImmunoBait quickly dislodges from the carrier erythrocyte in response to the physiological high shear stress in the metastatic lungs and gets precisely deposited at the metastatic sites. The engineered ImmunoBait gets retained in the metastatic lungs and continues to release the payload chemokine, which enables the re-establishment of the lost chemokine gradient and thus locally restores the immunological microenvironment at the metastatic sites. It has been further demonstrated that the restored local immune microenvironment leads to a significant improvement in the infiltration of effector immune cells, including Th1 CD4, effector CD8, NK, and activated dendritic cells, into the metastatic site. Promisingly, EASY was able to significantly inhibit the progression of lung metastasis and remarkably improve the animal survival in a breast cancer spontaneous lung metastasis model. EASY is one of the very first systemic administration approaches that can enable local immuno-restoration at the hard-to-reach lung metastatic sites and can be a potent strategy to modulating the local lung microenvironments by site-specific delivering a range of immunomodulatory agents.

Methods

Cell Lines and Animals

4T1 mammary carcinoma cell line (4T1-Luc) expressing luciferase were obtained from Imanis Life Sciences (MN, USA). 4T1-Luc cells were cultured in a humidified incubator maintained at 37° C. and 5% $CO_2$. They were cultured in RPMI-1640 media supplemented with 10% FBS, 1% Pen-Strep and 0.1 mg/mL G418. Human lung microvasculature endothelial cells (HLMVEC) and HLMVEC growth medium was purchased for Sigma Aldrich (MO, USA). HLMVEC were cultured in HLMVEC growth medium according to manufacturer's instructions. Cells were passaged 2-3 times before their use. Female Balb/c mice (7-8 weeks of age) were purchased from Charles River Laboratories (MA, USA). All experiments were performed according to the approved protocols by the Institutional Animal Care and Use Committee (IACUC) of the Faculty of Arts and Sciences (FAS), Harvard University, Cambridge.

ImmunoBait Preparation and Characterization

ImmunoBait, PLGA nanoparticles encapsulating CXCL10 were prepared using a double emulsion method. Briefly, 50 μg of CXCL10 was dissolved in 200 μL of 0.1% bovine serum albumin in PBS. This was added to 1 mL of dichloromethane containing 20 mg of PLGA. The mixture was briefly sonicated and then added dropwise to 11 mL of 1.5% polyvinyl alcohol (PVA) solution under constant stirring. The entire mixture was probe-sonicated for 40 seconds. The formed particles were kept under constant stirring overnight to remove the organic solvents. The particles were centrifuged at 12,000 g for 10 mins and the supernatant was analyzed for quantifying drug loading. The particles were then resuspended in de-ionized water and assessed for their size, zeta potential and polydispersity index using dynamic light scattering (Malvern Zen3600, PA, USA), scanning electron microscopy (Zeiss FESEM Supra 55VP, Zeiss FESEM Ultra 55, Germany) and transmission electron microscopy (JEOL 2100, MA, USA). The nanoparticles were washed for a total of two washes with deionized water before their final resuspension in PBS. For quantification and biodistribution studies, fluorescent ovalbumin/CXCL10 were encapsulated in PLGA using the method described above.

In Vitro Drug Release Study

CXCL10 containing nanoparticles (ImmunoBait) were resuspended in 1 mL PBS, FBS and complete medium (DMEM+10% FBS) and incubated at 37° C. on a tube revolver. At regular time points, the particles were centrifuged at 12,000 g for 10 mins and the supernatant was collected for analysis. The particles were further resuspended in 1 mL of fresh release media and incubated at 37° C. until the next time point. Samples were taken at 1, 2, 4, 6, and 12 h after starting the incubation. The cumulative release in each release media was quantified using ELISA.

Blood Collection and Processing

Murine whole blood was collected via cardiac puncture using a heparin pre-coated syringe and stored in BD Microtainer® blood collection tubes at 4° C. prior to use. Whole blood was centrifuged at 1,000 g for 10 mins at 4° C. to remove the serum and the buffy coat layers from the erythrocyte compartment. The isolated erythrocytes were further washed 3 times with cold 1×PBS and centrifuged at 650 g for 15 min at 4° C. before their final resuspension at a concentration of 10% hematocrit in 1×PBS. This solution will be regarded as erythrocyte stock solution in this study.

Assembly of ImmunoBait to Erythrocytes

Equal volumes of erythrocyte stock solution and ImmunoBait nanoparticle suspension were mixed in Axygen™ 1.5 mL Self-Standing Screw Cap Tubes and further thoroughly mixed by inversion and pipetting. The tubes were then rotated on a tube revolver (Thermo Fisher Scientific) for 40 mins. The hitchhiked erythrocytes were then pelleted by centrifugation at 100 g for 5 mins at 4° C., unabsorbed particles were carefully removed, and the pellet was washed again with 1 mL of 1×PBS to remove loosely bound particles. For attachment of anti-ICAM-1 antibody, ImmunoBait nanoparticles or hitchhiked erythrocyte pellet were resuspended in 0.5 mg/mL anti-ICAM-1 antibody solution for additional 20 mins. The hitchhiked erythrocytes were finally resuspended at 10% v/v in 1×PBS and used for further characterization or at 20% v/v in 1×PBS for in vivo studies.

Spontaneous Lung Metastasis Model Establishment

To establish the breast cancer spontaneous lung metastasis model, $1\times10^6$ 4T1-Luc cells were injected orthotopically into the left mammary fat pad of female Balb/c mice. Either 19 days (the early-stage model) or 32 days (the late-stage model) after inoculation, the primary tumor was surgically resected. 6 days after the primary tumor resection, mice were injected intraperitoneally with 150 μL of 30 mg/mL Xenolight-D-luciferin in saline. 15 mins after the injection, mice were imaged using in vivo imaging (IVIS Spectrum). Mice were randomized into different groups based on the primary tumor volume and bioluminescence intensity in the lungs 6 days after primary tumor resection.

In Vivo Biodistribution Studies in Disease Model

The early-stage or late-stage breast cancer lung metastasis model was established as described before. Seven days after the primary tumor resection, mice were injected intravenously with ImmunoBait, hitchhiked ImmunoBait, anti-ICAM-1 attached ImmunoBait and hitchhiked ImmunoBait with anti-ICAM-1 attached (n=3 for all groups) into the tail vein. ImmunoBait nanoparticles were fluorescently labeled by Alexa Fluor 647 that was conjugated to the albumin carrier protein. Mice were sacrificed at 20 mins and 6 h after the injection (n=3 per time point per group) and organs (liver, lungs, spleen, kidneys, heart, brain and blood) were harvested for further processing. For processing, 1 mL of cold RIPA lysis buffer (1×) was added to each organ and the organs were homogenized using a high shear homogenizer (IKA T-10 Basic® Ultra turrax, Germany) and the nanoparticle content was quantified by fluorescence on a plate reader (Tecan Safire 2®, Switzerland).

Efficacy Studies on In Vivo Breast Cancer Spontaneous Lung Metastasis Model

In the early-stage breast cancer spontaneous lung metastasis model, treatments were given starting one week after the primary tumor resection. Four injections were given over 10 days, i.e. day 26, 29, 32, and 35. The representative mice were imaged on days 25, 28, 31, 34, and 37, using in vivo imaging (IVIS Spectrum™). Briefly, mice were injected intraperitoneally with 150 μL of 30 mg/mL Xenolight™-D-luciferin in saline. 15 mins after the injection, mice were imaged using in vivo imaging. On day 37, the mice were euthanized, intratracheally injected with India ink solution and the lungs were excised and fixed using Feket's solution. The fixed lungs were used for counting of the surface nodules. Survival in the early-stage model was evaluated by having the injection schedule as described above (n=6). In the late-stage lung metastasis model, four doses of treatments were given every two days with the first dose being administered 7 days (on day 39) after primary tumor resection. Two days after the last dose (on day 50), mice were euthanized and nodules on excised lungs were counted.

Chemokine Gradient Assay

The time-course change of CXCL10 concentration in the blood and lung was measured in the early-stage lung metastasis model. 19 days after the tumor inoculation, tumors were surgically resected. 4, 10, 22 days after tumor resection, mice were euthanized, blood was collected by cardiac puncture and the lungs were excised (n=5 for all time points). For processing, 0.5 mL of cold tissue extraction buffer containing protease inhibitor was added to each lung and the lungs were homogenized using a high shear homogenizer (IKA T-10 Basic® Ultra turrax, Germany). CXCL10 content in the lungs and blood were quantified using ELISA.

The chemokine gradient assay was conducted on the early-stage lung metastasis model as follows. To evaluate chemokine gradient restoration capability of the therapy, early-stage spontaneous lung metastasis model was established as described in the previous context. One saline and three treatment groups (5× free CXCL10 chemokine, ImmunoBait with anti-ICAM-1, and erythrocyte hitchhiked ImmunoBait with anti-ICAM-1) were included into the study. Treatments were given starting one week after surgery. Two injection sets were given on day 7 and day 10 after surgery. (n=4-5 for each time point for each group). Mice were sacrificed at 20 mins and 6 h after the second injection, blood was collected by cardiac puncture and lungs were excised. Chemokine content in lungs and blood were quantified as described above.

Immune Cell and Cytokine Profiling

Different panels of antibody cocktails were made from CD45 (Biolegend, Cat no: 103116, Clone: 30-F11), CD3 (Biolegend, Cat no: 100218, Clone: 17A2), CD4 (Biolegend, Cat no: 100421, Clone: GK1.5), CD8a (Biolegend, Cat no: 100711, Clone: 53-6.7), NKp46 (Biolegend, Cat no: 137606, Clone: 29A1.4), CD11c (Biolegend, Cat no: 117307, Clone: N418), Granzyme B (Biolegend, Cat no: 372208, Clone: QA16A02), IFN-γ (Biolegend, Cat no: 505849, Clone: XMG1.2), IFN-γ (Biolegend, Cat no: 505806, Clone: XMG1.2), CD86 (Biolegend, Cat no: 105011, Clone: GL-1), and Am Cyan Live/dead cell staining kit (Thermo Fischer Scientific, MA, USA). All antibodies were diluted at optimized dilutions prior to their use.

For immune cell profiling, the early-stage spontaneous lung metastasis was established as described above. One saline and three treatment groups (5× free CXCL10 chemokine, ImmunoBait with anti-ICAM-1, and erythrocyte hitchhiked ImmunoBait with anti-ICAM-1) were included into the study. Treatments were given starting one week after surgery. Three injection sets were given on day 7, 10 and 13 after primary tumor resection. One day after the last injection, mice were euthanized, and lungs were excised. A single cell suspension of lung cells was formed using a Lung dissociation kit (Miltenyi Biotec, Germany) according to manufacturer's instructions. The cells were stained with antibodies mentioned above and analyzed by flow cytometry (BD LSR Analyser II™, NJ USA).

For cytokine profiling, model establishment and treatments were the same as described above. One day after the last injection, mice were euthanized, and lungs were excised. For processing, 0.5 mL of cold tissue extraction buffer containing protease inhibitor was added to each lung and the lungs were homogenized using a high shear homogenizer (IKA T-10 Basic® Ultra turrax, Germany). Cytokine profiling was carried out using LEGENDplex™ Mouse Inflammation Panel (Biolegend, CA, USA) according to manufacturer's instructions and analyzed using flow cytometry (BD LSR Analyser II, NJ USA). CXCL10 concentration was quantified by ELISA.

Statistical Analysis

All experiments were repeated at least three times. All statistical analyses were carried out using Graphpad prism™ 8 software. All data are presented as mean±SEM. Student's t test, one-way ANOVA with Tukey's HSD analysis, or Mann-Whitney test were used to determine significance. For the analysis of Kaplan-Meier survival curves, Log-rank test for trend was used. p values represent different levels of significance; $p<0.05$*; $p<0.01$; $p<0.001$*, $p<0.0001$****. All the flow cytometry analyses were carried out using FlowJo™ 10 software.

Supplementary Methods

Materials

All chemicals and reagents were obtained from Sigma Aldrich (MO, USA) and used without further purification, unless otherwise mentioned. CXCL10/IP-10, IL-10, IL-15, GM-CSF was obtained from PeproTech (NJ, USA). Nunc™ Lab-Tek™ II Chamber Slide™ System, cell staining buffer, G418 (Geneticin), mouse IP-10 ELISA kit, Alexa Fluor 647 Ovalbumin, Alexa Fluor 750 NHS reagent, Alexa Fluor 647 NHS reagent, phosphate buffered saline(1×), Axygen™ 1.5 mL Self-Standing Screw Cap Tubes were obtained from Thermo Fischer Scientific (MA, USA). Human whole blood and serum was obtained from BioIVT (NJ, USA). Xenolight-D-luciferin potassium salt was obtained from Perkin Elmer (MA, USA). Lithium heparin coated microtainer tubes were obtained from BD medical technology (MA, USA). LEGENDplex™ Mouse Inflammation Panel with Filter Plate and anti-ICAM-1 antibody (Cat no: 116102, Clone: YN 1/1.7.2) was obtained from BioLegend (CA, USA). Tissue dissociation tubes and lung dissociation kit were obtained from Miltenyi Biotec (Germany). Tissue Tek OCT compound was obtained from Sakura Finetek (CA, USA). 0.9% saline solution was obtained from Teknova (CA, USA). Paraformaldehyde was obtained from Electron Microscopy sciences (PA, USA). Surgical equipment was obtained from Braintree Scientific, Inc. (MA, USA).

Nanoparticle Internalization Studies

Nanoparticle internalization was confirmed using flow cytometry and confocal microscopy. For flow cytometry analysis, $2\times10^6$ HLMVEC cells were plated in a 12-well plate and allowed to adhere overnight. Plates were then aspirated, and 1 ml of fresh media was added to each well. 30 μg of Alexa Fluor 647 labeled nanoparticles were added to each well and allowed to incubate for 20 mins or 6 h at 37° C. in an incubator. After the stipulated time points, media in the wells was completely aspirated and washed 3 times with PBS and the cells were gently scrapped using a cell scrapper. These cells were analyzed by confocal microscope (Upright Zeiss LSM 710 NLO ready).

Hitchhiked Erythrocyte Characterizations and Biocompatibility

Hitchhiking efficiency and the nanoparticles loaded on erythrocytes were determined using fluorescence measurements. For quantification using fluorescence, 25 μL of erythrocytes were lysed using deionized water and the nanoparticle content was quantified using fluorescence on a plate reader (Tecan Safire 2®, Switzerland). Nanoparticle attachment to erythrocytes was confirmed using scanning electron microscopy (Zeiss FESEM Supra 55VP, Zeiss FESEM Ultra 55, Germany). Briefly, the hitchhiked erythrocytes were fixed using 2.5% glutaraldehyde solution and washed in an increasing ethanol gradient before being chemically dried using hexamethyldisilazane (HMDS). Finally, the samples were sputter coated (EMT 150T ES metal sputter coater, PA USA) prior to imaging.

For biocompatibility studies, osmotic fragility and agglutination assays were carried out as previously described.[1]

In Vitro Shear Studies

Nanoparticles were labeled by Alexa Fluor 647-OVA and used for the shear studies. For low shear studies, hitchhiked murine erythrocytes were incubated in 1 mL of FBS on a tube revolver at 12 rpm at 37° C. After incubation for 20 mins, the cells were pelleted by centrifugation at 250 g for 5 mins and resuspended to 10% v/v in 1×PBS. 25 μL of erythrocytes were then lysed using deionized water and the remaining drug content was quantified using fluorescence on a plate reader (Tecan Safire 2®, Switzerland).

For high shear studies, hitchhiked murine erythrocytes were incubated in 10 mL of FBS. A rotatory shear (6 Pa) was applied to erythrocytes in serum using a cylindrical couette viscometer (1 mm gap, AR-G2 rheometer, TA instruments) for 20 mins. The samples were maintained at 37° C. during the application of shear using a water jacket. These conditions simulate high shear physiological environment. After 20 mins, the cells were pelleted by centrifugation at 250 g for 10 mins and resuspended to 10% v/v in 1×PBS. 25 μL of erythrocytes were then lysed using deionized water and the remaining nanoparticle content was quantified using fluorescence on a plate reader (Tecan Safire 2®, Switzerland) and confirmed using scanning electron microscopy (Zeiss FESEM Supra 55VP, Zeiss FESEM Ultra 55, Germany).

Nanoparticle Distribution within the Lungs

For nanoparticle distribution within the diseased lungs, $1\times10^6$ 4T1-Luc cells were injected orthotopically into the left mammary fat pad of female Balb/c mice. 19 days after inoculation, tumors were surgically resected. 28 days after tumor resection, mice were injected with Alexa Fluor 647 labeled nanoparticles with anti-ICAM-1 and erythrocyte hitchhiked fluorescent nanoparticles with anti-ICAM-1. 20 mins after the injection, the mice were euthanized, and the intact lungs were collected. Lungs were washed twice with cold 1×PBS before being fixed in a 4% paraformaldehyde solution overnight. The fixed lungs were then frozen in Tissue Tek OCT compound (Sakura Finetek, CA, USA) and sectioned using a cryostat (Leica CM1950, Germany). The sectioned tissue was mounted using Fluroshield® to stain for DAPI (Ex/Em 340/488 nm) and were analyzed using confocal microscope (Upright Zeiss LSM 710 NLO ready, Germany).

In Vivo Biodistribution Studies in Healthy Mice

For biodistribution study with different PLGAs, healthy female Balb/c mice were used. Alexa Fluor 750-OVA encapsulating NPs and hitchhiked NPs (n=3 for all groups) were injected intravenously into the tail vein. Mice were sacrificed at 20 mins after the injection and organs (liver, lungs, spleen, kidneys, heart, brain and blood) were harvested for further processing. For comprehensive biodistribution, Alexa Fluor 750-OVA encapsulating NPs, hitchhiked NPs, Alexa Fluor 750-OVA encapsulating NPs with anti-ICAM-1 and hitchhiked NPs with anti-ICAM-1 (n=3 for free NPs and n=6 for hitchhiked NPs) were injected intravenously into the tail vein. Mice were sacrificed at 20 mins, 2 h, 6 h, and 24 h after the injection and organs (liver, lungs, spleen, kidneys, heart, brain and blood) were harvested for further processing. For processing, 1 mL of cold RIPA lysis buffer (1×) was added to each organ and the organs were homogenized using a high shear homogenizer (IKA T-10 Basic® Ultra turrax, Germany) and the nanoparticle content was quantified by fluorescence measurement on a plate reader (Tecan Safire 2®, Switzerland).

Late Stage Efficacy in a Breast Cancer Spontaneous Lung Metastasis Model

For the late stage efficacy, spontaneous lung metastasis model was established by orthotopic injection of $1\times10^6$ 4T1-Luc into the left mammary fat pad of female Balb/C mice. 32 days after the inoculation, tumors were surgically resected. Treatments were given starting one week after surgery. Four injections were given every two days. Two days after the last injection (on day 50), the mice were euthanized, intratracheally injected with India ink solution and the lungs were excised and fixed using Feket's solution as previously described.[2] The fixed lungs were used for counting of the surface nodules.

TABLE 4

Properties of four PLGA candidates.

| | PLGA-a | PLGA-b | PLGA-c | PLGA-d |
|---|---|---|---|---|
| L:G ratio* | 50:50 | 50:50 | 85:15 | 65:35 |
| End-group | Ester-end | Acid-end | Ester-end | Acid-end |

*Molar ratio of lactic acid to glycolic acid in the polymer

REFERENCES

1. Grivennikov, S. I., Greten, F. R. & Karin, M. Immunity, Inflammation, and Cancer. *Cell* 140, 883-899 (2010).
2. Ha, D. et al. Differential control of human Treg and effector T cells in tumor immunity by Fc-engineered anti-CTLA-4 antibody. *Proc Natl Acad Sci USA* 116, 609-618 (2019).
3. Hubbell, J. A., Thomas, S. N. & Swartz, M. A. Materials engineering for immunomodulation. *Nature* 462, 449-460 (2009).
4. Wing, J. B., Tanaka, A. & Sakaguchi, S. Human FOXP3(+) Regulatory T Cell Heterogeneity and Function in Autoimmunity and Cancer. *Immunity* 50, 302-316 (2019).
5. Tanoue, T. et al. A defined commensal consortium elicits CD8 T cells and anti-cancer immunity. *Nature* 565, 600-605 (2019).
6. Singhal, S. et al. Human tumor-associated monocytes/macrophages and their regulation of T cell responses in early-stage lung cancer. *Sci Transl Med* 11 (2019).
7. O'Brien, K. L. & Finlay, D. K. Immunometabolism and natural killer cell responses. *Nat Rev Immunol* 19, 282-290 (2019).
8. Li, Q. & Verma, I. M. NF-kappaB regulation in the immune system. *Nat Rev Immunol* 2, 725-734 (2002).
9. Zou, W. Regulatory T cells, tumour immunity and immunotherapy. *Nat Rev Immunol* 6, 295-307 (2006).
10. Libby, P. & Lichtman, A. I. Modulating Adaptive Immunity in Vascular Disease: CD4 to the Fore. *J Am Coll Cardiol* 73, 1824-1826 (2019).
11. Restifo, N. P., Dudley, M. E. & Rosenberg, S. A. Adoptive immunotherapy for cancer: harnessing the T cell response. *Nat Rev Immunol* 12, 269-281 (2012).
12. Carbo, A. et al. Systems modeling of molecular mechanisms controlling cytokine-driven CD4+ T cell differentiation and phenotype plasticity. *PLoS Comput Biol* 9, e1003027 (2013).
13. Salabarria, A. C. et al. Local VEGF-A blockade modulates the microenvironment of the corneal graft bed. *Am J Transplant* (2019).
14. Tan, R. P. et al. Bioactive Materials Facilitating Targeted Local Modulation of Inflammation. *JACC Basic Transl Sci* 4, 56-71 (2019).
15. Dellacherie, M. O., Seo, B. R. & Mooney, D. J. Macroscale biomaterials strategies for local immunomodulation. *Nature Reviews Materials* (2019).
16. Zhao, Z. M., Ukidve, A., Dasgupta, A. & Mitragotri, S. Transdermal immunomodulation: Principles, advances and perspectives. *Adv Drug Deliver Rev* 127, 3-19 (2018).
17. Zhao, Z., Ukidve, A., Krishnan, V. & Mitragotri, S. Effect of physicochemical and surface properties on in vivo fate of drug nanocarriers. *Adv Drug Deliv Rev* (2019).
18. Blanco, E., Shen, H. & Ferrari, M. Principles of nanoparticle design for overcoming biological barriers to drug delivery. *Nat Biotechnol* 33, 941-951 (2015).
19. Pardoll, D. M. The blockade of immune checkpoints in cancer immunotherapy. *Nat Rev Cancer* 12, 252-264 (2012).
20. Rosenberg, S. A. Decade in review-cancer immunotherapy: entering the mainstream of cancer treatment. *Nat Rev Clin Oncol* 11, 630-632 (2014).
21. Qian, Y. et al. Molecular-Targeted Immunotherapeutic Strategy for Melanoma via Dual-Targeting Nanoparticles Delivering Small Interfering RNA to Tumor-Associated Macrophages. *Acs Nano* 11, 9536-9549 (2017).
22. Riley, R. S., June, C. H., Langer, R. & Mitchell, M. J. Delivery technologies for cancer immunotherapy. *Nat Rev Drug Discov* 18, 175-196 (2019).
23. Yang, W. et al. In Situ Dendritic Cell Vaccine for Effective Cancer Immunotherapy. *Acs Nano* 13, 3083-3094 (2019).

24. Chen, D. S. & Mellman, I. Oncology meets immunology: the cancer-immunity cycle. *Immunity* 39, 1-10 (2013).
25. Nagarsheth, N., Wicha, M. S. & Zou, W. P. Chemokines in the cancer microenvironment and their relevance in cancer immunotherapy. *Nat Rev Immunol* 17, 559-572 (2017).
26. Homey, B., Muller, A. & Zlotnik, A. Chemokines: agents for the immunotherapy of cancer? *Nat Rev Immunol* 2, 175-184 (2002).
27. Makadia, H. K. & Siegel, S. J. Poly Lactic-co-Glycolic Acid (PLGA) as Biodegradable Controlled Drug Delivery Carrier. *Polymers-Basel* 3, 1377-1397 (2011).
28. Muro, S. et al. Control of endothelial targeting and intracellular delivery of therapeutic enzymes by modulating the size and shape of ICAM-1-targeted carriers. *Mol Ther* 16, 1450-1458 (2008).
29. Scherpereel, A. et al. Cell-selective intracellular delivery of a foreign enzyme to endothelium in vivo using vascular immunotargeting. *Faseb J* 15, 416-426 (2001).
30. Guo, P. et al. ICAM-1 as a molecular target for triple negative breast cancer. *P Natl Acad Sci USA* 111, 14710-14715 (2014).
31. Lee, S. J., Park, S. Y., Jung, M. Y., Bae, S. M. & Kim, I. S. Mechanism for phosphatidylserine-dependent erythrophagocytosis in mouse liver. *Blood* 117, 5215-5223 (2011).
32. Oldenborg, P. A. et al. Role of CD47 as a marker of self on red blood cells. *Science* 288, 2051-+(2000).
33. Brenner, J. S. et al. Red blood cell-hitchhiking boosts delivery of nanocarriers to chosen organs by orders of magnitude. *Nat Commun* 9 (2018).
34. Pan, D. C. et al. Nanoparticle Properties Modulate Their Attachment and Effect on Carrier Red Blood Cells. *Sci Rep-Uk*8 (2018).
35. Anselmo, A. C. et al. Delivering Nanoparticles to Lungs while Avoiding Liver and Spleen through Adsorption on Red Blood Cells. *Acs Nano* 7, 11129-11137 (2013).
36. Clancy-Thompson, E. et al. Melanoma Induces, and Adenosine Suppresses, CXCR3-Cognate Chemokine Production and T-cell Infiltration of Lungs Bearing Metastatic-like Disease. *Cancer Immunol Res* 3, 956-967 (2015).
37. Binnewies, M. et al. Understanding the tumor immune microenvironment (TIME) for effective therapy. *Nat Med* 24, 541-550 (2018).
38. Wang, H. & Mooney, D. J. Biomaterial-assisted targeted modulation of immune cells in cancer treatment. *Nat Mater* 17, 761-772 (2018).
39. Tokunaga, R. et al. CXCL9, CXCL10, CXCL11/CXCR3 axis for immune activation—A target for novel cancer therapy. *Cancer Treat Rev* 63, 40-47 (2018).
40. Hu, J. M. et al. CXCL9, CXCL10 and IFN gamma favor the accumulation of infused T cells in tumors following IL-12 plus doxorubicin treatment. *J Immunol* 196 (2016).
41. Pfirschke, C., Siwicki, M., Liao, H. W. & Pittet, M. J. Tumor Microenvironment: No Effector T Cells without Dendritic Cells. *Cancer Cell* 31, 614-615 (2017).
42. Zhu, J. F. & Paul, W. E. CD4 T cells: fates, functions, and faults. *Blood* 112, 1557-1569 (2008).
43. Quail, D. F. & Joyce, J. A. Microenvironmental regulation of tumor progression and metastasis. *Nat Med* 19, 1423-1437 (2013).
44. Palucka, K. & Banchereau, *J. Cancer* immunotherapy via dendritic cells. *Nat Rev Cancer* 12, 265-277 (2012).

References for Supplementary Information

1. Pan, D. et al. The Effect of Polymeric Nanoparticles on Biocompatibility of Carrier Red Blood Cells. *PLoS One* 11, e0152074 (2016).
2. Miretti, S. et al. A Mouse Model of Pulmonary Metastasis from Spontaneous Osteosarcoma Monitored In Vivo by Luciferase Imaging. *Plos One* 3 (2008).

Example 4: Lung Metastasis-Driven Cancer Immunotherapy for Local and Systemic Tumor Suppression Eliciting an immune response against tumor at their primary location is difficult due to immunosuppressive microenvironment and intrinsic immune inaccessibility. Metastasis, especially in lungs, exposes cancer cells and opens a unique opportunity for immunization. Described herein is a platform, erythrocyte anchored systemic immunotherapy, that leverages metastasis, converting the physiological adversity into a unique therapeutic opportunity for local and systemic tumor suppression. Briefly, chemokine nanoparticles were anchored to erythrocytes which enabled their dominant deposition in the vicinity of metastatic cancer cells in lungs while minimizing systemic accumulation, which led to a significant infiltration of effector immune cells and led to in-situ immunization without the need of any specific antigen. In vivo results based on a spontaneous breast cancer lung metastasis model showed that this strategy remarkably inhibited the progression of local lung metastasis and significantly extended the animal survival. Moreover, the in-situ immunization by this strategy elicited systemic immunity that significantly suppressed the growth of re-challenged distant tumors. These findings indicate that lung metastasis opens an effective opportunity for cancer vaccination and the erythrocyte anchored systemic immunotherapy is a potent strategy for leveraging this opportunity for treating various cancers.

Cancer immunotherapy has induced a paradigm shift in the approaches to treat cancer. Various immunotherapeutic approaches have been explored in the last few decades, amongst which, immune checkpoint inhibitors and adaptive T cell therapy have achieved significant clinical success recently.1-7 Particularly, cancer immunotherapy has shown significant impact in improving the overall as well as progression-free survival of patients that were thought to be medically incurable by conventional interventions such as chemotherapy.2, 8 One of the advantages of cancer immunotherapy is engaging body's own immune system against the defective cells, thereby having potential to induce an immunological memory and prevent recurrence.9, 10 Despite these prominent potentials of cancer immunotherapy, raising an immune response against tumor at their primary location remains a challenge. This is primarily attributed to the large size of the tumors that reduces the exposure of tumor cells and the immunosuppressive environment of the tumors that inhibits the induction of an anti-tumor immunity.11-13

In many patients, by the time cancer is diagnosed, tumor cells have already metastasized to a secondary organ.14, 15 Due to its unique physiological features, lung is a primary site for metastasis, with cells from different primary origins of the tumor, finally harboring into lungs and growing uncontrollably.16 Owing to its aggressive nature, metastasis is generally more difficult to manage than the primary tumors, with no standalone therapies currently available.17, 18 Induction of an effective immune response at the metastasis sites is also hampered by the rapid development of an immunosuppressive microenvironment. Particularly, the chemokine landscape at the metastatic sites undergoes endogenous changes, limiting the homing of effector immune cells and thereby blocking the immune responses.19-21 However, even with the quick change of its microenvironment, metastasis (especially early metastasis) usually exposes cancer cells to highly perfused and immunoactive organs such as the lung. This opens an opportunity for taking advantage of this unique physiology of metastasis for eliciting an active anti-cancer immune response.

Here, we leverage exposed cancer cells in the lungs using erythrocyte-mediated lung targeting,22, 23. Specifically, we deliver an unprecedented amount of immunoactive nanoparticles to co-localize with the metastatic cancer cells in the lung, a method we refer to as Erythrocyte Anchored Systemic Immunotherapy (EASI, also referred to herein interchangeably as "EH-ImmunoBait"), which controls progression of metastasis and generates an in situ adaptive response for systemic tumor suppression. We engineered ImmunoBaits, nanoparticles that encapsulate chemokine (CXCL10), capable of attracting effector immune cells, and anchored them onto the surface of erythrocytes. By engineering their interactions with the carrier erythrocytes, the ImmunoBaits specifically dislodge from the erythrocyte surface and accumulate in metastatic sites in the lungs. The site-specific accumulation of ImmunoBait restored the local chemokine gradient and attracts effector immune cells to elicit a localized cytotoxic immune response which in turn induced systemic immunity. Our in vivo results based on a spontaneous breast cancer lung metastasis model showed that EASI resulted in a decrease in the metastatic tumor burden and improved survival. Moreover, the in-situ immunization in the metastatic lungs led to systemic immunity, which suppressed distant tumor growth after tumor rechallenge. These findings highlight the ability of EASI to convert the biological adversity of metastasis into a unique therapeutic opportunity against metastatic cancers.

Engineering Material Properties of Nanoparticles for Optimal Targeting

Figure 35:
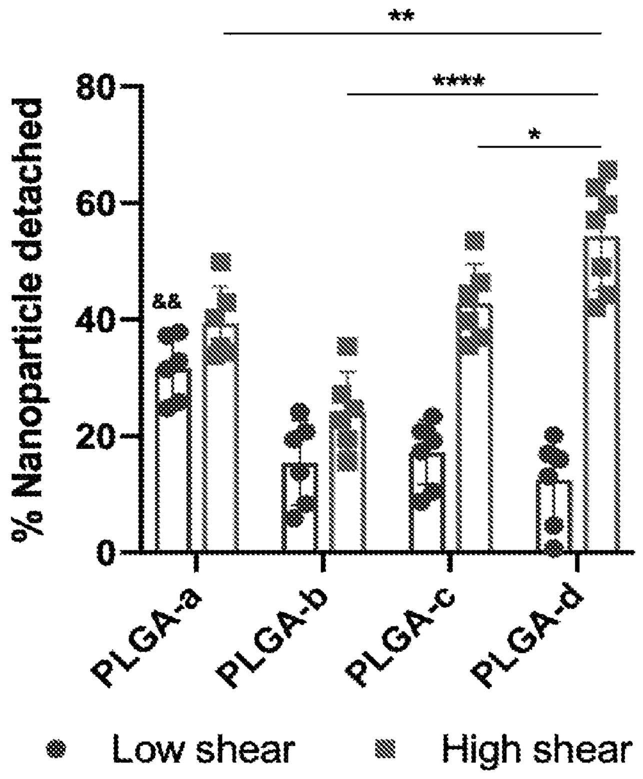

The anchoring of nanoparticles to erythrocytes is a non-covalent binding process which requires efficient surface contact and erythrocyte membrane spreading, and this process is mediated by non-covalent interactions between the erythrocyte membrane and nanoparticles including electrostatic interactions, hydrophobic interactions, and hydrogen bonding (FIGS. 34A-34E). With this understanding, we conducted a set of experiments to engineer the composition (lactic to glycolic acid ratio, L:G ratio) and surface chemistry (acid or ester end)24 of poly(lactic-co-glycolic acid) (PLGA) nanoparticles to achieve optimal organ targeting. To that effect, four different PLGA polymers (Table 5) were selected to prepare nanoparticles. In general, a high L:G ratio leads to a higher hydrophobicity. An acid-end (rather than ester-end) enables the formation of hydrogen bonds with cell membranes. Though different PLGA nanoparticles could anchor to the erythrocytes (FIG. 19), the PLGA nanoparticle with a high L:G ratio and an acid-end (PLGA-d), which has high hydrophobicity and ability to form hydrogen bonds, exhibited the highest binding efficiency to erythrocytes (FIG. 14A). The biocompatibility assays (FIG. 14B and FIGS. 20A-20C) indicated that PLGA-d caused relatively minimum damage to the carrier erythrocytes compared to the other designs. Interestingly, in vitro shear study experiments indicated that an acid-ended polymer with a higher L:G ratio led to a higher percentage of nanoparticle detachment at a high shear stress corresponding to that in the lung capillaries (6 Pa)25-27 and a lower premature detachment at a lower shear stress corresponding to that in the veins25, 26 (FIG. 14C, FIG. 35). PLGA-d showed maximum detachment at the high shear stress among all the PLGA candidates. Furthermore, in vivo biodistribution data (FIG. 22A) revealed that organ-specific targeting of different PLGA nanoparticles that hitchhiked on erythrocytes correlates with the in vitro shear data. Different PLGA nanoparticles that hitchhiked on erythrocytes were targeted to specific organs depending on their binding strength to erythrocytes. Overall, erythrocytes with PLGA-d anchored on them, exhibited the best lung targeting ability (FIG. 14D and FIG. 14E). Considering high binding efficiency, minimum damage to the carrier erythrocytes, and excellent targeting to the lung, PLGA-d (65:35 L:G ratio, acid-end) was established as the lead candidate and used for all the later studies in this example.

In vivo tracking of the erythrocyte hitchhiking system (FIGS. 36A-36F) indicated that the anchored nanoparticles were quickly detached from the carrier erythrocytes within 5 mins and deposited primarily in the lung while the carrier erythrocytes remained in circulation for at least 24 hrs. Lung deposition of hitchhiked nanoparticles is based on: 1) Mechano-induced nanoparticle transfer to the endothelium during mechanical squeezing of erythrocytes as they flow through narrow capillaries and 2) Shear-induced detachment of nanoparticles that shear-off in narrow lung capillaries. Presence of high capillary density and being the organ of first pass after intravenous administration, together, make lungs the primary site for particle deposition.23, 28 Upon particle desorption from the erythrocytes, robust interactions between the nanoparticle and endothelium must be rapidly achieved to assure prolonged particle retention. ICAM-1 has been reported to be overexpressed in the lung endothelium (especially in the diseased lungs)29-31 and certain cancers such as triple negative breast cancers.31, 32 Based on this, we explored whether the attachment of anti-ICAM-1 antibody (data not shown) could enhance the interactions between the detached nanoparticles and the lung endothelium. aICAM-1 antibody was efficiently attached to free nanoparticles and hitchhiked nanoparticles. Meanwhile, the attachment efficiency of aICAM-1 to free nanoparticles and hitchhiked nanoparticles was 15.4±6.7 μg antibody/mg nanoparticle and 6.5±3.4 μg antibody/mg nanoparticle, respectively. The attachment of anti-ICAM-1 antibody did not significantly influence the in vitro detachment of nanoparticles from erythrocytes under shear (FIG. 37). In a 2-D cell culture study, confocal laser scanning microscopy (CLSM) imaging data (FIG. 14F) indicated that the attachment of anti-ICAM-1 antibody to PLGA nanoparticles led to their enhanced interactions with the lung endothelial cells. Additionally, the time-course biodistribution data (FIG. 22B and FIG. 14G-14H) revealed that the attachment of anti-ICAM-1 antibody to nanoparticles that hitchhiked on erythrocytes significantly extended their retention in the lung, increasing the retention time from 20 mins to at least 6 hours.

ImmunoBait Anchoring onto Erythrocytes

Figures 14I, 14J, 14K, 14L, 14M:
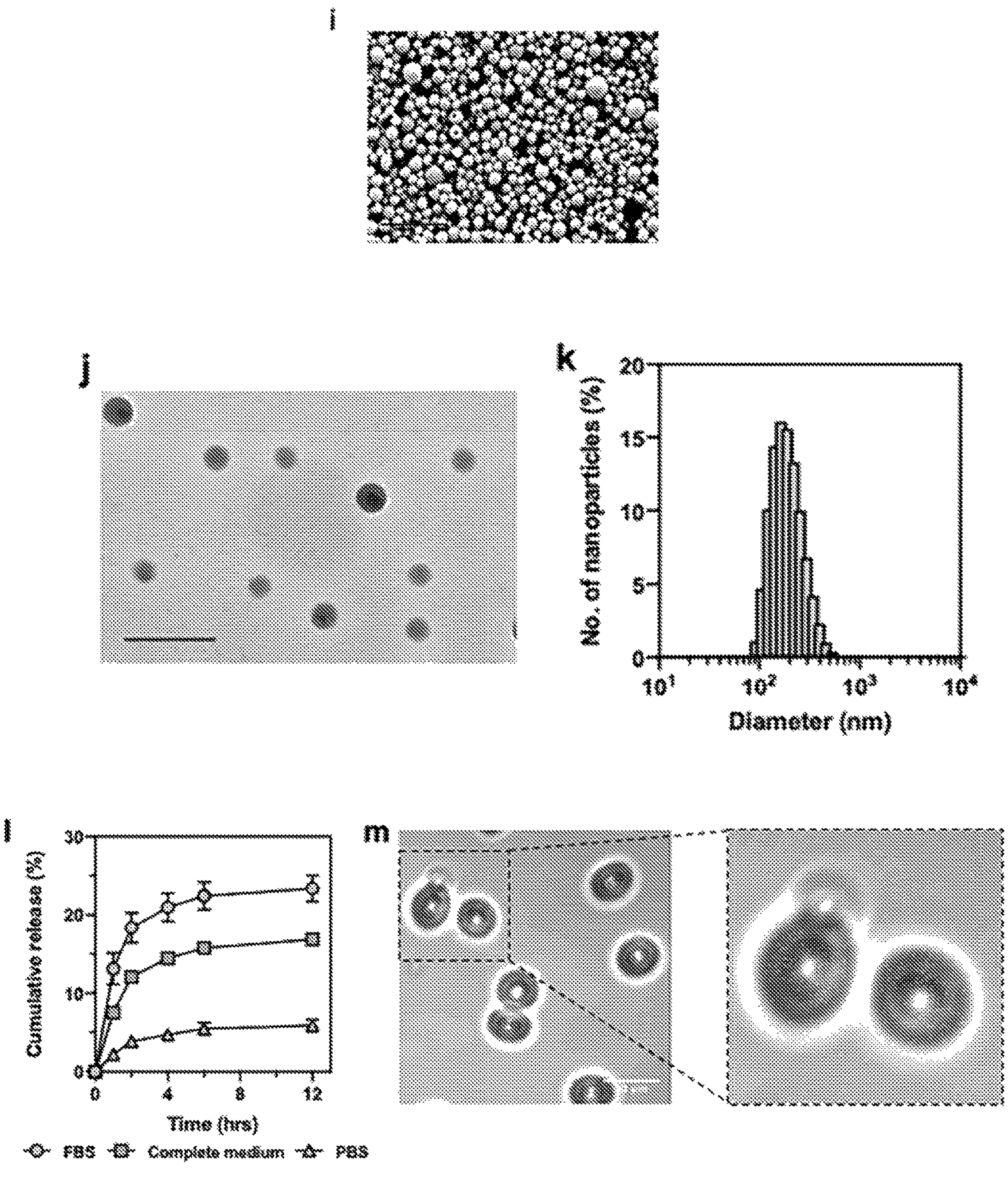
(FIG. 14I) Scanning electron microscopic (SEM) images of ImmunoBait. Scale bar, 1 μm.
(FIG. 14J) Transmission electron microscopic (TEM) images of ImmunoBait. Scale bar, 500 nm.
(FIG. 14K) Size distribution of ImmunoBait.
(FIG. 14L) Chemokine release kinetics from ImmunoBait in PBS, FBS, and complete medium (n=3).
(FIG. 14M) CLSM images of erythrocytes with ImmunoBait anchored on them. ImmunoBait was labeled with Alexa Fluor 647 which was conjugated to chemokine.

ImmunoBait particles with a loading of 1.88 μg/mg chemokine and encapsulation efficiency of 75%, were prepared using a double-emulsion method. Monodisperse, spherical ImmunoBait nanoparticles had an average diameter of 187.3 nm and a zeta-potential of −24.5 mV (FIG. 14I-14K). Release of chemokine from ImmunoBait exhibited a burst followed by a sustained release pattern (FIG.

Figures 14N, 14O, 14P, 14Q, 14R:
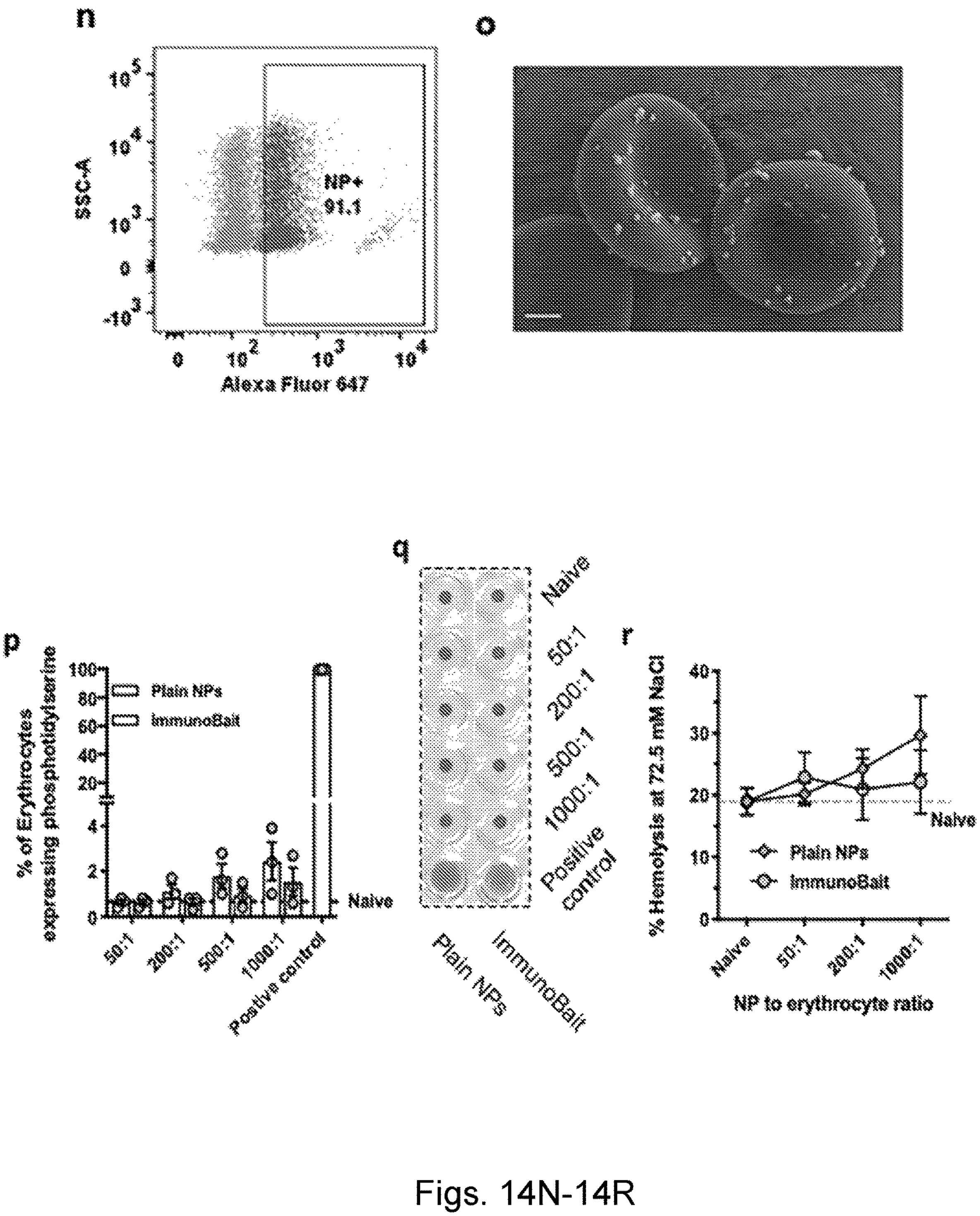
(FIG. 14N) Flow cytometry analysis of erythrocytes carrying Alexa Fluor 647 labeled ImmunoBait. ImmunoBait was labeled with Alexa Fluor 647 which was conjugated to chemokine. unboxed dots: plain erythrocytes; Boxed dots: erythrocytes carrying ImmunoBait.
(FIG. 14O) SEM images of ImmunoBait anchored on erythrocytes. Scale bar, 1 μm.
(FIG. 14P) Expression of phosphatidylserine on carrier erythrocytes after being hitchhiked by nanoparticles (n=3).
(FIG. 14Q) Agglutination of carrier erythrocytes hitchhiked by nanoparticles. 200 nm carboxylic polystyrene nanoparticles were used as a positive control in (FIG. 14P) and (FIG. 14Q).
Figures 38A, 38B:
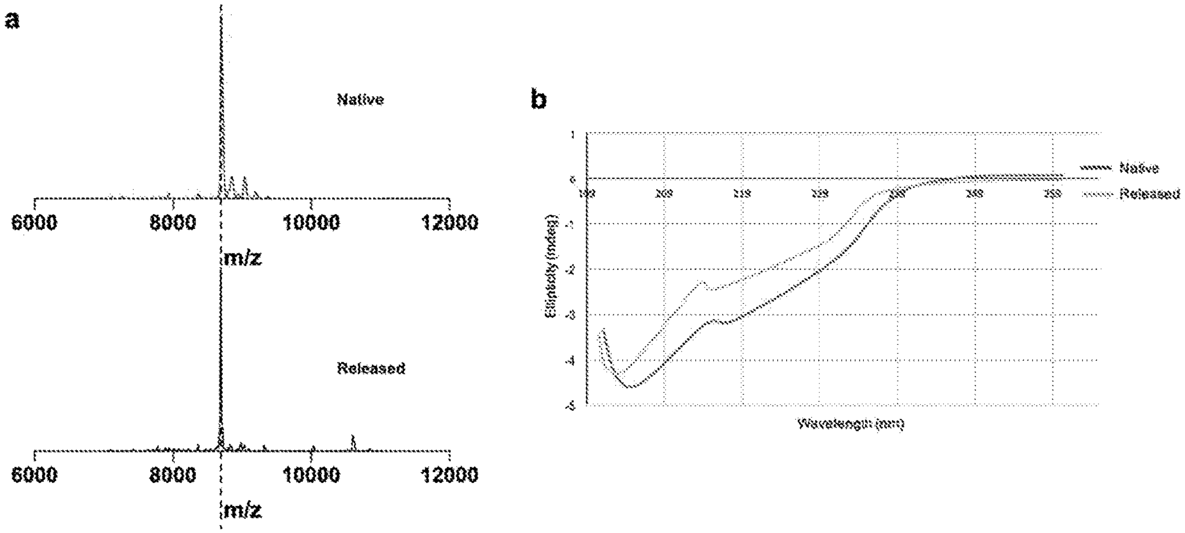
FIGS. 38A-38B depict the stability of CXCL10 following encapsulation into ImmunoBait.

14L). The released chemokine maintained good structural integrity, showing similar molecular weight and secondary structural patterns as the native chemokine (FIGS. 38A-38B). To test whether ImmunoBait can efficiently anchor to the erythrocytes, we labeled the chemokine with a fluorescent probe, Alexa Fluor 647. The CLSM data (FIG. 14M) indicated efficient anchoring of ImmunoBait onto mouse erythrocytes. By increasing the feed ratio of ImmunoBait to mouse erythrocytes, >90% of the mouse erythrocytes carried ImmunoBait (FIGS. 23A-23C and FIG. 14N). The scanning electron microscopy (SEM) imaging data confirmed efficient anchoring of ImmunoBait onto mouse erythrocytes (FIG. 14O). Apart from CXCL10, ImmunoBait that carried another chemokine (GM-CSF), cytokines (IL-2, IL-12, and IL-15), or an immune checkpoint inhibitor (anti-PD-1 antibody) were also efficiently anchored to mouse erythrocytes (FIG. 24). Furthermore, ImmunoBait could also anchor onto human erythrocytes, though at a lower binding efficiency (FIGS. 25A-25B).

Next, we performed a set of assays to detect any adverse effects caused to the carrier erythrocytes by the anchoring of ImmunoBait. Hitchhiking of ImmunoBait at all tested ratios did not cause obvious overexpression of surface phosphatidylserine (a marker for erythrocyte senescence and damage33, 34) on the carrier erythrocytes (FIG. 14P). In addition, the data from the agglutination assay28 (FIG. 14Q) and osmotic fragility assay35 (FIG. 26 and FIG. 14R) revealed that anchoring of ImmunoBait resulted in minimal changes to the agglutination and sensitivity to osmotic stress of the carrier erythrocytes. These biocompatibility studies indicated that the anchoring of ImmunoBait onto erythrocytes caused minimal damage to the carrier erythrocytes.

Figures 39A, 39B:
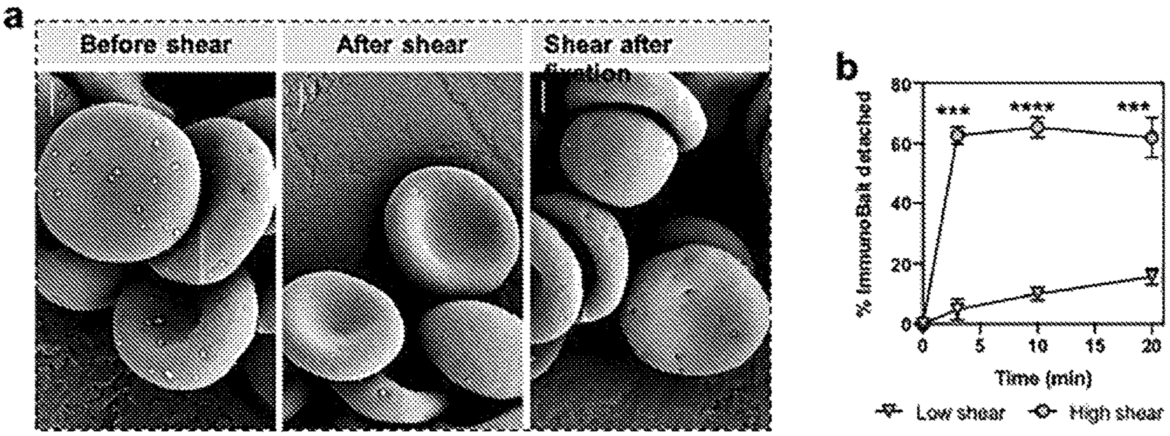
Figures 40A, 40B:
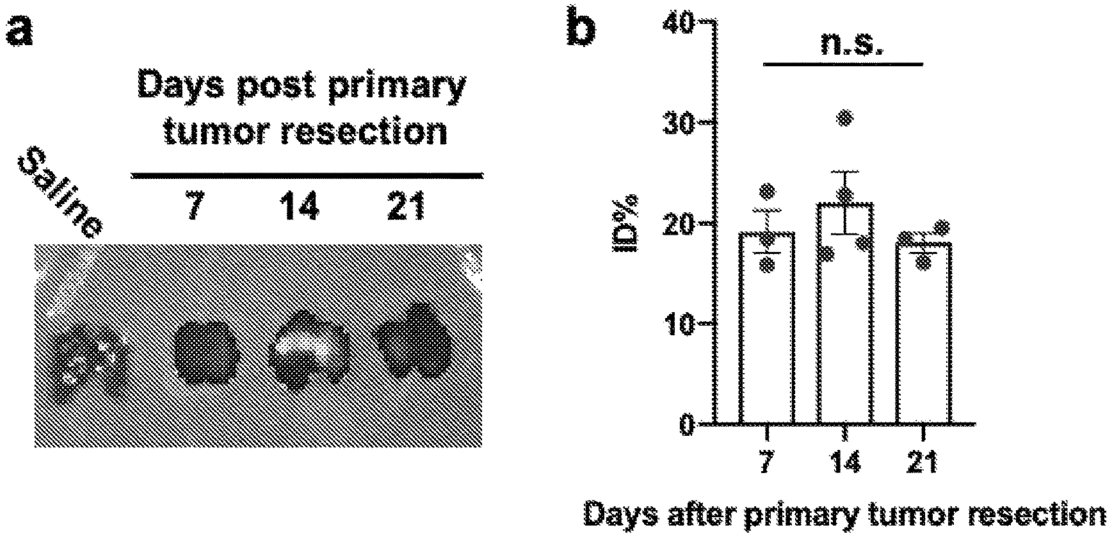
FIGS. 40A-40B depict lung accumulation of ImmunoBait delivered by EH with the progression of lung metastasis. On days 7, 14, and 21 after primary tumor resection, different sets of mice were IV administered with EASI with aICAM-1 (n=3-4). 20 mins after injections, mice were euthanized and organs were collected for fluorescence measurement using IVIS. ImmunoBait NPs were labeled by encapsulating AF647-Ovalbumin.
Figures 41A, 41B:
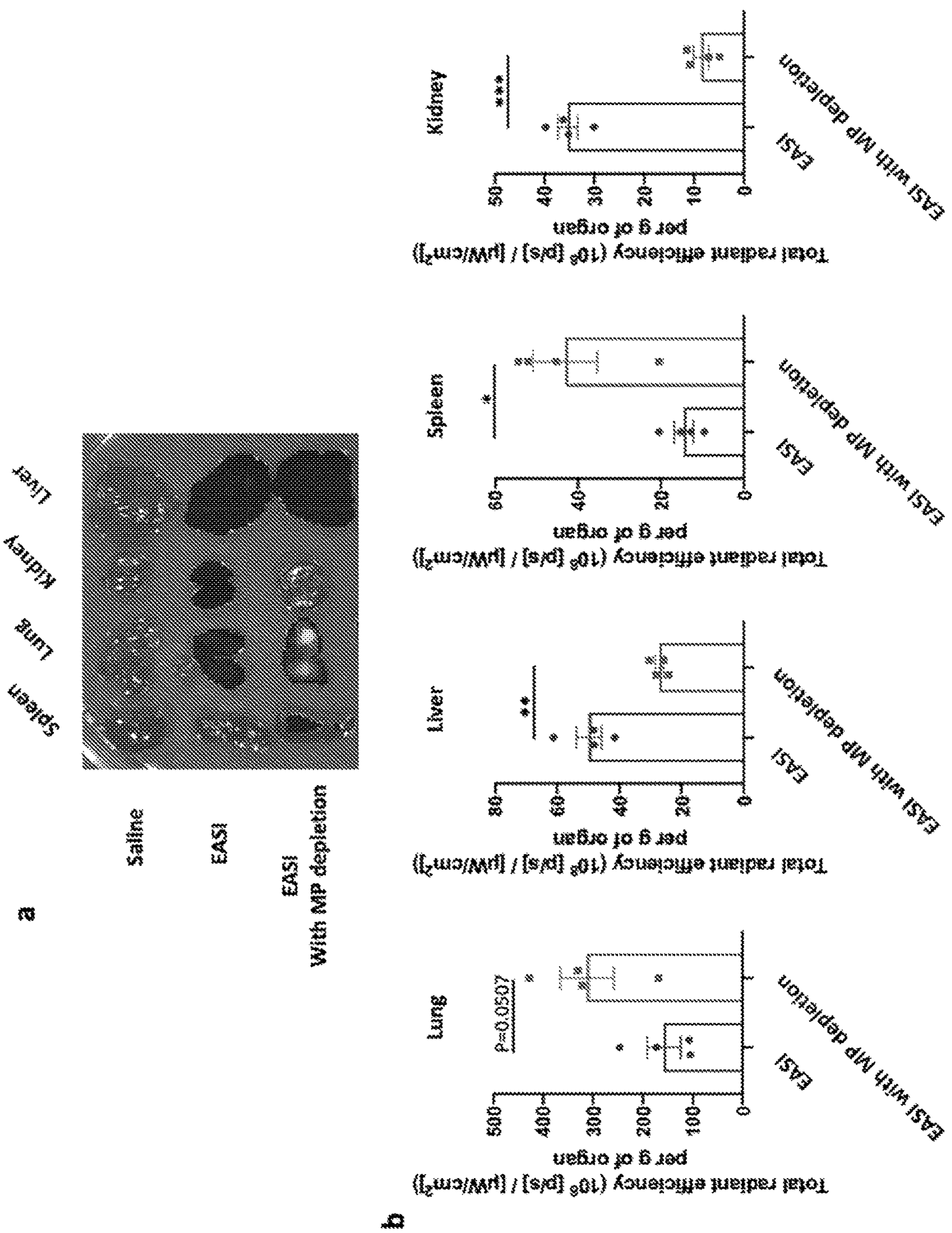
FIGS. 41A-41B demonstrate that ImmunoBait Nanoparticles delivered to metastatic lungs by erythrocyte hitchhiking were not entrapped in phagocytes. Phagocytes (mainly tissue macrophages) were depleted by IV administration of 200 μL of Clodrosome® containing 5 mg/mL Clodronate 48 h before IV injection of EASI. ImmunoBait NPs were labeled by encapsulating AF647-Ovabumin. 20 min after EASI administration, mice were euthanized and major organs including lung, liver, spleen, and kidney were collected and imaged using IVIS. Fluorescence intensity (radiant efficiency) of ROI was quantified and analyzed.

Targeted Delivery of ImmunoBait to the Metastatic Sites Using EASI LED to Restoration Of Local Chemokine Gradient In vitro shear study data (FIGS. 39A-39B) revealed that detachment of ImmunoBait from erythrocytes is shear-dependent and >60% of the nanoparticles were released from the carrier erythrocytes within 3 mins at the shear stress expected in the lungs (6 Pa)23, 25-27. Next, we conducted a biodistribution study in an early-stage breast cancer spontaneous lung metastasis model. As shown in FIGS. 16C-16E, by hitchhiking ImmunoBait on the erythrocytes, a decreased number of nanoparticles accumulated in the liver, which is consistent with the previous reports.23, 28 Significantly more ImmunoBait was delivered to the lungs that contained metastases in comparison to their free counterparts. The inclusion of anti-ICAM-1 antibody allowed ImmunoBait anchored onto erythrocytes to accumulate in diseased lungs ~27-fold higher than the particles alone, assessed 20 minutes after intravenous administration. Furthermore, anti-ICAM-1 antibody containing ImmunoBait was retained in the lungs for at least 6 hours. As shown in FIG. 16D, the enhanced delivery of ImmunoBait to the metastatic lungs resulted in an impressively high lung to blood ratio of 108, forming the basis for the establishment of payload gradients. Further biodistribution study indicated that ImmunoBait could be deposited in metastatic lungs at various stages of metastases with a similar efficiency (FIGS. 40A-40B), even in a late-stage model under advanced pathological conditions (FIG. 16F), indicating that the change of the tumor physiology minimally affects ImmunoBait deposition. Moreover, depletion of phagocytes did not reduce the deposition of ImmunoBait in metastatic lungs (FIGS. 41A-41B), indicating that ImmunoBait were not primarily taken up by lung phagocytes.

Figure 16O:
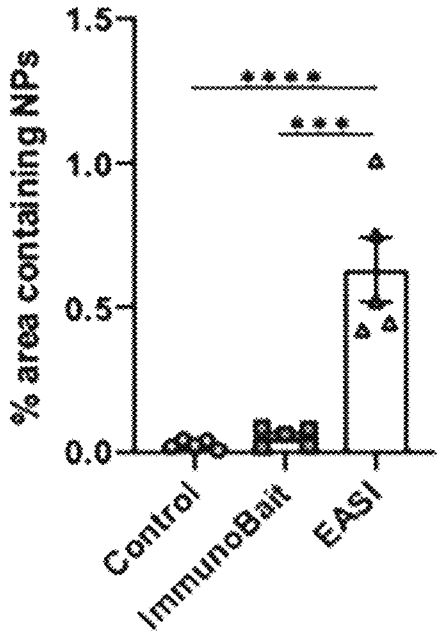
(FIG. 16O) Percent area containing ImmunoBait NPs calculated from confocal images as represented in (FIG. 16G) (n=5). Calculation was conducted in ImageJ. Significantly different (One-way ANOVA followed by Tukey's HSD test): * $p<0.001$, ** $p<0.0001$.

We then analyzed lung sections to investigate the distribution of ImmunoBait within metastatic lungs. As shown in FIGS. 16G and 16O, EASI was able to deliver a substantial amount of ImmunoBait to these hard-to-reach metastatic sites. Particularly, most of the ImmunoBait was distributed around the metastatic nodules while some also went deep into the metastatic nodules.

Figure 16R:
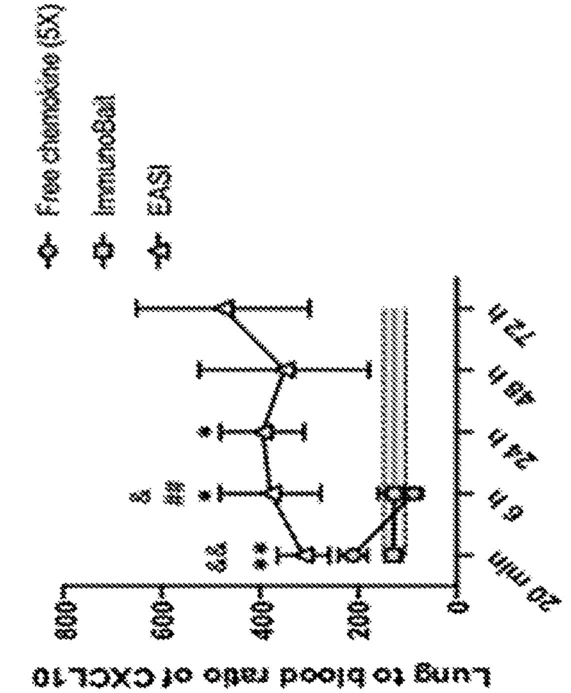
(FIG. 16R) Lung to blood ratio of CXCL10 chemokine concentration after administration (n=4-6). In (FIG. 16P-16**R), the horizontal bars indicate the mean±s.e.m. of the corresponding levels in control mice before treatments. Significantly different compared to the control before treatment (One-way ANOVA followed by Tukey's HSD test or student's t test): * $p<0.05$,  $p<0.01$, * $p<0.001$. Significantly different compared to the free chemokine (5×) group (One-way ANOVA followed by Tukey's HSD test or student's t test): ## $p<0.01$. Significantly different compared to the ImmunoBait group (One-way ANOVA followed by Tukey's HSD test or student's t test): & $p<0.05$, && $p<0.01$, &&&& $p<0.0001$. Data in (FIGS. 16O-16R) are presented as mean s.e.m.
Figure 16Q:
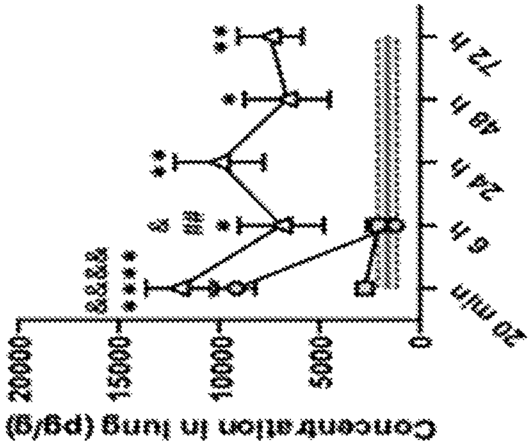
(FIG. 16Q) Concentration of CXCL10 chemokine in the lung after intravenous administration of CXCL10 formulations (n=4-6).
Figure 16P:
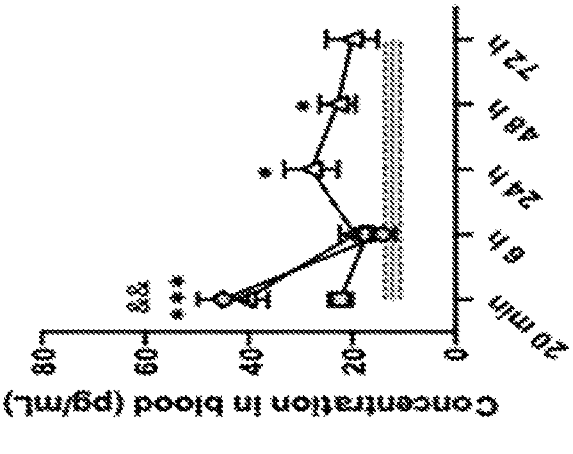
(FIG. 16P) Concentration of CXCL10 chemokine in the blood 20 min, 6 h, 24 h, 48 h, and 72 h after intravenous administration of CXCL10 formulations (n=4-6).
Figures 42A, 42B, 42C:
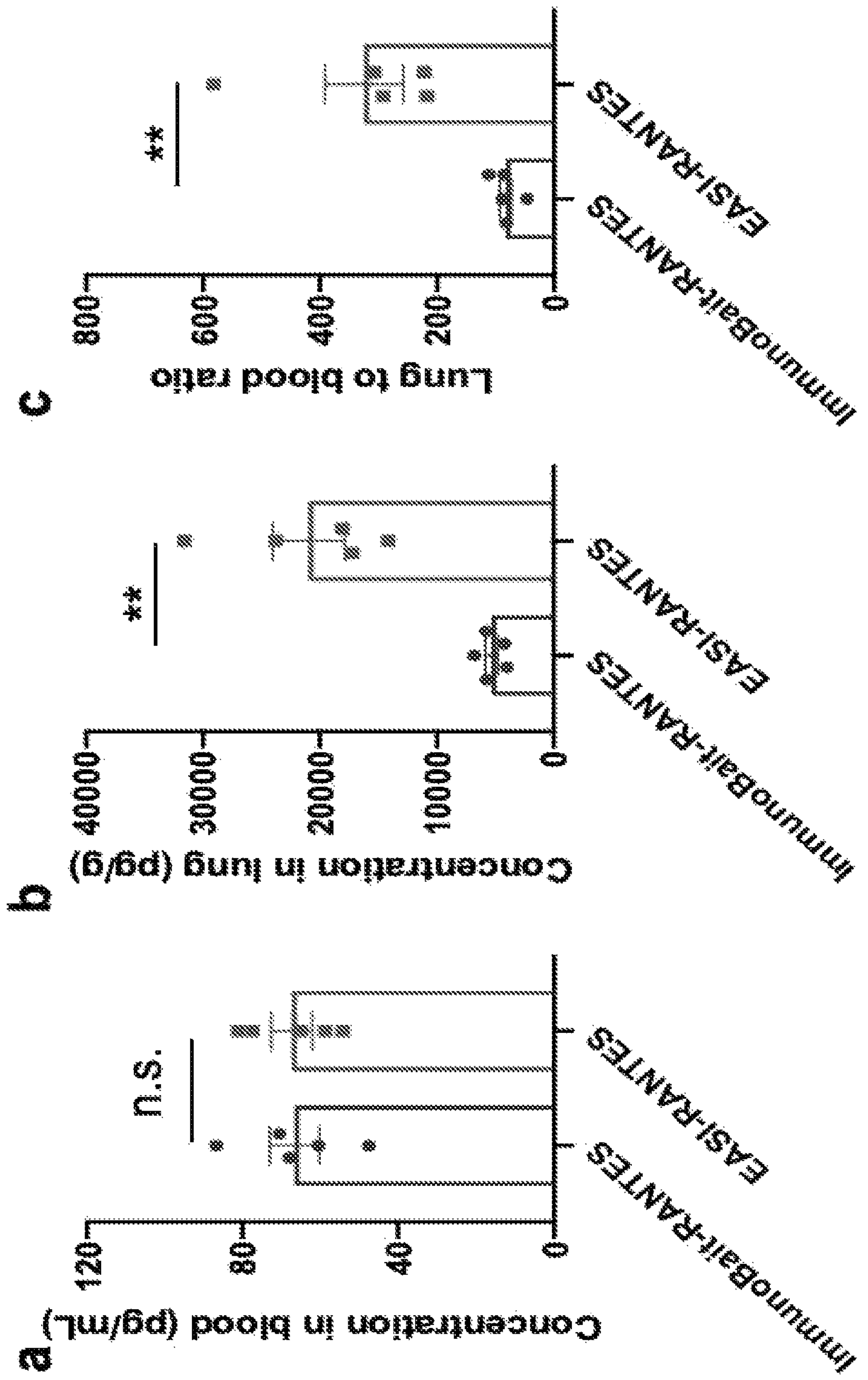
FIGS. 42A-42C demonstrate delivery of RANTES (a chemokine) by erythrocyte hitchhiking. ImmunoBait-RANTES was prepared by encapsulating RANTES in PLGA nanoparticles. Anti-ICAM-1 antibody was coated to ImmunoBait-RANTES. 6 h after IV administration of formulations, RANTES concentrations in the serum and lung homogenates were quantified by ELISA.

Next, we conducted a time-course study to monitor the CXCL10 chemokine gradients in the breast cancer spontaneous lung metastasis model (FIG. 16H). As shown in FIGS. 27A-27B and FIG. 16I, the inherent lung to blood CXCL10 chemokine gradient significantly dropped with the progression of lung metastasis, indicating the development of an immunosuppressive microenvironment in the metastatic lungs. To test whether EASI can lead to immuno-restoration, we performed a chemokine gradient assay (FIG. 16J). As shown in FIG. 16P-16R, EASI led to long-lasting restoration of chemokine gradients. The free ImmunoBait with anti-ICAM-1 antibody was not able to deliver enough chemokine to the lung and failed to establish a strong chemokine gradient. A challenging comparative control that delivered a 5× higher dose of free chemokine was used. The 5× free chemokine formulation delivered high contents of chemokine to both the blood and lung, by virtue of a high bioavailability, and created a weak chemokine gradient 20 mins after administration. However, this gradient could not be maintained. In a sharp comparison, EASI was able to deliver high concentrations of CXCL10 chemokine to the lungs and a strong chemokine gradient could be maintained for up to 72 hours. The longer duration of the chemokine gradient compared to ImmunoBait's retention time could have originated from the possibility that immune-restoration leads to endogenous expression of CXCL10 in the tumor microenvironment. Moreover, chemokine gradient assay indicated that apart from CXCL10, EASI can restore gradients of other chemokines such as RANTES (FIGS. 42A-42C).

Figures 43A, 43B:
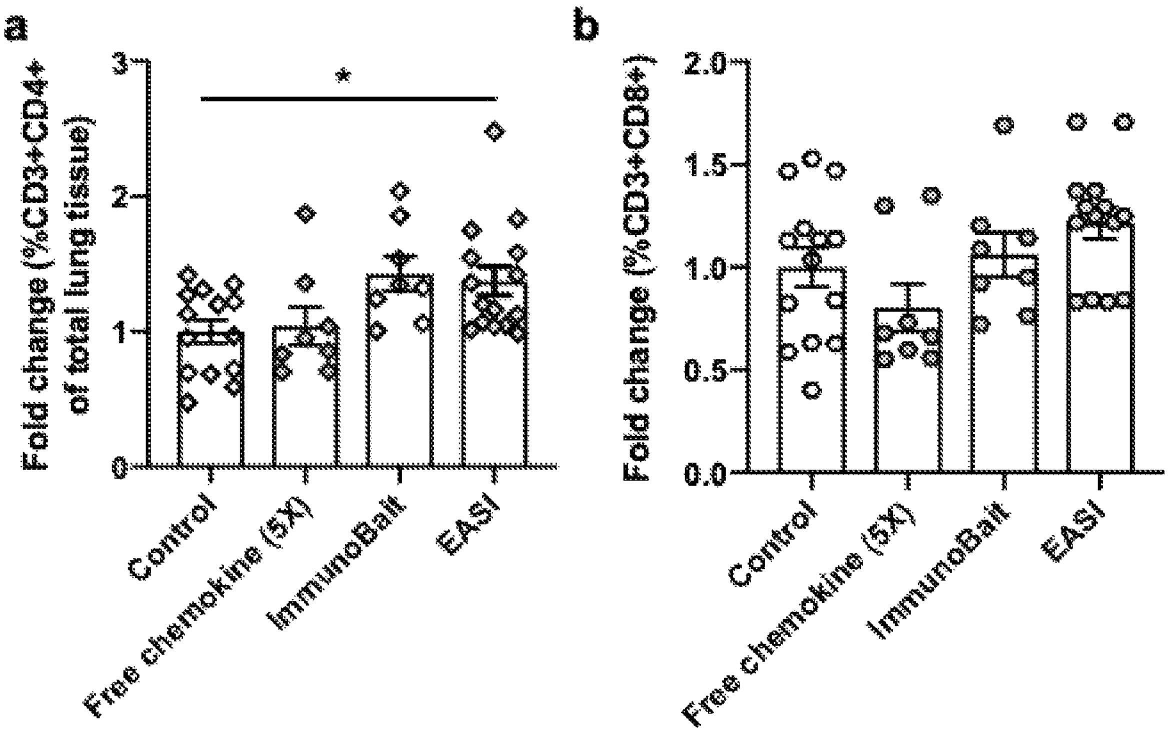
FIGS. 43A-43B depict immune cells in the metastatic lungs of mice under different treatments. The absolute percentage of (FIG. 43A) CD4 and (FIG. 43B) CD8 dendritic cells in the lungs were shown. Data are presented as mean±s.e.m. Significantly different (One-way ANOVA followed by Tukey's HSD test): *$p<0.05$.
Figures 44A, 44B:
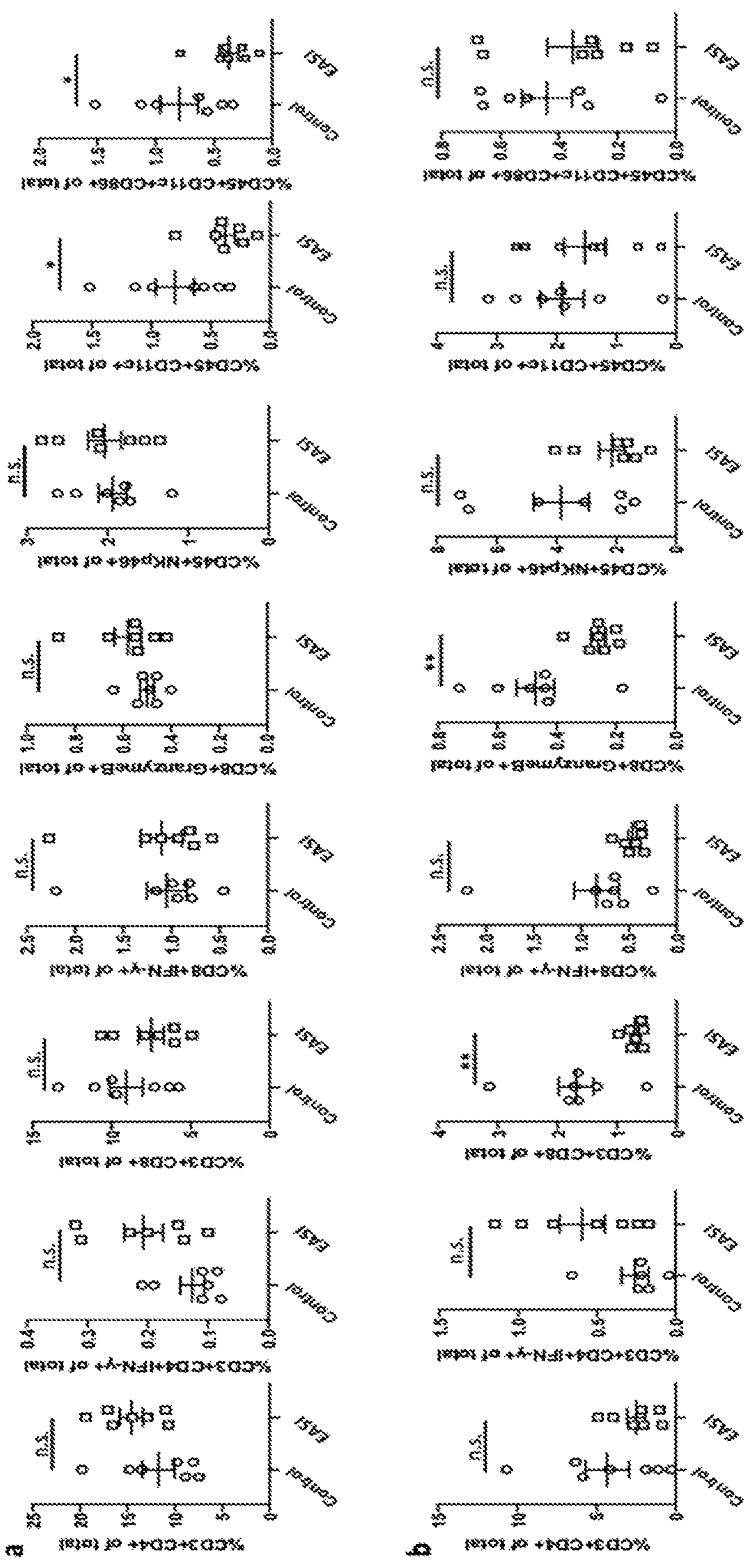
FIGS. 44A-44B depict immune cells in different organs of mice under different treatments. The absolute percentage of CD4 cells, Th1 CD4 cells, CD8 cells, effector CD8 cells, NK cells, dendritic cells, and activated dendritic cells in the (FIG. 44A) spleen and (FIG. 44B) liver were shown. Data are presented as mean±s.e.m. Significantly d

EASI LED to Local Effector Cell Infiltration that Significantly Inhibited the Progression Of Metastasis and Improved Survival To evaluate the in situ immune response elicited by the restoration of the chemokine gradients at the metastatic sites, we conducted a study to profile the immune cells in the metastatic lungs following different treatments (FIG. 18A). CXCL10 is a strong chemoattractant to specific classes of immune cells including Th1 CD4, effector CD8, and NK cells, all of which favor an anti-tumor response. 11, 36-38 As shown in FIG. 43A, EASI led to a 1.4-fold increase in the total CD4 cells as compared to the control (saline). Moreover, we observed significantly more (2.2-fold increase) IFN-γ+Th1 CD4 cells in the metastatic lungs treated by EASI in comparison to the saline group (FIG. 18B-18C). The total CD8 T cells in the metastatic lungs were not significantly different among various treatment groups (FIG. 43B). However, EASI significantly enhanced infiltration of IFN-γ+ CD8 cells (1.8-2.0-fold increase) and Granzyme B+CD8 cells (1.6-2.2-fold increase) over the other groups (FIG. 18D-18G). Apart from the adaptive immune cells, we also observed that EASI significantly changed the infiltration of innate immune cells (NK cells). A 1.4-1.8-fold higher NK cell infiltration was achieved by EASI as compared to the control and other treatment groups. The above immune cell profiling data evidently indicated that the immuno-restoration enabled by EASI significantly enhanced the infiltration of effector immune cells into the metastatic lungs. Specifically, Th1 CD4 cells secrete type 1 cytokines like IFN-γ and TNF-α, maintaining a pro-inflammatory environment that is favorable for the immunological control of tumors.39, 40 Effector CD8 cells and NK cells are the major contributors to drive direct cytotoxic killing of cancer cells.41, 42 Further, immune profiling in other organs (FIGS. 44A-44B) indicated that the tested immune cells in other organs including liver and spleen were less affected by EASI compared to that in the lung. Furthermore, the improved infiltration of immune cells significantly modulated the cytokine profile in the metastatic lungs. The inflammatory cytokine levels in the EASI group were generally higher than those in the control and other treatment groups (FIG. 32). Especially, as compared to the control and other treatments, EASI led to significantly higher concentrations of IFN-γ and TNF-α (FIG. 18L, 18M). More interestingly, the concentration of CXCL10 chemokine in the EASI group was also remarkably higher than in other groups, further confirming the successful immuno-restoration.

Figure 17I:
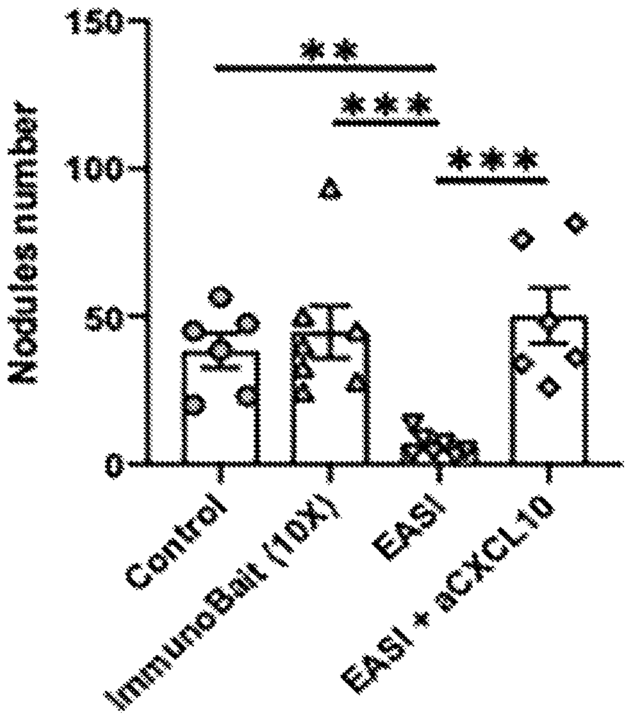
(FIG. 17I) Nodules number on excised lungs of mice on day 37 (n=6-7) receiving different treatments. Significantly different (Mann-Whitney test): p<0.01, *p<0.001. Data are presented as mean±s.e.m.
Figure 17J:
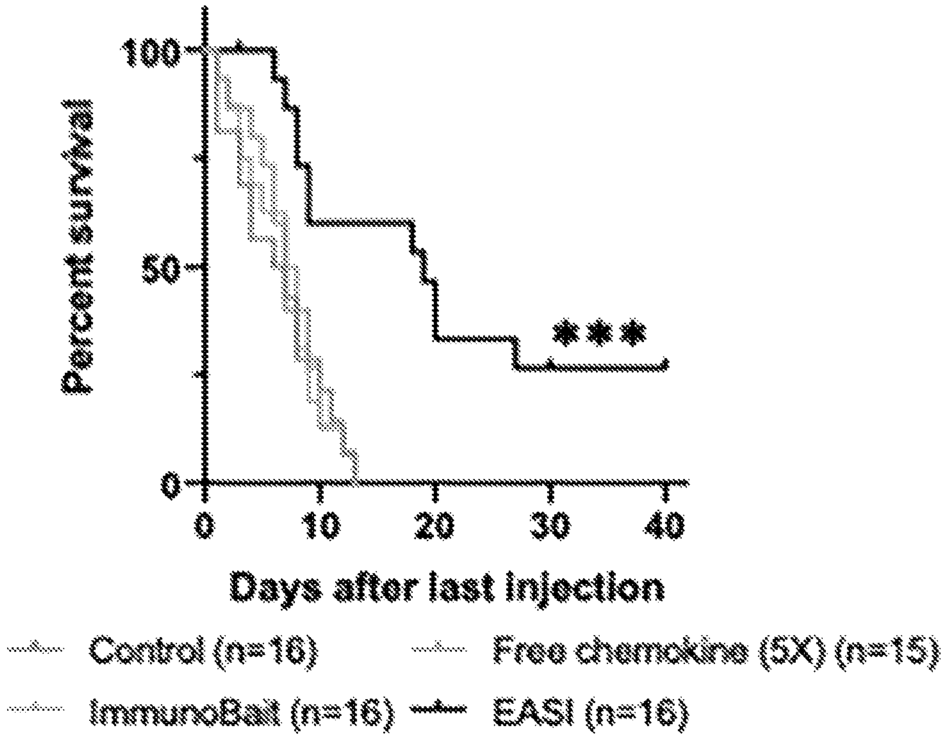
(FIG. 17J) Survival of mice under different treatments as displayed by Kaplan-Meier curves (n=15-16). Significantly different (Mantel-Cox test): ***p<0.001.
Figures 45A, 45B:
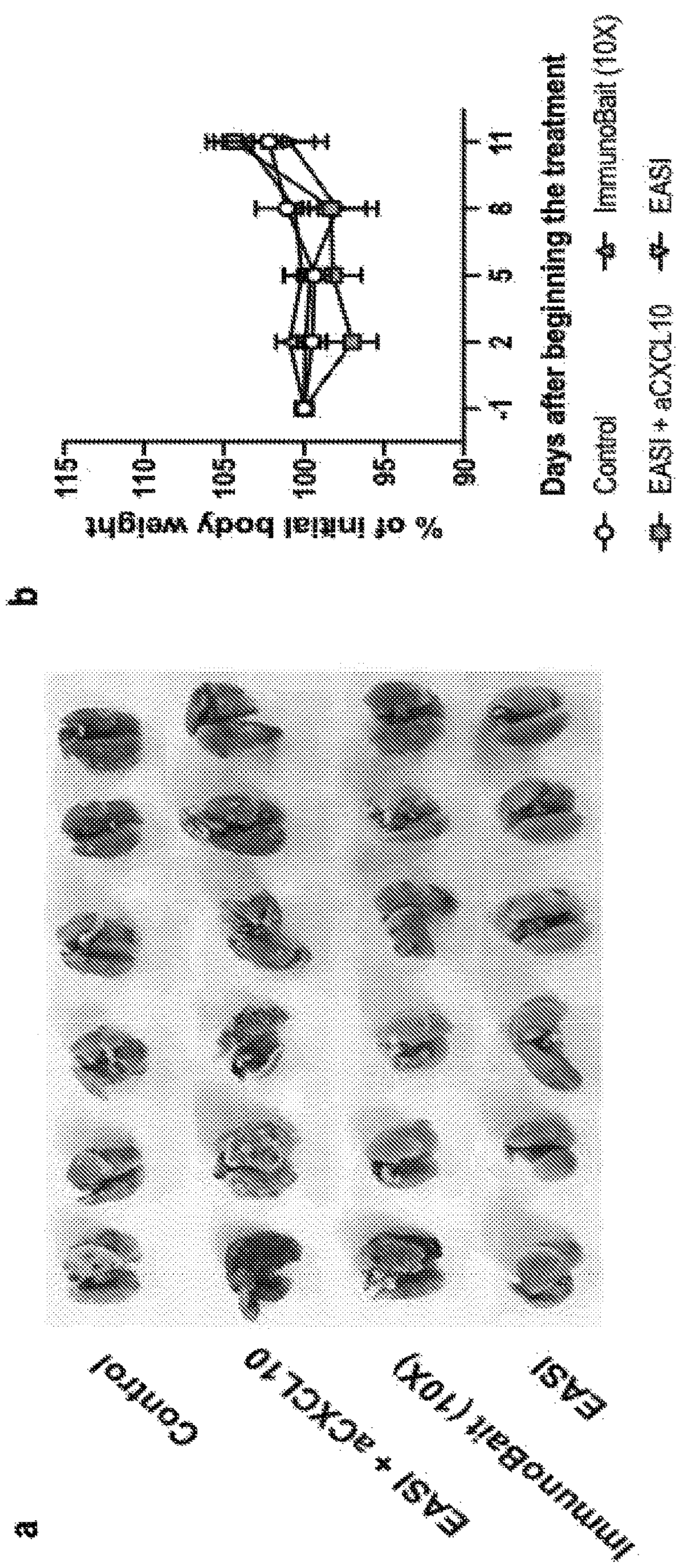
FIGS. 45A-45B depict the efficacy and safety evaluation of different formulations in inhibiting lung metastasis progression.

Immuno-restoration at the lung metastatic sites can modulate the local microenvironment to a "hot" state, which favors cytotoxic immune responses and has the potential to control the progression of lung metastasis.20, 43, 44 To test this hypothesis, we evaluated the efficacy of EASI for controlling lung metastasis in a breast cancer spontaneous lung metastasis model (FIG. 17A). As indicated by the bioluminescence imaging data (FIG. 17B), the EASI group exhibited remarkably slower progression of lung metastasis compared to other groups. Two days after the last dose, mice were euthanized and the surface nodules on excised lungs were counted. As shown in FIG. 17C, EASI exhibited a 3.5-fold and 6.0-fold better efficacy in inhibiting the progression of lung metastasis as compared to the 5× free chemokine and free ImmunoBait groups, respectively. Moreover, two out of eight mice in the EASI group had less than 2 visible nodules on day 37. In a separate set of experiments (FIG. 17I), a higher dose of free ImmunoBait (10×) did not lead to any anti-metastatic effect. Meanwhile, EASI was found to lose its anti-metastatic efficacy when CXCL10 was neutralized by the anti-CXCL10 antibody (FIG. 17I). The qualitative images of excised lungs confirmed higher efficacy of EASI over other treatments (FIG. 17E, FIG. 28 and FIG. 45A). Furthermore, the lung weight of mice treated by EASI is closer to that of the healthy mice in comparison to that of the other treatment groups (FIG. 17F). In addition, the body weight data (FIG. 17G and FIG. 45B) and the H&E staining data of mouse organs (FIG. 29) indicated that no obvious toxicity was associated with any of the treatments, including the higher doses of free chemokine (5×) and free ImmunoBait (10×). Next, we conducted a survival study in which mice received therapies according to the same schedule shown in FIG. 17A. The treatment by EASI significantly improved the animal survival compared to the control and other treatment groups, extending the median survival time by almost 3-fold (FIG. 17J). In addition, three of the sixteen mice in the EASI group survived throughout the entire study. Next, we studied the efficacy of EASI in inhibiting late-stage lung metastasis in a late-stage breast cancer spontaneous lung metastasis model (FIG. 30A). As shown in FIGS. 30B-30C, EASI resulted in a significantly reduced lung metastasis burden compared to the free ImmunoBait alone, indicating EASI also showed efficacy in the late-stage metastasis model.

Figures 33A, 33B, 33C, 33D, 33E, 33F, 33G, 33H, 33I, 33J:
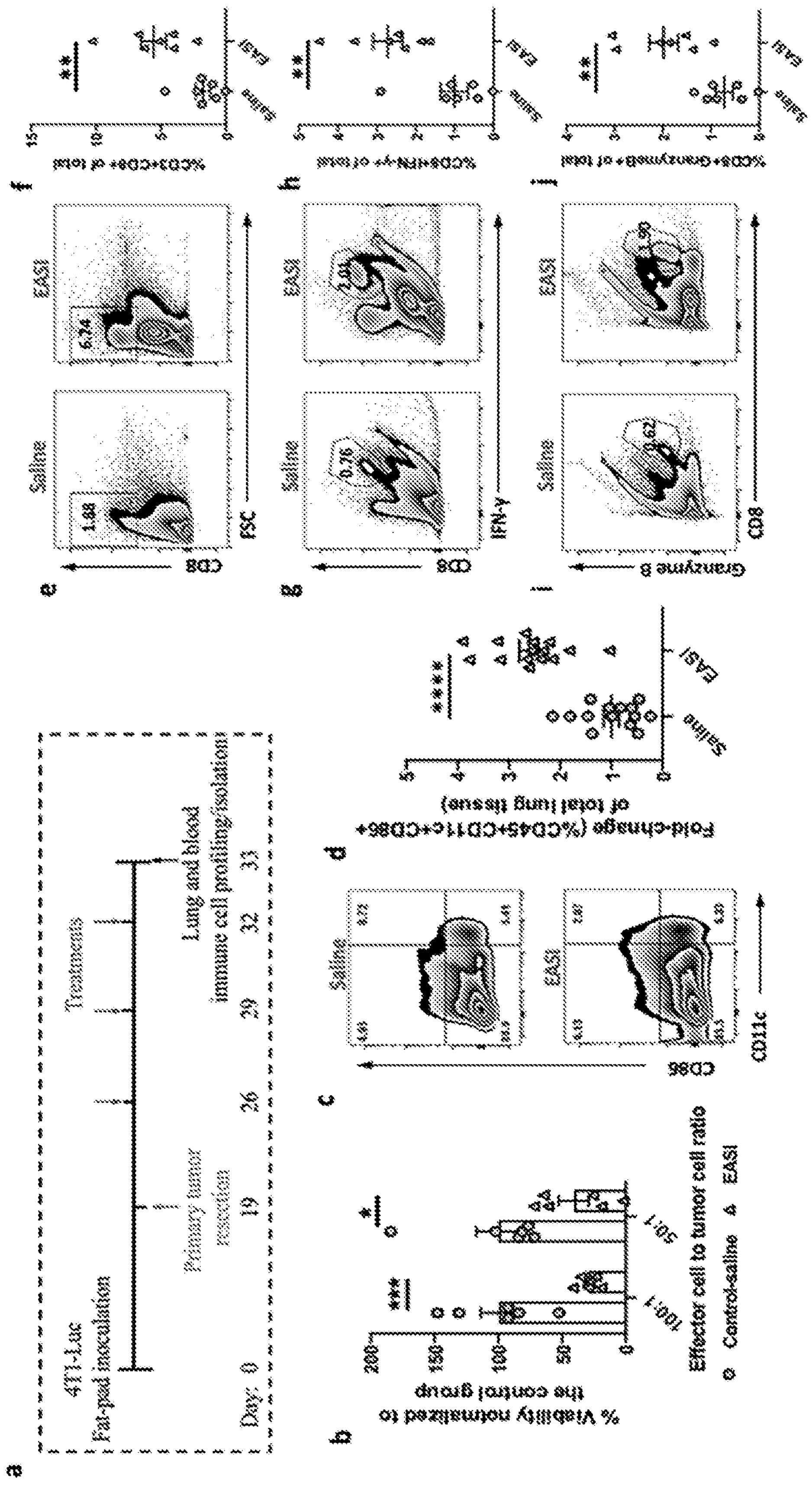
FIGS. 33A-33P demonstrate that EASI resulted in in situ immunization and systemic suppression of distant tumors.
(FIG. 33B) Viability of 4T1-Luc cells co-cultured with isolated lung lymphocytes at 50:1 or 100:1 effector cell to tumor cell ratios (n=6). Data were shown as normalized to the "Control-saline" group. Significantly different (student's t test): *p<0.05, ***p<0.001.
(FIG. 33C) Representative flow cytometry analysis images of CD11c+ CD86+ cells in the metastatic lung.
(FIG. 33D) The fold-change of absolute percentage of activated (CD86+) dendritic cells in the lung as compared to that of the control group (n=14-15).
(FIG. 33E) Representative flow cytometry analysis images of CD8 T cells in the blood.
(FIG. 33F) The absolute percentage of CD8 T cells in the blood.
(FIG. 33G) Representative flow cytometry analysis images of IFN-γ+ CD8 cells in the blood.
(FIG. 33H) The absolute percentage of IFN-γ+ CD8 cells in the blood.
(FIG. 33I) Representative flow cytometry analysis images of Granzyme B+ CD8 cells in the blood.
(FIG. 33J) The absolute percentage of Granzyme B+ CD8 cells in the blood. In (FIGS. 33B, 33D, 33F, 33H, and 33J), significantly different (student's t test): *p<0.05, p<0.01, **p<0.0001.
Figures 33K, 33L, 33M, 33N, 33O, 33P:
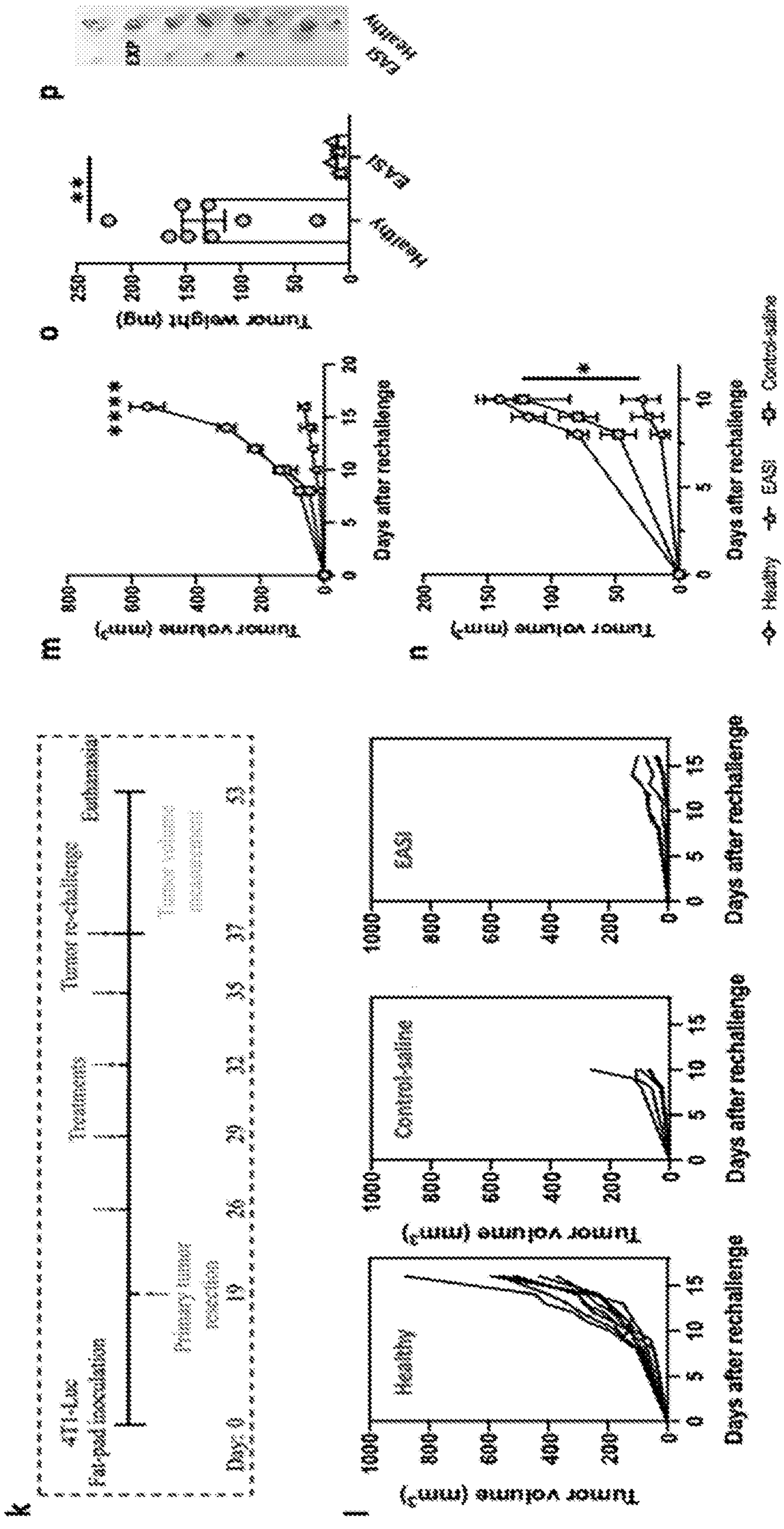
(FIG. 33K) Schedule for the tumor rechallenge study.
(FIG. 33L) Individual growth curve of the re-inoculated tumors in the tumor rechallenge study.
(FIG. 33M) Overall growth curve of re-inoculated tumors.
(FIG. 33N) Overall growth curve of re-inoculated tumors in the first 10 days after inoculation.
(FIG. 33O) Weight of extracted tumors 16 days after tumor rechallenge.
Figures 34A, 34B, 34C, 34D, 34E:
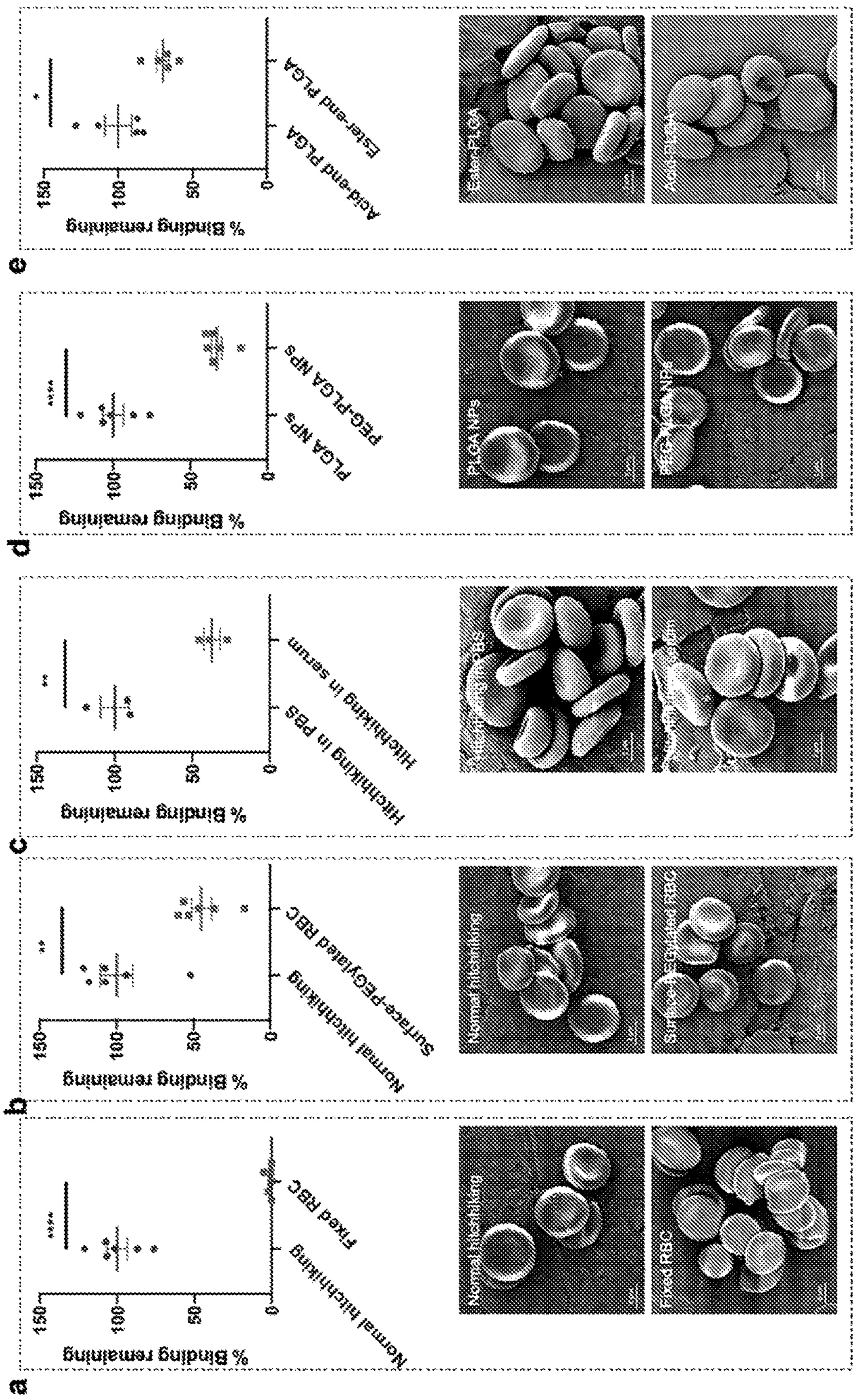
FIGS. 34A-34E depict the mechanisms of nanoparticles anchoring to erythrocytes. Relative binding efficiency and representative SEM images of nanoparticles anchoring to erythrocytes under different conditions.
Figures 46A, 46B:
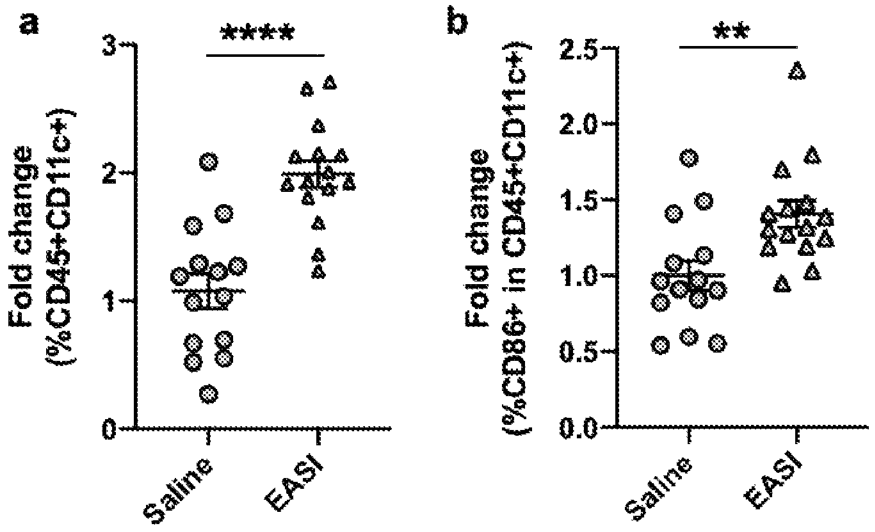
FIGS. 46A-46B depict dendritic cells in the metastatic lungs of mice under different treatments.
Figures 47A, 47B, 47C, 47D, 47E, 47F:
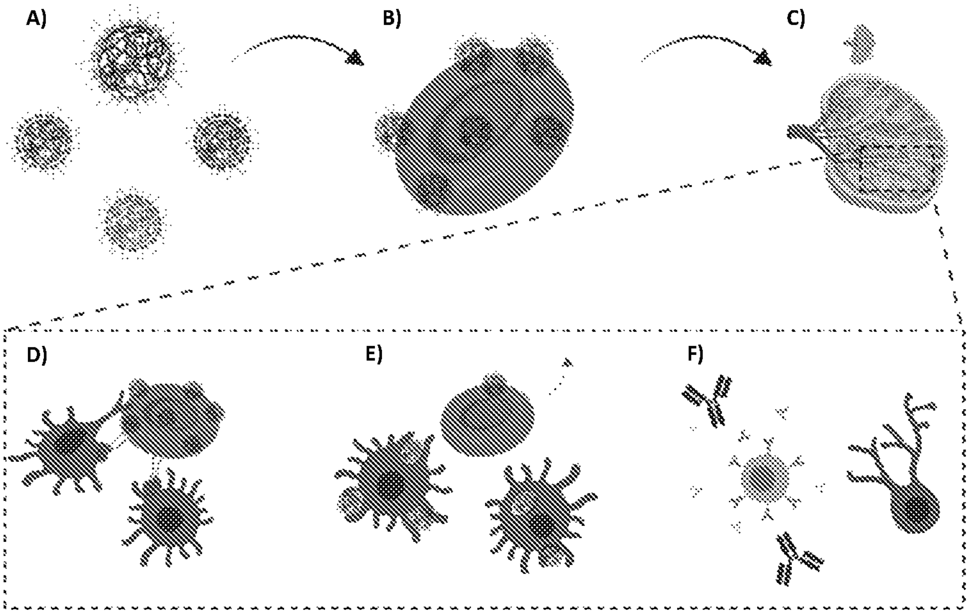
FIGS. 47A-47F depict a schematic for engineering a hand-off of nanoparticles at spleen via erythrocyte hitchhiking.

EASI Induced In Situ Immunization Leading to Systemic Immunity and Distant Tumor Suppression EASI resulted in enhanced infiltration of effector immune cells which were co-localized with the exposed metastatic cells in the lung that is an immune active organ. This opens an opportunity to take advantage of the exposed cancer cells to induce an in-situ immunization which could generate a systemic anti-tumor immunity. To test this hypothesis, we first isolated the lymphocytes from the metastatic lungs following EASI treatment (FIG. 33A) and co-cultured them with 4T1 cells. As shown in FIG. 33B, lymphocytes isolated from the EASI group led to a significantly higher tumor cell killing as compared to those from the saline group. Next, we assayed the antigen presenting cell (APC) landscape in the metastatic lungs. As shown in FIGS. 46A-46B, EASI resulted in significantly more dendritic cells (CD45+CD11c+) infiltrated into the metastatic lungs and these cells were in a more activated status. Particularly, 2.6-fold more activated dendritic cells (CD45+CD11c+CD86+) were present following the treatment by EASI as compared to the saline group (FIG. 33C-33D). These data indicated that EASI was able to enable in-situ antigen presentation and APC activation. The enhanced infiltration of dendritic cells may be caused by the improved infiltration of NK cells, as accumulating literature evidences suggest that NK cells stimulate recruitment of dendritic cells to tumor microenvironments.45-48 Also, the exposed tumor antigens caused by the enhanced tumor cell killing might have led to APC activation. Next, we tested if systemic immunity is generated by the in-situ immunization. As shown in FIG. 33E-33F, 3.1-fold more CD8 cells were present in the blood of mice treated by EASI as compared to the control. In addition, EASI resulted in 2.93-fold increase in IFN-γ+CD8 cells and 2.7-fold increase in Granzyme B+CD8 cells in the blood as compared to the control (saline) group (FIG. 33G-33J). These blood immune profiling data revealed that EASI induced a systemic immune response and generated more CD8 and effector CD8 cells. Further, we conducted a tumor rechallenge study to test if the systemic immunity generated by the in-situ immunization by EASI could lead to suppression of distant tumors (FIG. 33K). Two days after the last dose of therapies, distant tumors were inoculated on the right flank of mice. Apart from the "EASI" group, two control groups, "Healthy" (age-matched mice that received no prior tumor inoculation) and "Control-saline" (mice that received saline as treatment), were included in the study. As shown in FIG. 33L-33N, EASI significantly suppressed the growth of the re-inoculated distant tumors, as compared to the Healthy and Control-saline groups. The weight data (FIG. 33I) and qualitative images (FIG. 33P) of extracted tumors at the end of the study confirmed the better efficacy of EASI. All data in the tumor rechallenge study demonstrated that the focused local immuno-restoration in the metastatic lungs could induce in-situ immunization that generated a systemic immunity to inhibit systemic tumor development.

Discussion

Raising an immune response against tumor at their natural location is difficult due to the large size and immunosuppressive environment. Unlike the primary tumors, metastasis exposes cancer cells in immune active organs such as the lung and thus opens an opportunity for immunization. This is however difficult to implement due to the fact that metastatic sites quickly undergo endogenous changes to acquire an immunosuppressive status. In this work, by leveraging exposure in lungs, we have developed Erythrocyte Anchored Systemic Immunotherapy (EASI) that allows co-localization of large doses of immune activators with the exposed cancer cells in an immunoactive organ of lung, to induce in-situ immunization for local as well as systemic cancer suppression.

EASI builds on previously established concept of erythrocyte-mediated lung targeting.22, 23 However, unlike previous reports that focused on alleviating local conditions through lung targeting, EASI demonstrates a systemic outcome mediated by immune interactions in the lungs. Specifically, EASI exploits the exposure of cancer cells in the lungs to achieve in situ immunization that yields a systemic response. In contrast to other elegantly reported cellular delivery systems such as cellular "backpacking" 49-51 and ERY1-bound erythrocytes52, 53, which involve covalent or specific binding, EASI consists of ImmunoBait (chemokine nanoparticles) anchored onto erythrocytes via non-covalent spontaneous interactions. This design allows EASI to specifically dislodge and deposit ImmunoBait on the lung capillary endothelium, where circulatory tumor cells prefer to reside during metastasis, attributed to its narrow size and endogenous physiological changes. In addition, the attachment of anti-ICAM-1 antibody to ImmunoBait facilitated its co-localization with cancer cells, as ICAM-1 is overexpressed on lung endothelium (during metastasis)54 and certain type of cancer cells such as triple negative breast cancer.31

We demonstrated that the co-localization of ImmunoBait with local metastasis environment achieved by EASI could specifically restore the chemokine gradients at the lung metastatic sites. This local immune microenvironment modulation activated the immune cascade that leads to significant enhancement in the infiltration of effector immune cells, which subsequently drives strong therapeutic efficacy of inhibiting the progression of lung metastasis and improving animal survival. Moreover, the cytotoxic immune killing of cancer cells at the metastasis sites resulted in in-situ antigen presenting cell activation and subsequently induced an elevated generation of systemic CD8 and effector CD8 cells, which were able to resist the development of distant tumors. These data demonstrate that EASI converted the exposure of cancer cells during metastasis into a therapeutic opportunity for in-situ immunization. EASI offers a potential therapeutic approach to advanced cancer stages. Particularly, the systemic anti-cancer immune response elicited by the in-situ immunization can prevent tumor relapse or metastasis to other organs which often occurs in advanced cancer stage patients. Previous studies suggested that changing the injection sites, erythrocyte hitchhiking can target nanoparticles to organs immediately downstream the injection vessels.28 Considering this, EASI can be applied to induce in-situ immunization at metastasis in other organs other than the lung.

REFERENCES

1. Restifo, N. P., Dudley, M. E. & Rosenberg, S. A. Adoptive immunotherapy for cancer: harnessing the T cell response. Nat Rev Immunol 12, 269-281 (2012).
2. Pardoll, D. M. The blockade of immune checkpoints in cancer immunotherapy. Nat Rev Cancer 12, 252-264 (2012).
3. Rosenberg, S. A. Decade in review-cancer immunotherapy: entering the mainstream of cancer treatment. Nat Rev Clin Oncol 11, 630-632 (2014).
4. Qian, Y. et al. Molecular-Targeted Immunotherapeutic Strategy for Melanoma via Dual-Targeting Nanoparticles Delivering Small Interfering RNA to Tumor-Associated Macrophages. Acs Nano 11, 9536-9549 (2017).
5. Riley, R. S., June, C. H., Langer, R. & Mitchell, M. J. Delivery technologies for cancer immunotherapy. Nat Rev Drug Discov 18, 175-196 (2019).
6. Shah, N. J. et al. A biomaterial-based vaccine eliciting durable tumour-specific responses against acute myeloid leukaemia. Nat Biomed Eng 4, 40-51 (2020).
7. Neelapu, S. S. et al. Axicabtagene Ciloleucel CAR T-Cell Therapy in Refractory Large B-Cell Lymphoma. N Engl J Med 377, 2531-2544 (2017).
8. Fesnak, A. D., June, C. H. & Levine, B. L. Engineered T cells: the promise and challenges of cancer immunotherapy. Nat Rev Cancer 16, 566-581 (2016).
9. Sharma, P., Hu-Lieskovan, S., Wargo, J. A. & Ribas, A. Primary, Adaptive, and Acquired Resistance to Cancer Immunotherapy. Cell 168, 707-723 (2017).
10. Mellman, I., Coukos, G. & Dranoff, G. Cancer immunotherapy comes of age. Nature 480, 480-489 (2011).
11. Nagarsheth, N., Wicha, M. S. & Zou, W. P. Chemokines in the cancer microenvironment and their relevance in cancer immunotherapy. Nat Rev Immunol 17, 559-572 (2017).
12. Vijayan, D., Young, A., Teng, M. W. L. & Smyth, M. J. Targeting immunosuppressive adenosine in cancer. Nat Rev Cancer 17, 765 (2017).
13. Chauhan, V. P. et al. Reprogramming the microenvironment with tumor-selective angiotensin blockers enhances cancer immunotherapy. Proc Natl Acad Sci USA 116, 10674-10680 (2019).
14. Gupta, G. P. & Massague, J. Cancer metastasis: building a framework. Cell 127, 679-695 (2006).
15. Schroeder, A. et al. Treating metastatic cancer with nanotechnology. Nat Rev Cancer 12, 39-50(2011).
16. Institute, N.C. (National Cancer Institute, 2019).
17. Cardoso, F. et al. Locally recurrent or metastatic breast cancer: ESMO Clinical Practice Guidelines for diagnosis, treatment and follow-up. Ann Oncol 21 Suppl 5, v15-19 (2010).
18. Eckhardt, B. L., Francis, P. A., Parker, B. S. & Anderson, R. L. Strategies for the discovery and development of therapies for metastatic breast cancer. Nat Rev Drug Discov 11, 479-497 (2012).
19. Homey, B., Muller, A. & Zlotnik, A. Chemokines: agents for the immunotherapy of cancer?Nat Rev Immunol 2, 175-184 (2002).
20. Clancy-Thompson, E. et al. Melanoma Induces, and Adenosine Suppresses, CXCR3-Cognate Chemokine Production and T-cell Infiltration of Lungs Bearing Metastatic-like Disease. Cancer Immunol Res 3, 956-967 (2015).
21. Altorki, N. K. et al. The lung microenvironment: an important regulator of tumour growth and metastasis. Nat Rev Cancer 19, 9-31 (2019).
22. Zhao, Z., Ukidve, A., Gao, Y., Kim, J. & Mitragotri, S. Erythrocyte leveraged chemotherapy (ELeCt): Nanoparticle assembly on erythrocyte surface to combat lung metastasis. Sci Adv 5, eaax9250 (2019).
23. Anselmo, A. C. et al. Delivering Nanoparticles to Lungs while Avoiding Liver and Spleen through Adsorption on Red Blood Cells. Acs Nano 7, 11129-11137 (2013).
24. Makadia, H. K. & Siegel, S. J. Poly Lactic-co-Glycolic Acid (PLGA) as Biodegradable Controlled Drug Delivery Carrier. Polymers-Basel 3, 1377-1397 (2011).
25. Paszkowiak, J. J. & Dardik, A. Arterial wall shear stress: observations from the bench to the bedside. Vasc Endovascular Surg 37, 47-57 (2003).
26. Chatterjee, S. Endothelial Mechanotransduction, Redox Signaling and the Regulation of Vascular Inflammatory Pathways. Front Physiol 9, 524 (2018).

27. Malek, A. M., Alper, S. L. & Izumo, S. Hemodynamic shear stress and its role in atherosclerosis. Jama-J Am Med Assoc 282, 2035-2042 (1999).
28. Brenner, J. S. et al. Red blood cell-hitchhiking boosts delivery of nanocarriers to chosen organs by orders of magnitude. Nat Commun 9 (2018).
29. Muro, S. et al. Control of endothelial targeting and intracellular delivery of therapeutic enzymes by modulating the size and shape of ICAM-1-targeted carriers. Mol Ther 16, 1450-1458 (2008).
30. Scherpereel, A. et al. Cell-selective intracellular delivery of a foreign enzyme to endothelium in vivo using vascular immunotargeting. Faseb J 15, 416-426 (2001).
31. Guo, P. et al. ICAM-1 as a molecular target for triple negative breast cancer. P Natl Acad Sci USA 111, 14710-14715 (2014).
32. Guo, P. et al. Dual complementary liposomes inhibit triple-negative breast tumor progression and metastasis. Science Advances 5 (2019).
33. Lee, S. J., Park, S. Y., Jung, M. Y., Bae, S. M. & Kim, I. S. Mechanism for phosphatidylserine-dependent erythrophagocytosis in mouse liver. Blood 117, 5215-5223 (2011).
34. Oldenborg, P. A. et al. Role of CD47 as a marker of self on red blood cells. Science 288, 2051-+(2000).
35. Pan, D. C. et al. Nanoparticle Properties Modulate Their Attachment and Effect on Carrier Red Blood Cells. Sci Rep-Uk 8 (2018).
36. Tokunaga, R. et al. CXCL9, CXCL10, CXCL11/CXCR3 axis for immune activation—A target for novel cancer therapy. Cancer Treat Rev 63, 40-47 (2018).
37. Hu, J. M. et al. CXCL9, CXCL10 and IFN gamma favor the accumulation of infused T cells in tumors following IL-12 plus doxorubicin treatment. J Immunol 196 (2016).
38. Pfirschke, C., Siwicki, M., Liao, H. W. & Pittet, M. J. Tumor Microenvironment: No Effector T Cells without Dendritic Cells. Cancer Cell 31, 614-615 (2017).
39. Zhu, J. F. & Paul, W. E. CD4 T cells: fates, functions, and faults. Blood 112, 1557-1569 (2008).
40. Grivennikov, S. I., Greten, F. R. & Karin, M. Immunity, Inflammation, and Cancer. Cell 140, 883-899 (2010).
41. Hsu, J. et al. Contribution of NK cells to immunotherapy mediated by PD-1/PD-L1 blockade. J Clin Invest 128, 4654-4668 (2018).
42. Vivier, E., Ugolini, S., Blaise, D., Chabannon, C. & Brossay, L. Targeting natural killer cells and natural killer T cells in cancer. Nat Rev Immunol 12, 239-252 (2012).
43. Binnewies, M. et al. Understanding the tumor immune microenvironment (TIME) for effective therapy. Nat Med 24, 541-550 (2018).
44. Wang, H. & Mooney, D. J. Biomaterial-assisted targeted modulation of immune cells in cancer treatment. Nat Mater 17, 761-772 (2018).
45. Bottcher, J. P. et al. N K Cells Stimulate Recruitment of cDC1 into the Tumor Microenvironment Promoting Cancer Immune Control. Cell 172, 1022-+(2018).
46. Barry, K. C. et al. A natural killer-dendritic cell axis defines checkpoint therapy-responsive tumor microenvironments. Nat Med 24, 1178-1191 (2018).
47. Harizi, H. Reciprocal crosstalk between dendritic cells and natural killer cells under the effects of PGE2 in immunity and immunopathology. Cell Mol Immunol 10, 213-221 (2013).
48. Nguyen, K. B. & Spranger, S. Modulation of the immune microenvironment by tumor-intrinsic oncogenic signaling. J Cell Biol 219 (2020).
49. Schmid, D. et al. T cell-targeting nanoparticles focus delivery of immunotherapy to improve antitumor immunity. Nat Commun 8 (2017).
50. Tang, L. et al. Enhancing T cell therapy through TCR-signaling-responsive nanoparticle drug delivery. Nature Biotechnology 36, 707-+(2018).
51. Stephan, M. T., Moon, J. J., Um, S. H., Bershteyn, A. & Irvine, D. J. Therapeutic Cell Engineering Using Surface-Conjugated Synthetic Nanoparticles. J Immunother 33, 866-866 (2010).
52. Kontos, S., Kourtis, I. C., Dane, K. Y. & Hubbell, J. A. Engineering antigens for in situ erythrocyte binding induces T-cell deletion. P Natl Acad Sci USA 110, E60-E68 (2013).
53. Lorentz, K. M., Kontos, S., Diaceri, G., Henry, H. & Hubbell, J. A. Engineered binding to erythrocytes induces immunological tolerance to *E. coli* asparaginase. Sci Adv 1, e1500112 (2015).
54. Masuda, Y., Murata, Y., Hayashi, M. & Nanba, H. Inhibitory effect of MD-Fraction on tumor metastasis: Involvement of NK cell activation and suppression of intercellular adhesion molecule (ICAM)-1 expression in lung vascular endothelial cells. Biol Pharm Bull 31, 1104-1108 (2008).

Methods

Cell Lines and Animals

4T1 mammary carcinoma cell line (4T1-Luc) expressing luciferase were obtained from Imanis Life Sciences (MN, USA). 4T1-Luc cells were cultured in a humidified incubator maintained at 37° C. and 5% CO2. They were cultured in RPMI-1640 media supplemented with 10% FBS, 1% Pen-Strep and 0.1 mg/mL G418. Human lung microvasculature endothelial cells (HLMVEC) and HLMVEC growth medium was purchased for Sigma Aldrich (MO, USA). HLMVEC were cultured in HLMVEC growth medium according to manufacturer's instructions. Cells were passaged 2-3 times before their use. Female Balb/c mice (7-8 weeks of age) were purchased from Charles River Laboratories (MA, USA). All experiments were performed according to the approved protocols by the Institutional Animal Care and Use Committee (IACUC) of the Faculty of Arts and Sciences (FAS), Harvard University, Cambridge.

ImmunoBait Preparation and Characterization

ImmunoBait, PLGA nanoparticles encapsulating CXCL10 were prepared using a double emulsion method. Briefly, 50 μg of CXCL10 was dissolved in 200 μL of 0.1% bovine serum albumin in PBS. This was added to 1 mL of dichloromethane containing 20 mg of PLGA. The mixture was briefly sonicated and then added dropwise to 11 mL of 1.5% polyvinyl alcohol (PVA) solution under constant stirring. The entire mixture was probe-sonicated for 40 seconds. The formed particles were kept under constant stirring overnight to remove the organic solvents. The particles were centrifuged at 12,000 g for 10 mins and the supernatant was analyzed for quantifying drug loading. The particles were then resuspended in de-ionized water and assessed for their size, zeta potential and polydispersity index using dynamic light scattering (Malvern Zen3600, PA, USA), scanning electron microscopy (Zeiss FESEM Supra 55VP, Zeiss FESEM Ultra 55, Germany) and transmission electron microscopy (JEOL 2100, MA, USA). The nanoparticles were washed for a total of two washes with deionized water before their final resuspension in PBS. For quantification and biodistribution studies, fluorescent ovalbumin/CXCL10 were encapsulated in PLGA using the method described above.

Blood Collection and Processing

Murine whole blood was collected via cardiac puncture using a heparin pre-coated syringe and stored in BD Microtainer® blood collection tubes at 4° C. prior to use. Whole blood was centrifuged at 1,000 g for 10 mins at 4° C. to remove the serum and the buffy coat layers from the erythrocyte compartment. The isolated erythrocytes were further washed 3 times with cold 1×PBS and centrifuged at 650 g for 15 min at 4° C. before their final resuspension at a concentration of 10% hematocrit in 1×PBS. This solution will be regarded as erythrocyte stock solution in this study.

Anchoring of ImmunoBait to Erythrocytes

Equal volumes of erythrocyte stock solution and ImmunoBait nanoparticle suspension were mixed in Axygen™ 1.5 mL Self-Standing Screw Cap Tubes and further thoroughly mixed by inversion and pipetting. The tubes were then rotated on a tube revolver (Thermo Fisher Scientific) for 40 mins. The hitchhiked erythrocytes were then pelleted by centrifugation at 100 g for 5 mins at 4° C., unabsorbed particles were carefully removed, and the pellet was washed again with 1 mL of 1×PBS to remove loosely bound particles. For attachment of anti-ICAM-1 antibody, ImmunoBait nanoparticles or hitchhiked erythrocyte pellet were resuspended in 0.5 mg/mL anti-ICAM-1 antibody solution for additional 20 mins. The hitchhiked erythrocytes were finally resuspended at 10% v/v in 1×PBS and used for further characterization or at 20% v/v in 1×PBS for in vivo studies. The endotoxin levels of the hitchhiked samples for in vivo efficacy studies were evaluated by a Pierce™ LAL Chromogenic Endotoxin Quantification Kit (ThermoFisher). Assay results indicated that endotoxin levels in the samples were low (below 0.02 EU per dose).

Spontaneous Lung Metastasis Model Establishment

To establish the breast cancer spontaneous lung metastasis model, 1×106 4T1-Luc cells were injected orthotopically into the left mammary fat pad of female Balb/c mice. Either 19 days (the early-stage model) or 32 days (the late-stage model) after inoculation, the primary tumor was surgically resected. 6 days after the primary tumor resection, mice were injected intraperitoneally with 150 μL of 30 mg/mL Xenolight-D-luciferin in saline. 15 mins after the injection, mice were imaged using in vivo imaging (IVIS Spectrum). Mice were randomized into different groups based on the primary tumor volume and bioluminescence intensity in the lungs 6 days after primary tumor resection.

In Vivo Biodistribution Studies in Disease Model

The early-stage or late-stage breast cancer lung metastasis model was established as described before. For all the biodistribution studies, formulations containing 17 μg of nanoparticles were used. Seven days after the primary tumor resection, mice were injected intravenously with ImmunoBait, hitchhiked ImmunoBait, anti-ICAM-1 attached ImmunoBait and hitchhiked ImmunoBait with anti-ICAM-1 attached into the tail vein. ImmunoBait nanoparticles were fluorescently labeled by Alexa Fluor 647 or Alexa Fluor 750 that was conjugated to the albumin carrier protein. In the case of phagocyte depletion, mice were i.v. injected with 200 μL of Clodrosome® containing 5 mg/mL Clodronate 48 h before i.v. injection of hitchhiked samples, which has been shown to effectively deplete intravascular phagocytes28. Mice were sacrificed at 20 mins and 6 h after the injection and organs (liver, lungs, spleen, kidneys, heart, brain and blood) were harvested for further processing. For processing, 1 mL of cold RIPA lysis buffer (1×) was added to each organ and the organs were homogenized using a high shear homogenizer (IKA T-10 Basic® Ultra turrax, Germany) and the nanoparticle content was quantified by fluorescence on a plate reader (Tecan Safire 2®, Switzerland). Percent injected dose (ID %) was defined as the total nanoparticle fluorescence in a specific organ divided by the total nanoparticle fluorescence of all organs.

Efficacy Studies on In Vivo Breast Cancer Spontaneous Lung Metastasis Model

In the early-stage breast cancer spontaneous lung metastasis model, treatments were given starting one week after the primary tumor resection. ImmunoBait or hitchhiked ImmunoBait containing anti-ICAM-1 antibody was used in the efficacy and survival studies. Four injections were given over 10 days, i.e. day 26, 29, 32, and 35. For the hitchhiked ImmunoBait with anti-CXCL10 antibody group, immediately after i.v. administration of EASI, 100 μg of rat anti-mouse CXCL10 neutralizing antibody was administered intraperitoneally. The representative mice were imaged on days 25, 28, 31, 34, and 37, using in vivo imaging (IVIS Spectrum). Briefly, mice were injected intraperitoneally with 150 μL of 30 mg/mL Xenolight-D-luciferin in saline. 15 mins after the injection, mice were imaged using in vivo imaging. On day 37, the mice were euthanized, intratracheally injected with India ink solution and the lungs were excised and fixed using Feket's solution. The fixed lungs were used for counting of the surface nodules. Survival in the early-stage model was evaluated by having the injection schedule as described above (n=15-16). In the late-stage lung metastasis model, four doses of treatments were given every two days with the first dose being administered 7 days (on day 39) after primary tumor resection. Two days after the last dose (on day 50), mice were euthanized and nodules on excised lungs were counted. For the efficacy studies, the injected formulations contained 2.5 μg of CXCL10 chemokine, except that the free chemokine (5×) and free ImmunoBait (10×) contained 12.5 μg and 25 μg of CXCL10, respectively.

Chemokine Gradient Assay

The time-course change of CXCL10 concentration in the blood and lung was measured in the early-stage lung metastasis model. 19 days after the tumor inoculation, tumors were surgically resected. 4, 10, 22 days after tumor resection, mice were euthanized, blood was collected by cardiac puncture and the lungs were excised (n=5 for all time points). For processing, 0.5 mL of cold tissue extraction buffer containing protease inhibitor was added to each lung and the lungs were homogenized using a high shear homogenizer (IKA T-10 Basic® Ultra turrax, Germany). CXCL10 content in the lungs and blood were quantified using ELISA.

The chemokine gradient assay was conducted on the early-stage lung metastasis model as follows. To evaluate chemokine gradient restoration capability of the therapy, early-stage spontaneous lung metastasis model was established as described in the previous context. One saline and three treatment groups (5× free CXCL10 chemokine containing 12.5 μg CXCL10, ImmunoBait with anti-ICAM-1 containing 2.5 μg CXCL10, and erythrocyte hitchhiked ImmunoBait with anti-ICAM-1 containing 2.5 μg CXCL10) were included into the study. Treatments were given starting one week after surgery. Two injection sets were given on day 7 and day 10 after surgery. (n=4-6 for each time point for each group). Mice were sacrificed at 20 mins, 6 h, 24 h, 48 h, and 72 h after the second injection, blood was collected by cardiac puncture and lungs were excised. Chemokine content in lungs and blood were quantified as described above.

Immune Cell and Cytokine Profiling

Different panels of antibody cocktails were made from CD45 (Biolegend, Cat no: 103116, Clone: 30-F11), CD3 (Biolegend, Cat no: 100218, Clone: 17A2), CD4 (Biolegend, Cat no: 100421, Clone: GK1.5), CD8a (Biolegend, Cat no: 100711, Clone: 53-6.7), NKp46 (Biolegend, Cat no: 137606, Clone: 29A1.4), CD11c (Biolegend, Cat no: 117307, Clone: N418), Granzyme B (Biolegend, Cat no: 372208, Clone: QA16A02), IFN-γ (Biolegend, Cat no: 505849, Clone: XMG1.2), IFN-γ (Biolegend, Cat no: 505806, Clone: XMG1.2), CD86 (Biolegend, Cat no: 105011, Clone: GL-1), and Am Cyan Live/dead cell staining kit (Thermo Fischer Scientific, MA, USA). All antibodies were diluted at optimized dilutions prior to their use.

For immune cell profiling, the early-stage spontaneous lung metastasis was established as described above. One saline and three treatment groups (5× free CXCL10 chemokine containing 12.5 μg of CXCL10, ImmunoBait with anti-ICAM-1 containing 2.5 μg CXCL10, and erythrocyte hitchhiked ImmunoBait with anti-ICAM-1 containing 2.5 μg CXCL10) were included into the study. Treatments were given starting one week after surgery. Three injection sets were given on day 7, 10 and 13 after primary tumor resection. One day after the last injection, mice were euthanized. Blood was collected by cardiac puncture and organs including lung, liver, and spleen were excised. A single cell suspension of organ cells was formed using corresponding organ dissociation kits (Miltenyi Biotec, Germany) according to manufacturer's instructions. The cells were stained with antibodies mentioned above and analyzed by flow cytometry (BD LSR Analyser II, NJ USA).

For cytokine profiling, model establishment and treatments were the same as described above. One day after the last injection, mice were euthanized, and lungs were excised. For processing, 0.5 mL of cold tissue extraction buffer containing protease inhibitor was added to each lung and the lungs were homogenized using a high shear homogenizer (IKA T-10 Basic® Ultra turrax, Germany). Cytokine profiling was carried out using LEGENDplex™ Mouse Inflammation Panel (Biolegend, CA, USA) according to manufacturer's instructions and analyzed using flow cytometry (BD LSR Analyser II, NJ USA). CXCL10 concentration was quantified by ELISA.

Statistical Analysis

All experiments were repeated at least three times. All statistical analyses were carried out using Graphpad prism 8 software. All data are presented as mean±s.e.m. Student's t test, one-way ANOVA with Tukey's HSD analysis, or Mann-Whitney test were used to determine significance. For the analysis of Kaplan-Meier survival curves, Mantel-Cox test was used. p values represent different levels of significance; $p<0.05$*; $p<0.01$; $p<0.001$*, $p<0.0001$****. All the flow cytometry analyses were carried out using FlowJo™ 10 software.

Supplementary Methods

Materials

All chemicals and reagents were obtained from Sigma Aldrich (MO, USA) and used without further purification, unless otherwise mentioned. PLGA (50:50 acid-end, 50:50 ester-end, 85:15 ester-end, and 65:35 acid-end) was purchased from Sigma-Aldrich (MO, USA). mPEG-PLGA was purchased from PolySciTech (IN, USA). CXCL10/IP-10, IL-10, IL-15, and GM-CSF were obtained from PeproTech (NJ, USA). Nunc™ Lab-Tek™ II Chamber Slide™ System, cell staining buffer, G418 (Geneticin), mouse IP-10 ELISA kit, Alexa Fluor 647 Ovalbumin, Alexa Fluor 750 NHS reagent, Alexa Fluor 647 NHS reagent, phosphate buffered saline(1×), Axygen™ 1.5 mL Self-Standing Screw Cap Tubes, Pierce™ LAL Chromogenic Endotoxin Quantitation Kit, and CXCL10 monoclonal antibody were obtained from Thermo Fischer Scientific (MA, USA). Human whole blood and serum was obtained from BioIVT (NJ, USA). Xenolight-D-luciferin potassium salt was obtained from Perkin Elmer (MA, USA). Lithium heparin coated microtainer tubes were obtained from BD medical technology (MA, USA). LEGENDplex™ Mouse Inflammation Panel with Filter Plate, recombinant mouse RANTES (Cat no: 594208), and anti-ICAM-1 antibody (Cat no: 116102, Clone: YN 1/1.7.2; Cat no:353102, Clone: HA58) was obtained from BioLegend (CA, USA). Tissue dissociation tubes and lung dissociation kit were obtained from Miltenyi Biotec (Germany). Tissue Tek OCT compound was obtained from Sakura Finetek (CA, USA). 0.9% saline solution was obtained from Teknova (CA, USA). Paraformaldehyde was obtained from Electron Microscopy Sciences (PA, USA). Surgical equipment was obtained from Braintree Scientific, Inc. (MA, USA). Clodrosome® was obtained from Encapsula NanoSciences (TN, USA).

In Vitro Drug Release Study

CXCL10 containing nanoparticles (ImmunoBait) were resuspended in 1 mL PBS, FBS and complete medium (DMEM+10% FBS) and incubated at 37° C. on a tube revolver. At regular time points, the particles were centrifuged at 12,000 g for 10 mins and the supernatant was collected for analysis. The particles were further resuspended in 1 mL of fresh release media and incubated at 37° C. until the next time point. Samples were taken at 1, 2, 4, 6, and 12 h after starting the incubation. The cumulative release in each release media was quantified using ELISA. In addition, the released CXCL10 chemokine was characterized by MALDI-TOF and Circular Dichroism Spectrophotometer to detect any molecular weight and structural changes.

Nanoparticle Internalization Studies

Nanoparticle internalization was confirmed using confocal microscopy. For flow cytometry analysis, 2×106 HLMVEC cells were plated in a 12-well plate and allowed to adhere overnight. Plates were then aspirated, and 1 ml of fresh media was added to each well. 30 μg of Alexa Fluor 647 labeled nanoparticles were added to each well and allowed to incubate for 20 mins or 6 h at 37° C. in an incubator. After the stipulated time points, media in the wells was completely aspirated and washed 3 times with PBS and the cells were gently scrapped using a cell scrapper. These cells were analyzed by confocal microscope (Upright Zeiss LSM 710 NLO ready).

Erythrocyte PEGylation

PEGylation of erythrocytes were performed according to a previously reported method from our group.1 In brief, erythrocytes were incubated in PBS that contains 10 mg/mL Cyanuric chloride-functionalized 5-kDa m-PEG (C-mPEG, sigma Aldrich) for 30 mins. The C-mPEG formed covalent bonds with the amine groups on erythrocyte surface. Unreacted C-mPEG was eliminated by pelleting the erythrocytes by centrifugation followed by two washes using PBS. PEGylated erythrocytes were resuspended in PBS for use.

Hitchhiked Erythrocyte Characterizations and Biocompatibility

Hitchhiking efficiency and the nanoparticles loaded on erythrocytes were determined using fluorescence measurements. For quantification using fluorescence, 25 μL of erythrocytes were lysed using deionized water and the nanoparticle content was quantified using fluorescence on a plate reader (Tecan Safire 2®, Switzerland). Nanoparticle attachment to erythrocytes was confirmed using scanning electron microscopy (Zeiss FESEM Supra 55VP, Zeiss FESEM Ultra 55, Germany). Briefly, the hitchhiked erythrocytes were fixed using 2.5% glutaraldehyde solution and washed in an increasing ethanol gradient before being chemically dried using hexamethyldisilazane (HMDS). Finally, the samples were sputter coated (EMT 150T ES metal sputter coater, PA USA) prior to imaging. For biocompatibility studies, osmotic fragility and agglutination assays were carried out as previously described.2

In Vitro Shear Studies

Nanoparticles were labeled by Alexa Fluor 647-OVA and used for the shear studies. For low shear studies, hitchhiked murine erythrocytes were incubated in 1 mL of FBS on a tube revolver at 12 rpm at 37° C. After incubation for 20 mins, the cells were pelleted by centrifugation at 250 g for 5 mins and resuspended to 10% v/v in 1×PBS. 25 μL of erythrocytes were then lysed using deionized water and the remaining drug content was quantified using fluorescence on a plate reader (Tecan Safire 2®, Switzerland). For high shear studies, hitchhiked murine erythrocytes were incubated in 10 mL of FBS. A rotatory shear (2 Pa, 6 Pa, or 10 Pa) was applied to erythrocytes in serum using a cylindrical couette viscometer (1 mm gap, AR-G2 rheometer, TA instruments) for 20 mins. The samples were maintained at 37° C. during the application of shear using a water jacket. These conditions simulate high shear physiological environment. After 20 mins, the cells were pelleted by centrifugation at 250 g for 10 mins and resuspended to 10% v/v in 1×PBS. 25 μL of erythrocytes were then lysed using deionized water and the remaining nanoparticle content was quantified using fluorescence on a plate reader (Tecan Safire 2®, Switzerland) and confirmed using scanning electron microscopy (Zeiss FESEM Supra 55VP, Zeiss FESEM Ultra 55, Germany).

Nanoparticle Distribution within the Lungs

For nanoparticle distribution within the diseased lungs, 1×106 4T1-Luc cells were injected orthotopically into the left mammary fat pad of female Balb/c mice. 19 days after inoculation, tumors were surgically resected. 28 days after tumor resection, mice were injected with 17 μg Alexa Fluor 647 labeled nanoparticles with anti-ICAM-1 and erythrocyte hitchhiked fluorescent nanoparticles with anti-ICAM-1. 20 mins after the injection, the mice were euthanized, and the intact lungs were collected. Lungs were washed twice with cold 1×PBS before being fixed in a 4% paraformaldehyde solution overnight. The fixed lungs were then frozen in Tissue Tek OCT compound (Sakura Finetek, CA, USA) and sectioned using a cryostat (Leica CM1950, Germany). The sectioned tissue was mounted using Fluroshield® to stain for DAPI (Ex/Em 340/488 nm) and were analyzed using confocal microscope (Upright Zeiss LSM 710 NLO ready, Germany).

In Vivo Biodistribution Studies in Healthy Mice

For biodistribution study with different PLGAs, healthy female Balb/c mice were used. Alexa Fluor 750-OVA encapsulating NPs and hitchhiked NPs (n=3 for all groups) at a dose containing 17 μg NPs were injected intravenously into the tail vein. Mice were sacrificed at 20 mins after the injection and organs (liver, lungs, spleen, kidneys, heart, brain and blood) were harvested for further processing. For comprehensive biodistribution, Alexa Fluor 750-OVA encapsulating NPs, hitchhiked NPs, Alexa Fluor 750-OVA encapsulating NPs with anti-ICAM-1 and hitchhiked NPs with anti-ICAM-1 (n=3 for free NPs and n=6 for hitchhiked NPs) were injected intravenously into the tail vein. Mice were sacrificed at 20 mins, 2 h, 6 h, and 24 h after the injection and organs (liver, lungs, spleen, kidneys, heart, brain and blood) were harvested for further processing. For processing, 1 mL of cold RIPA lysis buffer (1×) was added to each organ and the organs were homogenized using a high shear homogenizer (IKA T-10 Basic® Ultra turrax, Germany) and the nanoparticle content was quantified by fluorescence measurement on a plate reader (Tecan Safire 2®, Switzerland).

Late-Stage Efficacy in a Breast Cancer Spontaneous Lung Metastasis Model

For the late-stage efficacy, spontaneous lung metastasis model was established by orthotopic injection of 1×106 4T1-Luc into the left mammary fat pad of female Balb/C mice. 32 days after the inoculation, tumors were surgically resected. Treatments were given starting one week after surgery. Four injections were given every two days. The injected doses are same as in the early-stage model. Two days after the last injection (on day 50), the mice were euthanized, intratracheally injected with India ink solution and the lungs were excised and fixed using Feket's solution as previously describe.3 The fixed lungs were used for counting of the surface nodules.

Tumor Rechallenge Study

The tumor rechallenge study was conducted in the early-stage breast cancer spontaneous lung metastasis model, treatments (Control-saline, EASI) were given starting one week after the primary tumor resection. Hitchhiked ImmunoBait containing anti-ICAM-1 antibody was used in the efficacy and survival studies. Four injections were given over 10 days, i.e. day 26, 29, 32, and 35. 2 days after the last injection (day 37), 1×106 4T1-Luc cells were subcutaneously inoculated to the right flank of diseases mice or age matched healthy mice that received no prior tumor inoculations. Mice in the Control-saline group was euthanized 10 days after tumor re-inoculation due to poor body conditions. Tumor growth was measured till day 53. On day 53, mice were euthanized and the weight of extracted tumors was measured.

Supplementary Results

Mechanism of Anchoring of Nanoparticles to Erythrocytes

Our hypothesis is that 1) the hitchhiking process is contact dependent, i.e. nanoparticles should be able to approach the RBC membrane clearly, spread the membrane and eventually get lodged into it, primarily due to non-covalent forces. 2) Post the membrane spreading, the particles are able to remain attached to the RBC membrane due to thermodynamic equilibrium between the membrane surface tension and non-covalent forces between the membrane and nanoparticle surface, including electrostatic interactions, hydrophobic interactions, and hydrogen bonding.

To test the first hypothesis, we first conjugated PEG onto the surface of erythrocytes to inhibit the surface contact of nanoparticles and erythrocyte membrane. According to FIG. 34B, the PEG on the RBC surface hindered the approach of nanoparticles towards the RBC, thereby reducing the hitchhiking efficiency by 50%. These data indicate that the anchoring of nanoparticles to erythrocyte surface is indeed contact dependent. Next, we fixed the erythrocytes to inhibit the spreading of erythrocyte membranes. As shown in FIG. 43A, in the case of fixed RBCs, the hitchhiking efficiency of RBCs dramatically reduced to zero, indicating that if the nanoparticles are not able to spread the membrane, they are unable to bind to the RBC membrane. This study indicates that the anchoring of nanoparticles requires membrane spreading, i.e. if the approach is hindered or the membrane chemically fixed to prevent stretching, the hitchhiking process gets drastically affected.

To test the second hypothesis, we conducted hitchhiking experiments in serum rather than PBS to inhibit the overall non-covalent interactions between nanoparticles and erythrocyte membranes. The serum proteins would form corona around the nanoparticles and also cover RBCs thereby masking/reducing overall nanoparticle-RBC interactions. As shown in FIG. 43C, in a sharp contrast to PBS, utilizing serum as the hitchhiking media reduced hitchhiking efficiency by 60%, indicating non-covalent interactions are largely responsible for the holding of nanoparticles onto erythrocyte membranes.

We hypothesize that the actual non-covalent forces responsible for holding the nanoparticles in place once the RBC membrane spreads include electrostatic interactions, hydrophobic interactions, and hydrogen bonding. In our previous study, we reported that positively charged nanoparticles bound to erythrocytes at a super high efficiency (>40%), suggesting the electrostatic interactions play a critical role in binding of nanoparticles to erythrocytes4. This is understandable because the erythrocyte membrane carries negative charge. However, negatively charged nanoparticles could also efficiently bind to erythrocytes, in which case electrostatic interactions do not involve. We hypothesize that hydrophobic interactions between nanoparticles and erythrocyte membranes are the major players in this case to hold nanoparticles in place. To test this hypothesis, we inhibited the hydrophobic interactions by covering the nanoparticles with hydrophilic PEG. As shown in FIG. 43D, in the case of PEG modified nanoparticles, the overall hitchhiking efficiency reduces by almost 75%, indicating that hydrophobic forces are vital in order for the process to happen efficiently. Apart from electrostatic and hydrophobic interactions, we hypothesize that other non-covalent interactions such as hydrogen bonding also plays a significant role in holding nanoparticles on erythrocyte membranes. To test this hypothesis, we compared the binding of ester-end and acid-end PLGA nanoparticles (of same composition) to erythrocytes. Ester-end PLGA nanoparticles are more hydrophobic while acid-end nanoparticles are able to form hydrogen bonding with cell membranes. As shown in FIG. 43E, when using ester-end nanoparticles instead of acid-end nanoparticles, the hitchhiking efficiency surprisingly reduced by 25%. This was unexpected, given that hitchhiking primarily was believed to be dominated by hydrophobic forces. This result indicates that H-bonding also controls hitchhiking to certain extent.

In summary, based on our data, the anchoring of nanoparticles to erythrocytes can follow the proposed mechanism: the nanoparticles approach the RBC membrane, and in absence of competitive shielding proteins/forces, spread the RBC membrane in a contact dependent manner. After this, nanoparticles are held in place due to non-covalent forces of attraction (electrostatic interactions, hydrophobic forces, and H-bonding) between the RBC membrane and the nanoparticle surface.

Detachment of PLGA Nanoparticles with Different Materials Properties from Erythrocytes Our mechanism study (FIGS. 43A-43E) indicates that both hydrophobic interactions and hydrogen bonding contribute to the binding of nanoparticles to erythrocytes. Under non-shear conditions, both H-bonding and hydrophobic interactions are sufficiently strong to hold nanoparticle on erythrocytes. PLGA-d has balanced hydrophobicity and hydrogen bonding ability, and thus show highest affinity to erythrocytes under non-shear conditions. However, H-bonding is relatively weaker than hydrophobic interactions. Therefore, under shear conditions, the weak hydrogen bond is easier to break down and leads to dislodgement of nanoparticles from erythrocytes. Since hydrogen bonding is a dominant force for PLGA-d binding to erythrocytes, more nanoparticles were dislodged from erythrocytes under shear conditions (FIG. 35).

Detachment of ImmunoBait from Erythrocytes In Vivo

Figures 36A, 36B, 36C, 36D, 36E, 36F:
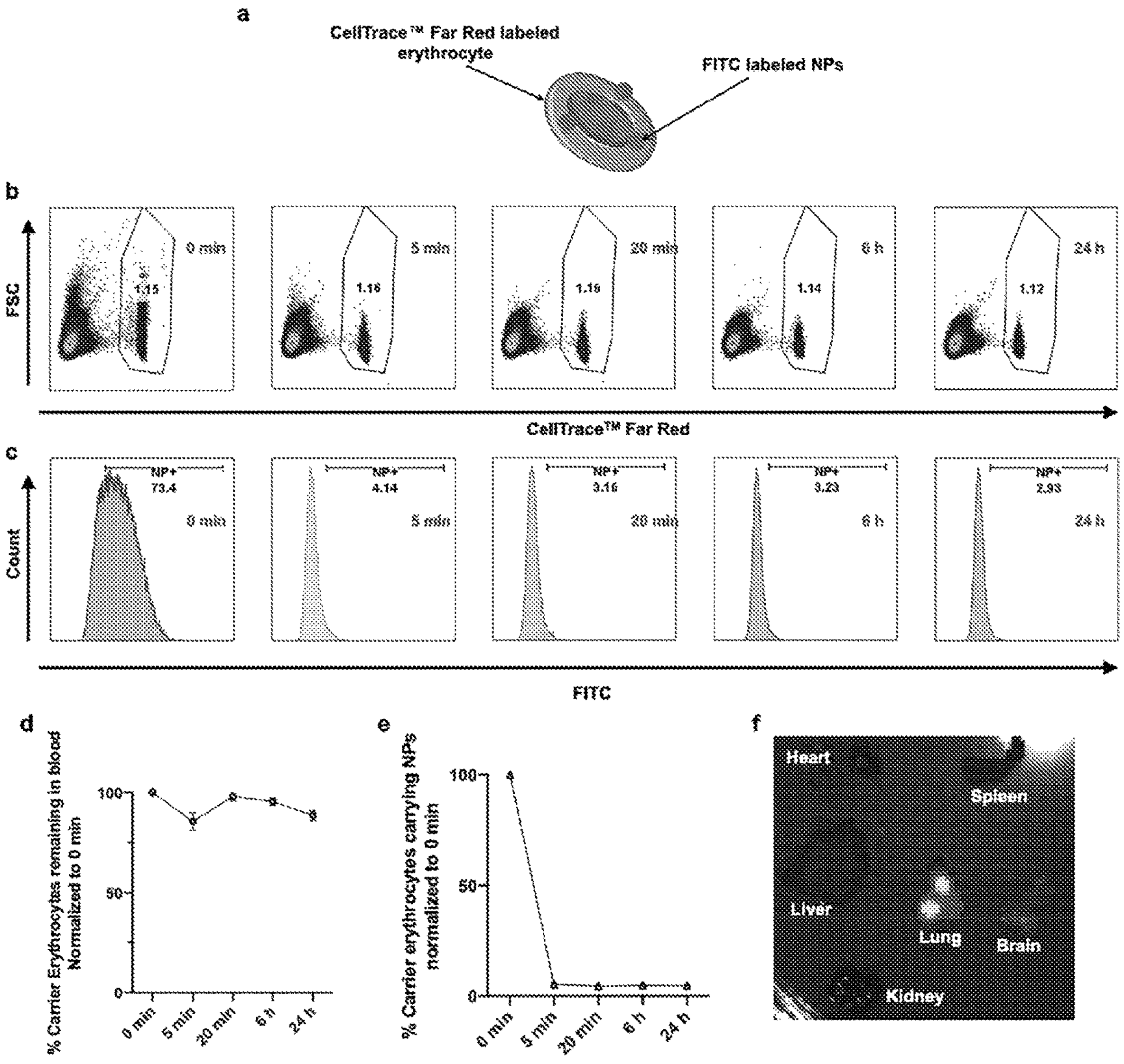
FIGS. 36A-36F depict characterization of the erythrocyte hitchhiking system in the blood after i.v. administration.
Figure 37:
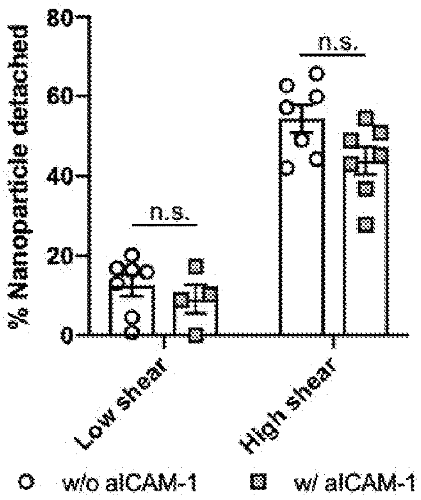

To further characterize the hitchhiked erythrocyte system in vivo, we double labeled the system in which the carrier erythrocytes were labeled by CellTrace™ Far Red and the nanoparticles were labeled by FITC (FIG. 36A). We injected the double labeled hitchhiked erythrocyte system and collected the blood at different time points and analyzed the hitchhiked system by flow cytometry. As shown in in FIG. 36B and FIG. 36D, the carrier erythrocytes remained in the blood for at least 24 hours. In contrast, as shown in FIG. 36C and FIG. 36E, most of the nanoparticles on the carrier erythrocytes (>95%) were quickly detached from the carrier erythrocytes in <5 min and the biodistribution data shown in FIG. 36F indicated the detached nanoparticles were most deposited in the lung. The data shown in FIGS. 36A-36F together with our previous studies5 indicate that nanoparticles anchored on erythrocytes are quickly sheared off at the first capillary bed they hit. In the case of intravenous injection, lung is the first capillary rich organ that the carrier erythrocytes see and hence deposit the most anchored nanoparticles there instead of other organs.

TABLE 5

Properties of four PLGA candidates.

| | PLGA-a | PLGA-b | PLGA-c | PLGA-d |
|---|---|---|---|---|
| L:G ratio* | 50:50 | 50:50 | 85:15 | 65:35 |
| End-group | Ester-end | Acid-end | Ester-end | Acid-end |

*Molar ratio of lactic acid to glycolic acid in the polymer

References for Supplementary Information

1. Chambers, E. & Mitragotri, S. Long circulating nanoparticles via adhesion on red blood cells: mechanism and extended circulation. Exp Biol Med (Maywood) 232, 958-966 (2007).
2. Pan, D. et al. The Effect of Polymeric Nanoparticles on Biocompatibility of Carrier Red Blood Cells. PLoS One 11, e0152074 (2016).
3. Miretti, S. et al. A Mouse Model of Pulmonary Metastasis from Spontaneous Osteosarcoma Monitored In Vivo by Luciferase Imaging. Plos One 3 (2008).
4. Zhao, Z., Ukidve, A., Gao, Y., Kim, J. & Mitragotri, S. Erythrocyte leveraged chemotherapy (ELeCt): Nanoparticle assembly on erythrocyte surface to combat lung metastasis. Sci Adv 5, eaax9250 (2019).
5. Brenner, J. S. et al. Red blood cell-hitchhiking boosts delivery of nanocarriers to chosen organs by orders of magnitude. Nat Commun 9 (2018).

Example 5: Erythrocyte-Driven Immunization Via Biomimicry of their Natural Antigen Presenting Function Erythrocytes naturally capture certain bacterial pathogens in circulation, kill them through oxidative stress, and present them to the antigen presenting cells (APCs) in the spleen. By leveraging this innate immune function of erythrocytes, we developed Erythrocyte Driven Immune Targeting (EDIT), which presents nanoparticles from the surface of erythrocytes to the APCs in the spleen. Antigenic nanoparticles were adsorbed on the erythrocyte surface. By engineering the number density of adsorbed nanoparticles, they were predominantly delivered in the spleen rather than lungs which is conventionally the target of erythrocyte-mediated delivery systems. Presentation of erythrocyte-delivered nanoparticles to the spleen led to improved antibody response against the antigen, higher central memory T cell response and lower regulatory T cell response, compared to the controls. Enhanced immune response slowed down tumor progression in a prophylaxis model. These findings indicate that EDIT is an effective strategy to enhance systemic immunity.

Red blood cells perform a unique function of capturing certain pathogens in blood and presenting them to the immune cells in the spleen. We developed a biomimetic strategy based on this innate immune function of red blood cells to deliver vaccine nanoparticles to the spleen. This "natural adjuvant" strategy induced strong vaccination responses without the need for foreign adjuvants.

Introduction

Erythrocytes, accounting for over 80% cells in the human body, serve the primary function of oxygen delivery to tissues. In addition to the oxygen transport, erythrocytes also perform several additional functions that are of high immunological relevance. For example, upon reaching the end of their natural lifespan, senescent erythrocytes are phagocytosed in the spleen in a non-inflammatory pathway (1). This unique mechanism has been elegantly exploited to develop tolerance to antigens for applications in autoimmune disorders and reducing anti-drug antibody production (2-4). Specifically, antigenic peptides, attached to erythrocyte membranes, are captured in the spleen along with senescent erythrocytes, thus generating a tolerogenic response to antigens due to non-inflammatory pathway of the capture unique to erythrocytes.

Recently, erythrocytes have been implicated in another interesting and contrasting innate immune function (5, 6). Specifically, they capture immune complexes and bacteria in circulation on their surface and hand them to Kupffer cells in the liver and professional antigen presenting cells (APCs) in the spleen without the capture of the carrier erythrocyte (7-11). Bacterial species in the blood such as *Staphylococcus* and *Propionibacterium* attach to erythrocyte membrane due to electrostatic attraction and are killed by oxycytosis by the carrier erythrocyte. Thereafter, erythrocytes hand them over to the cells in the liver and spleen, without themselves being sequestered (9, 12). While the exact mechanism of selective cargo uptake by APCs is unclear, transient membrane alteration induced by the bacterial cargo is implicated in the increased crosstalk between the erythrocytes and APCs (13, 14). Here, we leverage this innate and unique ability of erythrocytes to present antigens in the spleen to develop a biomimetic strategy for generating cellular and humoral immune responses to antigens (FIGS. 47A-47F).

Attachment of molecules to erythrocytes has been leveraged for several biomedical applications (15). A range of payloads including proteins (2-4), therapeutics (16) and nanoparticles (17-19) have been attached to erythrocyte surface or encapsulated within erythrocytes (20) for various therapeutic applications. The attachment of the cargo to the erythrocyte surface has been brought about by chemical conjugation (16), binding to specific receptors like Glycophorin A (4), sortagging (2) or passive adsorption (19), without compromising their physiological function of oxygen transport. All previous approaches of hitchhiking on erythrocytes are based on induction of minimal perturbation to the carrier erythrocytes, which has led to either their extended circulation or capture in the capillary endothelia after injection. (17, 19, 21). Here, we engineered a hitchhiking system that induces the delivery of the attached nanoparticles predominantly to the spleen instead of lungs to achieve cellular and humoral immunity, a process that we refer to as, Erythrocyte Driven Immune Targeting (EDIT).

Results

Synthesis and Characterization of Antigenic Cargo

Figures 48A, 48B, 48C, 48D, 48E, 48F, 48G:
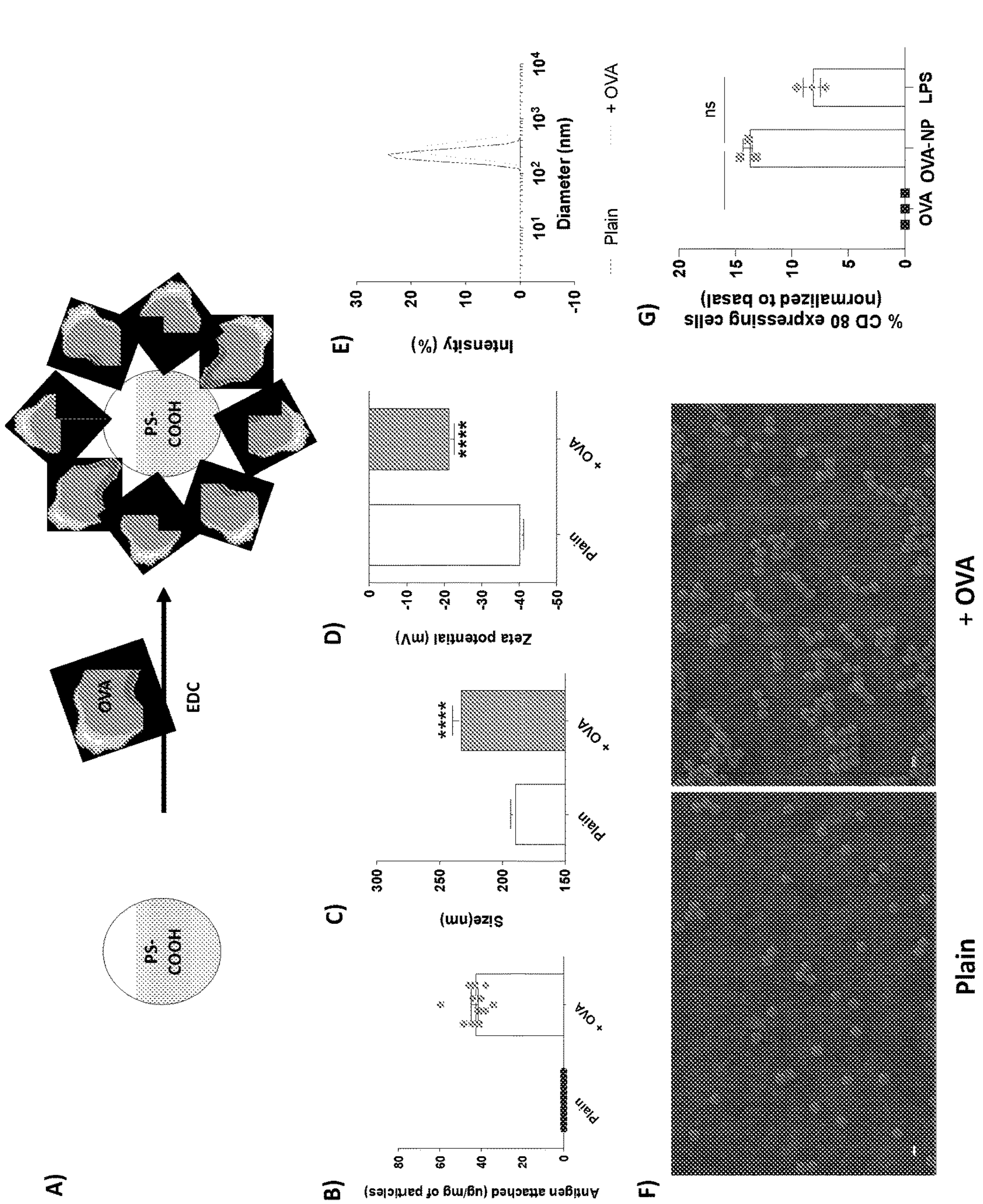
FIGS. 48A-48G depict the characterization of protein capped nanoparticles.
Figures 52A, 52B:
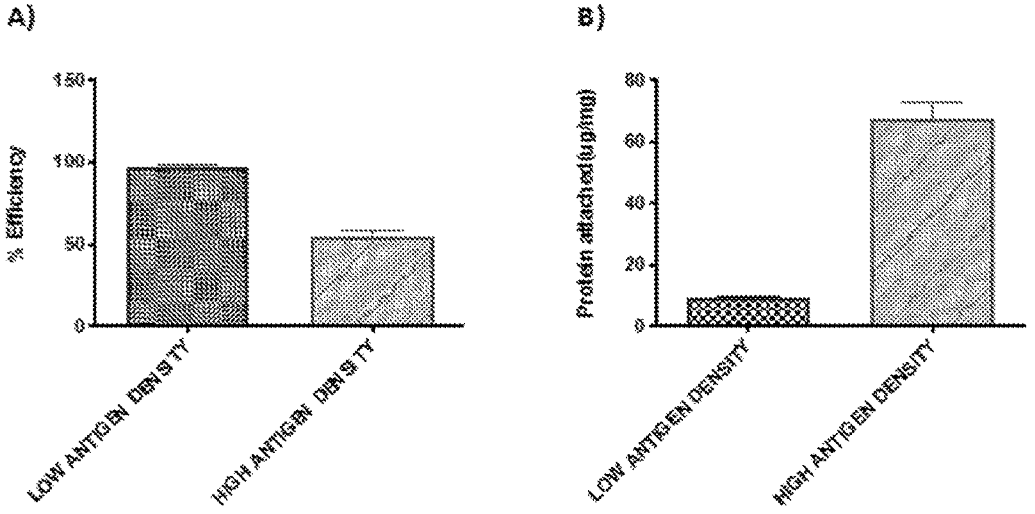
FIGS. 52A-52B depict the attachment of different amount of proteins on the surface of 200 nm polystyrene carboxylate nanoparticles.

Ovalbumin (OVA) was selected as a model antigen and was capped on the surface of 200 nm polystyrene carboxylate (PS—COOH) to generate protein-capped nanoparticles (NPs) that were attached to erythrocytes (FIG. 48A). OVA was attached to 200 nm NPs using the 1-Ethyl-3-(3-dimethylaminopropyl) carbodiimide (EDC) chemistry, as previously reported (22). Loading of OVA on NPs could be controlled over a wide range (FIG. 52A-52B), however, an intermediate loading of 43 ug/mg of particles was used for the remainder of the studies (FIG. 48B). OVA attachment to nanoparticles was confirmed by size and zeta potential measurements. OVA attachment increased the hydrodynamic size of NPs from 191 nm to 234 nm (FIG. 48C). Further, conjugation of the carboxylate groups on the NPs was also evident from the decrease in zeta potential from −40.4 mV to −21.4 mV (FIG. 48D). OVA conjugation did not affect NP polydispersity (FIG. 48E). This was further confirmed by performing scanning electron microscopy (SEM). SEM images of plain and conjugated nanoparticles show monodisperse nanoparticles (FIG. 48F) in both cases, indicating that OVA conjugation had a negligible effect on polydispersity.

Figures 53A, 53B:
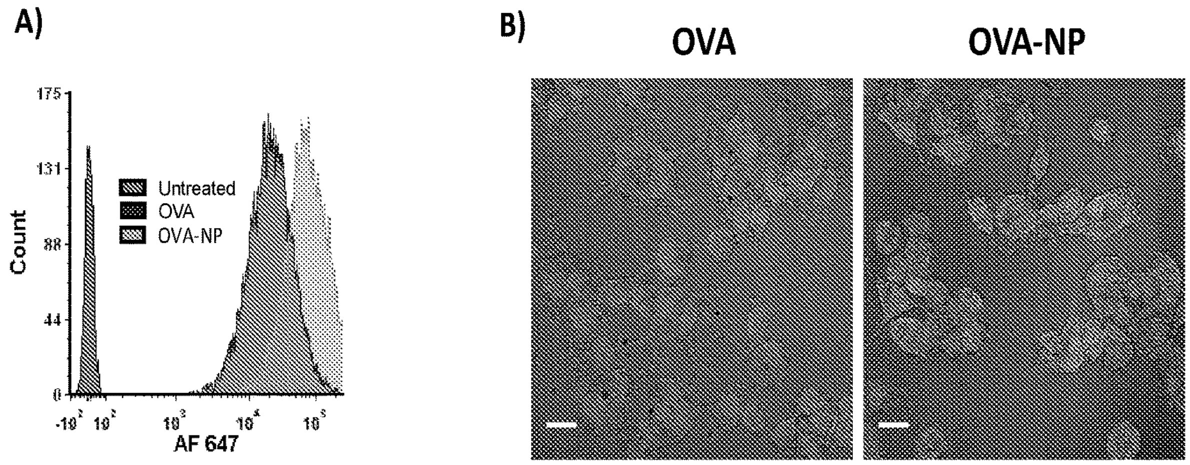
FIGS. 53A-53B depict the internalization of OVA-NP by dendritic cells.
Figures 54A, 54B, 54C, 54D:
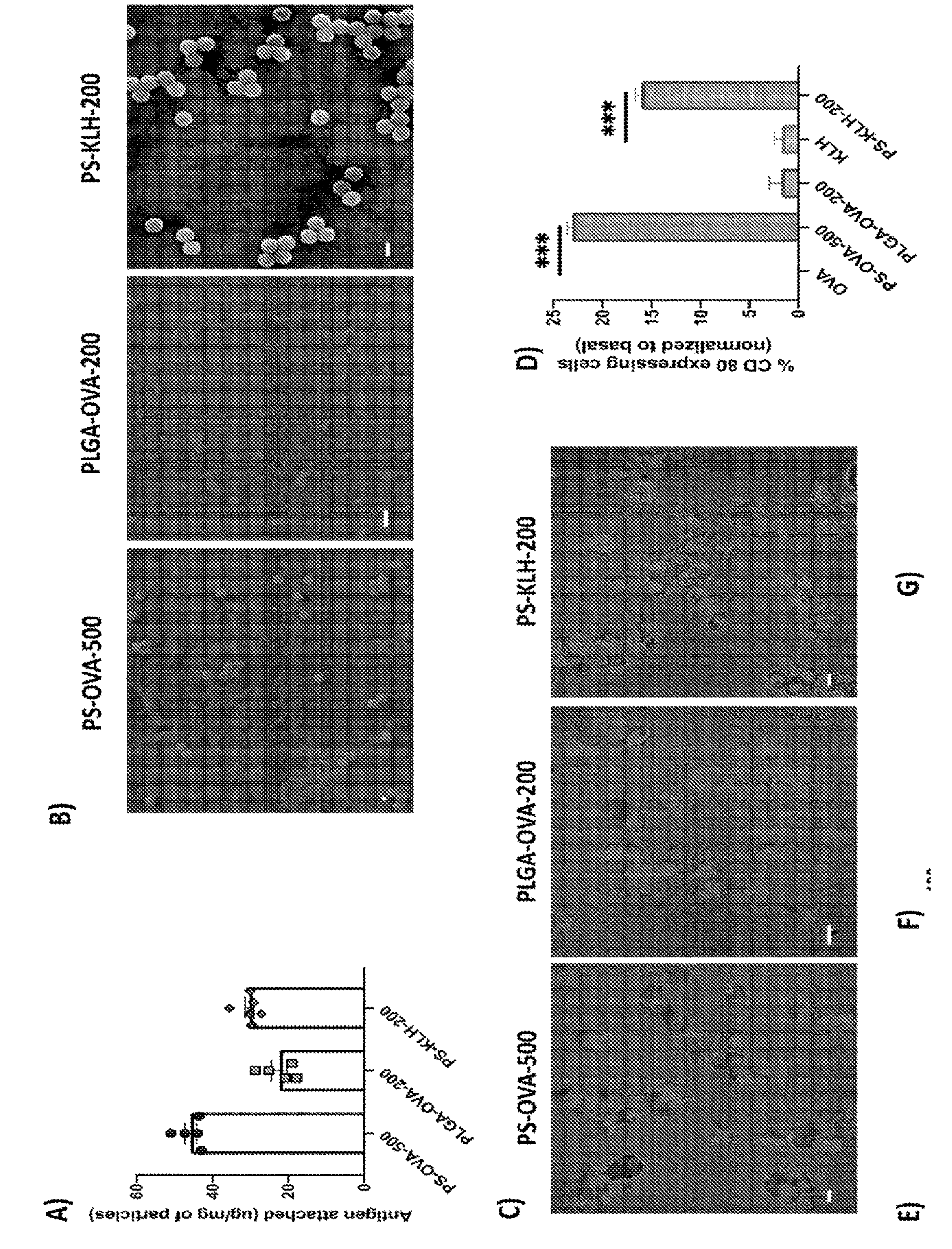
FIGS. 54A-54D depict particle combinations for EDIT platform.

Apart from characterization of physicochemical properties, we also characterized the OVA-NPs for internalization by and activation of dendritic cells. Both OVA and OVA-NPs were taken up by dendritic cells (FIG. 53A). However, OVA-NPs were taken up in significantly higher quantities compared to free OVA, which was also confirmed by confocal scanning laser microscopy (CLSM) images (FIG. 53B). Co-stimulatory effect on dendritic cells, evaluated in terms of CD80 upregulation, revealed that OVA-NPs significantly upregulated CD80 expression compared to their soluble counterpart and were comparable to positive control, lipopolysaccharide (LPS) (FIG. 48G). We also capped 500 nm PS with OVA, 200 nm PLGA with OVA (PLGA-OVA-200) and 200 nm PS—COOH with subunit 1 of Keyhole limpet hemocyanin (KLH) (PS-KLH-200) to confirm the generality of this approach. Respective proteins were attached to different particle types using the same EDC chemistry Physicochemical properties of these combination particles were evaluated (Table 6) and these particles were also characterized for their ability to get internalized by the dendritic cells and consequently activate them (FIG. 54A-54D). All particles were monodispersed and showed excellent internalization by and activation of dendritic cells. Though bare nanoparticles are themselves capable of maturating the cells (23), they are not of specific consequence in assessing the benefits of hitchhiking OVA-NPs and hence were not included in the study.

Figures 49A, 49B, 49C, 49D, 49E, 49F, 49G:
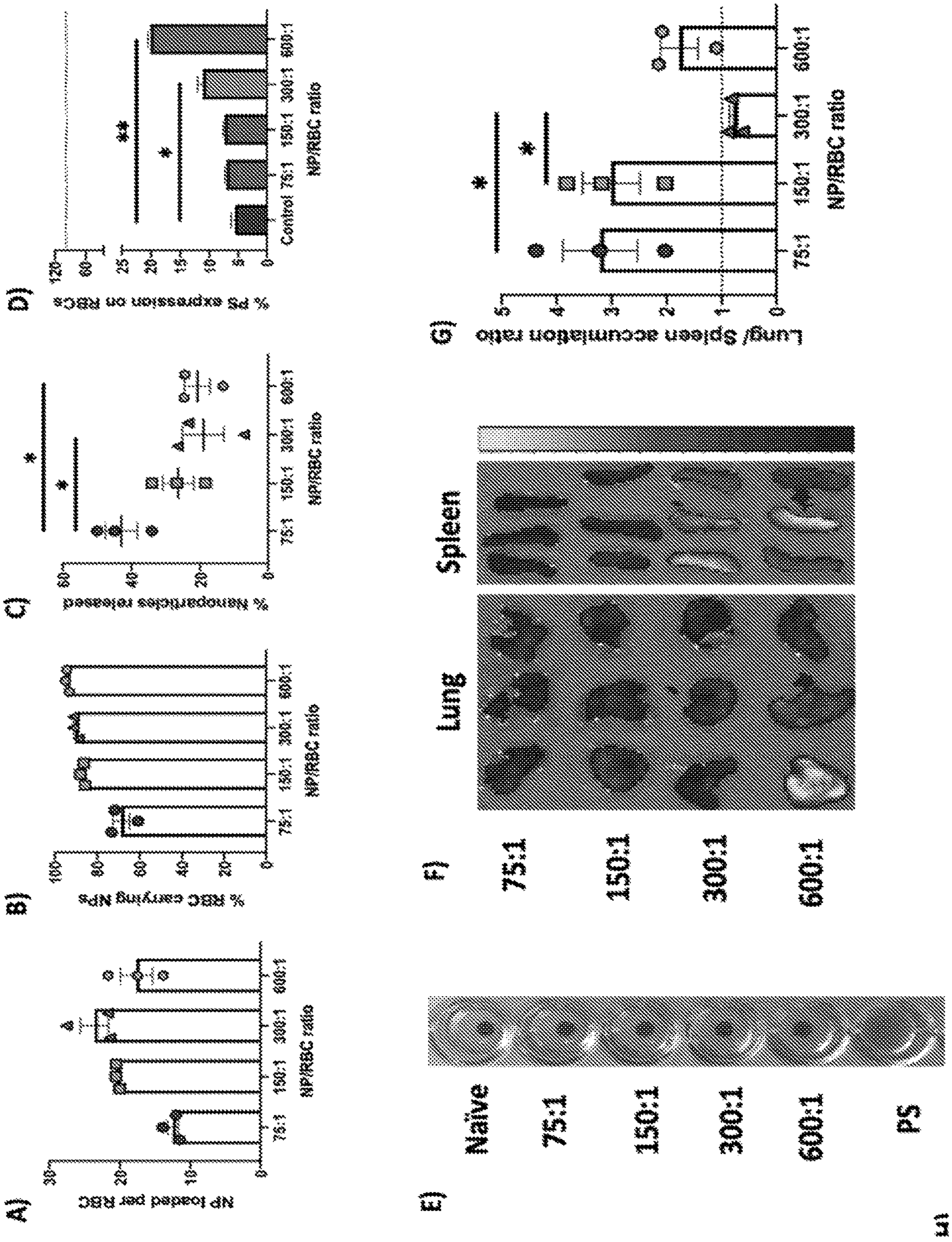
FIGS. 49A-49K depict engineering nanoparticle-erythrocyte hitchhiking parameters to achieve spleen targeting.
Figures 55A, 55B, 55C:
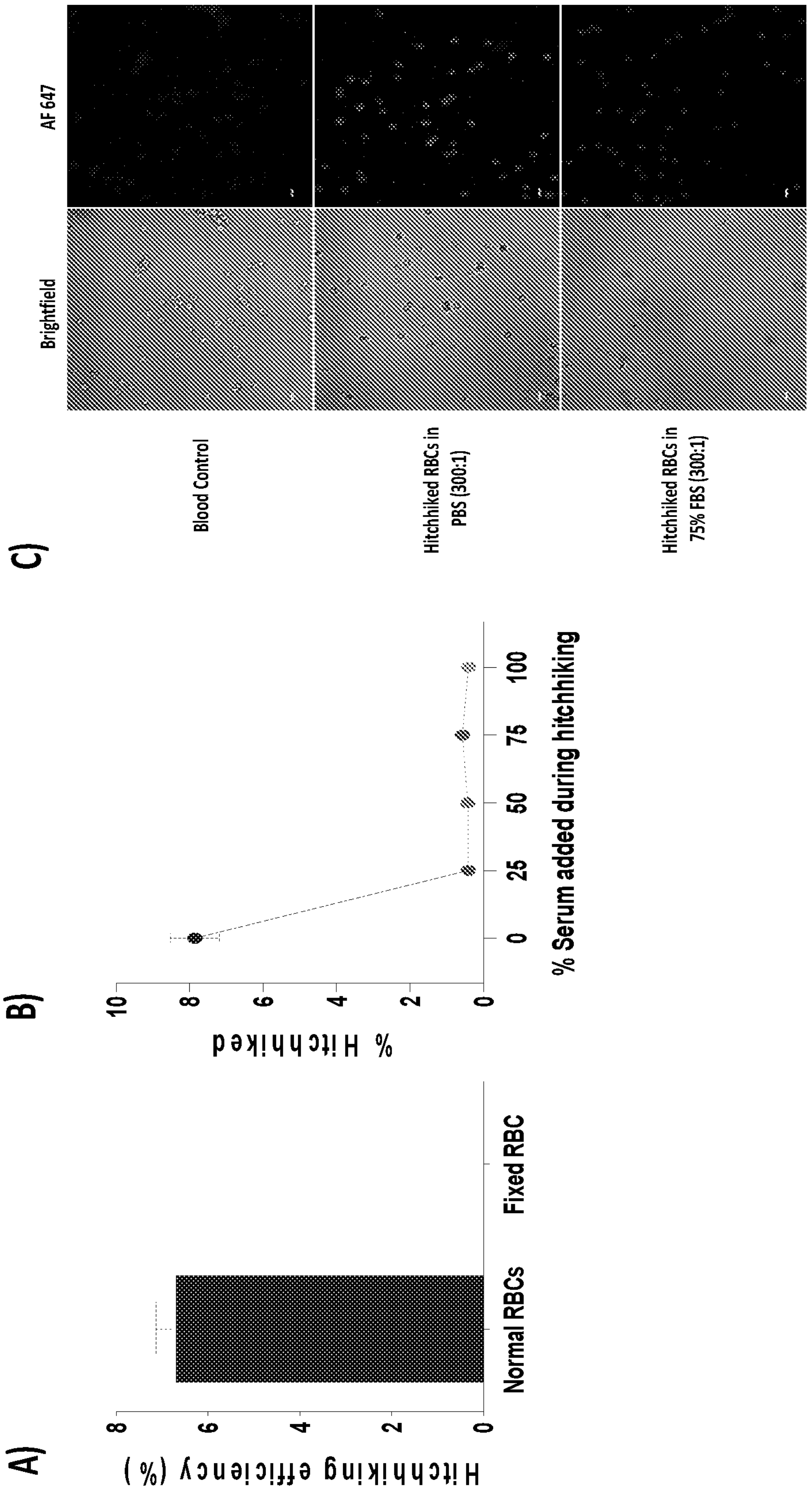
FIGS. 55A-55C depict mechanistic understanding of erythrocytes-nanoparticle binding.
Figures 56A, 56B, 56C:
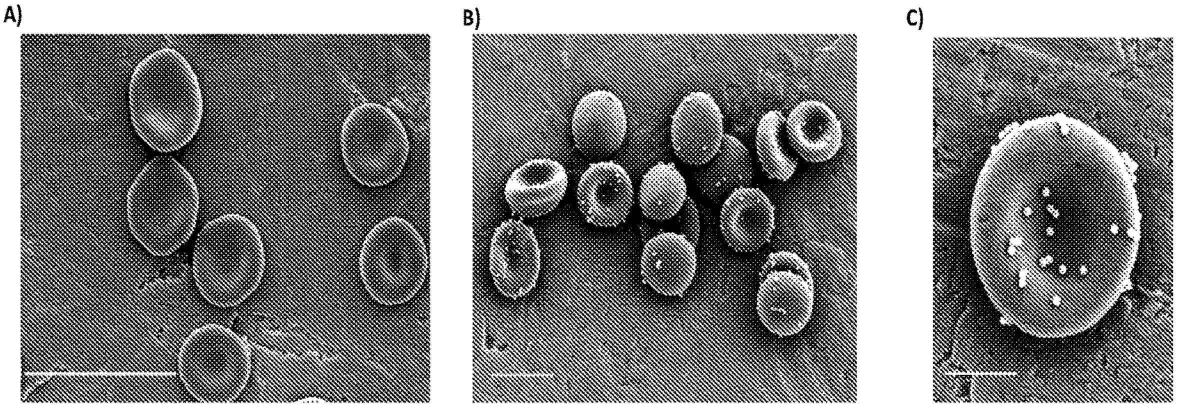
FIGS. 56A-56C depict scanning electron micrographs of nanoparticles hitchhiked on erythrocytes.

Engineering Nanoparticle-Erythrocyte Hitchhiking to Achieve a Hand-Off in the Spleen Hitchhiking of nanoparticles occurs through two steps that are physical in nature (17, 19, 24); adsorption of nanoparticles on erythrocyte surface to initiate the contact and spreading of the membrane around the nanoparticles to enhance the adhesion strength. Either one of them is not sufficient. If nanoparticles don't make a contact with the erythrocyte, the adhesion is not initiated and if the membrane spreading is inhibited, the adhesion is weak, and the nanoparticles fall off during washing. Introduction of competitor proteins (serum) during attachment essentially inhibits the hitchhiking. This inhibitory effect is seen even at 25% addition of serum. At the same time, by using glutaraldehyde fixed RBCs, our data demonstrate that rigidifying the membrane nearly eliminates hitchhiking (FIG. 55A-55C). As the NP:Erythrocyte ratio during incubation increased from 75:1 to 300:1, the number of nanoparticles that attached to erythrocytes increased from 12 to 24 per cell. However, further increasing the ratio to 600:1 surprisingly decreased nanoparticle loading to about 18 per erythrocyte, possibly due to the presence of excessive nanoparticles in the hitchhiking suspension, thereby hampering the necessary erythrocyte-nanoparticle interactions (FIG. 49A). The presence of nanoparticles on the erythrocytes was confirmed by SEM (FIG. 56A-56C) and flow cytometry analyses of hitchhiked erythrocytes. Particularly, percentage of erythrocytes carrying nanoparticles increased from 68% at a ratio of 75:1 to >95% at a ratio of 600:1 (FIG. 49B).

Erythrocyte hitchhiking has been previously explored for lung targeting since the nanoparticles on the erythrocyte surface are sheared off in the lungs owing to high shear stress and squeezing of erythrocytes due to close contact with the endothelium in lung capillaries (17, 18). Reducing lung uptake is essential to enabling nanoparticle-carrying erythrocytes escape lungs and deliver their cargo in other organs, in this case, spleen. To that effect, we tested the in vitro shear resistance of hitchhiked nanoparticles as a function of NP:Erythrocyte ratio at a shear stress of 6 Pa which corresponds to lung capillaries. Release of NPs from erythrocytes decreased with increasing loading from 75:1 to 600:1 (FIG. 49C), likely due to the stiffening of erythrocytes at high particle loadings (24). Thus, sufficient fluidity/shear resistance at higher nanoparticle loadings is needed to escape the mechanical dislodgement of particles in the lungs.

Figures 57A, 57B:
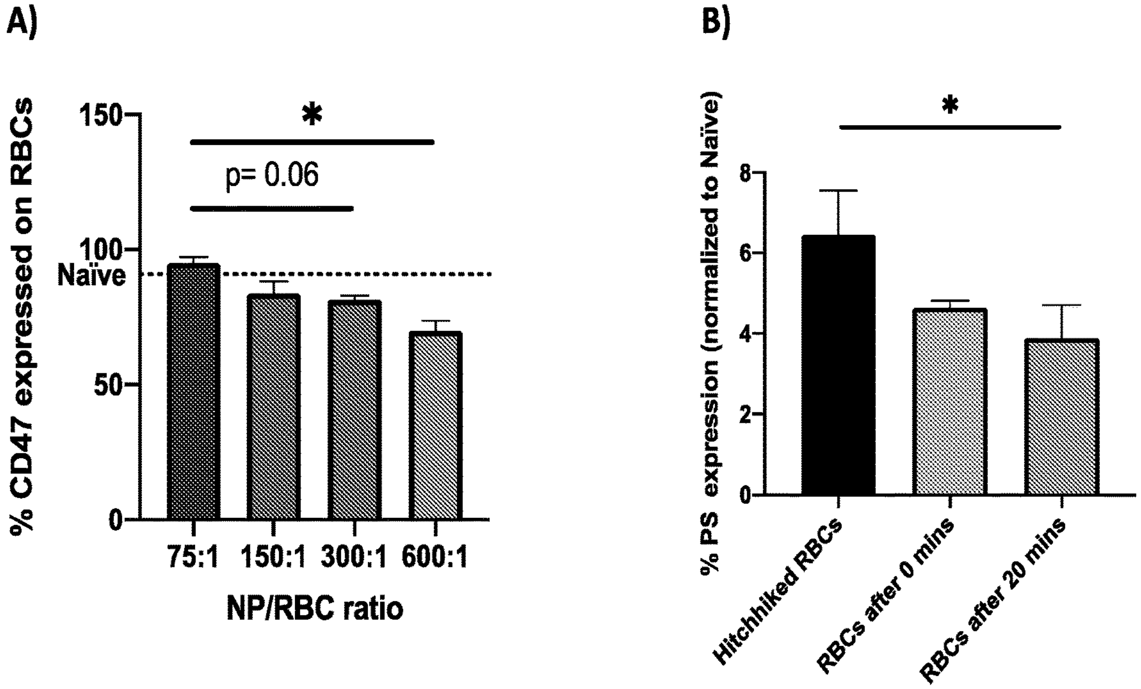
FIGS. 57A-57B depict changes in the surface marker expressions on erythrocyte membranes.

Spleen targeting was mediated by maintaining sufficient loading, shear resistance to escape mechanical dislodgement in the lungs and induction of erythrocyte membrane alterations to prompt capture in the spleen. The extent of alterations in the erythrocyte in the membrane was controlled by NP dose. Erythrocyte membrane alteration was quantified in terms of expression of phosphatidyl serine on the erythrocyte membrane. Incubation of erythrocytes at an NP:Erythrocyte ratio of 300:1 and 600:1 caused a moderate increase in the expression of phosphatidyl serine compared to unloaded naïve erythrocytes (FIG. 49D). Hitchhiking process also decreased CD47 expression, possibly due to physical masking by the nanoparticles (FIG. 57A). Further, optical agglutination assay indicated that there is no visual aggregation/rouleaux formation of erythrocytes incubated with nanoparticles compared to positive control polystyrene beads which formed matrix shaped aggregates (FIG. 49E). The lack of aggregation indicates that NP-hitchhiking erythrocytes can be injected in vivo (25).

Figures 49H, 49I, 49J, 49K:
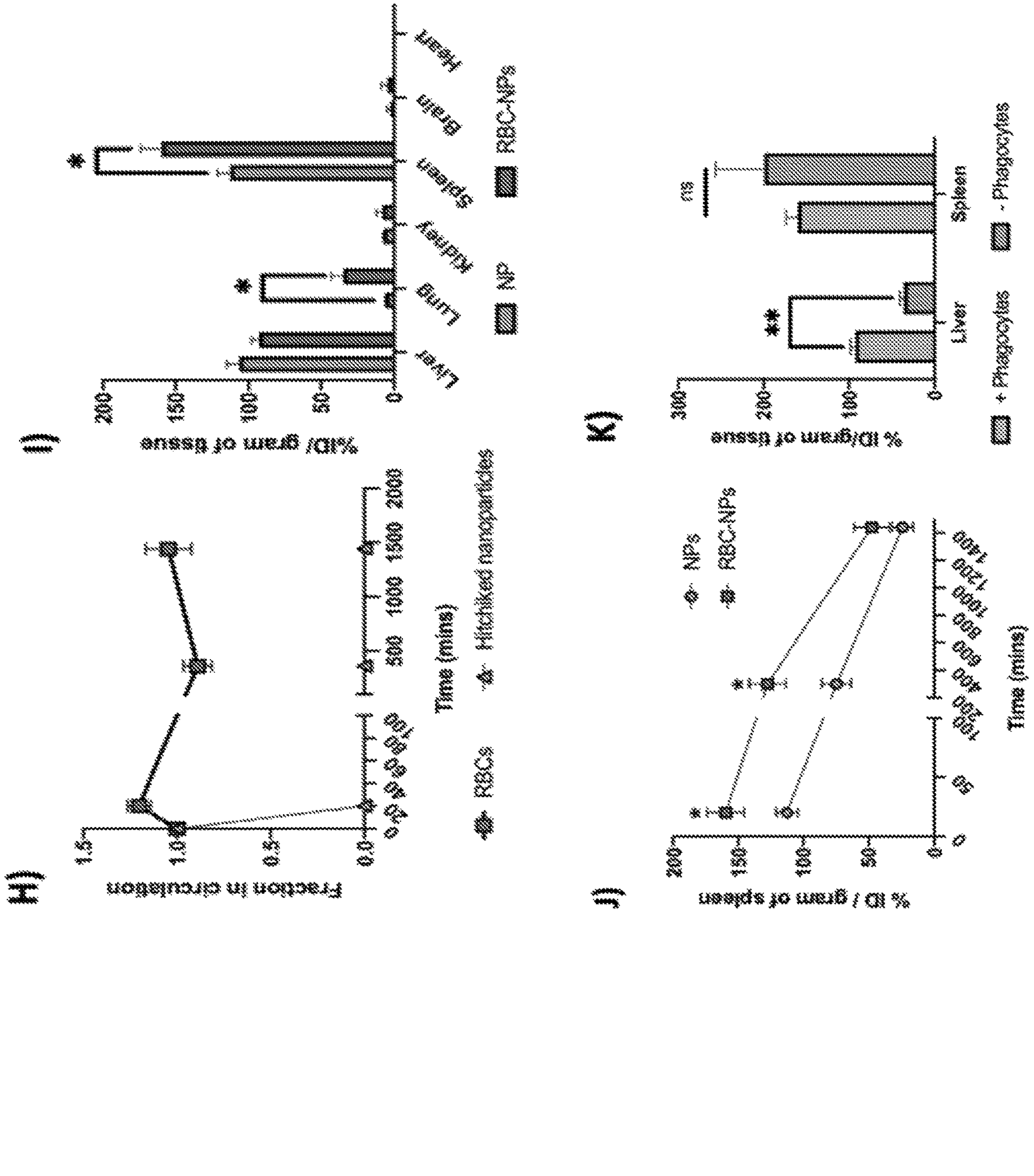

Effect of the nanoparticle loading on in vivo nanoparticle distribution was evaluated by performing biodistribution 20 min after intravenous injection of all different loading ratios but injecting the same volume of erythrocytes. Fluorescent intensities of harvested organs, particularly lungs and the spleen were evaluated (FIG. 49F). Low NP:Erythrocyte ratios (75:1 and 150:1) led to high lung:spleen accumulation ratio (~3) whereas high loading (NP: Erythrocyte ratio of 300:1 showed higher spleen accumulation than lung accumulation (lung:spleen ratio ~0.8). Increasing the ratio further to 600:1 again favored lung accumulation possibly due to lower nanoparticle attachment than that of 300:1 (FIG. 49A). The PS expression data (FIG. 49D) indicate that the erythrocyte membrane is most impacted at an incubation ratio of 600:1. Collectively, these findings indicate that 300:1 is the optimal loading ratio for spleen targeting, e.g., under these conditions (FIG. 49G). Hence, NP:Erythrocyte ratio of 300:1 was selected for the remainder of the studies. The lung:spleen accumulation ratio for our optimal system is less than 1 (<40% ID/g in lungs). This ratio in a typical study on erythrocyte hitchhiking nanoparticles targeting lungs is ~10 (to >100% ID/g in the lungs) (17). We also evaluated pharmacokinetics of the injected hitchhiked nanoparticles (NP: Erythrocyte ratio of 300:1) by separately tracking erythrocytes and nanoparticles by flow cytometry. The fraction of injected erythrocytes did not change with time (<24 h) after injection, while the hitchhiked nanoparticles rapidly disappeared out of the blood stream with less than 1% remaining in the circulation as early as 20 mins after the injection, indicating rapid clearance from the bloodstream (FIG. 49H). This clearly indicated that erythrocytes were able to quickly deliver their payloads to specific organs while themselves resisting clearance, possibly due to decrease in the phosphatidyl serine expression on hitchhiked erythrocytes after nanoparticle hand-off (FIG. 57B).

Figures 58A, 58B:
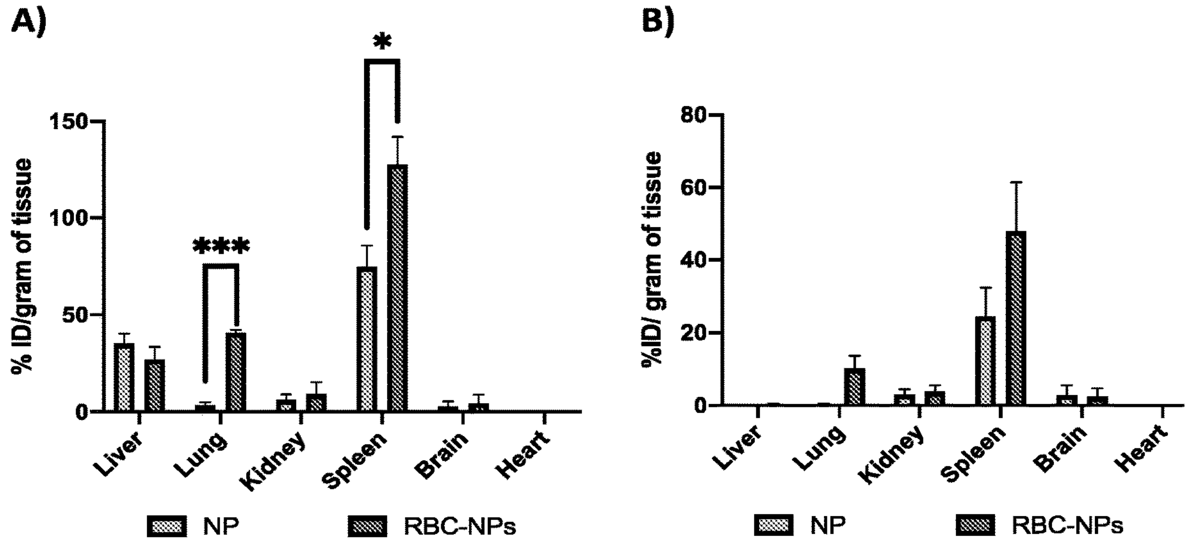
FIGS. 58A-58B depict the biodistribution of hitchhiked and free nanoparticles 6 h and 24 h after intravenous injections.
Figures 59A, 59B, 59C, 59D:
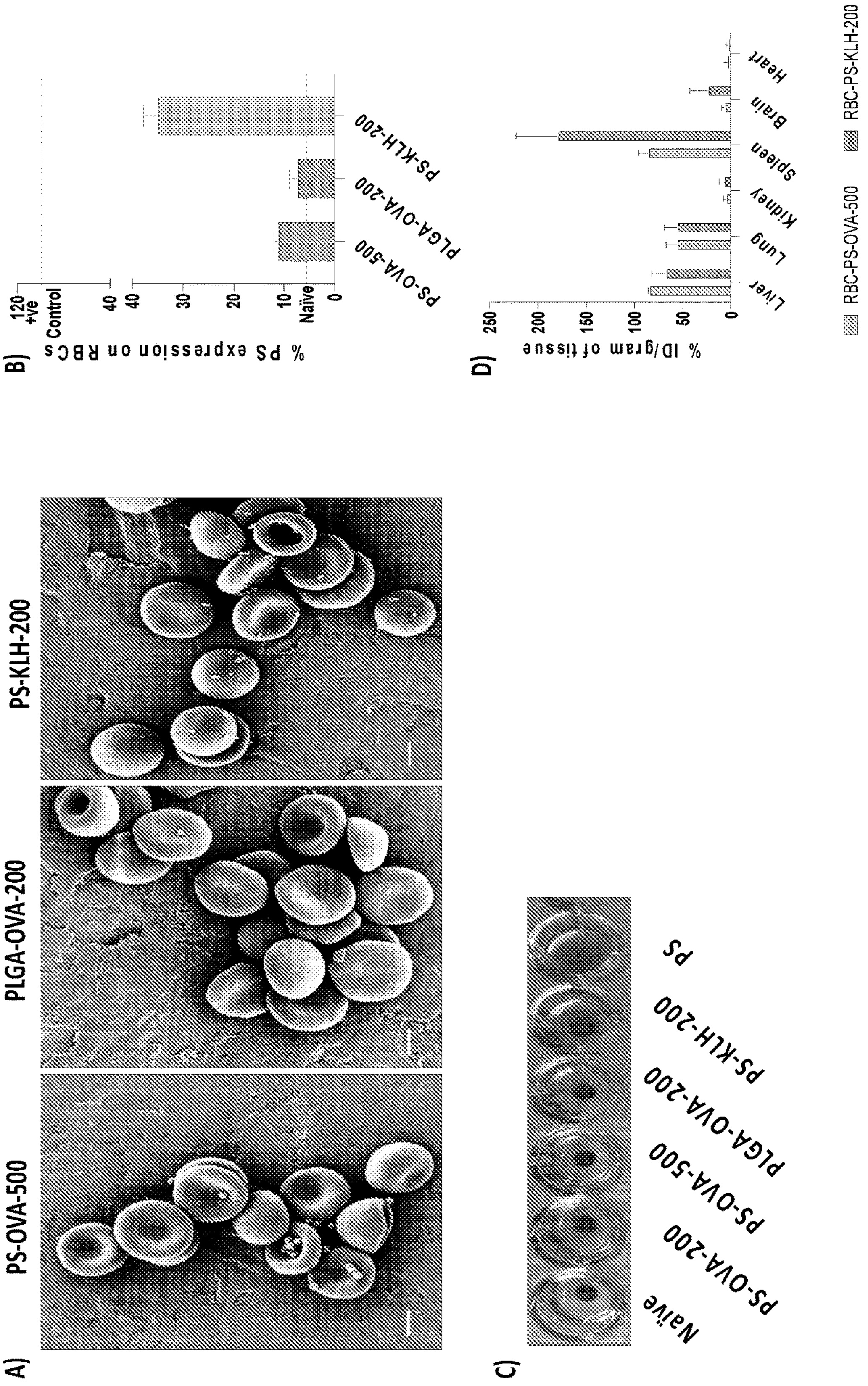
FIGS. 59A-59D depict the potential of EDIT to deliver different nanoparticle combinations to spleen.

Next, we performed a time course biodistribution of hitchhiked nanoparticles at 20 mins, 6 h and 24 h after intravenous injection and compared it to the biodistribution of equivalent free nanoparticles (FIG. 49I, 58A-58B). Free nanoparticles accumulated in the liver and spleen. Erythrocyte-hitchhiked NPs exhibited higher spleen accumulation (FIG. 49J). Our study represents the first time that a splenic dose of ~150% ID/g was achieved using erythrocyte hitchhiking. The higher accumulation (~1.5-fold improvement over control) in spleen was significant even after 6 h compared to free nanoparticles and was maintained for up to 24 h after injection (FIG. 49J). Further studies revealed that other particle combinations studied were also able to induce transient damage and this strategy was capable of carrying out hand-offs for a variety of particles (FIG. 59A-59D).

To assess whether the nanoparticles delivered by erythrocytes to the spleen are picked up by phagocytes or by professional antigen presenting cells (APCs), we carried out phagocyte depletion in mice using clodronate (26) and performed biodistribution at 20 mins post the injection of hitchhiked nanoparticles and two immunologically active organs, liver and spleen were evaluated for changes in delivery efficiency. Clodronate liposomes transiently incapacitate the macrophages in the reticuloendothelial system in hepatic sinuses and spleen (26). This intervention leads to delegation of the functions of recognition, phagocytosis and presentation of foreign compounds to other cells including dendritic cells taking over antigen-presenting functions in the host defense. Phagocyte depletion significantly reduced the liver uptake (~2.5 fold) but caused no significant change in the splenic uptake, indicating that nanoparticles in the spleen are viable and internalized by APCs and not phagocytosed (FIG. 49K).

Immunological Consequences of Nanoparticle Hand-Off in the Spleen

Figures 50A, 50B, 50C:
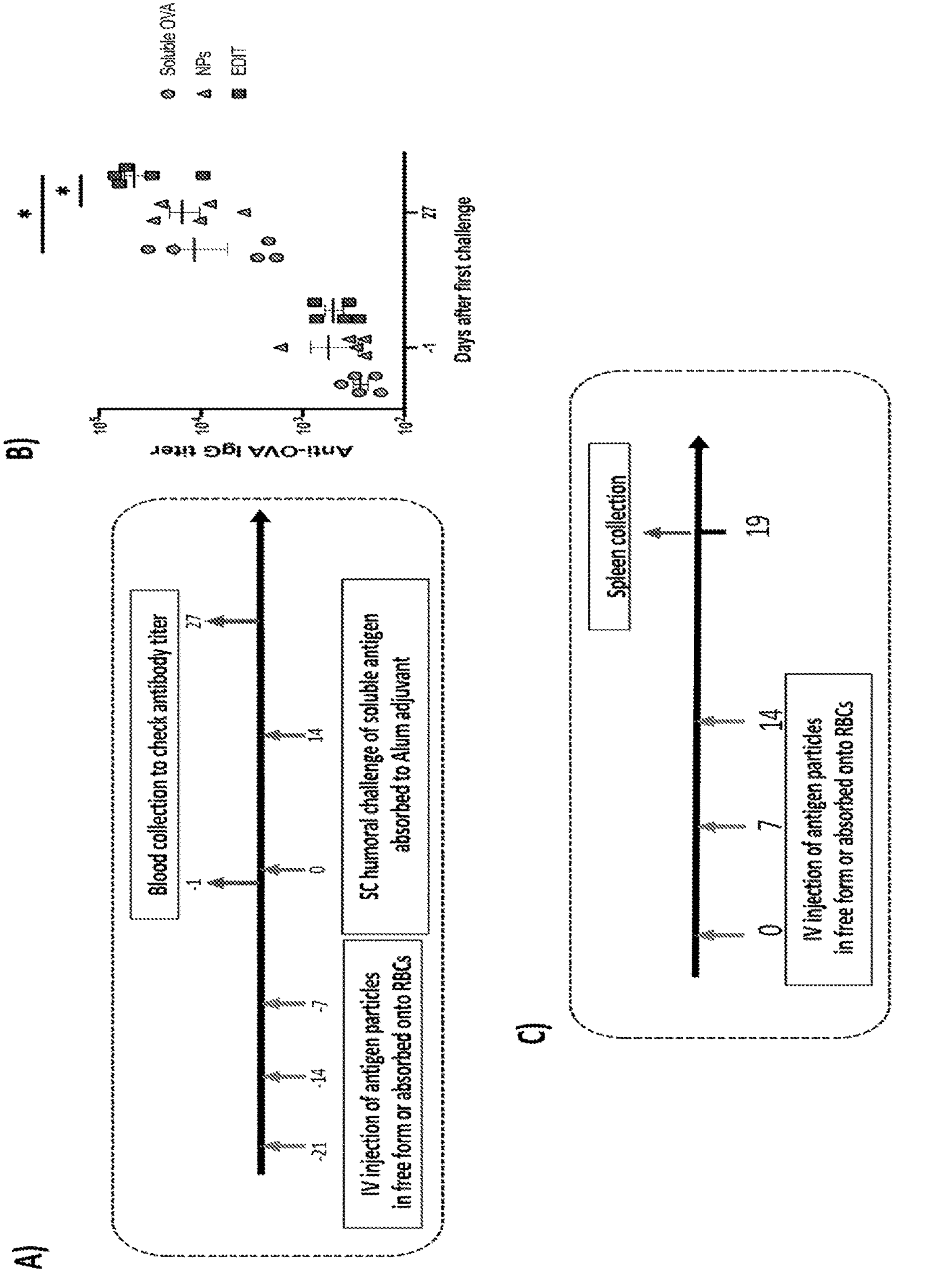
FIGS. 50A-50I depict the immunological consequences of nanoparticle spleen hand-off.

We characterized both the humoral and the cellular responses of hitchhiked nanoparticles delivered to the spleen from erythrocyte surface. For humoral immunity, we used a vaccination schedule comprising of one injection per week, for 3 weeks followed by two alum based-humoral challenges (FIG. 50A). Anti-OVA antibody (IgG) titer, one day before the challenge (Day −1), indicated no significant differences between hitchhiked OVA-NPs, free OVA-NPs or soluble OVA. Antibody titers evaluated 13 days after the last challenge were highest for hitchhiked OVA-NPs (EDIT), significantly higher than those for free nanoparticles (~3 fold) and soluble protein (~4 fold). No difference was found between OVA-NPs and free OVA (FIG. 50B). This demonstrated the ability of EDIT to induce higher OVA specific humoral responses compared to the other groups.

Figures 50D, 50E, 50F, 50G, 50H, 50I:
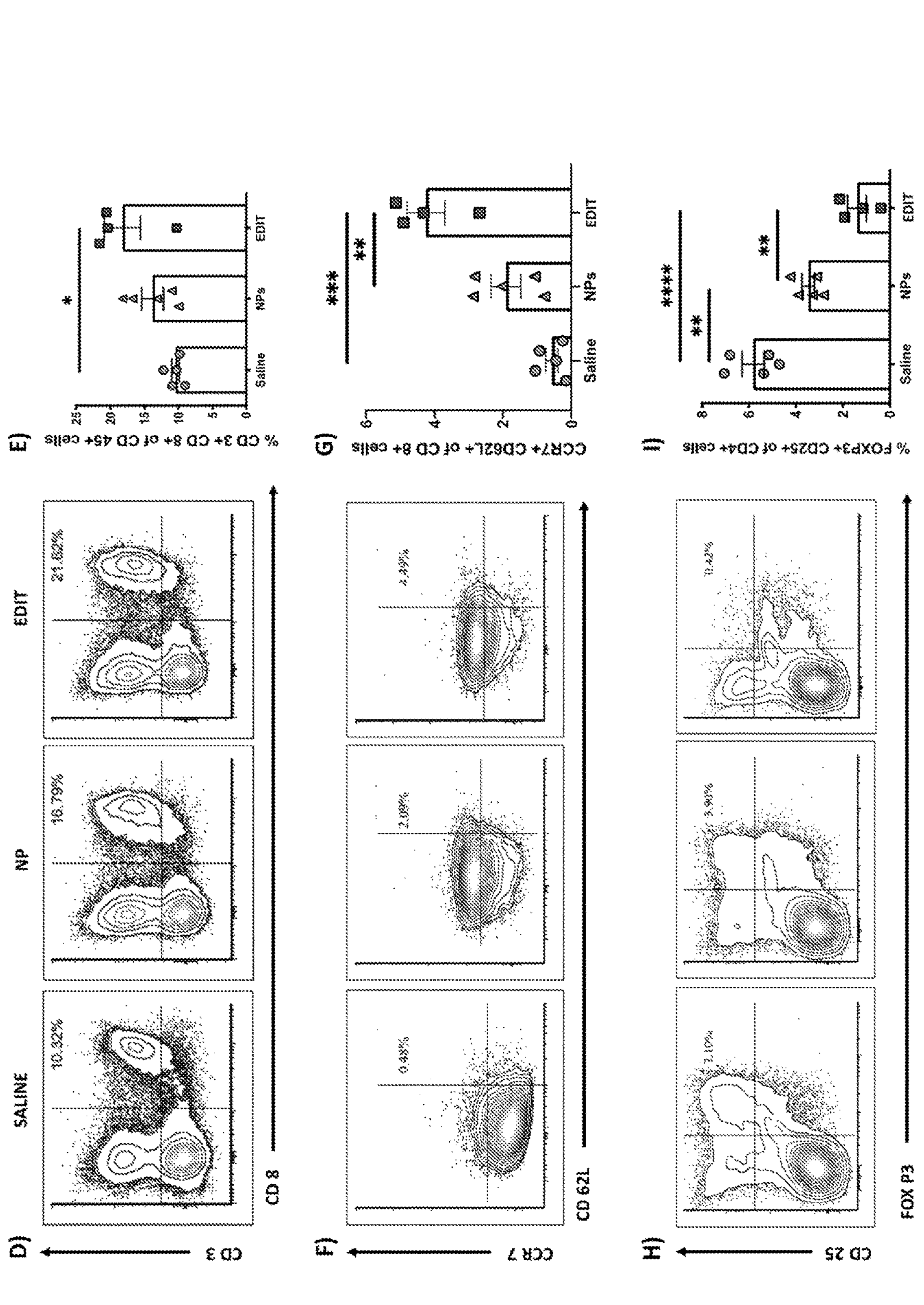
Figures 60A, 60B:
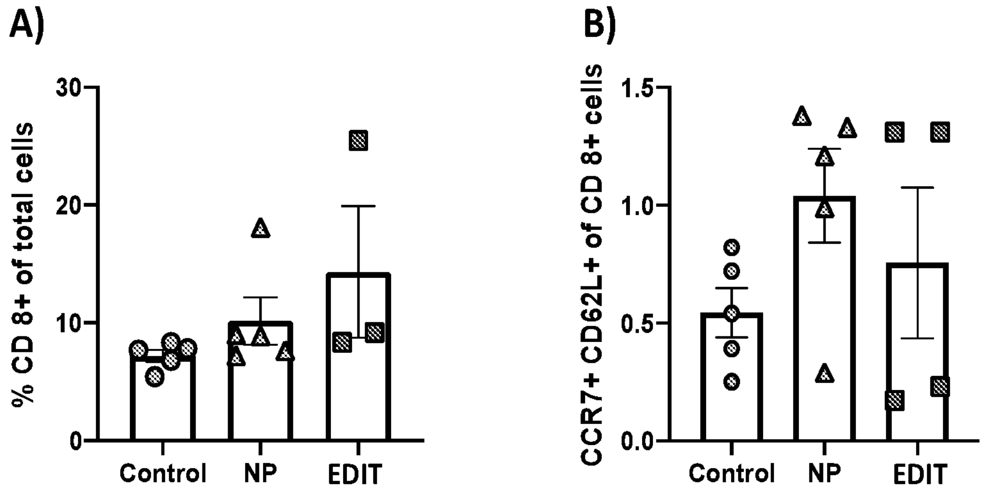
FIGS. 60A-60B depict the immunological consequences of enhanced delivery in the lung.

Cellular immunity generated by EDIT was also assessed. Mice were immunized by EDIT or OVA-NPs once a week for 3 weeks, and comprehensive immune profiling from the harvested splenocytes was performed 5 days after the last vaccination (FIG. 50C). Flow cytometry analysis indicated that EDIT showed significant enhancement in CD3+CD8+ cells in the spleen compared to the control group (A1.7 fold). Interestingly, free nanoparticles (NPs) alone did not show the same effect (FIG. 50D-50E). Carrying out a deeper analysis of CD8 subtypes, we found that CCR7+CD62L+ T cells, which correspond to a group of antigen-experienced T cells (27, 28), were remarkably increased in EDIT compared to both free NPs and the control group. Specifically, EDIT had 8-fold and 2.2-fold more antigen-experienced cells than untreated and OVA-NP groups, respectively (FIG. 50F-50G). Furthermore, our analysis also revealed that the increase in antigen-experienced central memory T cells, is also associated with a corresponding decrease in the CD25+ FOXP3+ regulatory T cell phenotype, with EDIT having 4-fold and 2.5-fold less Treg cells than untreated or OVA-NP group respectively (FIG. 50H-50I). No significant cellular immune effects were seen locally in the lung tissue (FIG. 60A-60B), indicating that spleen delivery and consequent systemic effects are more dominant.

Figures 51A, 51B, 51C:
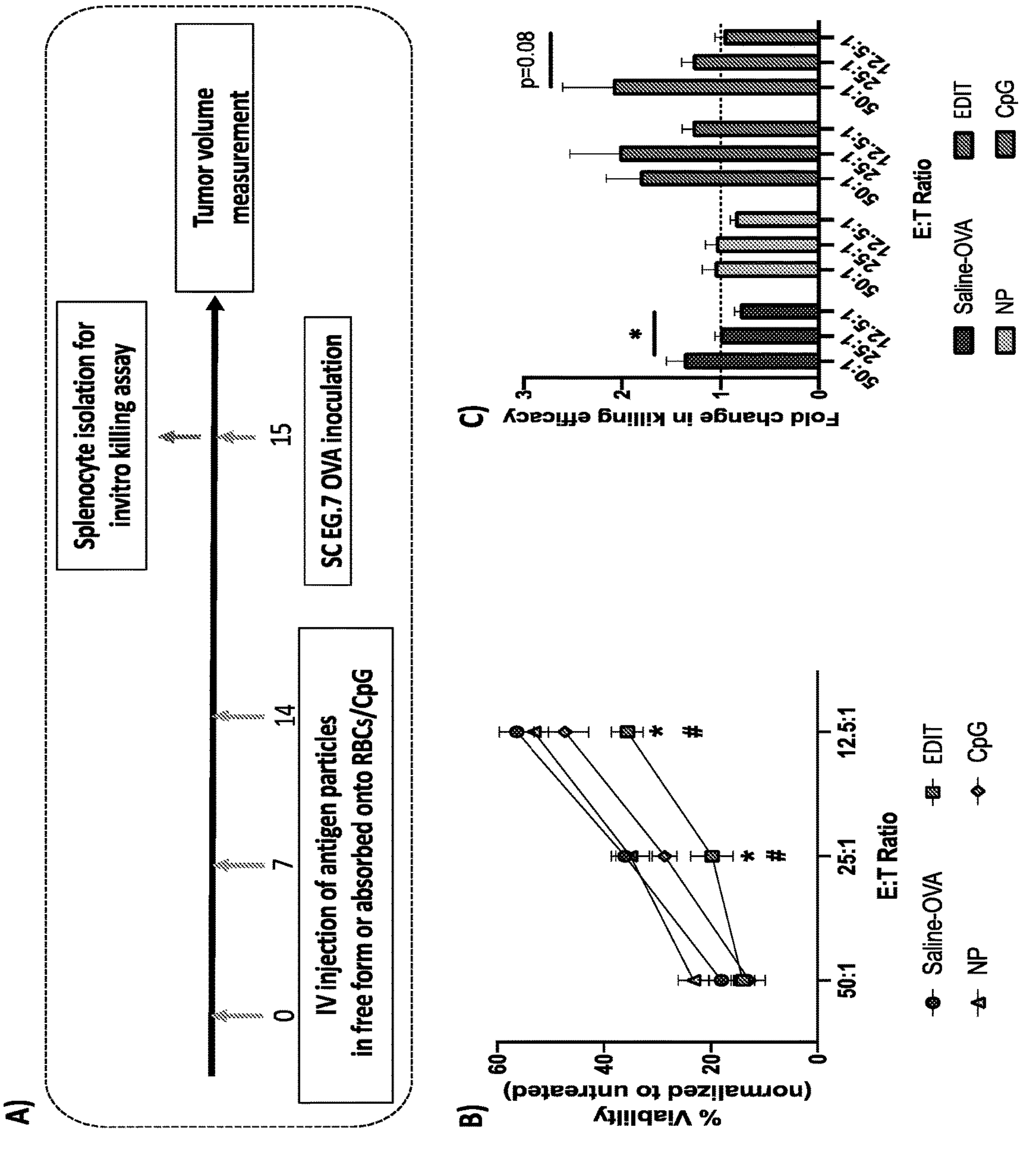
FIGS. 51A-51I depict the therapeutic extension of immune modulation of hitchhiked nanoparticles for vaccination.
Figures 51D, 51E, 51F, 51G, 51H, 51I:
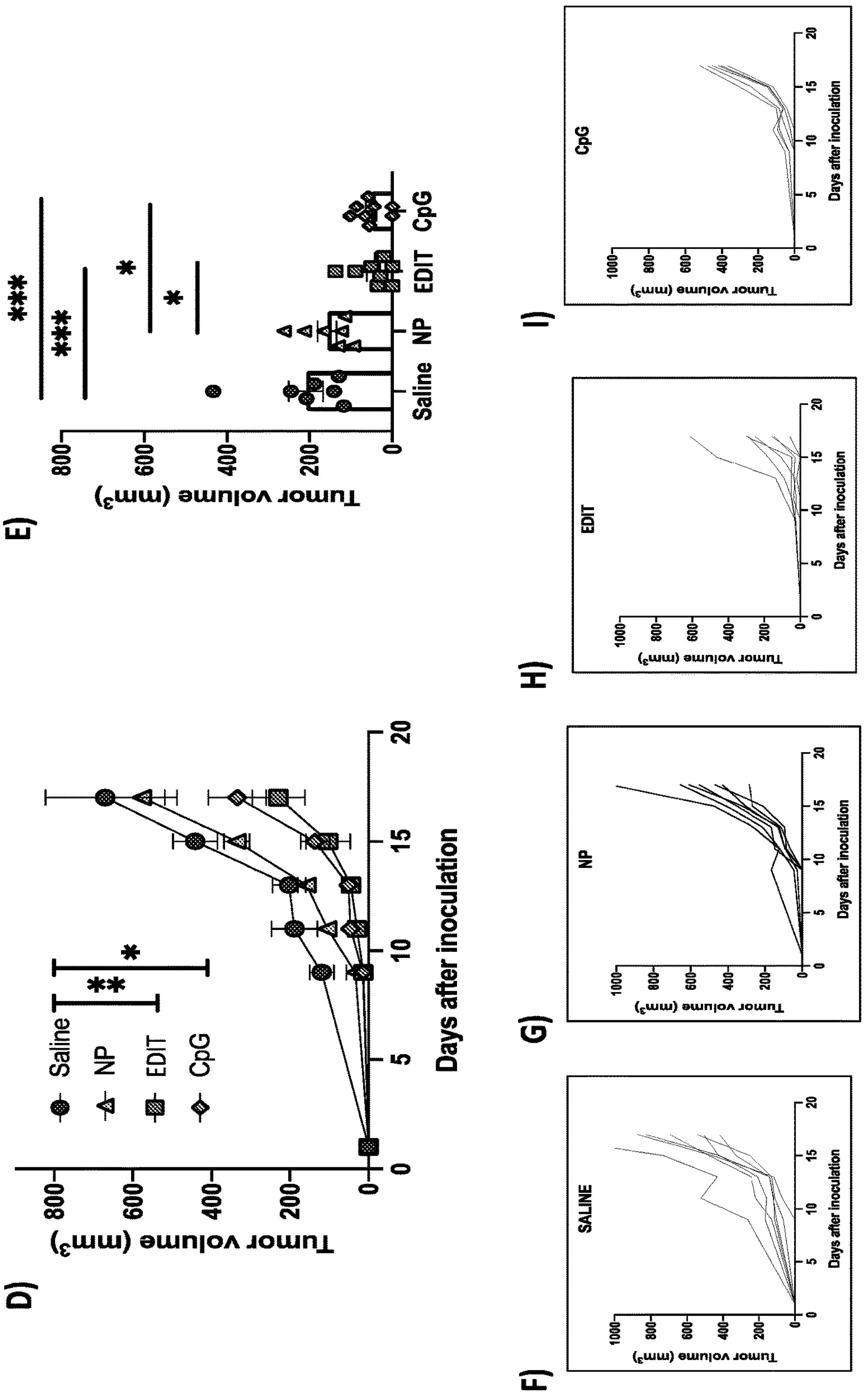
Figure 61:
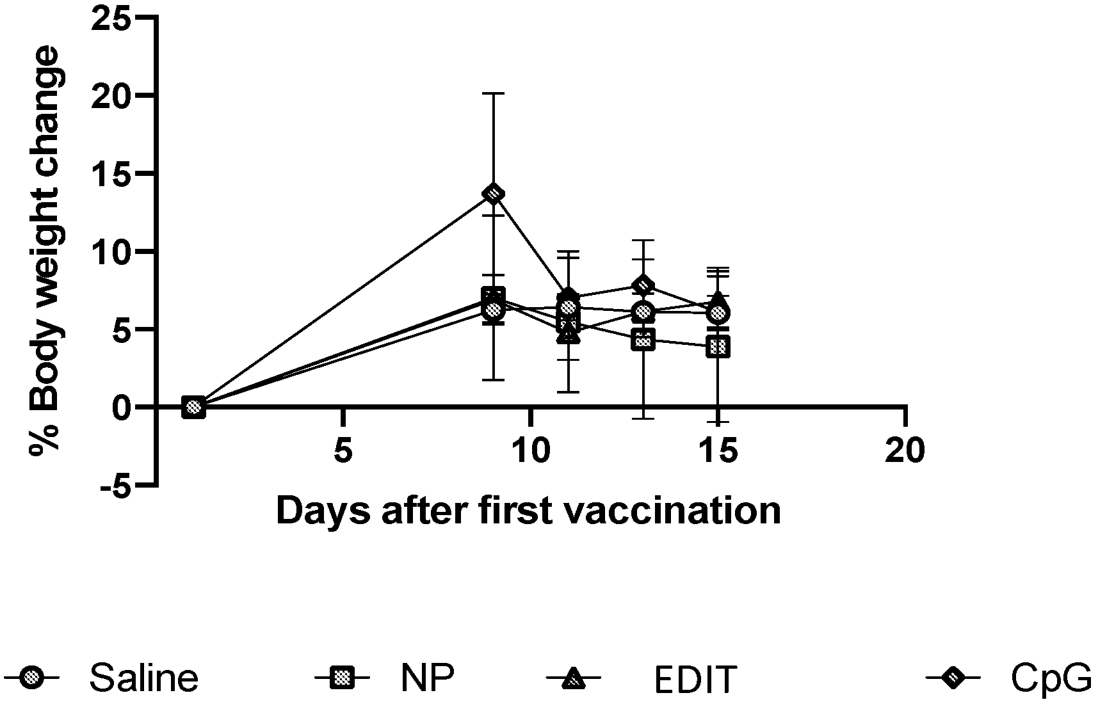
FIG. 61 depicts body weight change after vaccination treatments for the prophylactic studies. Data expressed as mean±s.e.m.

Enhanced Immune Response Improves Interventional Window in a Prophylactic Tumor Model To test the ability of EDIT to induce a cellular therapeutic response, we designed a prophylactic vaccination study, where the mice were immunized once a week for 3 weeks with OVA, EDIT or free OVA-NPs. CpG was used as a positive control. One day after the last vaccination, mice were challenged by subcutaneous inoculation of EG-7 OVA cells and tumor growth was monitored (FIG. 51A). None of the treatment groups induced obvious toxicities during vaccination as indicated by the body weight (FIG. 61). Also, after the last vaccination, splenocytes were isolated from mice injected with different treatment groups to evaluate their in vitro specific target cell killing ability. Splenocytes from mice immunized with EDIT demonstrated significant specific killing even at low effector to target (E:T) ratios (FIG. 51B). Only EDIT group maintained the fold-change of killing efficiency above 1 for all the ratios tested (FIG. 51C). Both these studies indicated that EDIT induced higher OVA specific responses compared to any other vaccination. Tumor growth kinetics clearly demonstrate EDIT immunization was effective. Specifically, 17 days after tumor inoculation, EDIT immunization resulted in ~2.9-fold slower growth as compared to the control group, but the free NP group exhibited no significant difference compared to the control group (FIG. 51D), while on day 13, EDIT resulted in ~4.6 fold and ~3.5 fold compared to the control and NP group (FIG. 51E). In other words, central memory induced by EDIT immunization successfully manifests in effector immune responses against EG-7 OVA when stimulated with the antigen and is able to significantly slow down the tumor growth rate as effectively as the positive control, CpG, without the need for a foreign adjuvant. Free NPs on their own show no such memory effects. Individual tumor growth curves from all different treatment groups indicate that in control and NP groups, growth curves exponentiate far more quickly as compared to EDIT and CpG groups (FIG. 51F-51I). Remarkably, one mouse from the EDIT group remained tumor free throughout the course of the study. EDIT significantly prolonged the tumor exponentiation, thereby increasing the window for therapeutic interventions with alternate strategies.

Discussion

Erythrocytes play an important role in maintaining physiological homeostasis by carrying out the process of oxygenation. However, erythrocytes are also an active member of the innate immune system. It has been reported that certain pathogens can attach to the erythrocyte cell membrane, get neutralized by oxidative species from within the erythrocytes and ultimately are physically handed off to the immune cells in spleen (8, 9). This offers a genuine opportunity to develop a biomimetic strategy to target spleen, Erythrocyte Driven Immune Targeting (EDIT), which leverages antigen presentation to spleen from the surface of erythrocyte.

Conventionally, erythrocyte hitchhiking has been explored for lung targeting applications since the shear stresses experienced by stretched erythrocytes in lung capillaries is able to dislodge the particles in lungs (17, 18). This makes it challenging to deliver the cargo to the spleen. The dominant factor in skewing the distribution of nanoparticles from the lung to the spleen was the initial feed ratio of nanoparticle to erythrocytes. Modulation of this parameter helped in improving shear resistance in the lungs, thus allowing a smaller fraction of nanoparticles to detach in the lungs, and thus making a larger fraction available to target elsewhere. At the same time, the slight alteration induced to the erythrocyte membrane enabled spleen as a natural target. In vitro shear studies indicated that increasing NP:Erythrocyte feed ratios significantly reduced shear-induced detachment. Higher nanoparticle density on hitchhiked erythrocytes for higher NP:Erythrocyte feed ratios is the likely cause for this improved shear resistance. Highly loaded erythrocytes are more rigid, thus resisting the biomechanical stretching in the lung capillaries (24) and thereby reducing lung accumulation. The natural pathway of pathogen transfer from the surface of erythrocytes to the APCs in the spleen has been unclear, however, membrane alteration caused by adherent pathogens has been strongly implicated. This attribute was engineered in our system by controlling the NP:Erythrocyte ratio in the feed and assessing temporary damage in terms of phosphatidyl serine upregulation. Phosphatidyl serine upregulation is known to promote interactions of dendritic cells with the erythrocytes (13, 14). This, combined with the masking of CD47 receptors at higher nanoparticle to erythrocytes ratios, likely makes the nanoparticles on the "missing self" erythrocyte more prone to uptake by these cells (29).

Based on the effect of NP:Erythrocyte ratio on in vitro shear resistance and transient phosphatidyl serine expression, an optimal NP:Erythrocyte ratio of 300:1 was selected. This ratio also led to efficient delivery and sustained presence of nanoparticles in the spleen. In contrast to the past studies involving erythrocytes or their membranes, where their senescence was exploited for targeting spleen, in our case, only particles are delivered to the spleen, while the erythrocytes continue to remain in circulation, indicating that the damage to erythrocyte membrane is temporary, sufficient for spleen hand-off but does not cause the erythrocytes themselves to be sequestered. Thus, EDIT offers a new pathway for targeting the spleen, particularly the antigen presenting cells in the spleen. Phagocyte depletion studies illustrated that particles in spleen are not located within the phagocytes, indicating their presence within APCs which could be exploited for immunomodulation.

Overall, for therapeutic evaluation of the humoral and cellular immune responses, respective OVA challenges were received after the treatments were given and therapeutic outcomes were monitored. Thus, by the design of these experiments, we were able to track the memory responses to our prophylactic vaccinations. Humoral and cellular immune responses showed a strong vaccination effect, with EDIT exhibiting 3-fold higher antibody titer, 2.2-fold higher antigen experienced central memory T cells and 2.5-fold lower regulatory T cells, compared to free nanoparticles. Moreover, the outcomes were assessed by ELISA (for Anti-OVA IgG antibody) and specific cell killing assay (for splenocyte cytotoxicity), indicating that these responses are highly specific.

This adjuvant effect can be effectively used for vaccinations against blood-borne infections, such as malaria, and the overall concept can be extrapolated to develop systemic or tissue-specific memory responses following intravenous vaccinations (17, 30). As a proof of concept, the immune response generated by EDIT was successfully utilized to drive therapeutic responses in a prophylaxis model. EDIT-mediated immunization was able to significantly slow down the tumor growth by increasing the equilibrium phase of cancer immunity cycle (31), performing equally as good as a foreign adjuvant CpG, thereby increasing the window of therapeutic interventions. Several differences can be noted between strategies of CpG and EDIT. Unlike CpG, which is a non-native molecule, RBC here acts a natural adjuvant. Further, CpG is generally admixed with the vaccine, thus allowing it to diffuse away from the injection site, which can raise potential safety concerns. In contrast, EDIT is active only when the nanoparticle is attached to the perturbed erythrocyte, which inherently improves the safety profile. Finally, our data confirm that EDIT can incorporate nanoparticles beyond 200 nm PS including those of different sizes, synthetic materials or biological materials.

Thus, EDIT offers a new perspective for vaccination strategies. Several adjuvants have been reported in the literature and used in the clinic (32). Often, the adjuvants are of non-human origin and that is the principal reason why an immune response gets triggered. Such adjuvant-based strategies are based on mixing the antigen with some kind of foreign chemical/material that stimulates the immune system, as the first Gaston Ramon's alum adjuvant. In contrast, we report erythrocyte-mediated delivery of the antigen that stimulates the immune response acting as a 'natural adjuvant. Adjuvant free therapies based on the most "self" cell of the body represents a unique way of propelling developments of safe vaccines.

In summary, we have developed a biomimetic strategy that exploits the innate immune function of the erythrocytes to engineer an efficient nanoparticle hand-off to the spleen. Fundamentally, it represents a novel pathway to deliver nanoparticles to the spleen, that does not involve extensive modifications to the nanoparticles themselves. Nanoparticle hand-off by EDIT led to a strong immunological memory that can drive therapeutic responses. This platform is a versatile strategy to target nanoparticles to the spleen without specific modifications.

Materials and Methods

Materials

Carboxylic acid polystyrene nanoparticles were purchased from Polysciences, Inc. (PA, USA). PLGA nanoparticles and Hexamethyldisilazane (HMDS) were purchased from Sigma Aldrich (MO, USA). GM-CSF was obtained from PeproTech (NJ, USA). Nunc™ Lab-Tek™ II Chamber Slide™ System, cell staining buffer, Alexa Fluor 647 Ovalbumin, Alexa Fluor 647 NHS reagent, and phosphate buffered saline (1×), 1-Ethyl-3-(3-dimethylaminopropyl) carbodiimide (EDC), 2-(N-morpholino) ethanesulfonic acid (MES) were obtained from Thermo Fischer Scientific (MA, USA). Lithium heparin coated microtainer tubes were obtained from BD medical technology (MA, USA). Tissue dissociation tubes and lung dissociation kit were obtained from Miltenyi Biotec (Germany). 0.9% saline solution was obtained from Teknova (CA, USA). Paraformaldehyde was obtained from Electron Microscopy sciences (PA, USA). Clodrosome® was obtained from Encapsula NanoSciences (TN, USA). All fluorescent probe conjugated antibodies for immune cell staining were purchased from Biolegend (CA, USA).

Preparation and Characterization of Antigen-Coated Polystyrene Nanoparticles

Antigen-coated polystyrene nanoparticles were prepared using an EDC-based method. Briefly, 2 mg of polystyrene nanoparticles with carboxylic acid surface groups (PS—COOH) was suspended in MES buffer (pH 5.5) for 15 mins to activate the carboxylic group. 1 mg of antigen protein was subsequently added and allowed for reaction for 4 h under gentle shaking at room temperature. Unconjugated protein was eliminated by centrifugation of the nanoparticles at 12000 g for 15 mins. Protein conjugation efficiency was measured by quantifying the unconjugated protein in the supernatant using a fluorescence-based method. Protein coated nanoparticles were washed twice using deionized (DI) water. The particles were resuspended in DI water and assessed for their size, zeta potential and polydispersity index using dynamic light scattering (Malvern Zen3600, PA, USA) and scanning electron microscopy (Zeiss FESEM Supra 55VP, Zeiss FESEM Ultra 55, Germany). Nanoparticles were resuspended in 1×PBS immediately before their use. Antigen-coated PLGA nanoparticles were prepared using the same method.

Internalization of Nanoparticles by Dendritic Cells (DCs) and Activation of DCs by Nanoparticles JAWII DCs (ATCC® CRL-11904™) were obtained from ATCC (VA, USA). They were cultured in Alpha minimum essential medium with ribonucleosides, deoxyribonucleosides, 4 mM L-glutamine, 1 mM sodium pyruvate and 5 ng/ml murine GM-CSF, 80%; fetal bovine serum, 20%. Internalization of antigen-coated nanoparticles was evaluated by flow cytometry and confocal microscopy. For flow cytometry analysis, $2\times10^6$ JAWII DCs were seeded in a 12-well plate and allowed to adhere overnight. Media was replaced before adding nanoparticles. 30 μg of Alexa Fluor 647 labeled antigen-coated nanoparticles were added to each well and allowed to incubate for 24 h at 37° C. Media was then removed and cells were washed 3 times using PBS. The cells were gently scrapped using a cell scrapper. These cells were analyzed by flow cytometry (BD LSR Analyzer II, CA, USA). For confocal microscopy, 2×105 JAWII DCs were seeded to a 2-well chamber and treated similarly as for the flow cytometry analysis. After washing cells with PBS, cells were fixed with 4% (paraformaldehyde) PFA for 10 mins. Cells were then permeabilized with 0.01% Triton-X100 and cell nucleus was stained with DAPI. The processed cells were imaged by confocal microscopy (Upright Zeiss LSM 710 NLO ready).

To evaluate the activation of DCs by antigen-coated nanoparticles, $2\times10^6$ JAWII DCs were seeded in a 12-well plate and allowed to adhere overnight. Cells were incubated with antigen-coated nanoparticles using the same protocol for flow cytometry analysis of nanoparticle uptake. After treatment, cells were washed three times with PBS and detached from the wells using 0.25% Trypsin/EDTA solution. The cells were washed twice using flow staining buffer and stained for CD80 using PE-CD80 antibody (Biolegend, CA, USA). The stained cells were analyzed by flow cytometry (BD LSR Analyzer II, CA, USA).

Hitchhiking of Antigen-Coated Nanoparticles to Red Blood Cells (RBCs)

Mouse whole blood was collected via terminal cardiac puncture using a heparin coated syringe and stored in BD Microtainer blood collection tube. After sitting for >30 min on ice, the collected whole blood was centrifuged at 1000 g for 10 mins at 4° C. to remove the serum and buffy coat layer. The RBC layer was washed three times using cold PBS and centrifuged at 650 g for 15 mins at 4° C. The washed RBCs were resuspended in PBS at a hematocrit of 10% (RBC stock solution) and stored at 4° C. for later use.

The hitchhiking of antigen-coated nanoparticles to RBCs was conducted using a previously reported method(18). In brief, equal volume of antigen-coated nanoparticles was mixed with equal volume of 10% RBC stock solution by inversion and pipetting. The mixture was then rotated on a revolver at 12 rpm for 40 mins. The hitchhiked RBCs were separated from unbound nanoparticles by centrifugation at 100 g for 5 mins at 4° C. The hitchhiked samples were then washed twice using PBS and finally resuspended in PBS at a 10% (v/v) concentration for further characterization and later use. The number of hitchhiked nanoparticles on RBCs was quantified using a fluorescence-based method. 25 μL of hitchhiked RBC samples (with known number of RBCs) were lysed using DI water, and the nanoparticle concentration was quantified by measuring the fluorescence of nanoparticles on a plate reader. The percentage of RBCs carrying nanoparticles for different nanoparticle-to-RBC ratios was determined using flow cytometry (BD LSR Analyzer II, CA, USA) using Alexa Fluor 647 fluorescence and confirmed by confocal microscopy (Upright Zeiss LSM 710 NLO ready, Germany). Scanning electron microscopy (SEM) (Zeiss FESEM Supra 55VP, Zeiss FESEM Ultra 55) was used to confirm the hitchhiking of antigen-coated nanoparticles to RBCs. Briefly, hitchhiked samples were fixed for 1 h using 4% glutaraldehyde. They were washed twice with PBS to remove unreacted glutaraldehyde. Next, fixed hitchhiked cells were subjected to successive washes with increasing ethanol concentration (50-100% v/v) before finally resuspending them in Hexamethyldisilazane (HMDS) followed by imaging. In vitro shear studies were performed as described before (18) Briefly, hitchhiked RBCs were resuspended in 10 ml of fetal bovine serum and a rotary shear of 6 Pa was applied for 20 mins using a couette viscometer (AR-G2,TA Instruments, DE, USA). The nanoparticle remaining attached were quantified using fluorescence as described before.

The impact of nanoparticle hitchhiking on the carrier RBCs was evaluated by the agglutination assay(25) and the phosphatidylserine (PS) assay (24) as reported before. In brief, for the agglutination assay, naïve or hitchhiked RBCs of 1% hematocrit were dispensed onto a 96-well U-bottom plate. The plate was allowed to sit at 37° C. for 1 h and the agglutination was then assessed. 200 nm carboxylic acid polystyrene nanoparticle hitchhiked RBCs were used as a positive control considering its reported damage to the carrier erythrocytes. For the PS assay, naïve and hitchhiked RBCs of 0.01% hematocrit were incubated with fluorescent Annexin V-Alexa Fluor 488 (binding to PS) for 15 min in buffer containing 2 mM $CaCl_2$. After staining, samples were analyzed using flow cytometry (BD LSR Analyzer II, CA, USA).

Animals

Female Balb/c and C57BL/6 mice (7-9 weeks of age) were purchased from Charles River Laboratories (MA, USA). All animal experiments were performed according to the approved protocols by the Institutional Animal Care and Use Committee of the Faculty of Arts and Sciences, Harvard University, Cambridge.

Biodistribution Study

All biodistribution studies were performed in healthy female Balb/c mice. Alexa Fluor 647 labeled antigen was used to prepare antigen-coated nanoparticles for the biodistribution studies. In brief, female Balb/c mice (7-9 weeks of age) were intravenously administered with free or hitchhiked antigen nanoparticles at a dose containing 7 ug antigen. For studies involving phagocyte depletion, phagocytes were depleted by i.v. administration of 200 μL of Clodrosome® containing 5 mg/mL Clodronate 48 h before i.v. injection of formulations. 20 min, 6 h, or 24 h after formulation administration, mice were euthanized and major organs including blood, liver, spleen, kidney, heart, lung, and brain were extracted. The extracted organs were imaged using in vivo imaging (PerkinElmer IVIS Spectrum, MA, USA). Fluorescence in organs were quantified using IVIS software by analyzing the ROI of organs. Percent injected dose (ID %) of nanoparticles accumulated in organs was estimated by dividing the fluorescence in the organ of interest with the total fluorescence in all the tested organs.

For the in vivo tracking of hitchhiked system, RBCs were labeled by CellTrace™ CFSE and antigen-coated nanoparticles were labeled by Alexa Fluor 647. The double labeled hitchhiked system was i.v. administered to female Balb/c mice (7-9 weeks of age). Blood was collected at predetermined time points (0 min, 20 min, 6 h, and 24 h after administration). The collected Blood was diluted in flow staining buffer at a 1:100 dilution and analyzed by flow cytometry (BD LSR Analyzer II, CA, USA).

Characterization of Immune Responses Induced by EDIT

The humoral and cellular immune response induced by EDIT were assessed in healthy Balb/c mice. To evaluate the humoral response, female Balb/c mice (7 weeks of age) were i.v. administered with free Ovalbumin (OVA), OVA-coated nanoparticles, and hitchhiked OVA-coated nanoparticles at a dose containing 7 μg of OVA, on days 0, 7, and 14. Subsequently, 7 and 14 days after the three doses of immunization, mice were subcutaneously challenged with two doses of OVA adjuvanted with Alum (7 ug OVA and 70 ug Alum). Blood was collected one day before the first dose of challenge and 13 days after the second dose of challenge. Anti-OVA IgG antibody titer in the collected blood was measure by ELISA using a previously reported method.(33)

To evaluate the cellular response, female Balb/c mice (7 weeks of age) were i.v. administered with saline, ovalbumin (OVA)-coated nanoparticles, and hitchhiked OVA-coated nanoparticles at a dose of 7 μg of OVA every week for three doses (on day 0, 7, and 14). 5 days after the last dose (on day 19), spleen and lung of mice were collected. A single cell suspension of organ cells was formed using corresponding organ dissociation kits (Miltenyi Biotec, Germany) according to manufacturer's instructions. The cells were stained with antibodies and analyzed by flow cytometry (BD LSR Analyser II, NJ USA). Different panels of antibody cocktails were made from CD45 (Biolegend, Cat no: 103116, Clone: 30-F11), CD3 (Biolegend, Cat no: 100218, Clone: 17A2), CD4 (Biolegend, Cat no: 100421, Clone: GK1.5), CD8a (Biolegend, Cat no: 100711, Clone: 53-6.7), NKp46 (Biolegend, Cat no: 137606, Clone: 29A1.4), CD11c (Biolegend, Cat no: 117307, Clone: N418), Granzyme B (Biolegend, Cat no: 372208, Clone: QA16A02), IFN-γ (Biolegend, Cat no: 505849, Clone: XMG1.2), IFN-γ (Biolegend, Cat no: 505806, Clone: XMG1.2), CD86 (Biolegend, Cat no: 105011, Clone: GL-1), and Am Cyan Live/dead cell staining kit (Thermo Fischer Scientific, MA, USA). All antibodies were diluted at optimized dilutions prior to their use.

Tumor Studies

EG-7 OVA (ATCC® CRL-2113™) was obtained for ATCC (VA, USA). Cells were cultured in RPMI 1640 medium with 2 mM L-glutamine adjusted to contain 1.5 g/L sodium bicarbonate, 4.5 g/L glucose, 10 mM HEPES and 1.0 mM sodium pyruvate and supplemented with 0.05 mM 2-mercaptoethanol and 0.4 mg/ml G418, 90%; fetal bovine serum, 10%. Cells of low passage number were passaged 2-3 times before their in vivo use.

The efficacy of EDIT in controlling the growth of EG-7 OVA tumors was studied in a prophylactic model. Female C57BL/6 mice (7 weeks of age) were immunized with free OVA (in saline), OVA nanoparticles, hitchhiked OVA nanoparticles, and free OVA+CpG ODN 1826 (10 ug) at a dose containing 7 ug OVA, on days 0, 7, and 14. One day after the last immunization (on day 15), $5\times10^5$ EG-7 OVA cells were subcutaneously inoculated into the right mammary fat-pad. The tumor size and body weight of mice were monitored after tumor inoculation.

Statistical Analysis

All statistical analyses were carried out using Graphpad prism 8 software. Normality tests were used to determine normality. Student's t test and one-way ANOVA with Tukey's HSD test were used to determine significance: $p<0.05$*; $p<0.01$; $p<0.001$*, $p<0.0001$****. All the flow cytometry analyses were carried out using FCS Express 7.0 software.

REFERENCES

1. T. R. Klei, S. M. Meinderts, T. K. van den Berg, R. van Bruggen, From the Cradle to the Grave: The Role of Macrophages in Erythropoiesis and Erythrophagocytosis. *Front Immunol* 8, 73 (2017).
2. N. Pishesha et al., Engineered erythrocytes covalently linked to antigenic peptides can protect against autoimmune disease. *Proc Natl Acad Sci USA* 114, 3157-3162 (2017).
3. K. M. Lorentz, S. Kontos, G. Diaceri, H. Henry, J. A. Hubbell, Engineered binding to erythrocytes induces immunological tolerance to *E. coli* asparaginase. *Sci Adv* 1, e1500112 (2015).
4. S. Kontos, I. C. Kourtis, K. Y. Dane, J. A. Hubbell, Engineering antigens for in situ erythrocyte binding induces T-cell deletion. *Proc Natl Acad Sci USA* 110, E60-68 (2013).
5. H. L. Anderson, I. E. Brodsky, N. S. Mangalmurti, The Evolving Erythrocyte: Red Blood Cells as Modulators of Innate Immunity. *J Immunol* 201, 1343-1351 (2018).
6. V. Pretini et al., Red Blood Cells: Chasing Interactions. *Front Physiol* 10, 945 (2019).
7. J. Baum, R. H. Ward, D. J. Conway, Natural selection on the erythrocyte surface. *Mol Biol Evol* 19, 223-229 (2002).
8. H. Minasyan, Mechanisms and pathways for the clearance of bacteria from blood circulation in health and disease. *Pathophysiology* 23, 61-66 (2016).
9. H. Minasyan, Phagocytosis and oxycytosis: two arms of human innate immunity. *Immunol Res* 66, 271-280 (2018).
10. C. Halma et al., Elimination of soluble 123I-labeled aggregates of IgG in patients with systemic lupus erythematosus. Effect of serum IgG and numbers of erythrocyte complement receptor type 1. *Arthritis Rheum* 34, 442-452 (1991).
11. J. C. Edberg, E. Wright, R. P. Taylor, Quantitative analyses of the binding of soluble complement-fixing antibody/dsDNA immune complexes to CR1 on human red blood cells. *J Immunol* 139, 3739-3747 (1987).
12. C. Damgaard et al., Viable bacteria associated with red blood cells and plasma in freshly drawn blood donations. *PLoS One* 10, e0120826 (2015).
13. D. B. Nguyen et al., Regulation of phosphatidylserine exposure in red blood cells. *Cell Physiol Biochem* 28, 847-856 (2011).
14. D. Z. de Back, E. B. Kostova, M. van Kraaij, T. K. van den Berg, R. van Bruggen, Of macrophages and red blood cells; a complex love story. *Front Physiol* 5, 9 (2014).
15. C. H. Villa, A. C. Anselmo, S. Mitragotri, V. Muzykantov, Red blood cells: Supercarriers for drugs, biologicals, and nanoparticles and inspiration for advanced delivery systems. *Adv Drug Deliv Rev* 106, 88-103 (2016).
16. K. Danielyan et al., Cerebrovascular thromboprophylaxis in mice by erythrocyte-coupled tissue-type plasminogen activator. *Circulation* 118, 1442-1449 (2008).
17. J. S. Brenner et al., Red blood cell-hitchhiking boosts delivery of nanocarriers to chosen organs by orders of magnitude. *Nat Commun* 9, 2684 (2018).
18. Z. Zhao, A. Ukidve, Y. Gao, J. Kim, S. Mitragotri, Erythrocyte leveraged chemotherapy (ELeCt): Nanoparticle assembly on erythrocyte surface to combat lung metastasis. *Sci Adv* 5, eaax9250 (2019).
19. A. C. Anselmo et al., Delivering nanoparticles to lungs while avoiding liver and spleen through adsorption on red blood cells. *ACS Nano* 7, 11129-11137 (2013).
20. V. Bourgeaux, J. M. Lanao, B. E. Bax, Y. Godfrin, Drug-loaded erythrocytes: on the road toward marketing approval. *Drug Des Devel Ther* 10, 665-676 (2016).
21. Z. Zhao, A. Ukidve, V. Krishnan, S. Mitragotri, Effect of physicochemical and surface properties on in vivo fate of drug nanocarriers. *Adv Drug Deliv Rev* 143, 3-21 (2019).
22. S. Kumar, A. C. Anselmo, A. Banerjee, M. Zakrewsky, S. Mitragotri, Shape and size-dependent immune response to antigen-carrying nanoparticles. *J Control Release* 220, 141-148 (2015).
23. S. U. Frick et al., Functionalized polystyrene nanoparticles trigger human dendritic cell maturation resulting in enhanced CD4+ T cell activation. *Macromol Biosci* 12, 1637-1647 (2012).
24. D. C. Pan et al., Nanoparticle Properties Modulate Their Attachment and Effect on Carrier Red Blood Cells. *Sci Rep* 8, 1615 (2018).
25. D. Pan et al., The Effect of Polymeric Nanoparticles on Biocompatibility of Carrier Red Blood Cells. *PLoS One* 11, e0152074 (2016).
26. S. G. Moreno, Depleting Macrophages In Vivo with Clodronate-Liposomes. *Methods Mol Biol* 1784, 259-262 (2018).
27. M. D. Martin, V. P. Badovinac, Defining Memory CD8 T Cell. *Front Immunol* 9, 2692 (2018).
28. H. Unsoeld, H. Pircher, Complex memory T-cell phenotypes revealed by coexpression of CD62L and CCR7. *J Virol* 79, 4510-4513 (2005).

29. T. Yi et al., Splenic Dendritic Cells Survey Red Blood Cells for Missing Self-CD47 to Trigger Adaptive Immune Responses. *Immunity* 43, 764-775 (2015).

30. P. A. Darrah et al., Prevention of tuberculosis in macaques after intravenous BCG immunization. *Nature* 577, 95-102 (2020).

31. D. S. Chen, I. Mellman, Oncology meets immunology: the cancer-immunity cycle. *Immunity* 39, 1-10 (2013).

32. A. Di Pasquale, S. Preiss, F. Tavares Da Silva, N. Garcon, Vaccine Adjuvants: from 1920 to 2015 and Beyond. *Vaccines* (*Basel*) 3, 320-343 (2015).

33. Z. Zhao et al., Engineering of a hybrid nanoparticle-based nicotine nanovaccine as a next-generation immunotherapeutic strategy against nicotine addiction: A focus on hapten density. *Biomaterials* 123, 107-117 (2017).

TABLE 6

Physicochemical properties of different particle combinations

| Particle | Size (nm)* | Polydispersity (PDI)* | Zeta potential (mV)* |
|---|---|---|---|
| PS-OVA-500 | 540.93 ± 13.03 | 0.072 ± 0.031 | −21.5 ± 0.1 |
| PLGA-OVA-200 | 155.73 ± 1.03 | 0.064 ± 0.033 | −21.26 ± 0.2 |
| PS-KLH-200 | 261.43 ± 2.98 | 0.073 ± 0.01 | −3.08 ± 0.21 |

*Data presented as mean ± s.e.m.

What is claimed herein is:

1. A composition comprising:

a) an erythrocyte; and b) more than 20 particles located on the cell surface of the erythrocyte, each particle comprising:

i) poly(lactic-co-glycolic acid) (PLGA); and ii) at least one therapeutic agent.

2. The composition of claim 1, wherein the PLGA comprises ester ends and/or acid ends.

3. The composition of claim 1, wherein the at least one therapeutic agent is selected from the group consisting of:

a chemotherapeutic agent; an antigen; a steroid; an immunosuppressant agent; an immunostimulatory agent; a virus; a small molecule; a peptide; a nucleic acid; and a chemokine.

4. The composition of claim 3, wherein the at least one chemotherapeutic agent is selected from the group consisting of:

doxorubicin; camptothecin; paclitaxel; docetaxel; 5-fluorouracil; gemcitabine; methotrexate; and a combination of any of the foregoing.

5. The composition of claim 3, wherein the at least one therapeutic agent is an antigen.

6. The composition of claim 1, wherein the PLGA comprises a L:G ratio with more L than G.

7. The composition of claim 1, wherein the PLGA comprises a L:G ratio of about 85:15.

8. The composition of claim 1, wherein the PLGA comprises a L:G ratio of about 65:35.

9. The composition of claim 1, wherein the PLGA comprises a L:G ratio of about 85:15 and ester ends.

10. The composition of claim 1, wherein the PLGA comprises a L:G ratio of about 65:35 and acid ends.

11. The composition of claim 1, wherein the at least one therapeutic agent is present at a concentration of at least 100 μg per $3\times10^8$ erythrocytes.

12. The composition of claim 1, wherein the diameter of the particle is from about 100 nm to about 10 μm.

13. The composition of claim 1, wherein the particle further comprises one or more cell adhesive molecules.

14. The composition of claim 13, wherein the one or more cell adhesive molecules is localized to a region of the particle surface.

15. The composition of claim 13, wherein the one or more cell adhesive molecule is selected from the group consisting of:

an antibody reagent that binds specifically to a molecule on a red blood cell; a peptide that binds specifically to a molecule on a red blood cell; a cell adhesive polymer; a cell adhesive polyelectrolyte; and a ligand for a receptor on a red blood cell.

16. The composition of claim 15, wherein the one or more cell adhesive polyelectrolytes comprise hyaluronic acid, hyaluronic acid-aldehyde, and/or poly(allylamine) hydrochloride.

17. The composition of claim 15, wherein the one or more cell adhesive polymers is a polyphenol or metal-polyphenol network.

18. A method of delivering a therapeutic agent to a cell in a subject, the method comprising administering to the subject a composition of claim 1, wherein the therapeutic agent is a chemotherapeutic agent or a chemokine.

19. A method of treating cancer and/or a tumor in a subject in need thereof, the method comprising administering to the subject a composition of claim 1.

20. A method of stimulating an immune response in a subject in need thereof, the method comprising administering to the subject a composition of claim 1, wherein the therapeutic agent is an antigen, an immunostimulatory agent, or a chemokine.

21. A method of decreasing or suppressing an immune response in a subject in need thereof, the method comprising administering to the subject a composition of claim 1, wherein the therapeutic agent is an immunomodulatory agent or a steroid.

* * * * *